(12) United States Patent
Min et al.

(10) Patent No.: US 12,203,065 B2
(45) Date of Patent: Jan. 21, 2025

(54) METHOD FOR CULTURING NATURAL KILLER CELL, USING TRANSFORMED T CELL

(71) Applicant: GC CELL CORPORATION, Seoul (KR)

(72) Inventors: Bokyung Min, Yongin-si (KR); Gyeong Min PArk, Yongin-si (KR); Hyun Ah Kim, Yongin-si (KR); Bitna Yang, Yongin-si (KR); Yu Kyeong Hwang, Yongin-si (KR); Hyojin Kim, Yongin-si (KR)

(73) Assignee: GC Cell Corporation (KR)

( * ) Notice: Subject to any disclaimer, the term of this patent is extended or adjusted under 35 U.S.C. 154(b) by 776 days.

(21) Appl. No.: 16/613,601

(22) PCT Filed: May 25, 2018

(86) PCT No.: PCT/KR2018/005983
§ 371 (c)(1),
(2) Date: Nov. 14, 2019

(87) PCT Pub. No.: WO2018/217064
PCT Pub. Date: Nov. 29, 2018

(65) Prior Publication Data
US 2020/0108096 A1    Apr. 9, 2020

(30) Foreign Application Priority Data
May 26, 2017  (KR) ........................ 10-2017-0065180

(51) Int. Cl.
*C12N 5/0783*   (2010.01)
*A61K 39/00*    (2006.01)

(52) U.S. Cl.
CPC ........ *C12N 5/0638* (2013.01); *A61K 39/4613* (2023.05); *A61K 39/4644* (2023.05); *C12N 5/0636* (2013.01); *C12N 5/0646* (2013.01); *C12N 2501/25* (2013.01); *C12N 2502/1157* (2013.01); *C12N 2510/00* (2013.01)

(58) Field of Classification Search
CPC .... A61K 35/17; C12N 5/0638; C12N 5/0646; C12N 2501/25; C12N 2502/1157; C12N 2510/00
USPC ...................................................... 424/93.71
See application file for complete search history.

(56) References Cited

U.S. PATENT DOCUMENTS

| | | | |
|---|---|---|---|
| 5,882,650 | A | 3/1999 | Ennis |
| 9,062,287 | B2 | 6/2015 | Ideno et al. |
| 9,834,753 | B2 | 12/2017 | Min et al. |
| 11,766,456 | B2 | 9/2023 | Min et al. |
| 2003/0068306 | A1 | 4/2003 | Dilber |
| 2007/0048290 | A1 | 3/2007 | Tsai |
| 2008/0138833 | A1 | 6/2008 | Braun et al. |
| 2010/0178276 | A1 | 7/2010 | Sadelain et al. |
| 2012/0045423 | A1 | 2/2012 | Har-Noy |
| 2013/0011376 | A1 | 1/2013 | Peled et al. |
| 2014/0050710 | A1 | 2/2014 | Gonzalez et al. |
| 2014/0080148 | A1 | 3/2014 | Spanholtz |
| 2015/0152387 | A1 | 6/2015 | Lee et al. |
| 2017/0319621 | A1 | 11/2017 | Min et al. |
| 2019/0037831 | A1 | 2/2019 | Hwang et al. |
| 2019/0336533 | A1 | 11/2019 | Hwang et al. |
| 2021/0147803 | A1 | 5/2021 | Hwang et al. |
| 2021/0179733 | A1 | 6/2021 | Lee et al. |
| 2021/0268025 | A1 | 9/2021 | Min |
| 2024/0050478 | A1 | 2/2024 | Min et al. |

FOREIGN PATENT DOCUMENTS

| | | |
|---|---|---|
| CA | 2977472 | 9/2016 |
| CN | 102911918 A | 2/2013 |
| CN | 103068973 | 4/2013 |
| CN | 102112600 | 9/2014 |
| CN | 102911918 | 12/2014 |
| CN | 104204194 | 12/2014 |
| CN | 104321425 | 1/2015 |
| CN | 105602899 | 5/2016 |
| CN | 106222141 | 12/2016 |
| CN | 106222141 A | 12/2016 |
| CN | 108300693 | 7/2018 |
| CN | 108300697 | 7/2018 |
| EP | 2856876 | 4/2015 |

(Continued)

OTHER PUBLICATIONS

Hassell et al., "Adaptation to non-ammoniagenic medium and selective substrate feeding lead to enhanced yields in animal cell cultures," Journal of Cell Science, Jul. 1990, 96(3):501-508.
KR Office Action in Korean Appln. No. 10-2019-7030133, dated May 23, 2022, 9 pages (with English Translation).
Condiotti, R., et al., "Ex Vivo Expansion of Cd56+ Cytotoxic Cells from Human Umbilical Cord Blood, " Experimental Hematology 29(2001):104-113, Elsevier Science Inc, Netherlands (Jan. 2001).
Denman, C.J., "Membrane-Bound Il-21 Promotes Sustained Ex Vivo Proliferation of Human Natural Killer Cells, " PLoS One 7(1):e30264, Public Library of Science, United States (2012).
Fujisaki, H., et al., "Expansion of Highly Cytotoxic Human Natural Killer Cells For Cancer Cell Therapy," Cancer Research 69(9):4010-4017, American Association for Cancer Research, United States (May 2009).

(Continued)

*Primary Examiner* — Yan Xiao
(74) *Attorney, Agent, or Firm* — Fish & Richardson P.C.

(57) ABSTRACT

A method for culturing natural killer cells uses genetically modified T cells. The method for culturing natural killer cells, using genetically modified T cells enables the effective proliferation and production of natural killer cells from a smaller amount of source cells. In addition, the method enhances the cytolytic activity of natural killer cells. Therefore, the method for culturing natural killer cells, using genetically modified T cells may be suitable for various applications in commercializing cell therapy products. Further, the natural killer cells produced by the culturing method can be useful as a cell therapy product.

30 Claims, 79 Drawing Sheets
Specification includes a Sequence Listing.

(56) References Cited

FOREIGN PATENT DOCUMENTS

| | | | |
|---|---|---|---|
| EP | 3633029 | 4/2020 | |
| JP | 2004-501110 | 1/2004 | |
| JP | 2008-544760 | 12/2008 | |
| JP | 2010-501173 | 1/2010 | |
| JP | 2010-523083 | 7/2010 | |
| JP | 2011-529341 | 12/2011 | |
| JP | 2012-521215 | 9/2012 | |
| JP | 2013-006793 | 1/2013 | |
| JP | 2013-027385 | 2/2013 | |
| JP | 2013-071915 | 4/2013 | |
| JP | 2015-502756 | 1/2015 | |
| JP | 2015-513403 | 5/2015 | |
| JP | 2018-520993 | 8/2015 | |
| JP | 5840837 | 1/2016 | |
| JP | 5840837 B2 | 1/2016 | |
| JP | 2017-525370 | 9/2017 | |
| JP | 2018-501779 | 1/2018 | |
| JP | 7039623 | 3/2022 | |
| KR | 10-2008-0008060 | 1/2008 | |
| KR | 10-2009-0121694 | 11/2009 | |
| KR | 10-2010-0011586 | 2/2010 | |
| KR | 10-2010-0012586 | 2/2010 | |
| KR | 10-1035556 | 5/2011 | |
| KR | 10-1133185 | 5/2011 | |
| KR | 10-2011-0132618 | 12/2011 | |
| KR | 10-2012-0091012 | 8/2012 | |
| KR | 10-1298012 | 8/2013 | |
| KR | 10-2014-0123503 | 10/2014 | |
| KR | 10-1520534 | 5/2015 | |
| KR | 10-2016-0063114 | 6/2016 | |
| KR | 10-2016-0066837 | 6/2016 | |
| KR | 10-1644984 | 8/2016 | |
| KR | 10-1706524 | 2/2017 | |
| WO | WO 97/05239 | 2/1997 | |
| WO | WO 1997/032970 | 9/1997 | |
| WO | WO 98/06822 | 2/1998 | |
| WO | WO 2005014637 | * 2/2005 | ............ C07K 14/47 |
| WO | WO 2005/007116 | 12/2006 | |
| WO | WO 2007/111677 | 10/2007 | |
| WO | WO 2008/023874 | 2/2008 | |
| WO | WO 2008/121420 | 10/2008 | |
| WO | WO 2008/133845 | 11/2008 | |
| WO | WO 2008/138214 | 11/2008 | |
| WO | WO 2009/060865 | 5/2009 | |
| WO | WO 2009/132192 | 10/2009 | |
| WO | WO-2009132283 A2 * | 10/2009 | ......... A61K 39/0008 |
| WO | WO 2009/151183 | 12/2009 | |
| WO | WO 2010/013947 | 5/2010 | |
| WO | WO 2010/110734 | 9/2010 | |
| WO | WO 2011/080740 | 7/2011 | |
| WO | WO 2013/094988 | 6/2013 | |
| WO | WO 2014/188680 | 11/2014 | |
| WO | WO-2015157386 A1 * | 10/2015 | ............ A61K 35/17 |
| WO | WO 2016069993 | * 5/2016 | ........... C07K 14/705 |
| WO | WO 2016/085248 | 6/2016 | |
| WO | WO 2016/154585 | 9/2016 | |
| WO | WO-2016139463 A1 * | 9/2016 | ............ A61K 35/76 |
| WO | WO 2017/135631 | 8/2017 | |
| WO | WO 2018/124766 | 7/2018 | |
| WO | WO 2018/197859 | 11/2018 | |
| WO | WO 2018/217064 | 11/2018 | |
| WO | WO 2019/098682 | 5/2019 | |
| WO | WO 2019/182392 | 9/2019 | |
| WO | WO 2020/055040 | 3/2020 | |
| WO | WO 2020/101361 | 5/2020 | |
| WO | WO 2021/235894 | 11/2021 | |
| WO | WO 2022/133056 | 6/2022 | |
| WO | WO 2022/133057 | 6/2022 | |
| WO | WO 2022/133061 | 6/2022 | |
| WO | WO 2022/216144 | 10/2022 | |
| WO | WO 2022/216811 | 10/2022 | |
| WO | WO 2022/216813 | 10/2022 | |
| WO | WO 2022/216815 | 10/2022 | |
| WO | WO 2022/216826 | 10/2022 | |
| WO | WO 2022/216831 | 10/2022 | |
| WO | WO 2022/216837 | 10/2022 | |
| WO | WO 2023/080895 | 5/2023 | |
| WO | WO 2023/081317 | 5/2023 | |

OTHER PUBLICATIONS

Gong, W., et al., "Ex Vivo Expansion of Natural Killer Cells With High Cytotoxicity By K562 Cells Modified to Co-Express Major Histocompatibility Complex Class I Chain-Related Protein A, 4-1BB Ligand, and Interleukin-15, " Tissue Antigens 76(6):467-475, Wiley Blackwell, England (Dec. 2010).

Goodier, M.R and Londei, M, "Lipopolysaccharide Stimulates the Proliferation of Human Cd56+Cd3- Nk Cells: A Regulatory Role of Monocytes and Il-10, " Journal of Immunology 165(1):139-147, American Association of Immunologists, United States (Jul. 2000).

Written Opinion for International Application No. PCT/KR2018/005983, Korean Intellectual Property Office, Republic of Korea, mailed on Feb. 8, 2019, 12 pages.

Kim et al., "Engineering Conferences International ECI Digital Archives Scale-up study for ex-vivo expansion of allogeneic natural killer cells in stirred-tank bioreactor, Hyuang Jin nam Sang Hyun Lee Recommended Citation," Advancing Manufacture of Cell and Gene Therapies VI, Jan. 2019, 3 pages.

Ando et al., "Extensive generation of human cord blood CD34 stem cells from Lin 2CD34 cells in a long-term in vitro system" Exp. Hematol., 2000 28:690-9.

Bae et al., "Development of NK cell expansion methods using feeder cells from human myelogenous leukemia cell line," Blood Research, Sep. 2014, 49(3):154-61.

Baek et al., "Ex Vivo Expansion of Natural Killer Cells Using Cryopreserved Irradiated Feeder Cells," Anticancer Res., Jan. 2013, 33:2011-2020.

Berg et al., "Clinical Grade Ex Vivo-Expanded Human Natural Killer Cells Upregulate Activating Receptors and Death Receptor Ligands and Have Enhanced Cytolytic Activity against Tumor Cells," Cytotherapy, 2009, 11(3):41-355.

Boissel et al., "Umbilical Cord Mesenchymal Stem Cells Increase Expansion of Cord Blood Natural Killer Cells," Biology of Blood and Marrow Transplantation, Sep. 2008, 14(9):1031-8.

Byers "What Can Randomized Controlled Trials Tell US About Nutrition and Cancer Prevention?," Cancer Journal, 1999, 49(6):353-61.

Carlens et al., "A New Method for In Vitro Expansion of Cytotoxic Human CD3-CD56+ Natural Killer Cells, " Human Immunology, Oct. 2001, 62(10):1092-8.

Castriconi et al., "Human NK cell infusions prolong survival of metastatic human neuroblastoma-bearing NOD/scid mice" Cancer Immunol. Immunother., Nov. 2007, 56(11):1733-42.

Childs and Berg, "Bringing natural killer cells to the clinic: ex vivo manipulation," Hematology Am. Soc. Hematol. Educ. Program, 2013. 2013(1):234-46.

Condiotti et al., "Ex vivo expansion of CD56+ cytotoxic cells from human umbilical cord blood," Experimental Hematol., 2001, 29(1):104-13.

Dahlberg et al., "Natural Killer Cell-Based Therapies Targeting Cancer: Possible Strategies to Gain and Sustain Anti-Tumor Activity," Front. Immunol., 2015, 6:1-19).

Denman et al, "Membrane-Bound IL-21 Promotes Sustained Ex Vivo Proliferation of Human Natural Killer Cell" PloSONE, 2012, 7(1):e30264.

Dermer, "Another Anniversary for the War on Cancerm," Bio/Technology, 1994, 12:320.

Dewan et al., "Role of natural killer cells in hormone-independent rapid tumor formation and spontaneous metastasis of breast cancer cells in vivo" Breast Cancer Res. Treatment, 2007, 104(3):267-75.

Dunne et al., "Selective Expansion and Partial Activation of Human NK Cells and NK Receptor-Positive T Cells by IL-2 and IL-15," J. Immunol., 2001167(6):3129-38.

Edwards et al., "The Remarkable Flexibility of the Human Antibody Repertoire; Isolation of Over One Thousand Different Antibodies to a Single Protein, BLyS," JMB, 2003, 334:103-18.

(56) References Cited

OTHER PUBLICATIONS

Extended European Search Report in European Appln. No. 18805231.0, dated May 7, 2021, 10 pages.
Freshney, "Culture of Animal Cells, A Manual of Basic Technique," Alan R. Liss, Inc., 1983, 1-4.
Frias et al., "Generation of functional natural killer and dendritic cells in a human stromal-based serum-free culture system designed for cord blood expansion" Experimental Hematology, 2008, 36(1):61-8.
Fujisaki et al., "Expansion of Highly Cytotoxic Human Natural Killer Cells for Cancer Cell Therapy," Cancer Res., May 1, 2009,69(9):4010-7.
GenBank Accesion No. CAA56284.1, "OX 40 ligand/ gp 34 [*Homo sapiens*]", dated Oct. 7, 2008, 2 pages.
GenBank Accession No. LN874322.1, "TPA_inf: *Homo sapiens* mRNA for tumor necrosis factor ligand 5A (TNLG5A gene)," dated Nov. 28, 2019, 2 pages.
GenBank Accestion No. NM_001768.7, "*Homo sapiens* CD8a molecule (CD8A), transcript variant 1, mRNA" dated Feb. 27, 2020, 4 pages.
GenBank Accestion No. NM_003326.5, "*Homo sapiens* TNF superfamily member 4 (TNFSF4), transcript variant 1, mRNA" dated Nov. 23, 2018, 4 pages.
GenBank Accestion No. NM_003811.4, "*Homo sapiens* TNF superfamily member 9 (TNFSF9), mRNA" dated Nov. 22, 2018, 4 pages.
GenBank Accestion No. NM_021803.3, "*Homo sapiens* interleukin 21 (IL21), transcript variant 1, mRNA," dated Jun. 17, 2018, 3 pages.
Goel et al., "Plasticity within the Antigen-Combining Site May Manifest as Molecular Mimicryin the Hurnoral Immune Response," J. Immunol., 2004, 173:7358-67.
Gong et al., "Ex vivo expansion of natural killer cells with high cytotoxicity by K562 cells modified to co express major histocompatibility complex class I chain-related protein A, 4-1 BB ligand, and interleukin-15," Tissue Antigens, 2010, 76(6):467-75.
Goodier et al., "Lipopolysaccharide Stimulates the Proliferation of Human CD56+CD3-NK Cells: A Regulatory Role of Monocytes and IL-10," J. Immunology, 2000, 165(1):139-47.
Holmes et al., "A Human NK Cell Activation/Inhibition Threshold Allows Small Changes in the Target Cell Surgace Phenotype to Dramatically Alter Susceptibility to NK Cells," J. Immunol., 2011, 186:1538-45.
iwai-chem.co.jp [online] "DataSheet: CellGro/CellGenix GMP Serum-free StemCell GrowthMedium (SCGM) Xeno-free", May 16, 2011, via Internet Archive: Wayback Machine URL <https://web.archive.org/web/20140124200115/http://www.iwai-chem.co.jp/products/cellgenix/20802-0500.pdf>, retrieved on Jul. 23, 2021, URL<http://www.iwai-chem.co.jp/products/cellgenix/20802-0500.pdf>, 1 page.
Kelly et al., "Memory CD4+ T Cells Are Required for Optimal NK Cell Effector Functions against the Opportunistic Fungal Pathogen Pneumocystis murina", J. Immunology, 2013, 190:285-95.
Keridiles et al., "T cell regulation of natural killer cells", J. Experimental Medicine, Jun. 2013, 210(6):1065-8.
Khan and Salunke, "Adjustable Locks and Flexible Keys: Plasticity of Epitope-Paratope Interactions in Germline Antibodies," J. Immunol., 2014, 192(11):5398-405.
Kim et al., "Ex vivo activation and expansion of natural killer cells from patients with advanced cancer with feeder cells from healthy volunteers", Cytotherapy, 2013, 15:231-41.
Koehl et al., "IL-2 activated NK cell immunotherapy of three children after haploidentical stem cell transplantation, " Blood Cells Molecules & Disease, Nov.-Dec. 2004, 33(3):261-6.
Lim et al., "Ex Vivo Expansion of Highly Cytotoxic Human NK Cells by Cocultivation with Irradiated Tumor Cells for Adoptive Immunotherapy," Cancer Res., Apr. 15, 2013, 73(8):2598-607.
Lim et al., "GMP-Compliant, Large-Scale Expanded Allogeneic Natural Killer Cells Have Potent Cytolytic Activity against Cancer Cells In Vitro and In Vivo," PlosOne, Jan. 2013, 8(1):1-9.

Lloyd et al., "Modelling the human immune response: performance of a human antibody repertoire against a 10 broad panel of therapeutically relevant antigens," Protein Engineering, Eng. Design & Selection, 2009, 22(3):159-68.
Miller et al., "Role of monocytes in the expansion of human activated natural killer cells, " Blood, Nov. 1992, 80(9):2221-9.
Min, "Identification of NK cell costimulatory receptors for large-scale expansion of NK cells for adoptive immunotherapy in cancer patients ," Thesis for the degree of Doctor ,2018, http://library.kaist.ac.kr/search/detail/view.do?bibCtrlNo=827940&flag=dissertation.
Mingari et al., "In Vitro Proliferation and Cloning of CD3-CD16+ Cells from Human Thymocyte Precursors", J. Exp. Med., Jul. 1991, 174:21-6.
Miyahira, "Types of Immune Cells Present in Human PBMC," Sanguine Bio Researcher Blog, Nov. 22, 2012, 3 pages.
Morris et al., "A high-efficiency system of natural killer cell cloning," Journal of Immunological Methods,2005, 307(1-2):24-33.
North et al., "Tumor-Primed Human Natural Killer Cells Lyse NK-Resistant Tumor Targets: Evidence of a Two-Stage Process in Resting NK Cell Activation," J. Immunology, 2007, 178(1):85-94.
PCT International Search Preliminary Report on Patentability in International Appln. No. PCT/KR2018/005983, dated Nov. 26, 2019, 13 pages.
PCT International Search Report and Written Opinion in International Appln. No. PCT/KR2018/005983, dated Feb. 8, 2019, 17 pages.
Perez et al., "A potential role for hydrocortisone in the positive regulation of IL-15-activated NK-cell proliferation and survival," Blood, Jul. 2005, 106(1):158-66.
Poggi et al., "Extrathymic differentiation of T lymphocytes and natural killer cells from human embryonic liver precursors", Proc. Natl. Acad. Sci. USA, May 1993, 90:4465-9.
Poosarla et al., "Computational De Novo Design of Antibodies Binding to a Peptide With High Affinity," Biotechn. Bioeng., 2017, 114(6): 1331-42.
Siegler et al., "Good manufacturing practice-compliant cell sorting and large-scale expansion of single KIR-positive alloreactive human natural killer cells for multiple infusions to leukemia patients," Cytotherapy, 2010, 12:750-63.
Sigmaaldrich.com, "Sigma-Aldrich H9", retrieved on Nov. 15, 2019, retrieved from URL <https://www.sigmaaldrich.com/catalog/productUsigma/cb_85050301?1ang=en&region=US&cm_sp=Insite -_- prodRecCold_xviews-_-prodRecCold10-1>, 3 pages.
Torres and Casadevall, "The immunoglobulin constant region contributes to affinity and specificity," Trend. Immunol., Jan. 2008, 29(2): 91-7.
Vansdol et al., "Generation of Functional CD56+ Natural Killer (NK) Cells from Ex Vivo Expanded Human Cord Blood (CB) Hematopoietic Stem Cells", Blood, 2000, Abstract#424, 96(11):128b.
Vitale et al., "Effect of Tumor Cells and Tumor Microenvironment on NK-cell Function" Euro. J. Immunol., 2014, 44:1582-92.
www.thermofisher.com [online] "CTS (TM) AIM V (R) Medium", Aug. 24, 2015, retrieved from URL<http://www.thermofisher.com/order/catalog/product/0870112BK?ICID=search-product>, 4 pages.
Xiao-Hong et al., "Ex vivo expansion of highly purified NK cells from human peripheral blood", Zhongguo shi yan xue ye xue za zhi . . . , Apr. 2007, 15(2):373-7.
Zips et al., "New AntiCancer Agents: In Vitro and In Vivo Evaluation" In vivo, 2005, 19:1-8.
Ncbi, NCBI Reference Sequence No. LN874322.1, Jun. 8, 2016, 3 pages.
NCBI, NCBI Reference Sequence No. CAA56284.1, Oct. 7, 2008, 2 pages.
Duk Seong Bae et al., "Development of NK cell expansion methods using feeder cells from human myelogenous leukemia cell line," Blood Research, Sep. 2014, pp. 154-161 (9 pages), vol. 49, No. 3.
International Search Report of PCT/KR2018/005983 dated Feb. 8, 2019.
KR Office Action in Korean Application No. 10-2019-7030133, dated Jan. 19, 2022, 6 pages (with English translation).
Park et al., "CD4 T-cells transduced with CD80 and 4-1BBL mRNA induce long-term CD8 T-cell responses resulting in potent antitumor effects," Vaccine, Nov. 2014, 32: 6919-6926.

(56) References Cited

OTHER PUBLICATIONS

Ahn et al., "Irradiated and Activated Autologous PBMCs Induce Expansion of Highly Cytotoxic Human NK Cells In Vitro," Journal of Immunotherapy, Sep. 2013, 36(7):373-381.
Almishri et al., "TNFα augments cytokine-induced NK Cell IFNγ production through TNFR2," Journal of Innate Immunity, 2016, 8(6):617-629.
Carson et al., "A potential role for interleukin-15 in the regulation of human natural killer cell survival.," The Journal of Clinical Investigation, Mar. 1, 1997, 99(5):937-943.
Choi et al., "Donor-Derived Natural Killer Cells Infused after Human Leukocyte Antigen-Haploidentical Hematopoietic Cell Transplantation: A Dose-Escalation Study," Biology of Blood and Marrow Transplantation, 2014, 20(5):696-704.
Croft, "Control of immunity by the TNFR-related molecule OX40 (CD134)," Annual Review of Immunology, 2010, 28(1):57-78.
Granzin et al., "Shaping of Natural Killer Cell Antitumor Activity by Ex Vivo Cultivation," Frontiers in Immunology, Apr. 26, 2017, 8:458, 18 pages.
Lee et al., "Expansion of cytotoxic natural killer cells using irradiated autologous peripheral blood mononuclear cells and anti-CD16 antibody," Scientific Reports, Sep. 11, 2017, 7(1):1-13.
Mason et al., "Regulation of NK cells through the 80-kDa TNFR (CD120b)," Journal of Leukocyte Biology, Aug. 1, 1995, 58(2):249-255.
Min et al., "Harnessing novel engineered feeder cells expressing activating molecules for optimal expansion of NK cells with potent antitumor activity," Cellular & Molecular Immunology, Sep. 27, 2021, 19(2):296-298.
Min et al., "Optimization of Large-Scale Expansion and Cryopreservation of Human Natural Killer Cells for Anti-Tumor Therapy," Immune Network, Jan. 1, 20118, 18(4):e31, 13 pages.
Parkhurst et al., "Adoptive Transfer of Autologous Natural Killer Cells Leads to High Levels of Circulating Natural Killer Cells but Does Not Mediate Tumor Regression," Clinical Cancer Research, Oct. 1, 2011, 17(19):6287-6297.
Parrish-Novak et al., "Interleukin 21 and its receptor are involved in NK cell expansion and regulation of lymphocyte function," Nature, Nov. 2, 2000, 408(6808):57-63.
Parrish-Novak et al., "Interleukin-21 and the IL-21 receptor: novel effectors of NK and T cell responses," Journal of Leukocyte Biology, Nov. 1, 2002, 72(5):856-863.
Sakamoto et al., "Phase I clinical trial of autologous NK cell therapy using novel expansion method in patients with advanced digestive cancer," Journal of Translational Medicine, Aug. 25, 2015, 13:277, 13 pages.
Shuford et al., "4-1BB Costimulatory Signals Preferentially Induce CD8+ T Cell Proliferation and Lead to the Amplification In Vivo of Cytotoxic T Cell Responses," The Journal of Experimental Medicine, Jul. 7, 1997, 186(1):47-55.
Turaj et al., "Augmentation of CD134 (OX40)-dependent NK anti-tumour activity is dependent on antibody cross-linking," Scientific Reports, Feb. 2018, 8(1):1-11.
Wendt et al., "Interleukin-21 differentially affects human natural killer cell subsets," Immunology, Dec. 2007, 122(4):486-495.
Wilcox et al., "Signaling through NK cell-associated CD137 promotes both helper function for CD8+ cytolytic T cells and responsiveness to IL-2 but not cytolytic activity," The Journal of Immunology, Oct. 15, 2002, 169(8):4230-4236.
Willoughby et al., "OX40: Structure and function—What questions remain?," Molecular Immunology, Mar. 2017, 83:13-22.
Xu et al., "Essential role of the TNF-TNFR2 cognate interaction in mouse dendritic cell-natural killer cell crosstalk," Blood, Apr. 15, 2007, 109(8):3333-3341.

Yang et al., "Phase I Study of Random Healthy Donor-Derived Allogeneic Natural Killer Cell Therapy in Patients with Malignant Lymphoma or Advanced Solid Tumors," Cancer Immunology Research, Mar. 1, 2016, 4(3):215-224.
AU Office Action in Australian Appln. No. 2018271755, dated Jun. 29, 2021, 3 pages.
JP Office Action in Japanese Appln. No. 2019-565241, dated Jun. 22, 2021, 10 pages (with English translation).
Li et al., "Expansion of NK cells from PBMCs using immobilized 4-1BBL and interleukin-21", International Journal of Oncology, 2015, 47:335-342.
U.S. Appl. No. 14/367,813, filed Jun. 20, 2014, Min et al.
U.S. Appl. No. 15/527,752, filed May 18, 2017, Min et al.
U.S. Appl. No. 16/702,978, filed Dec. 4, 2019, Min et al.
U.S. Appl. No. 17/040,661, filed Jan. 14, 2021, Hwang et al.
U.S. Appl. No. 17/220,865, filed Apr. 1, 2021, Min et al.
U.S. Appl. No. 17/293,835, filed May 13, 2021, Kim et al.
Carswell et al., "Culture of Human T Cells in Stirred Bioreactors for Cellular Immunotherapy Applications: Shear, Proliferation, and the IL-2 Receptor," Biotechnology & Bioengineering, May 5, 2000, 68(3):328-338.
Granzin et al., "'Fully automated expansion and activation of clinical-grade natural killer cells for adoptive immunotherapy," Cytotherapy, May 2015, 17(5):621-632.
Granzin et al., "Highly efficient IL-21 and feeder cell-driven ex vivo expansion of human NK cells with therapeutic activity in a xenograft mouse model of melanoma," OncoImmunology, 2016, 5(9):e1219007.
Granzin, "Highly Efficient Activation and Expansion of Natural Killer Cells For Clinical Use in Cancer Immunotherapy," Dissertation for the Degree of Doctor of Natural Sciences, Combined Faculties for the Natural Sciences and for Mathematics of the Ruperto-Carola University of Heidelberg, Germany, Apr. 25, 2016, 136 pages.
Min et al., "Harnessing novel engineered feeder cells expressing activating molecules for optimal expansion of NK cells with potent antitumor activity," Cellular & Molecular Immunology, 2022, 19(2):296-298 (Supplemental Figure S4 only).
Peirson et al., "Production of Human Natural Killer Cells for Adoptive Immunotherapy Using a Computer-Controlled Stirred-Tank Bioreactor, " Journal of Hematotherapy, 1996, 5(5):475-483.
Valle et al., "Heterogeneous CD3 Expression Levels in Differing T Cell Subsets Correlate with the In Vivo Anti-CD3-Mediated T Cell Modulation," The Journal of Immunology, 2015, 194:2117-2127.
CN Office Action in Chinese Application No. 201880034893.8, dated Feb. 11, 2023, 17 pages (with English Translation).
GenBank Accession No. LN874322.1, "TPA_inf: *Homo sapiens* mRNA for tumor necrosis factor ligand 5A (TNLG5A gene)," dated Jun. 8, 2016, 2 pages.
U.S. Appl. No. 18/455,003, filed Aug. 24, 2023, Min et al.
Cheng et al., "NK cell-based immunotherapy for malignant diseases," Cell. Mol. Immunol., May 2013, 10(3):230-252.
GenBank Accession No. NM_000594.3, "*Homo sapiens* tumor necrosis factor (TNF), mRNA," Sep. 30, 2018, 4 pages.
GenBank Accession No. NM_003811.3, "*Homo sapiens* TNF superfamily member 9 (TNFSF9), mRNA," May 21, 2018, 4 pages.
GenPept Accession No. NP_003317, "tumor necrosis factor ligand superfamily member 4 isoform 1 [*Homo sapiens*]," Oct. 21, 2018, 3 pages.
GenPept Accession No. PDB:2OQP_A, "Chain A, Interleukin-21," May 17, 2018, 2 pages.
Mock et al., "Automated manufacturing of chimeric antigen receptor T cells for adoptive immunology using CliniMACs Prodigy," Cytotherapy, Aug. 2016, 18(8):1002-1011.
Office Action in Canadian Application No. 3,062,130, dated Jan. 19, 2024, 4 pages.

* cited by examiner

[Fig. 1a]
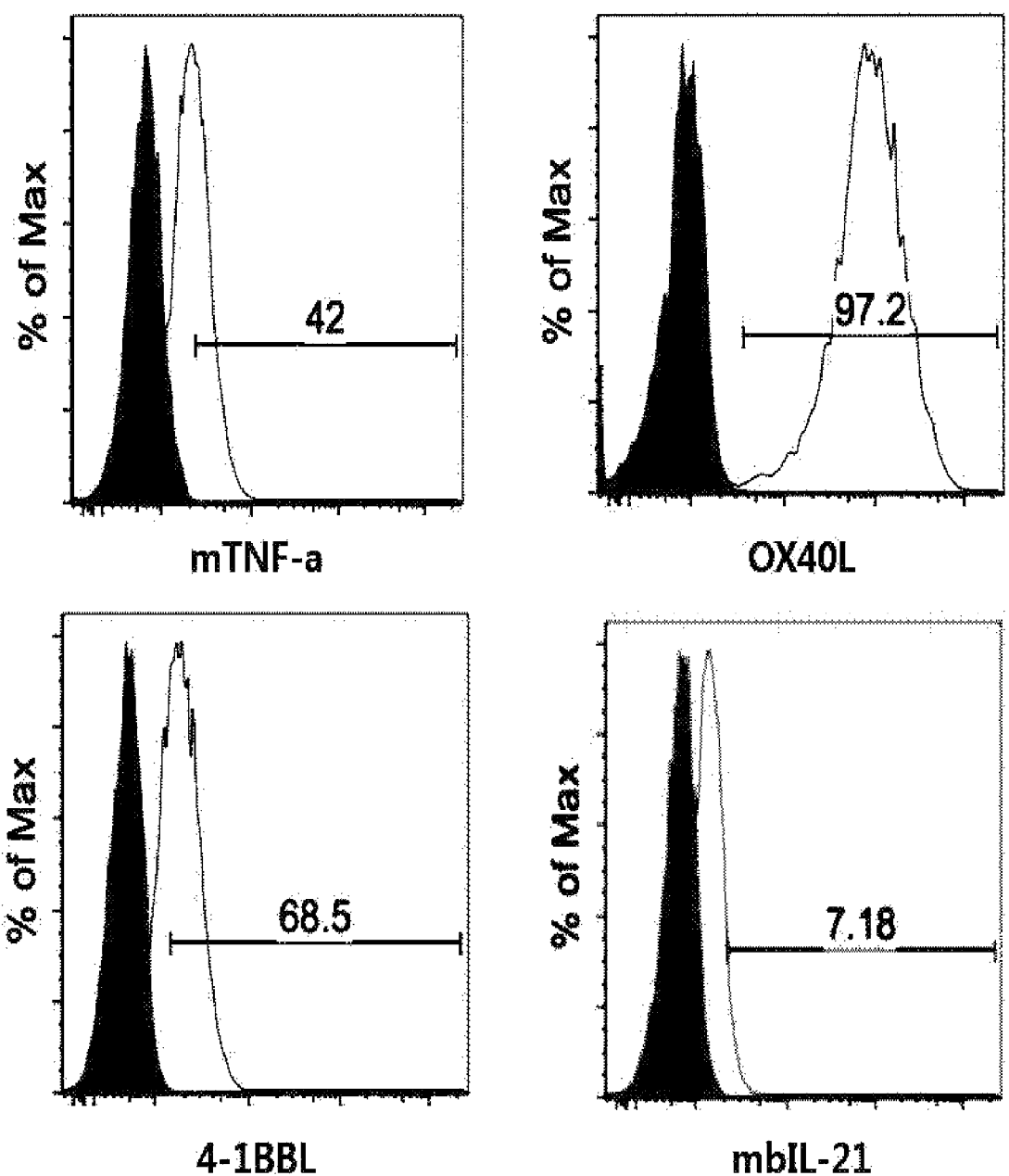

[Fig. 1b]
Hut78 feeder cells
Double gene transduction
(a) mTNF-a/OX40L
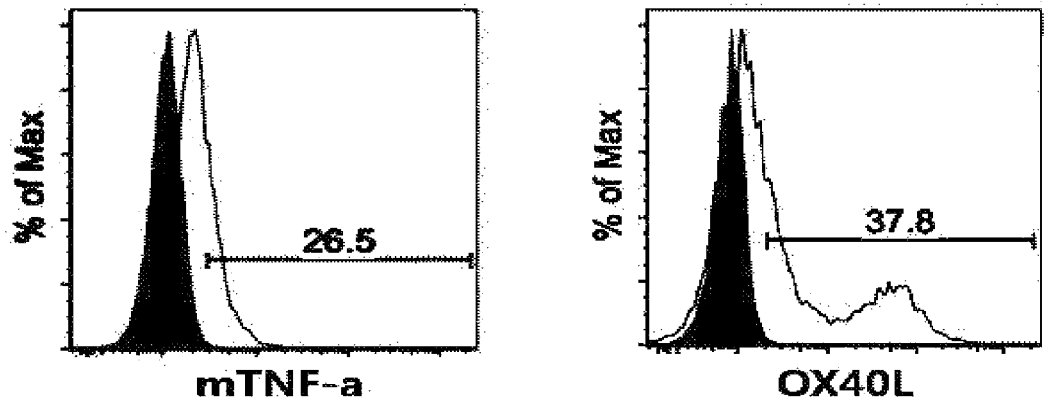
(b) mTNF-a/4-1BBL
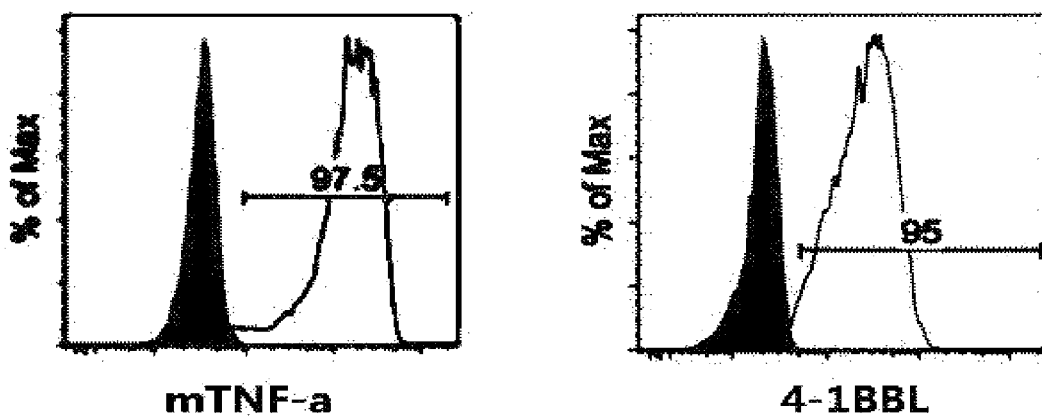
(c) mbIL-21/ 4-1BBL
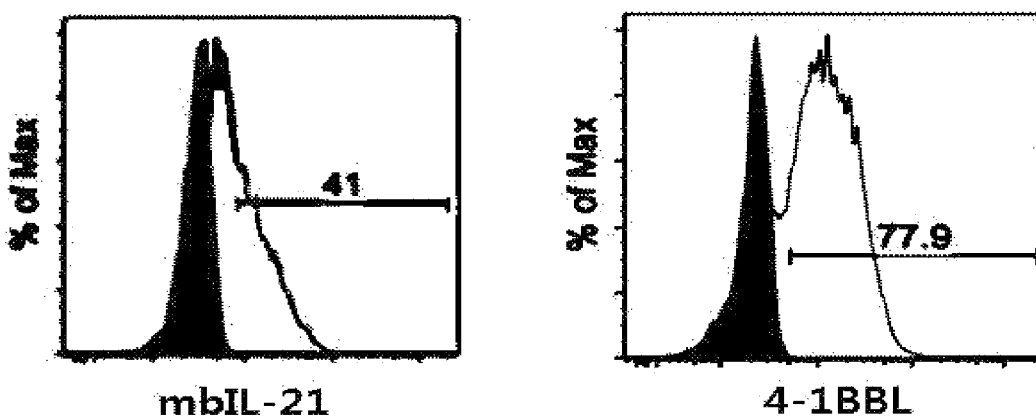

[Fig. 1c]
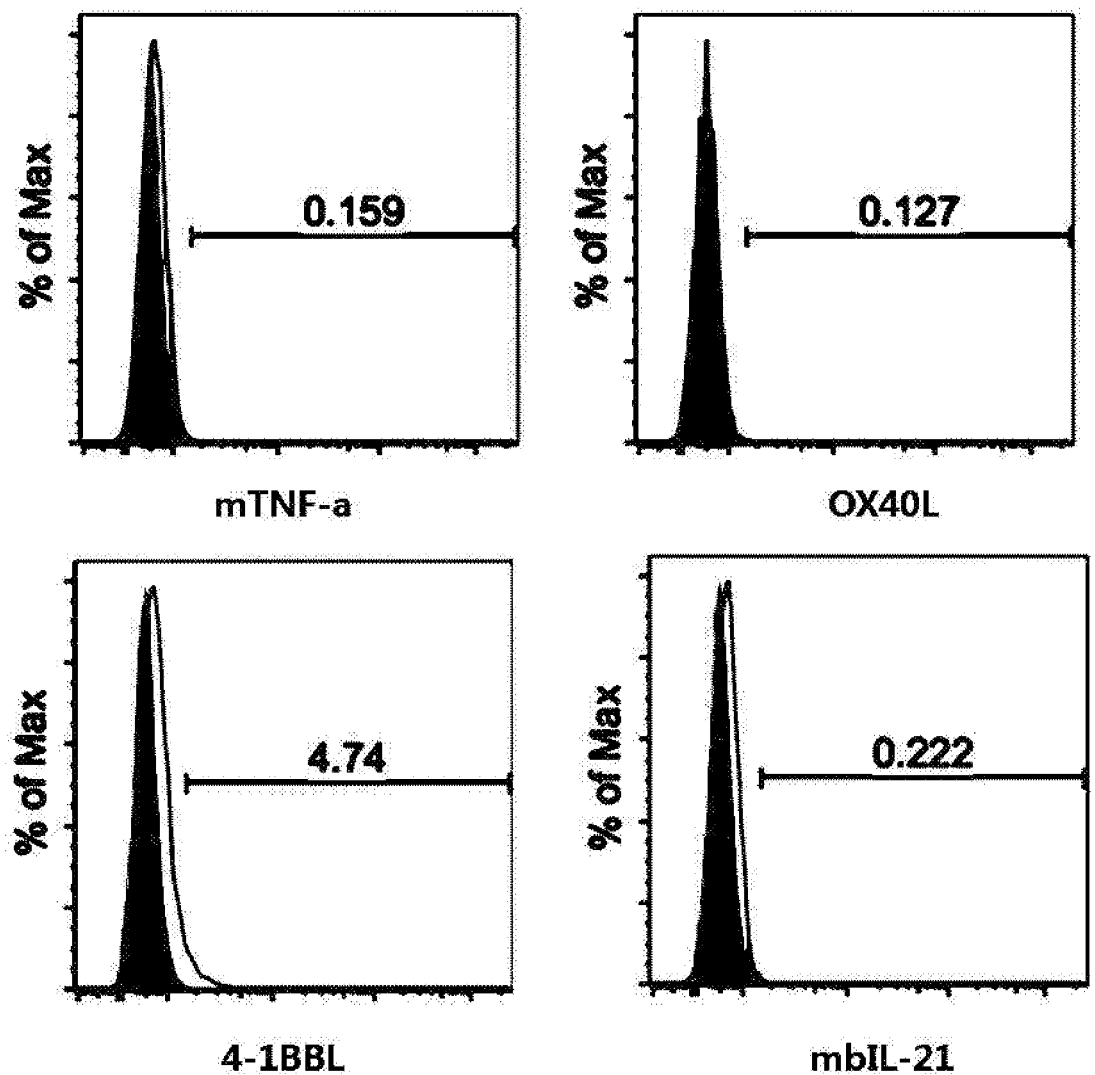

[Fig. 1d]
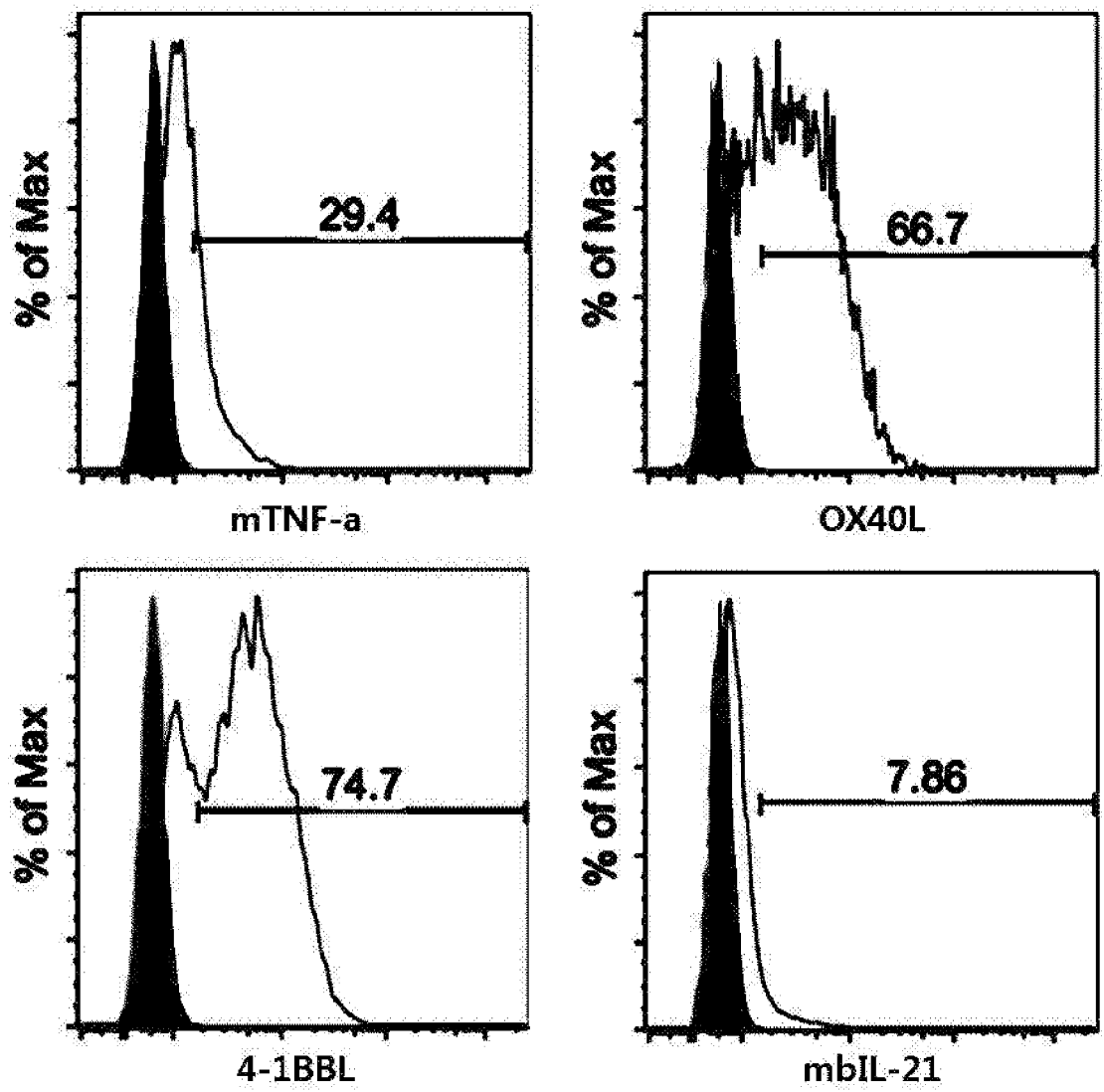

[Fig. 1e]
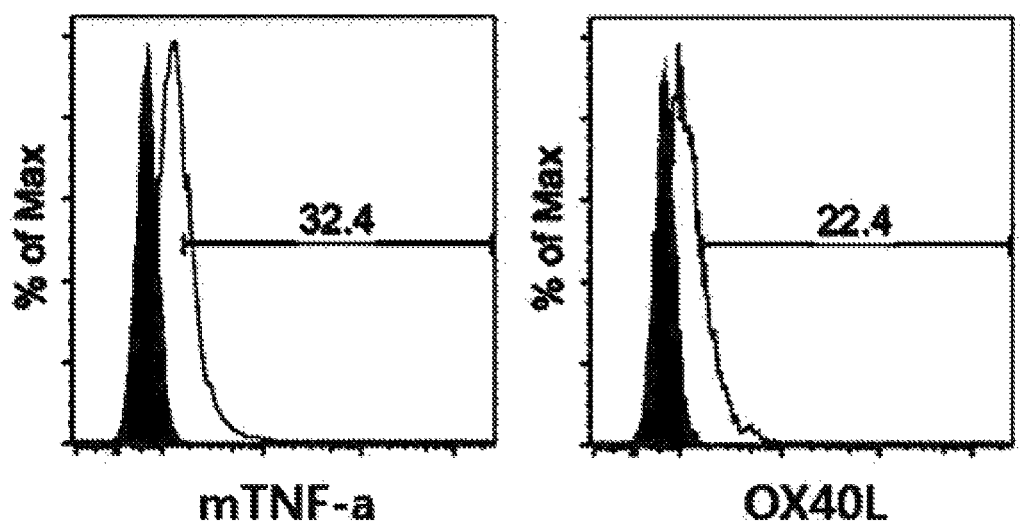
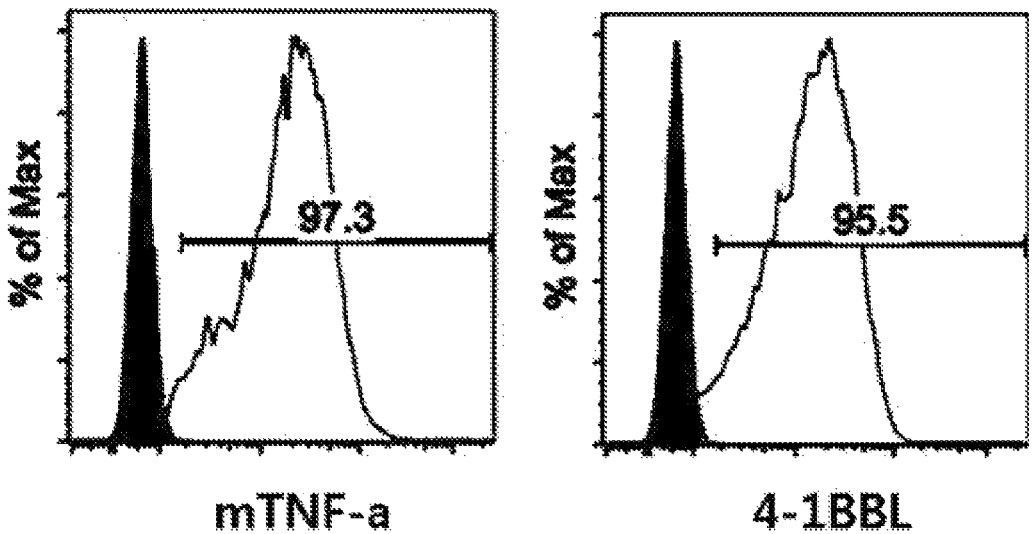

[Fig. 1f]
Hut78 feeder cells
Double gene transduction
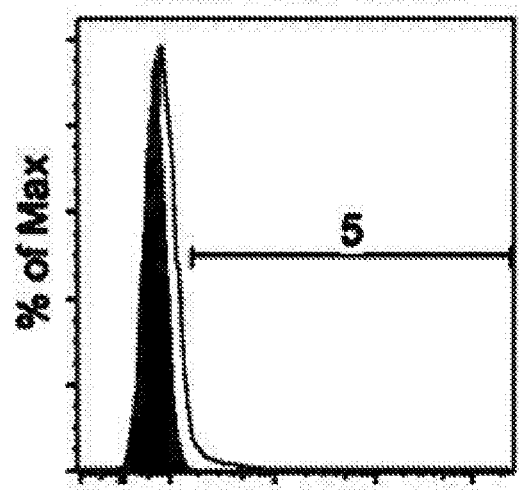
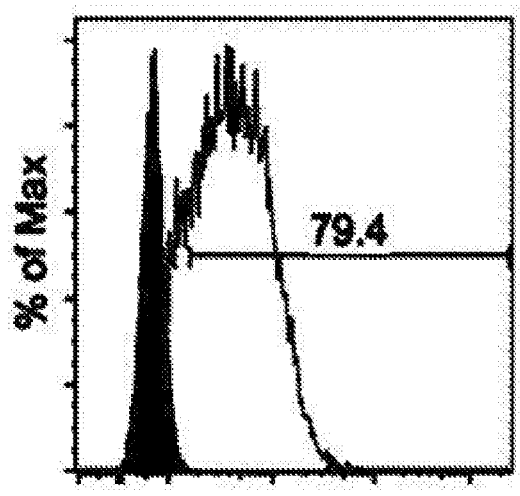
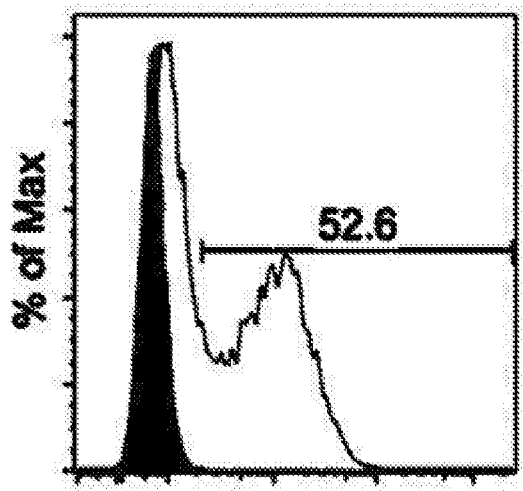
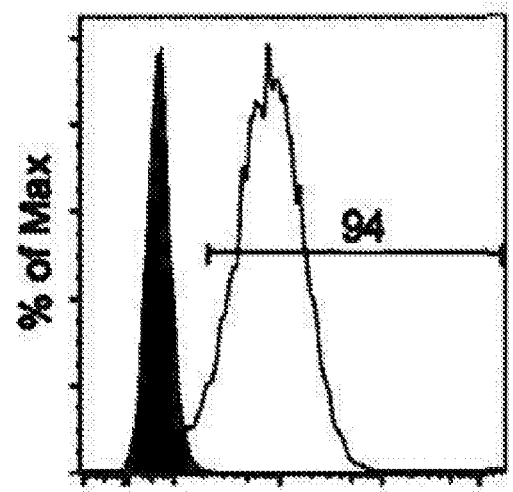

[Fig. 1g]
Hut78 feeder cells
Triple gene transduction
mTNF-a/mbIL-21/4-1BBL
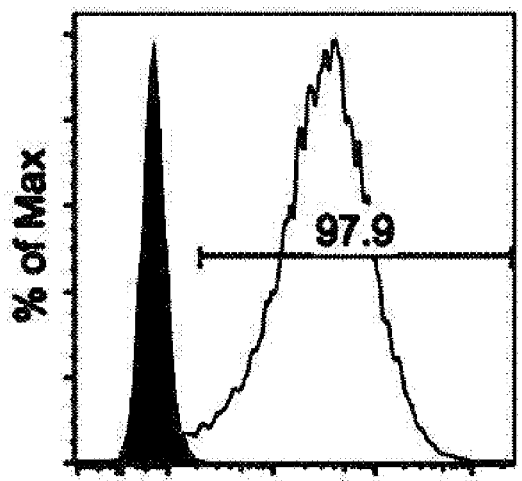
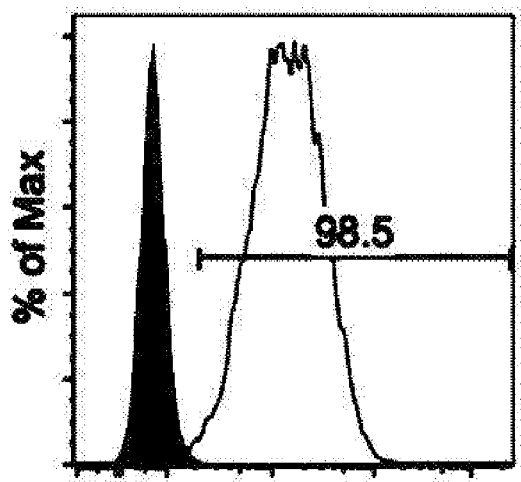
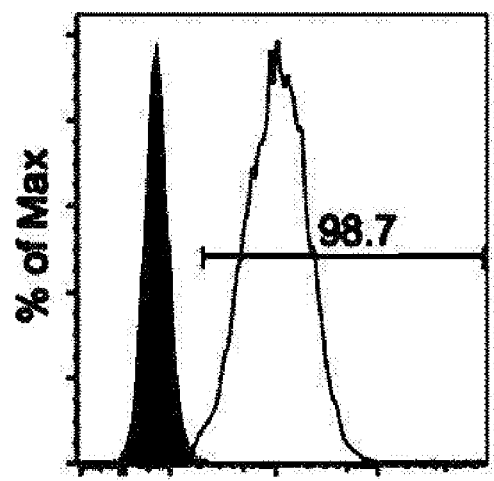

[Fig. 1h]
Hut78 feeder cells
Quadruple gene transduction
mTNF-a/mbIL-21/OX40L/4-1BBL
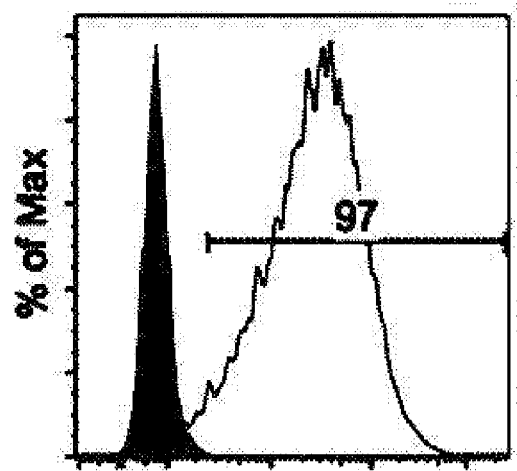
mTNF-a
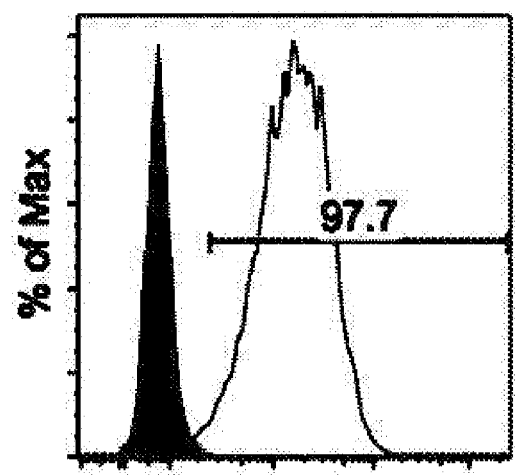
mbIL-21
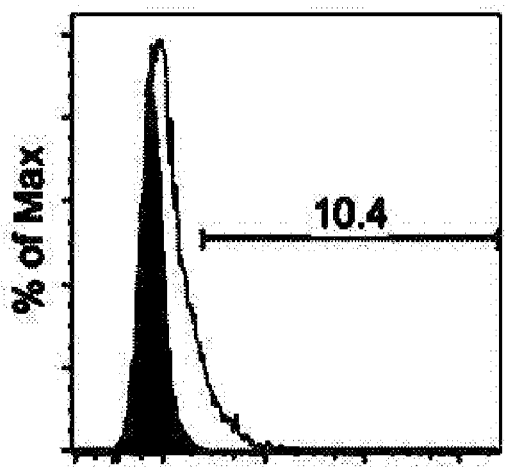
OX40L
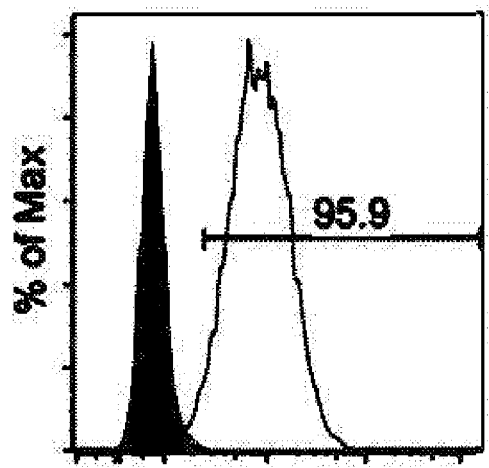
4-1BBL

[Fig. 2a]
H9 feeder cells
Single gene transduction
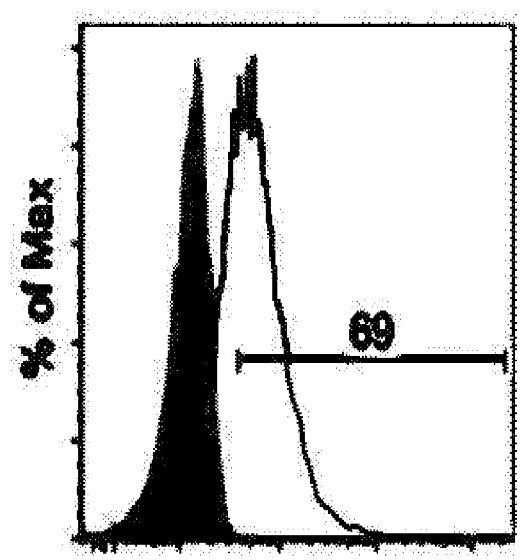
mTNF-a
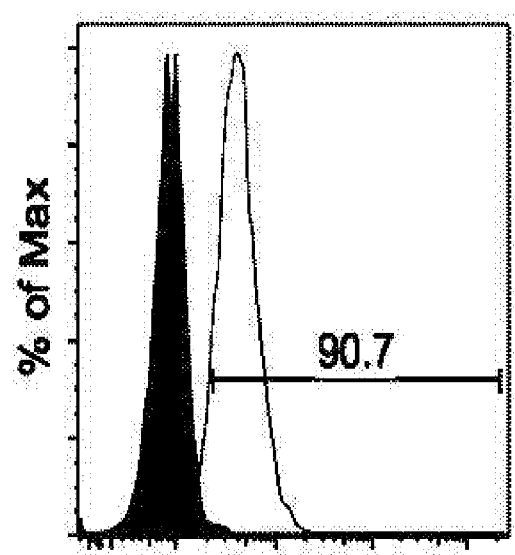
4-1BBL
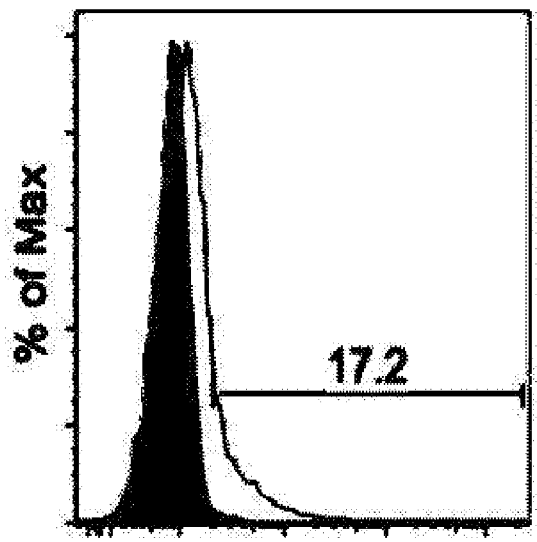
mbIL-21

[Fig. 2b]
H9 feeder cells
Double gene transduction
mTNF-a/4-1BBL
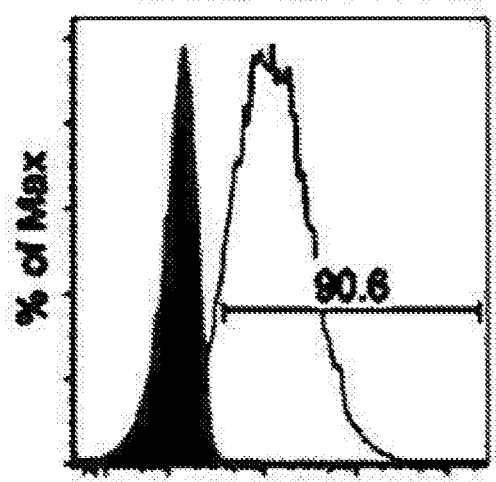
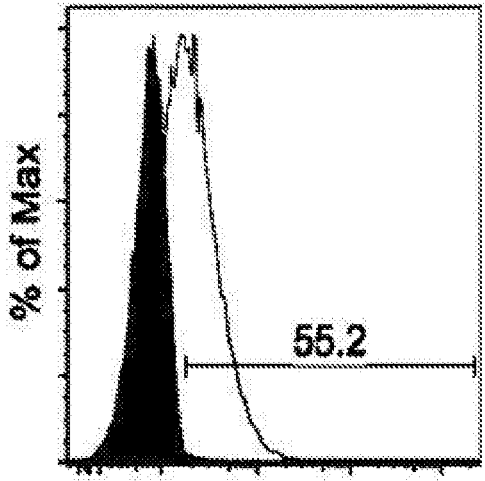
mbIL-21/ 4-1BBL
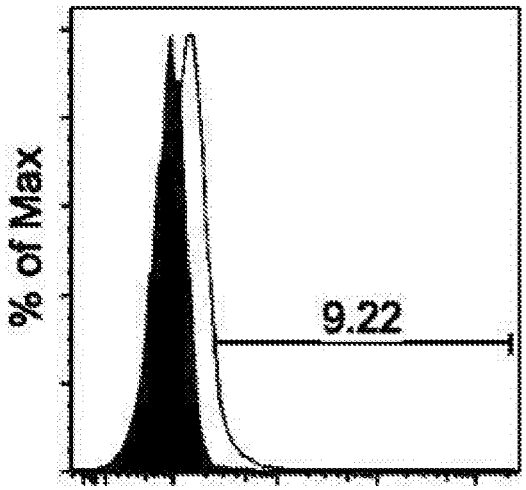
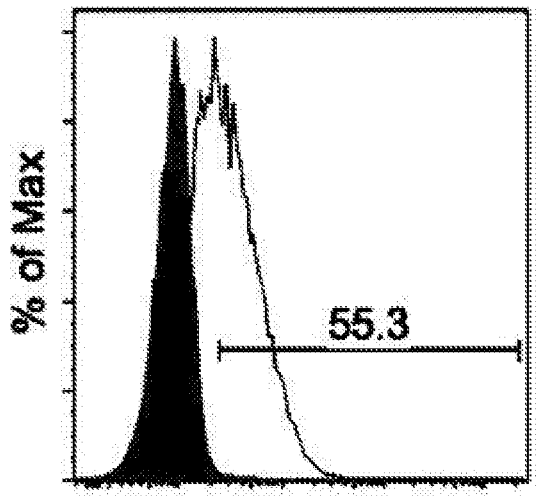

[Fig. 3a]
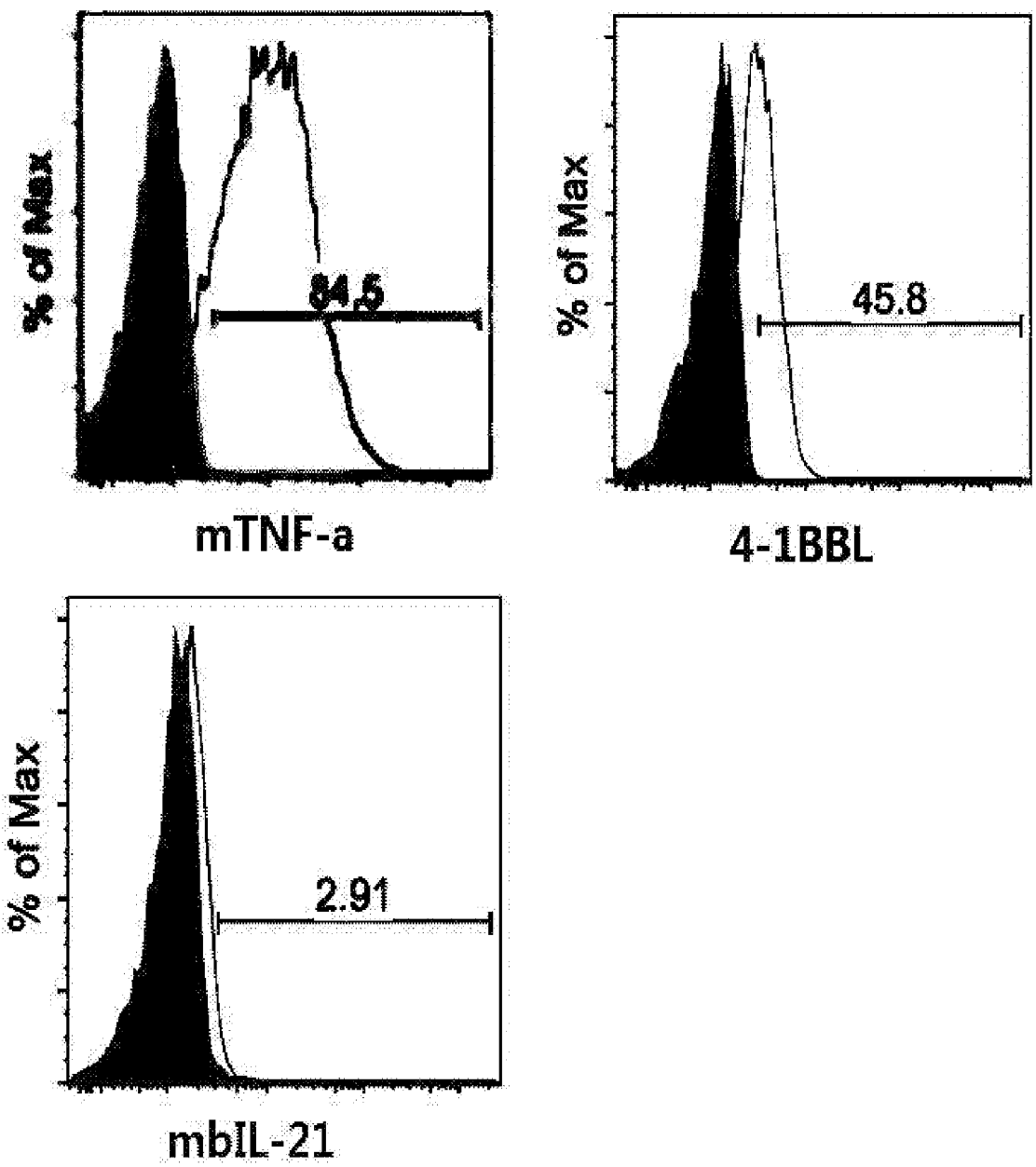

[Fig. 3b]
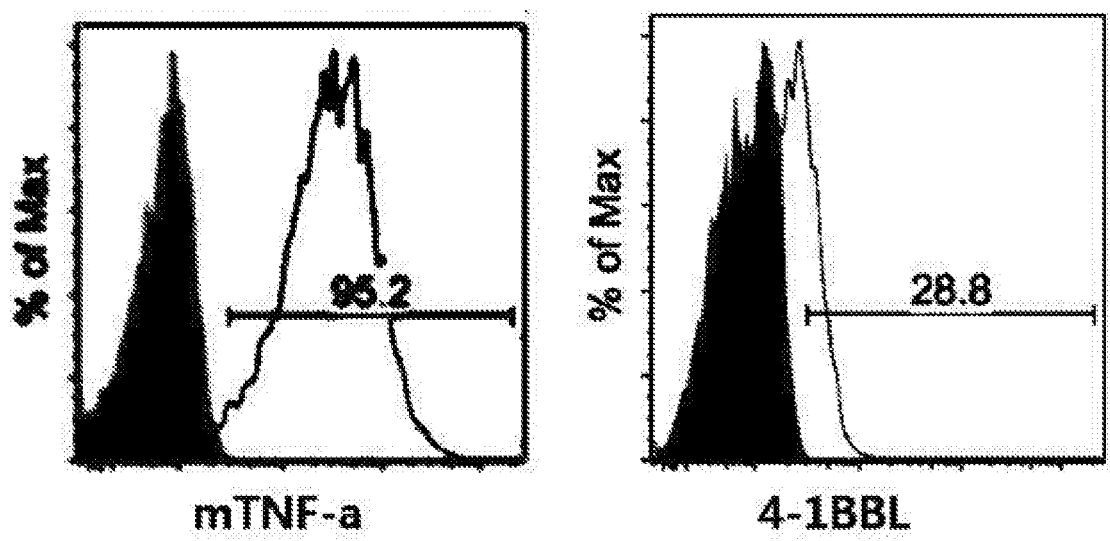
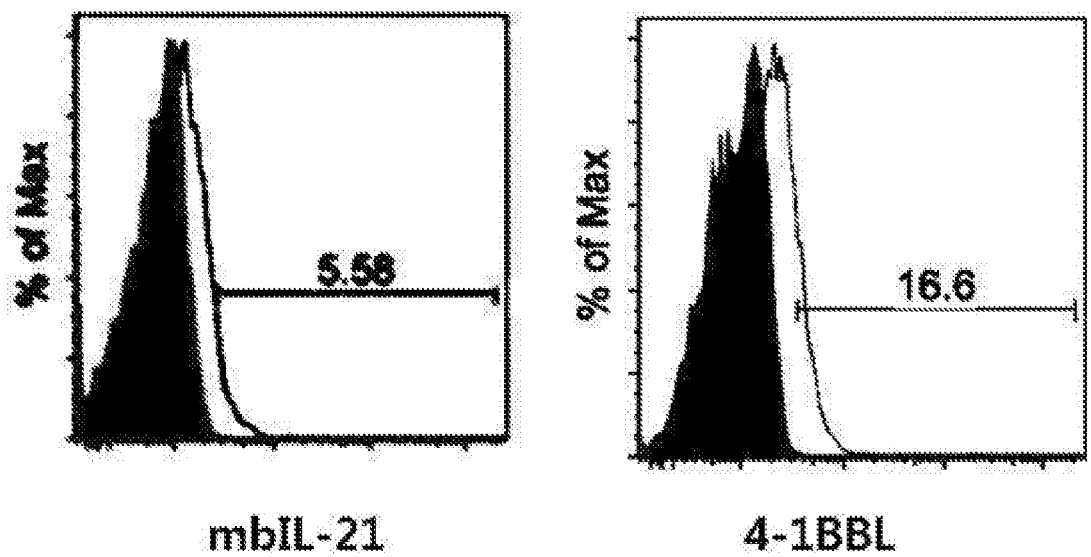

[Fig. 4a]
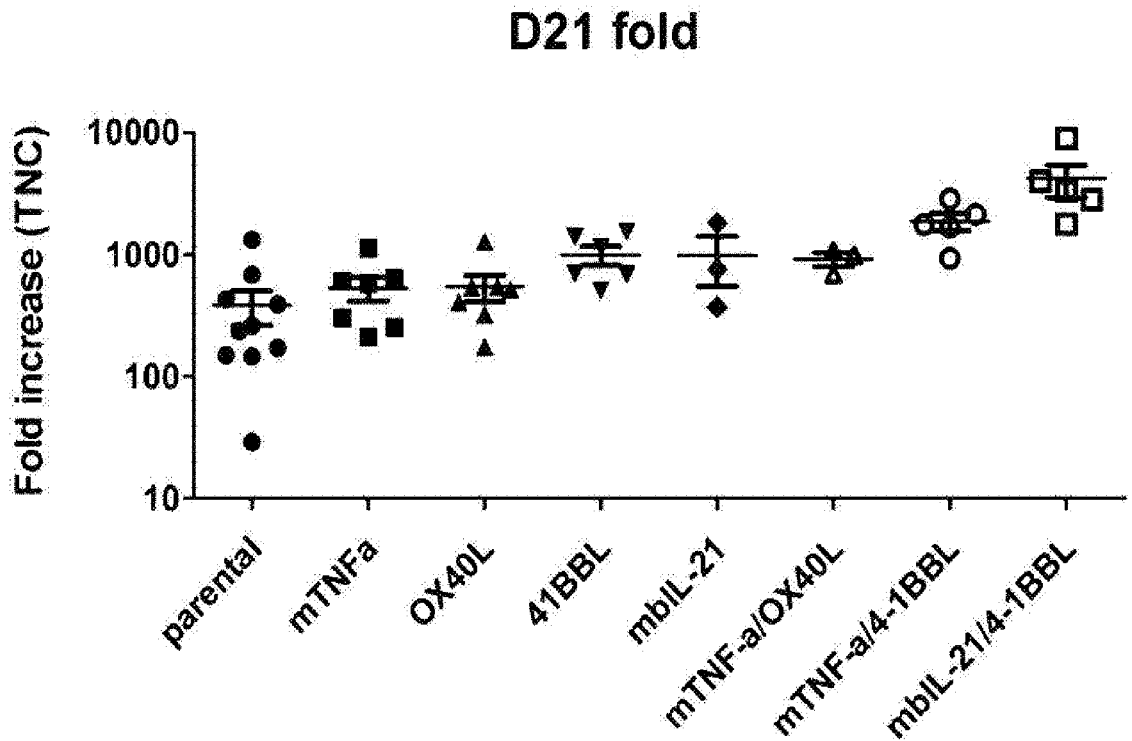
[Fig. 4b]
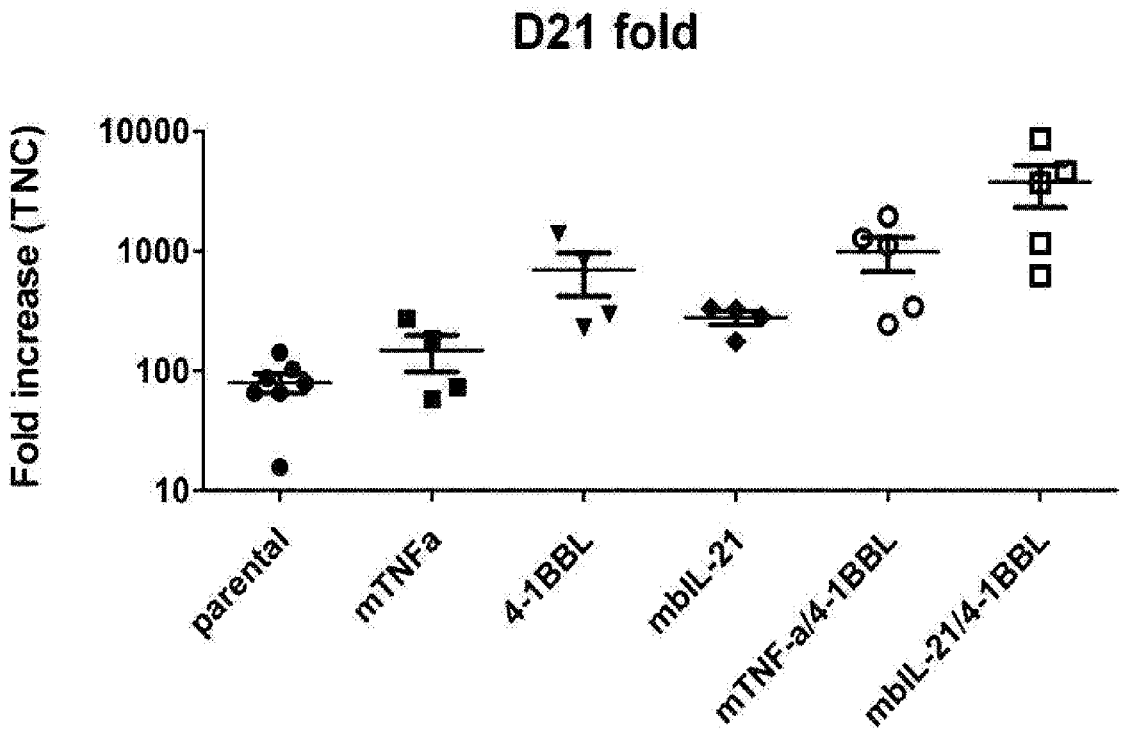

[Fig. 4c]
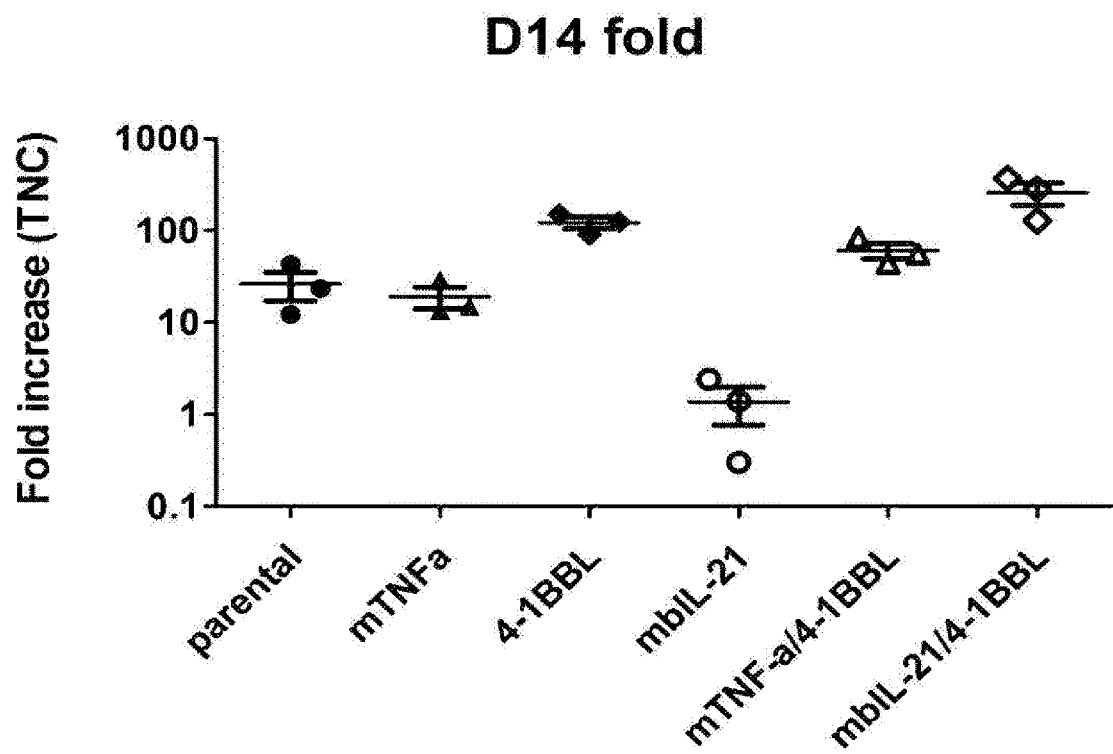

[Fig. 4d]
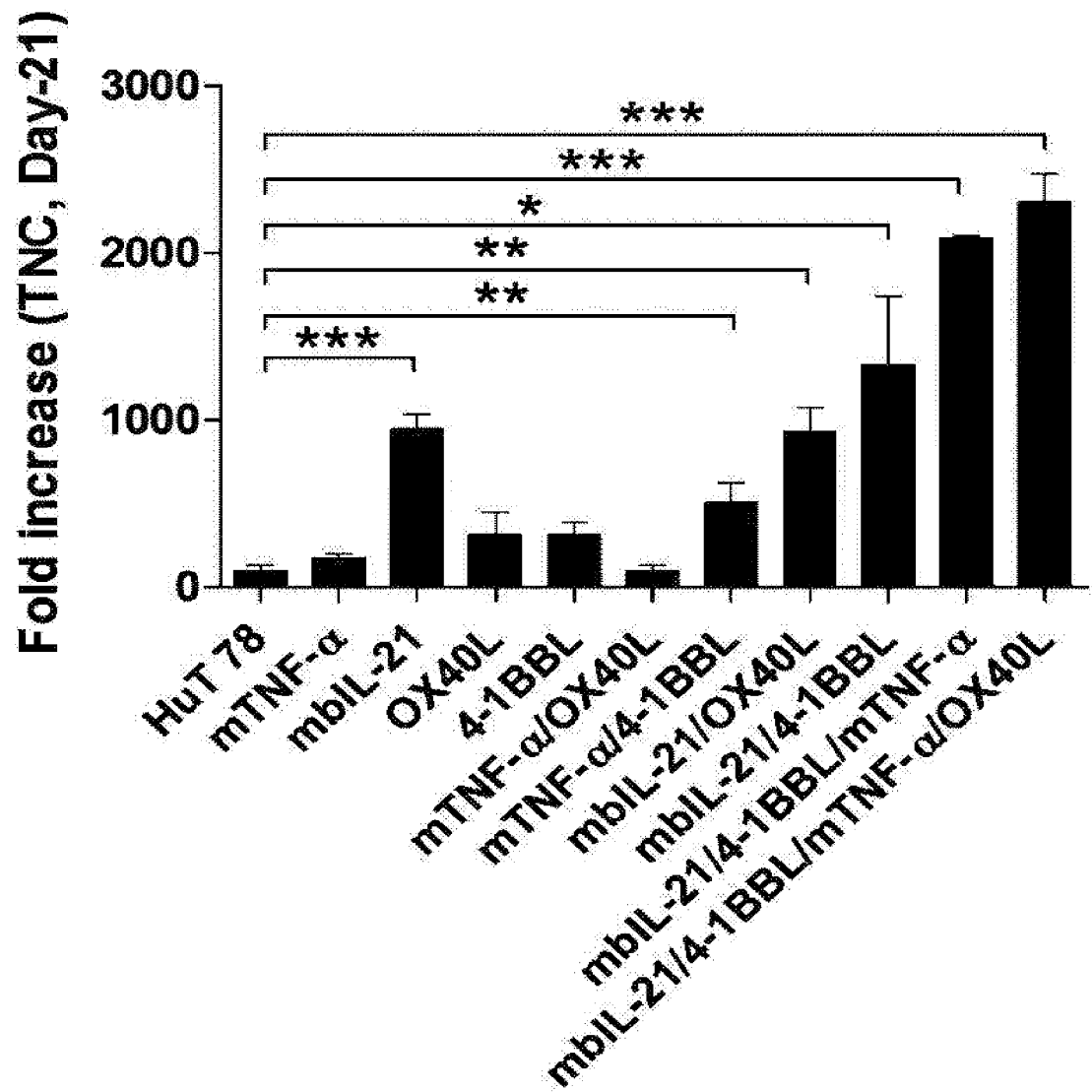

[Fig. 5a]
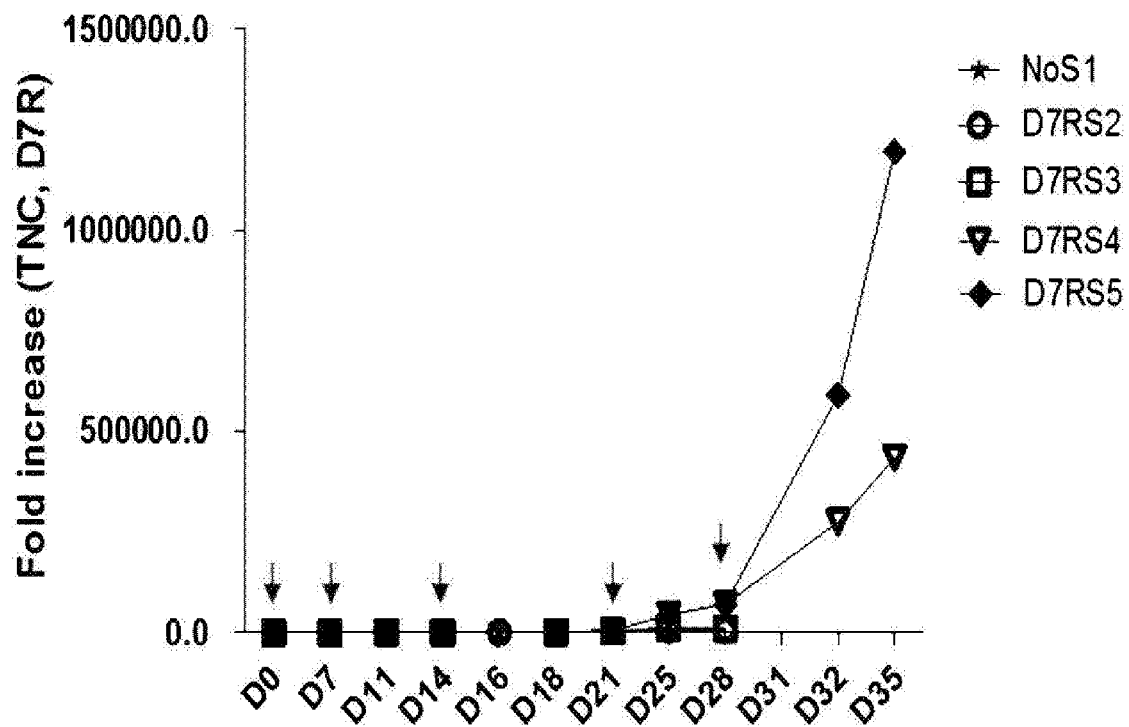
[Fig. 5b]
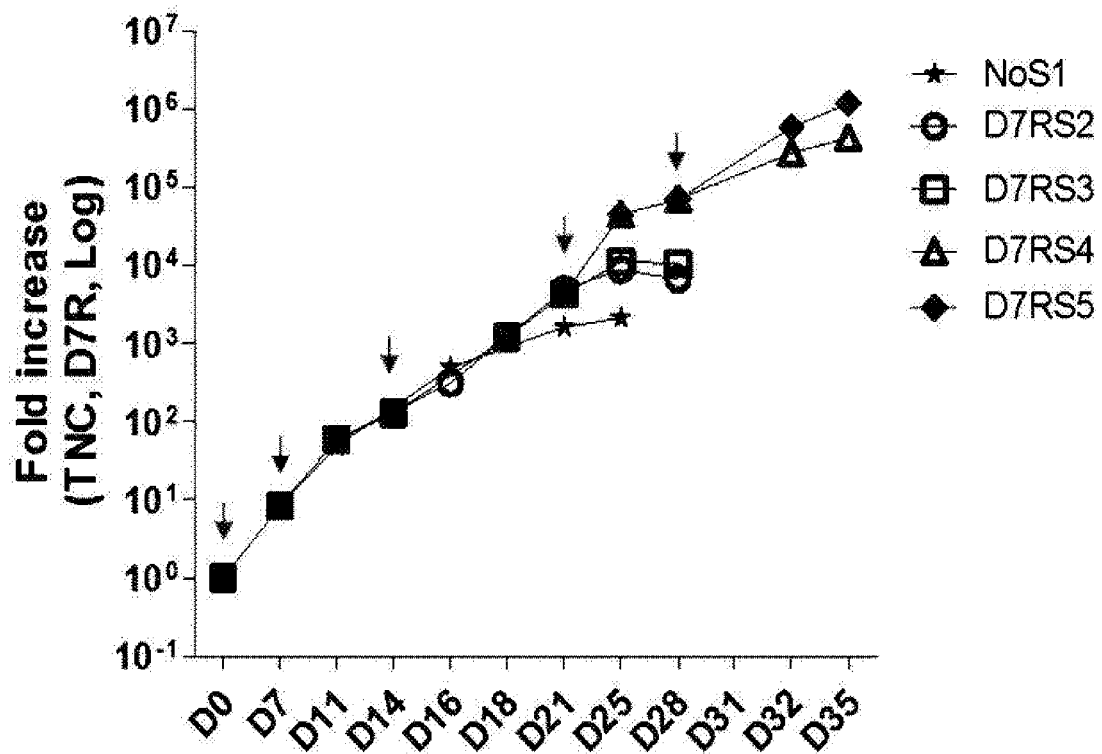

[Fig. 5c]
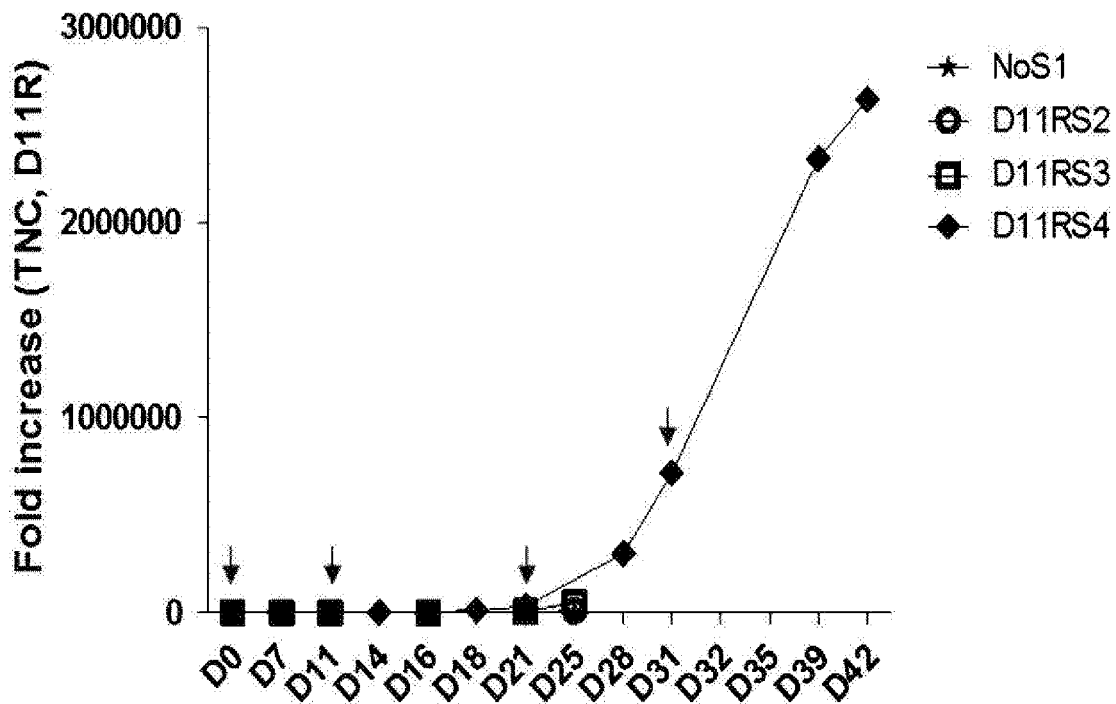
[Fig. 5d]
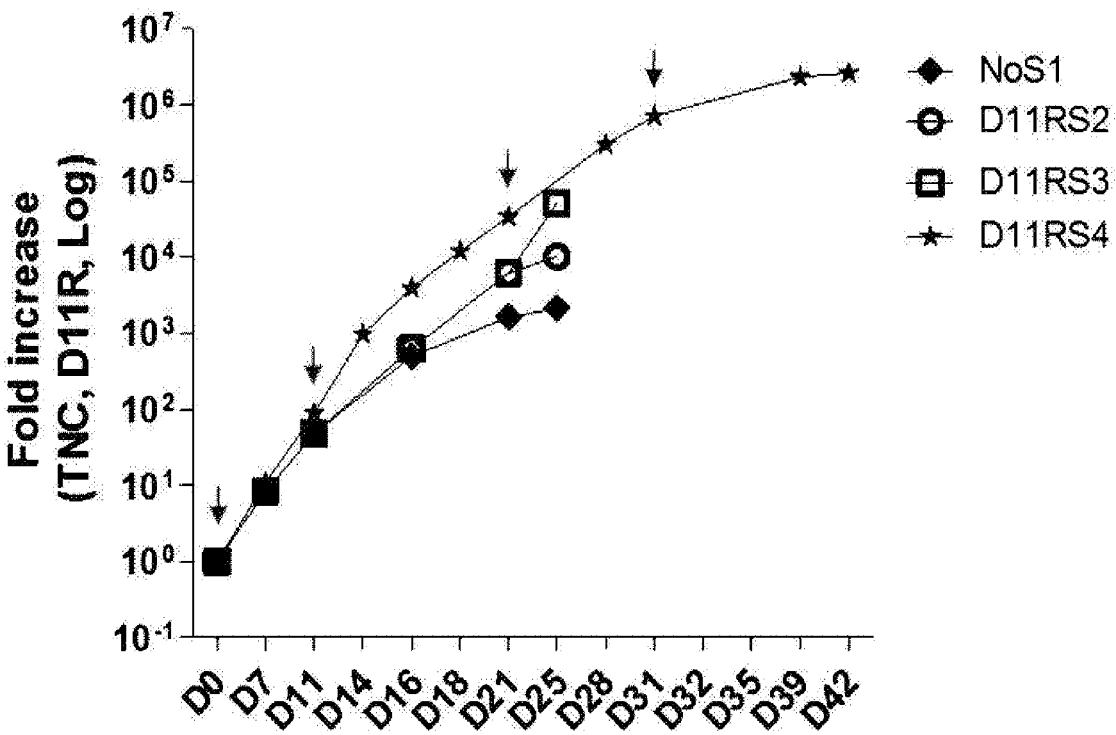

[Fig. 6a]
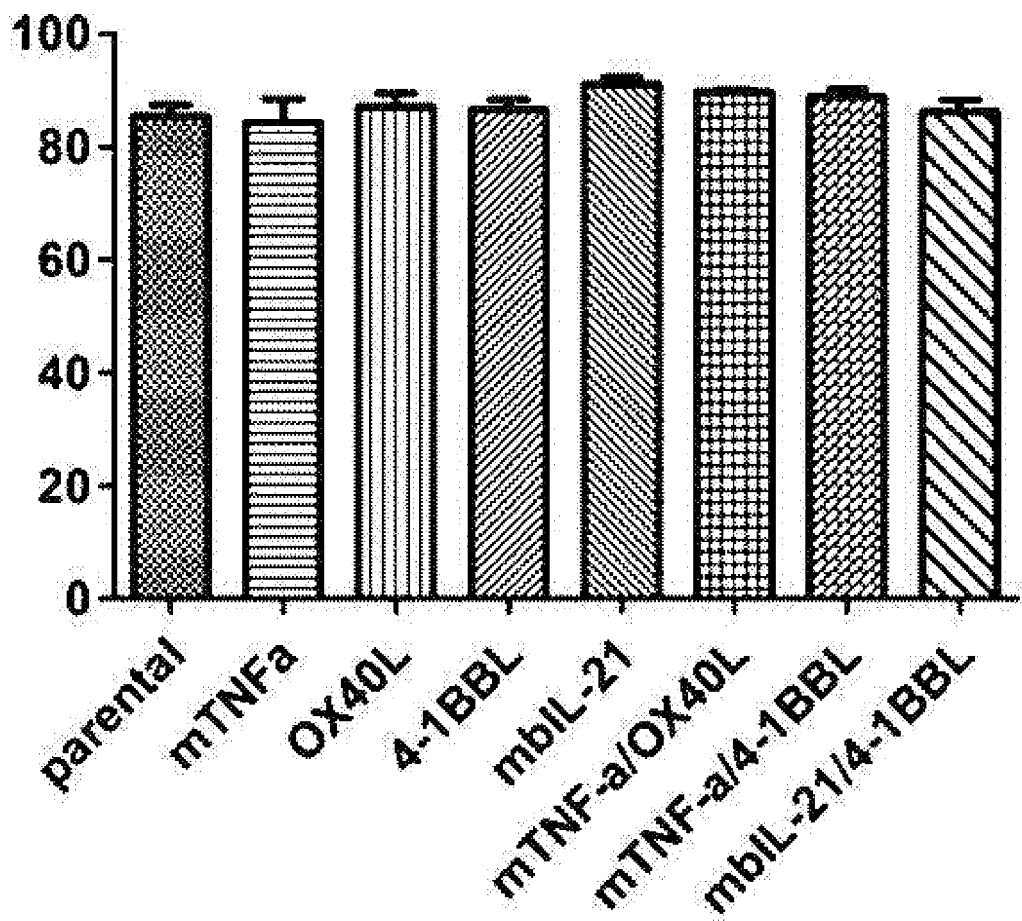

[Fig. 6b]
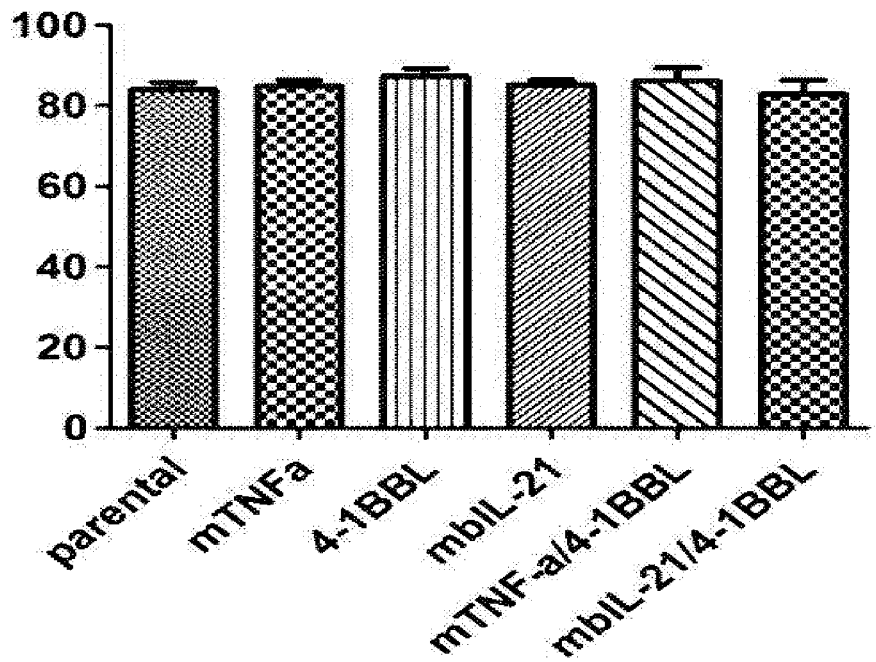
[Fig. 6c]
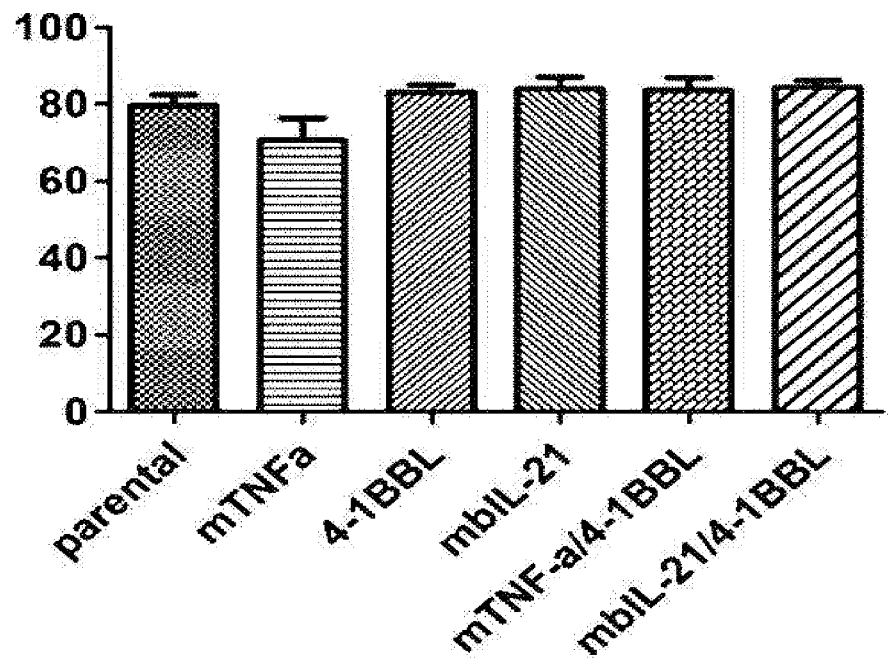

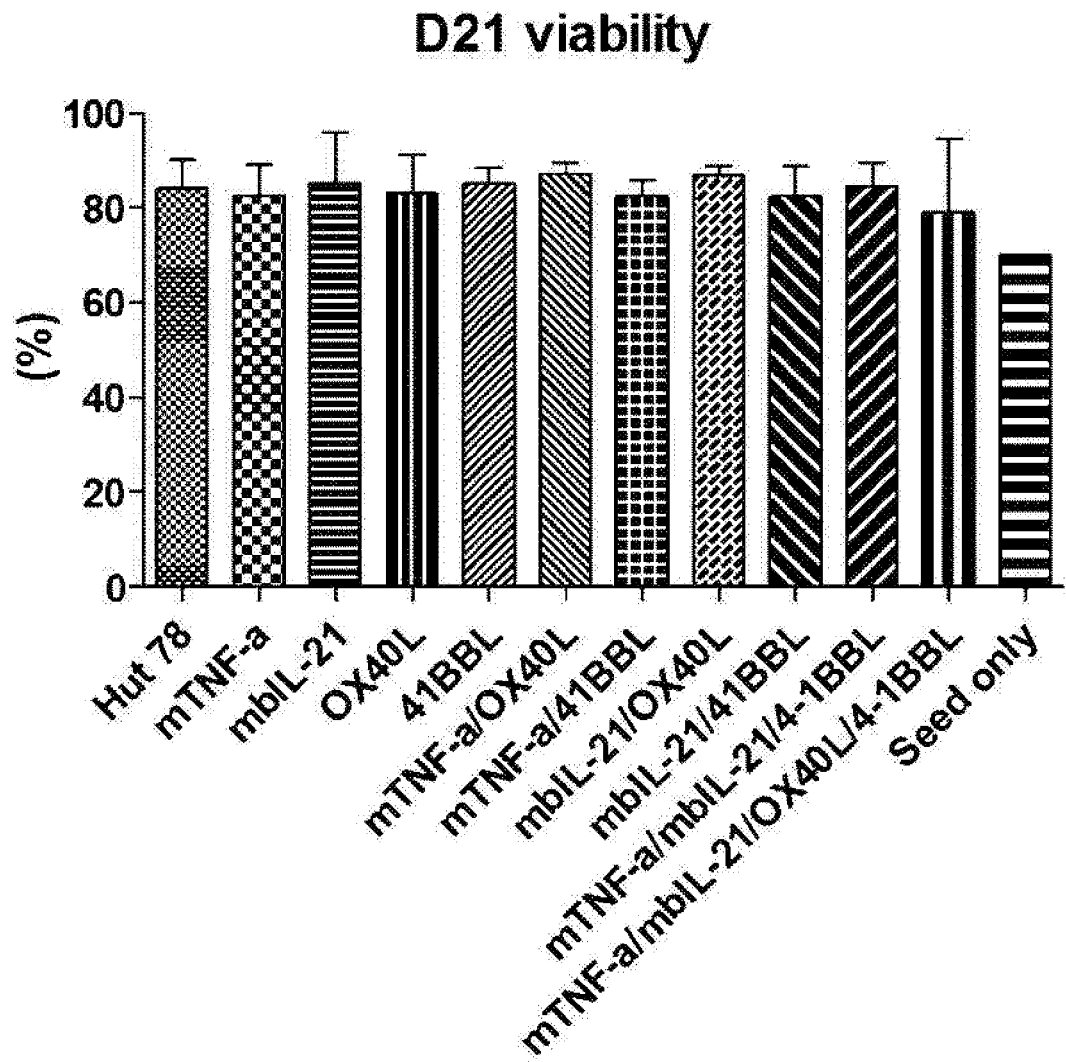
[Fig. 6d]

[Fig. 7a]
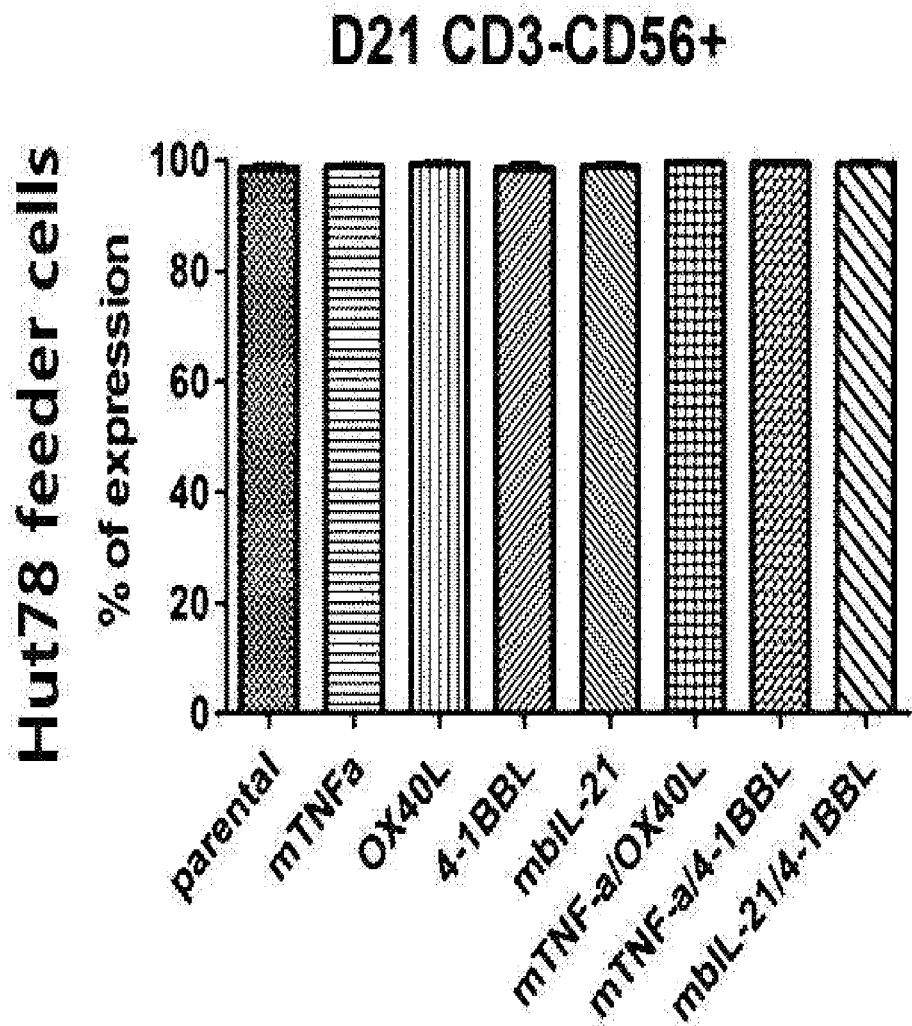

[Fig. 7b]
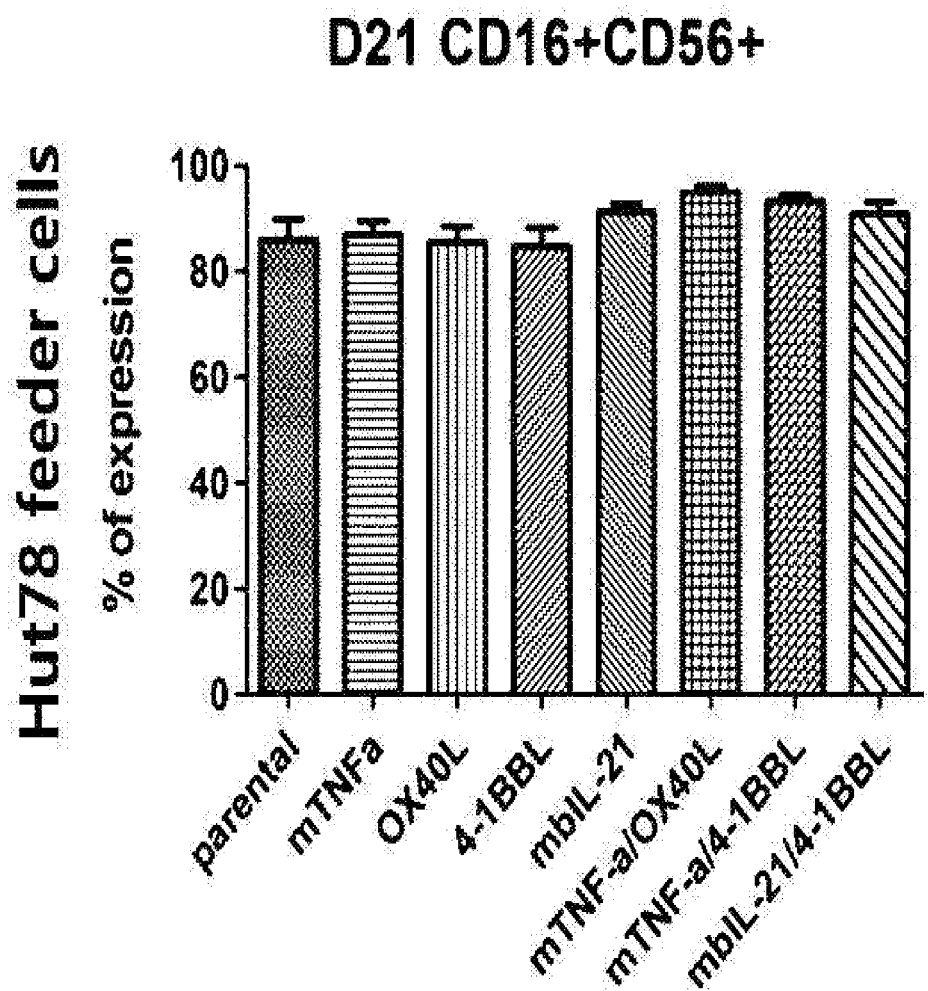

[Fig. 7c]
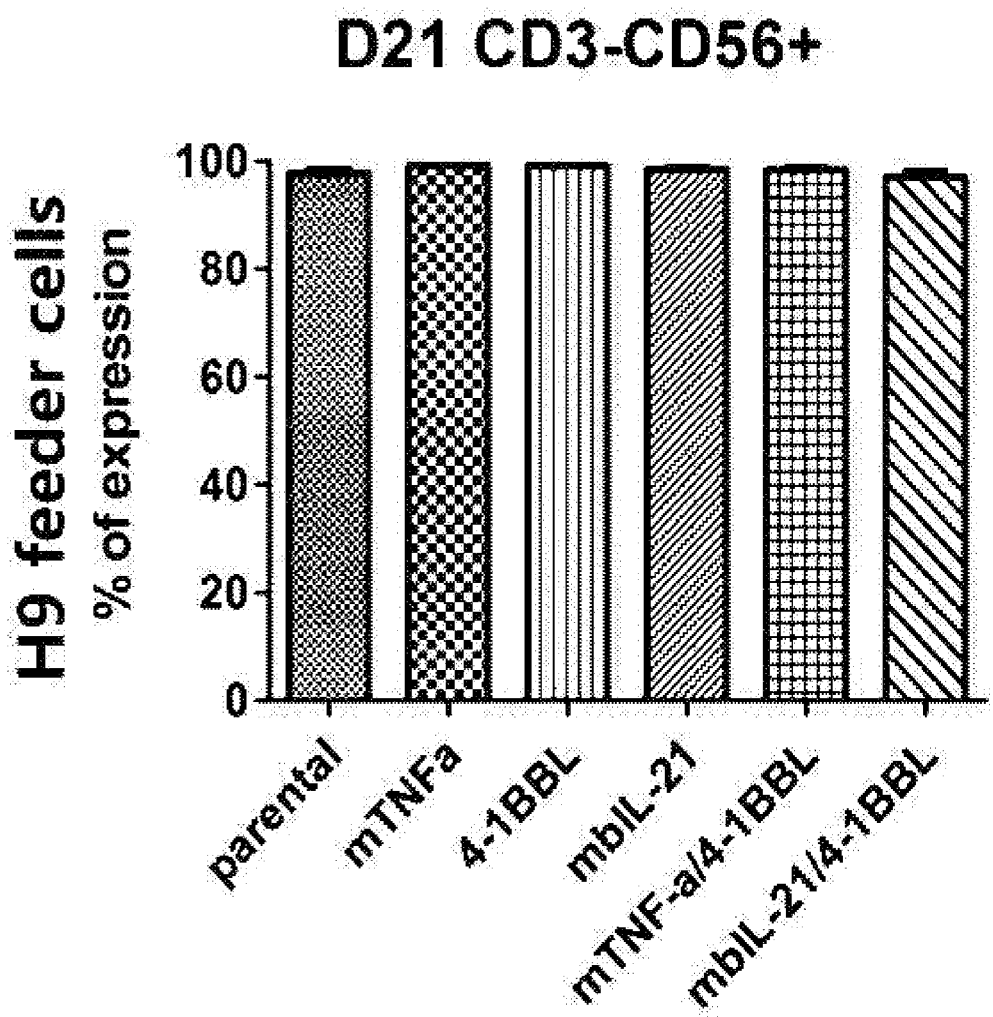

[Fig. 7d]
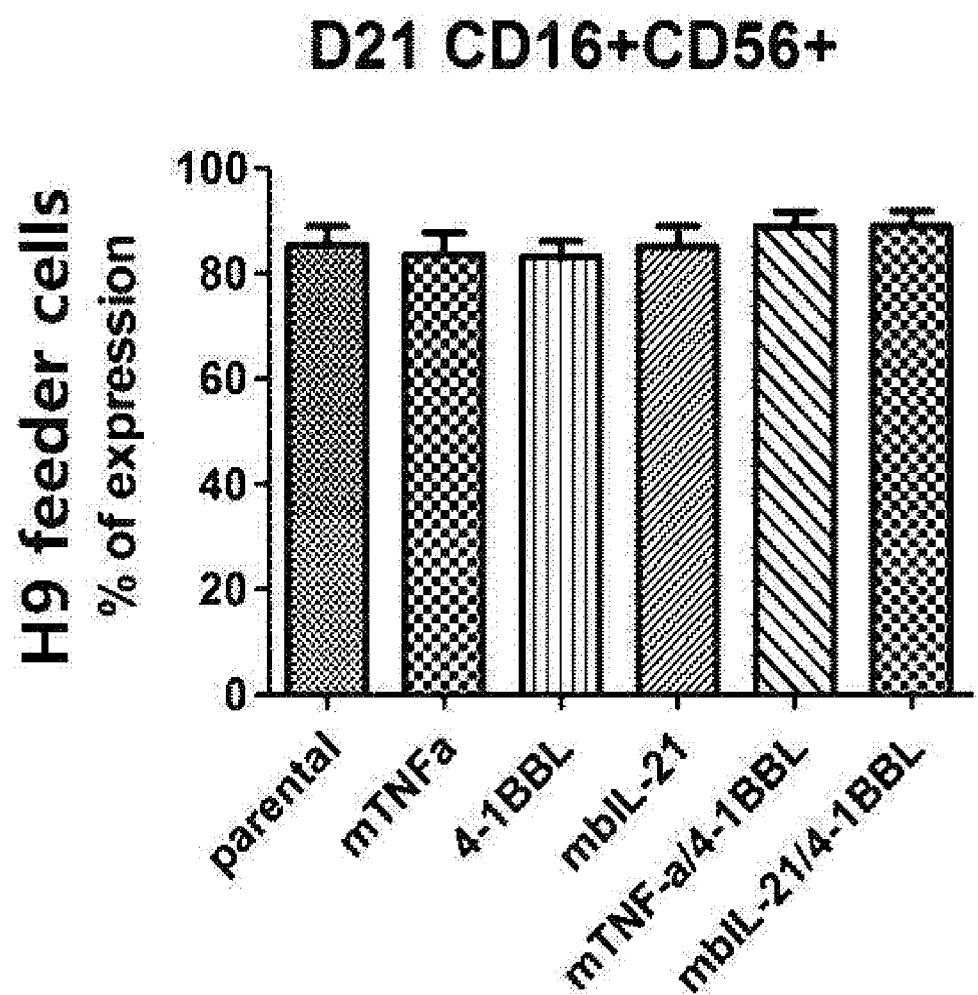

[Fig. 7e]
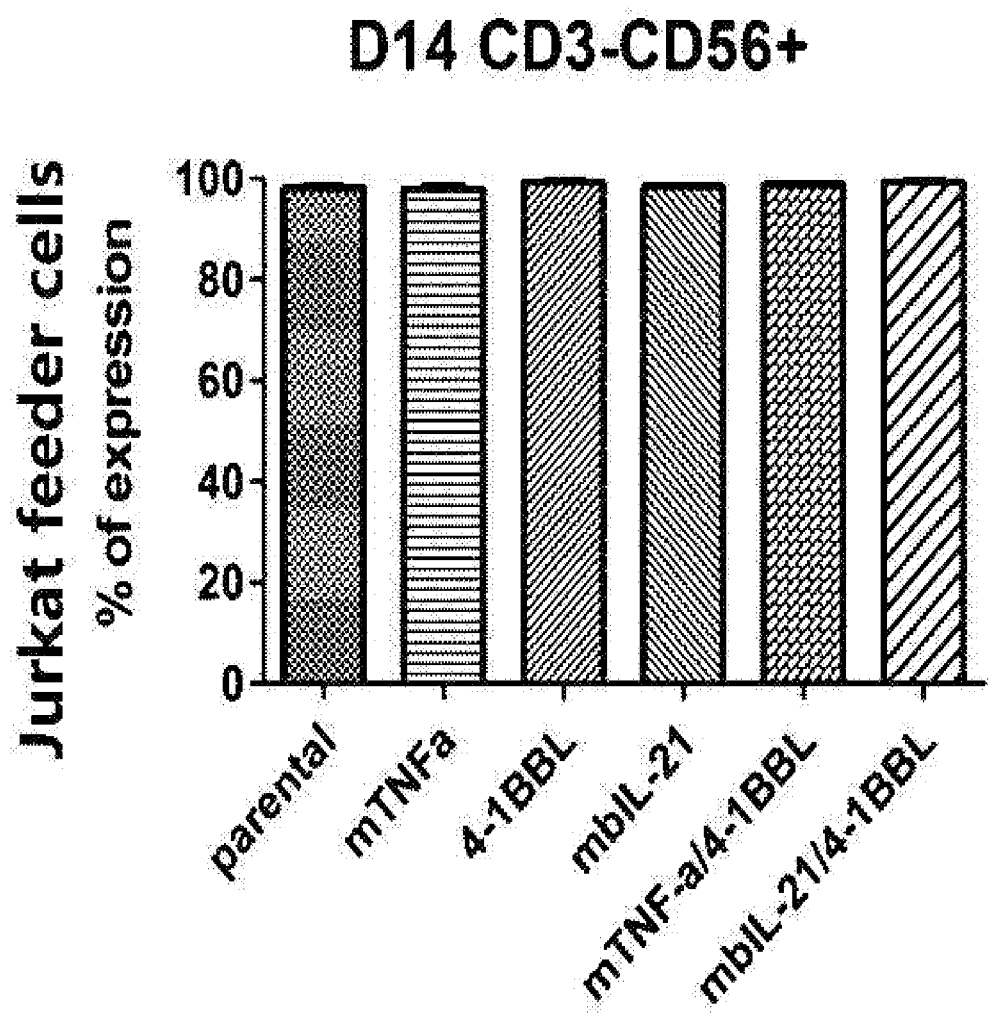

[Fig. 7f]
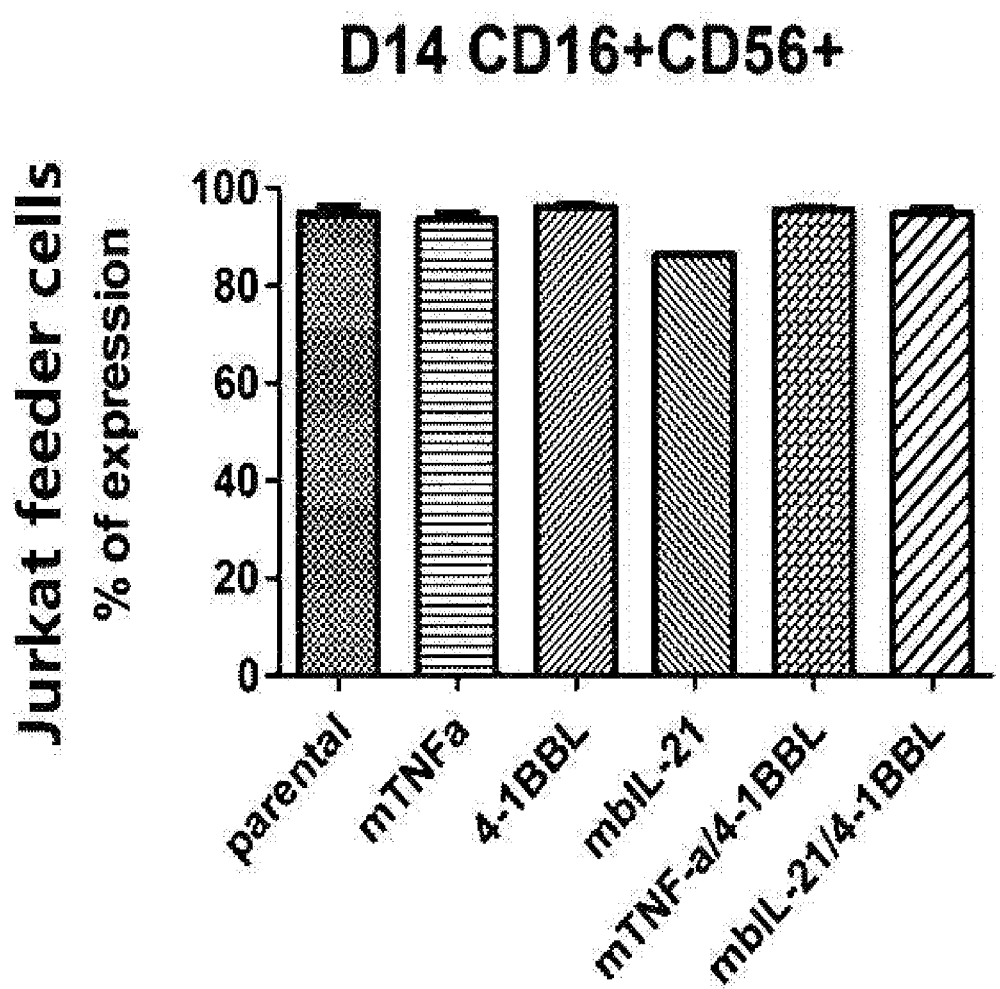

[Fig. 7g]
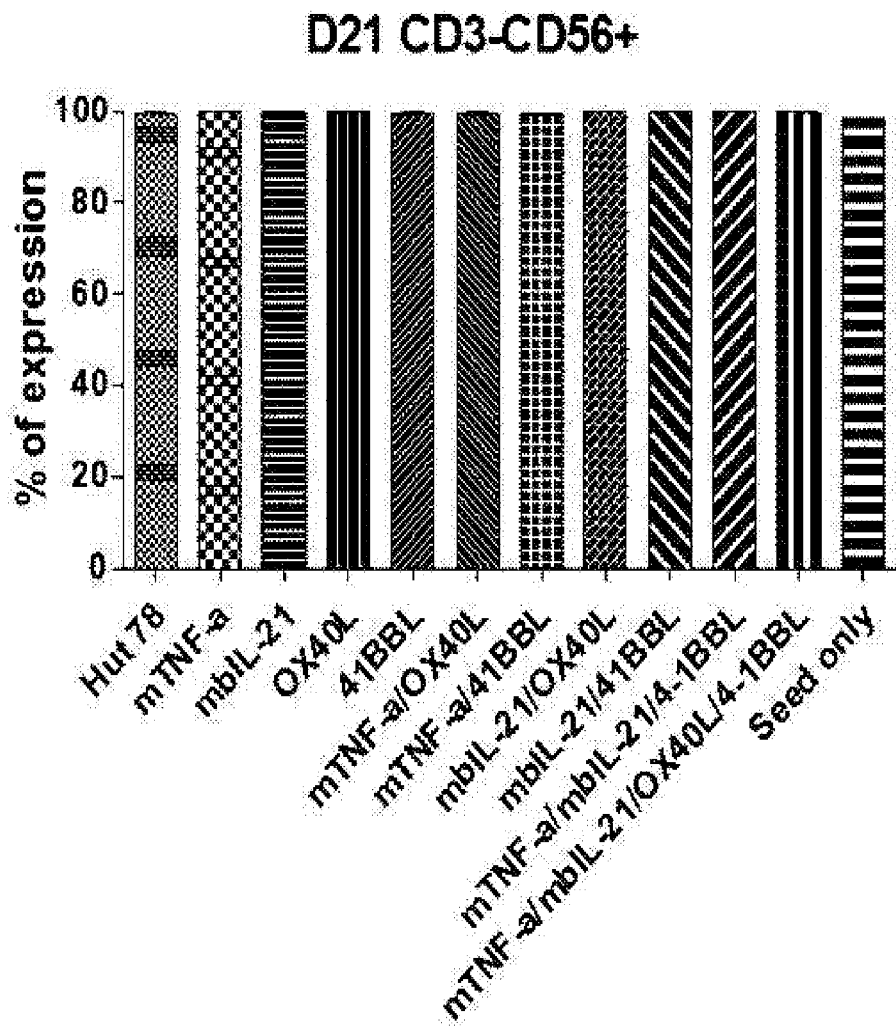

[Fig. 7h]
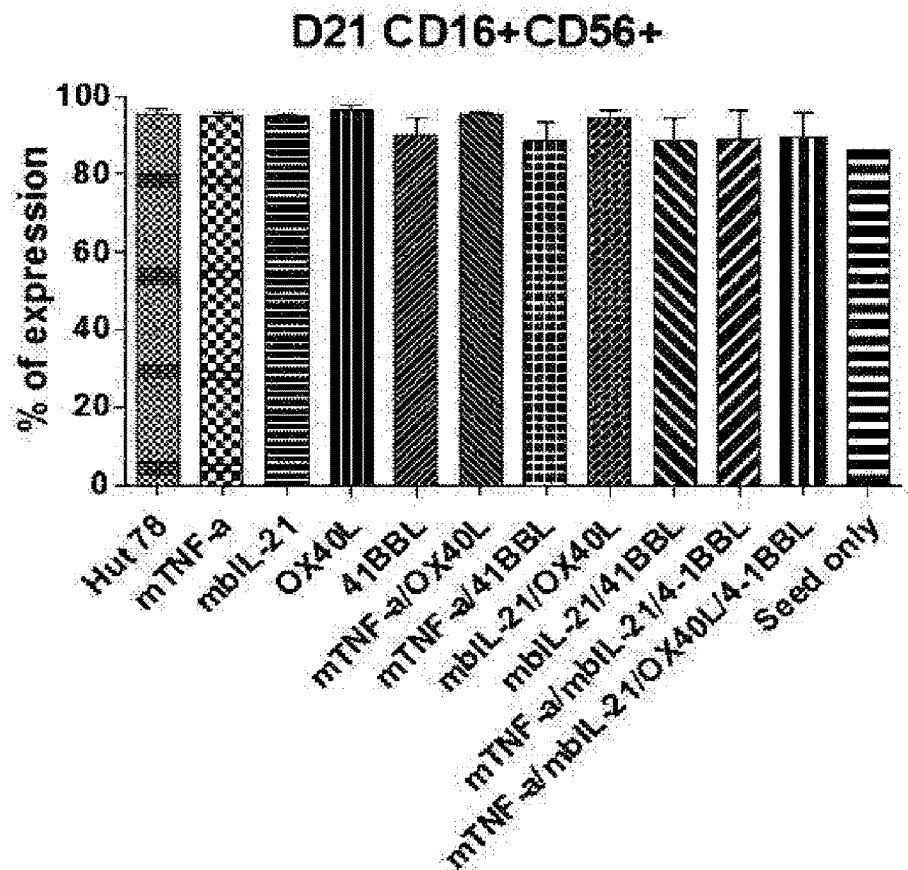
[Fig. 8a]
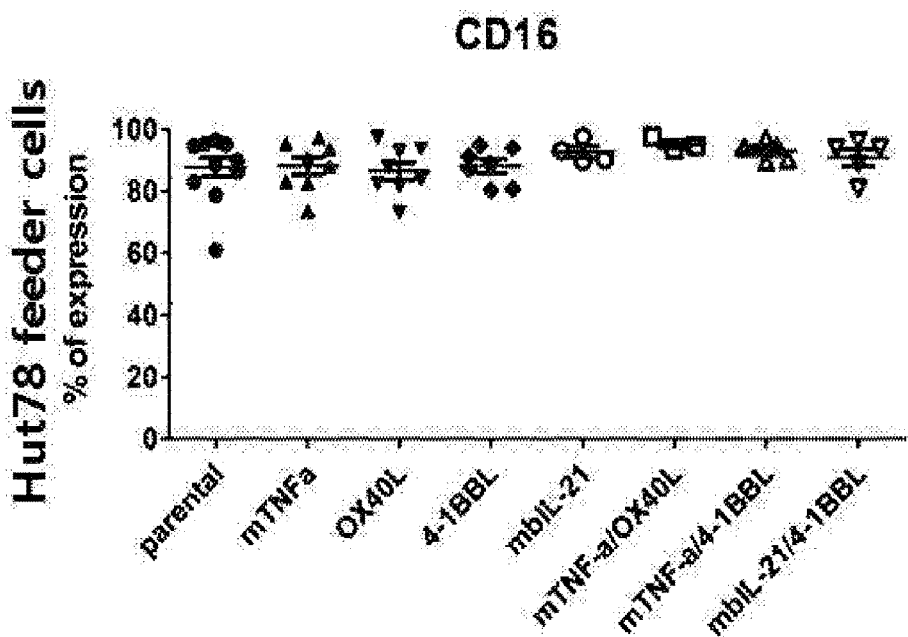

[Fig. 8b]
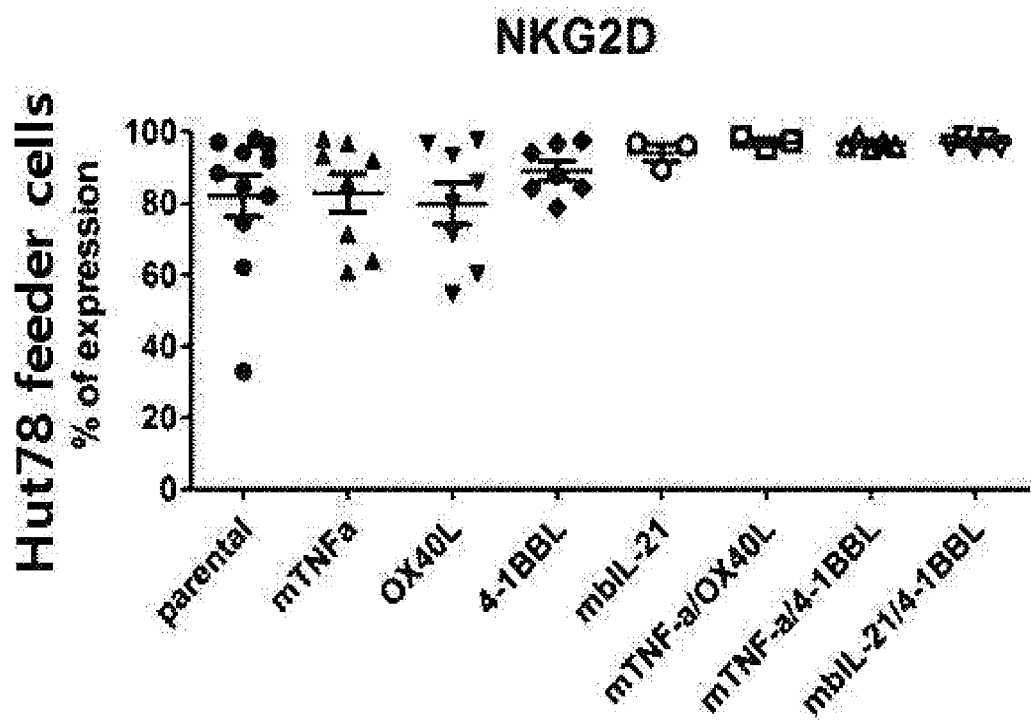
[Fig. 8c]
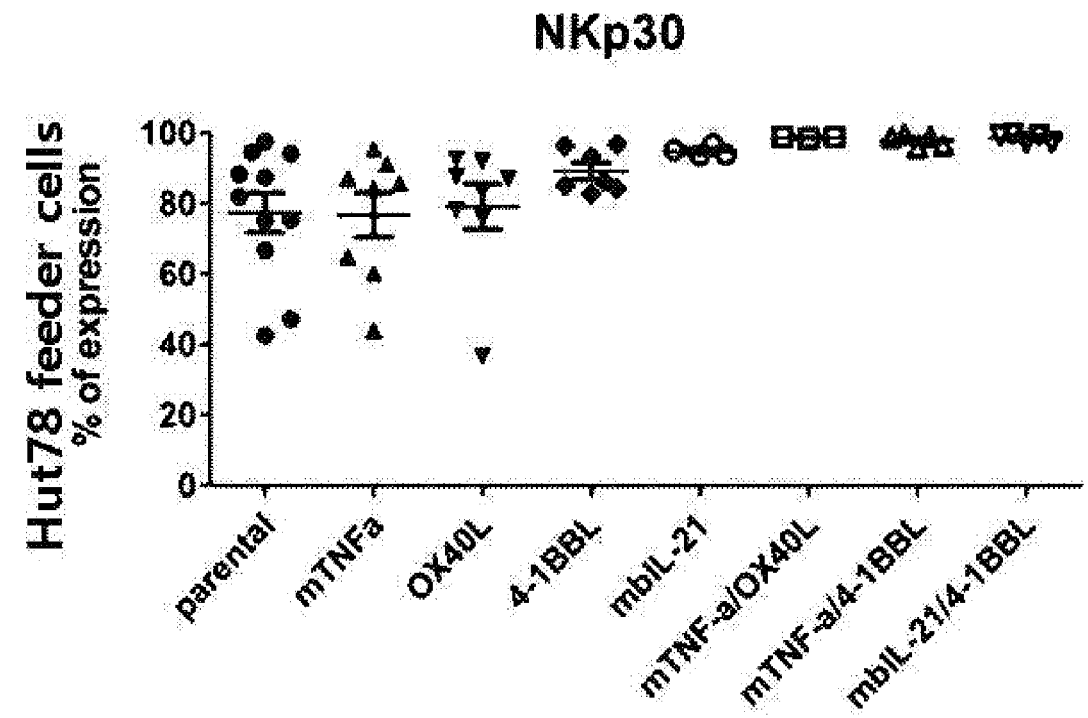

[Fig. 8d]
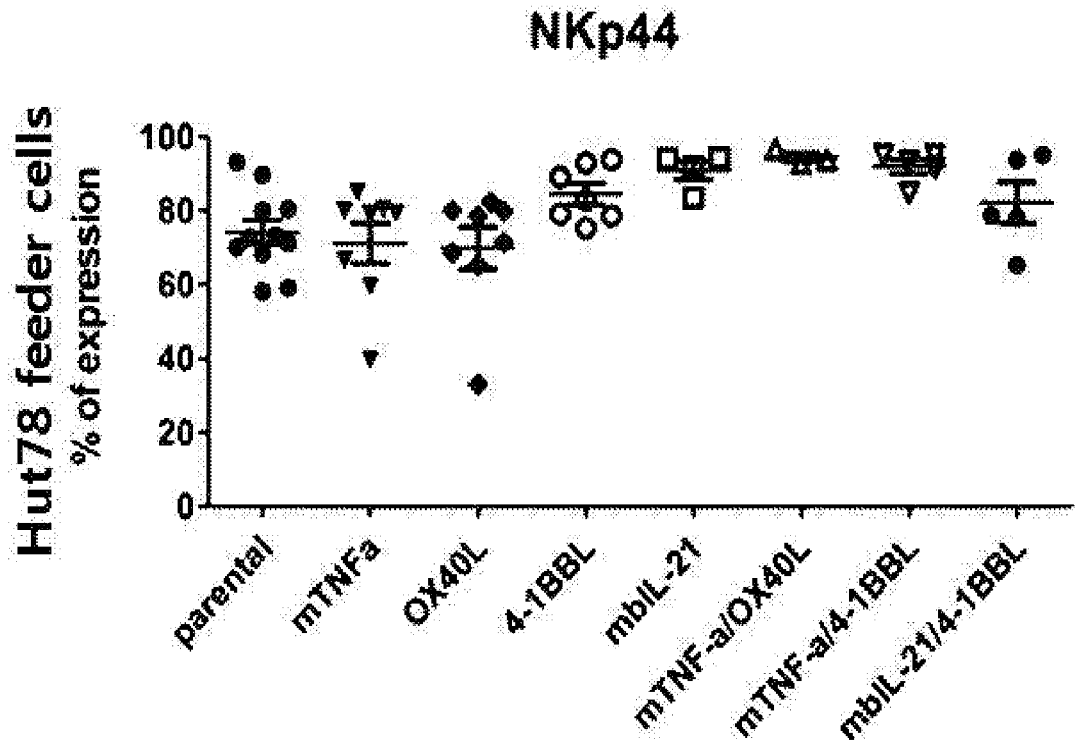
[Fig. 8e]
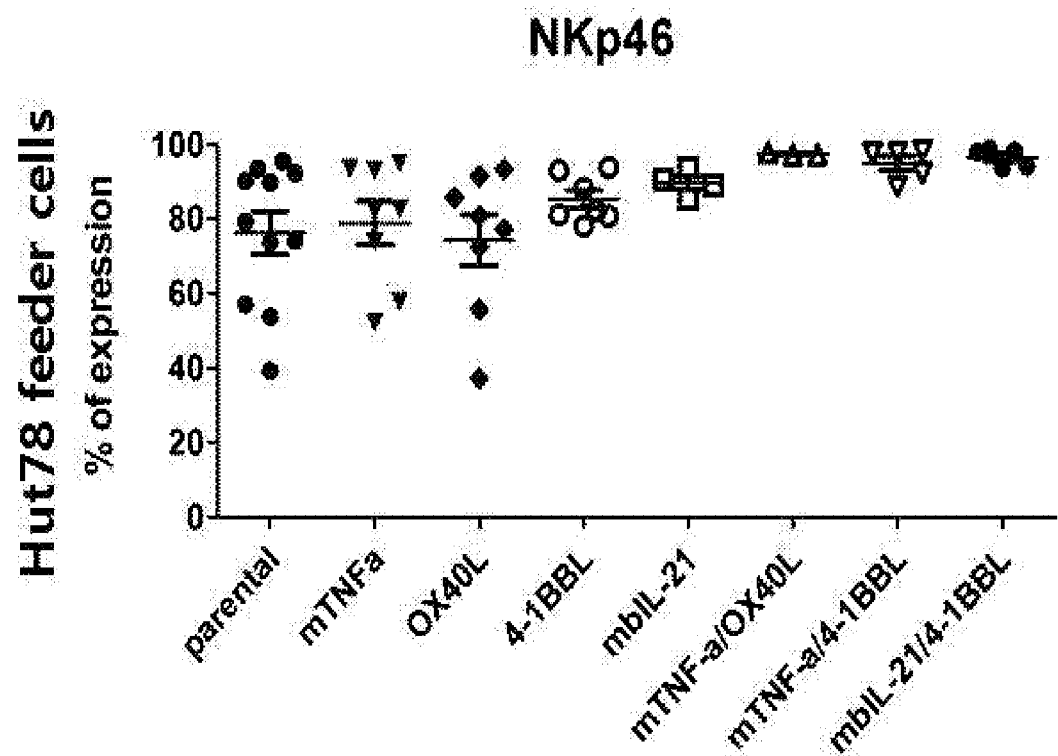

[Fig. 8f]
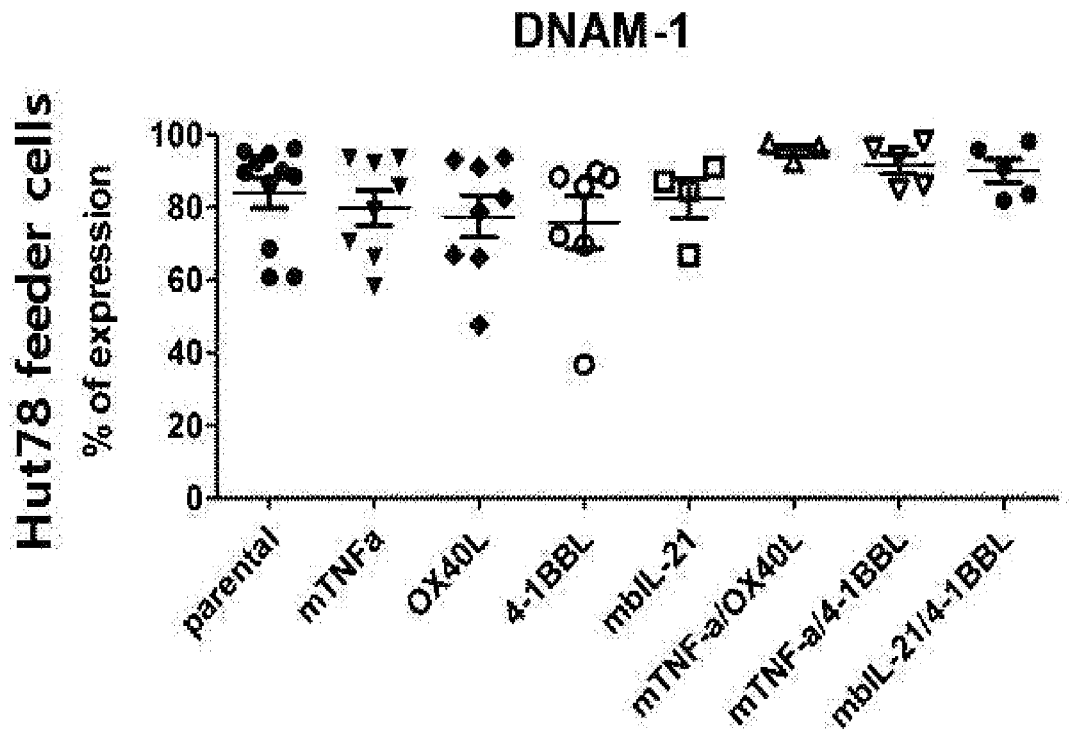
[Fig. 8g]
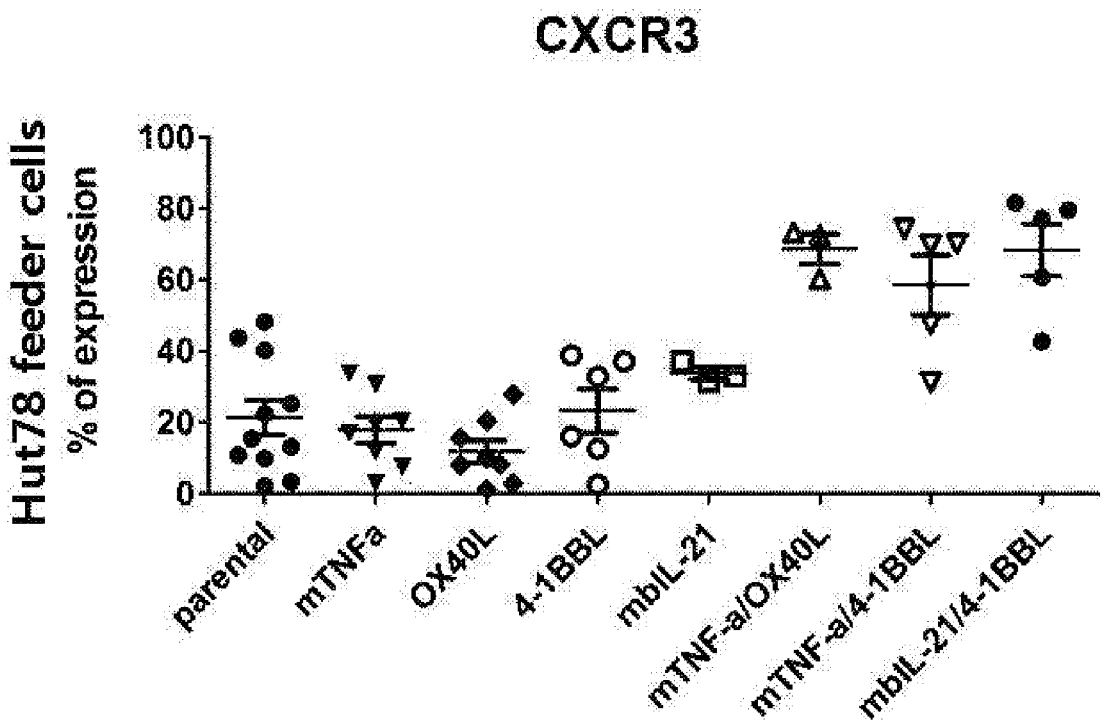

[Fig. 9a]
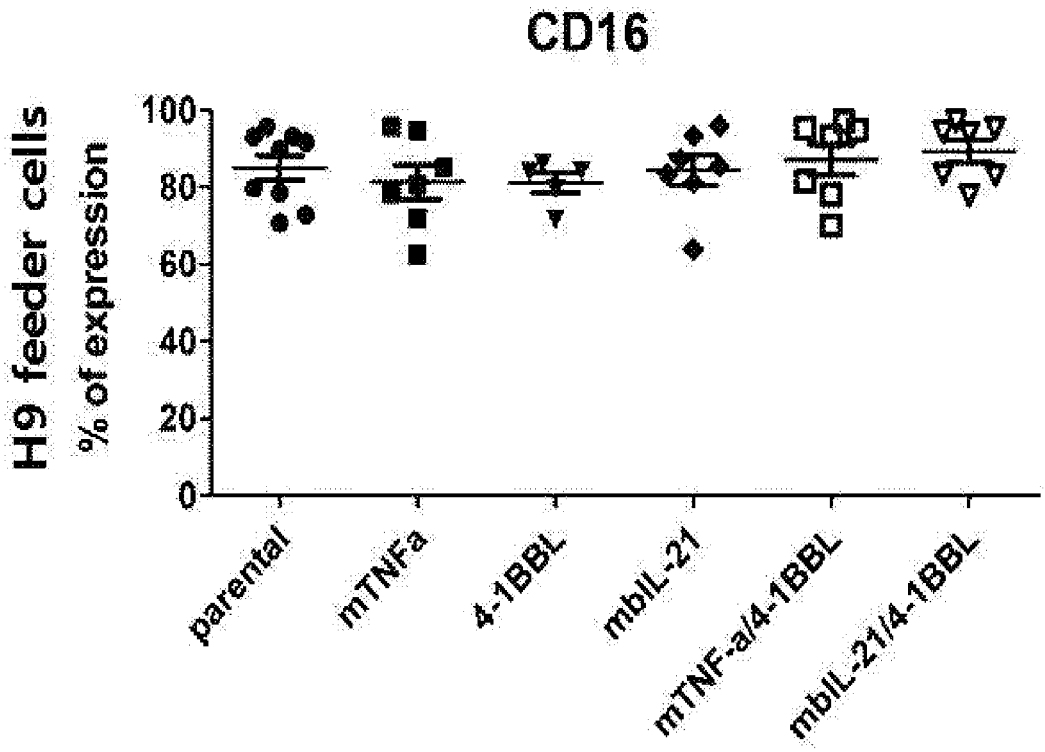
[Fig. 9b]
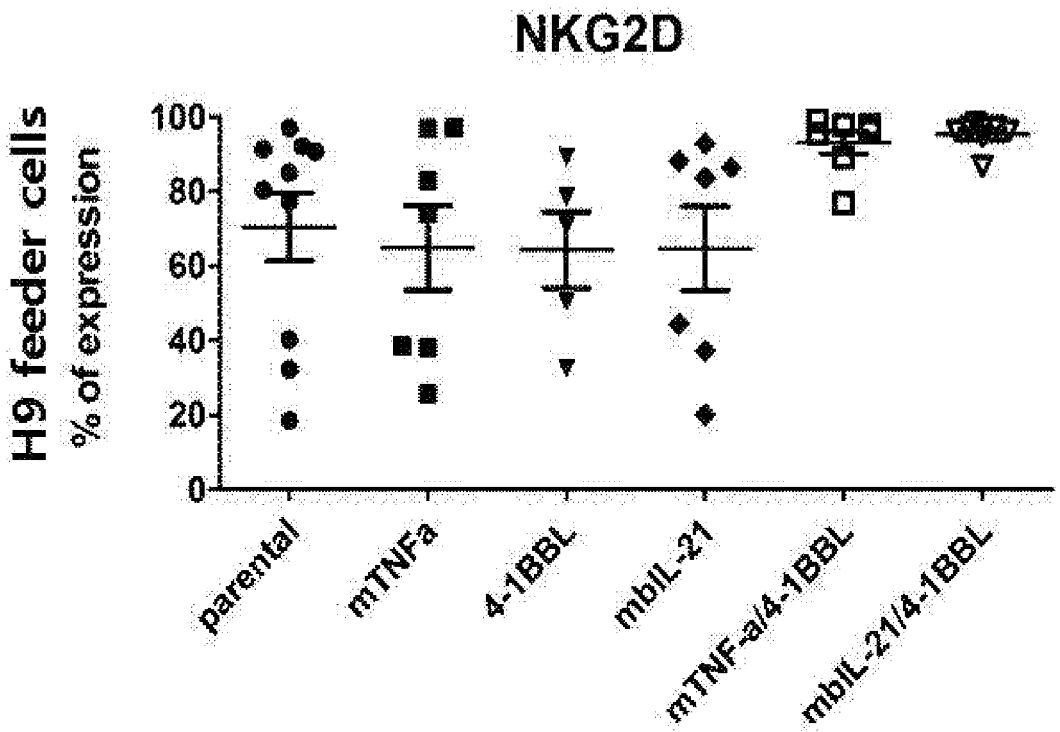

[Fig. 9c]
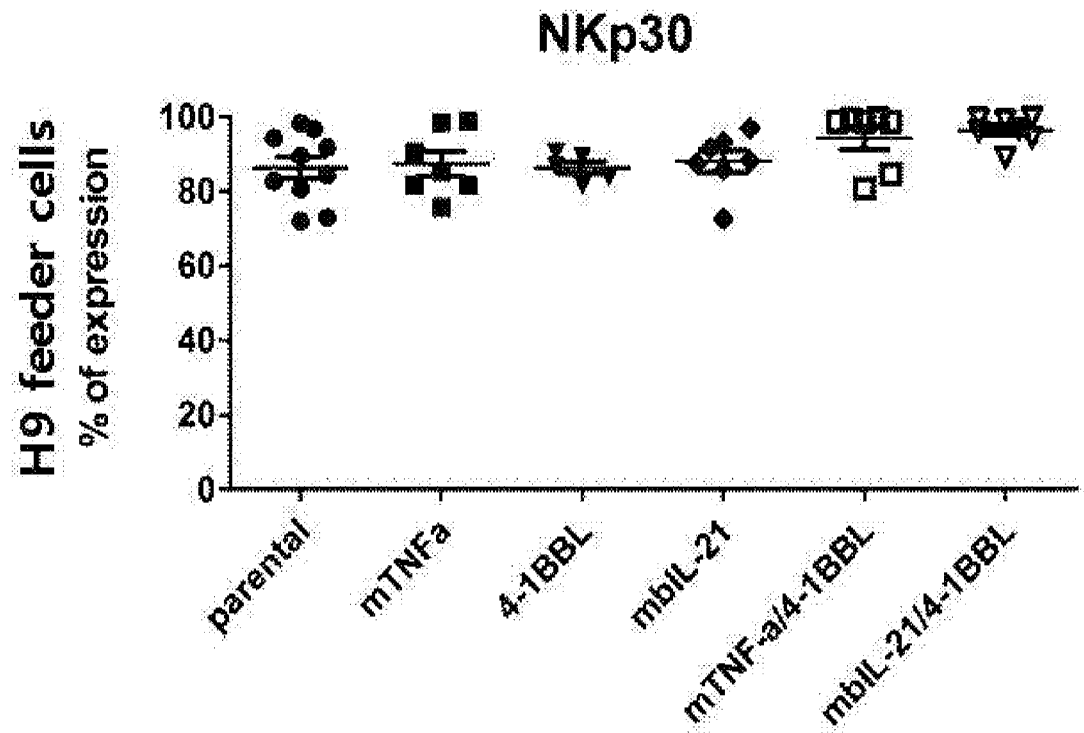
[Fig. 9d]
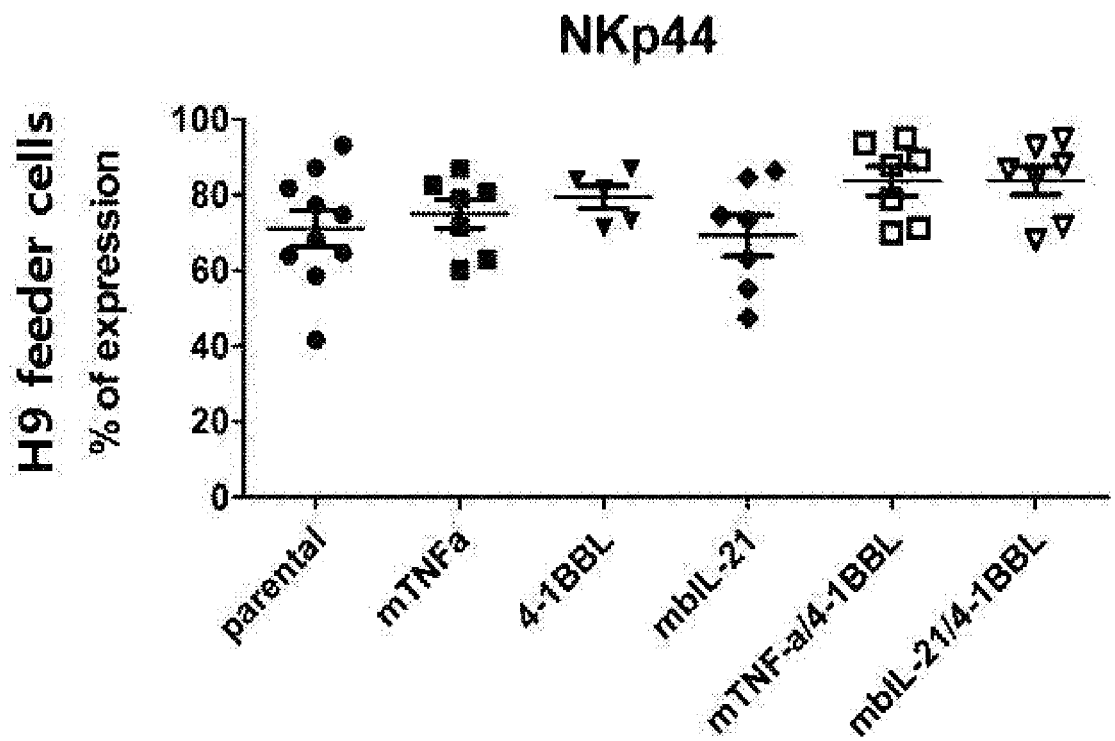

[Fig. 9e]
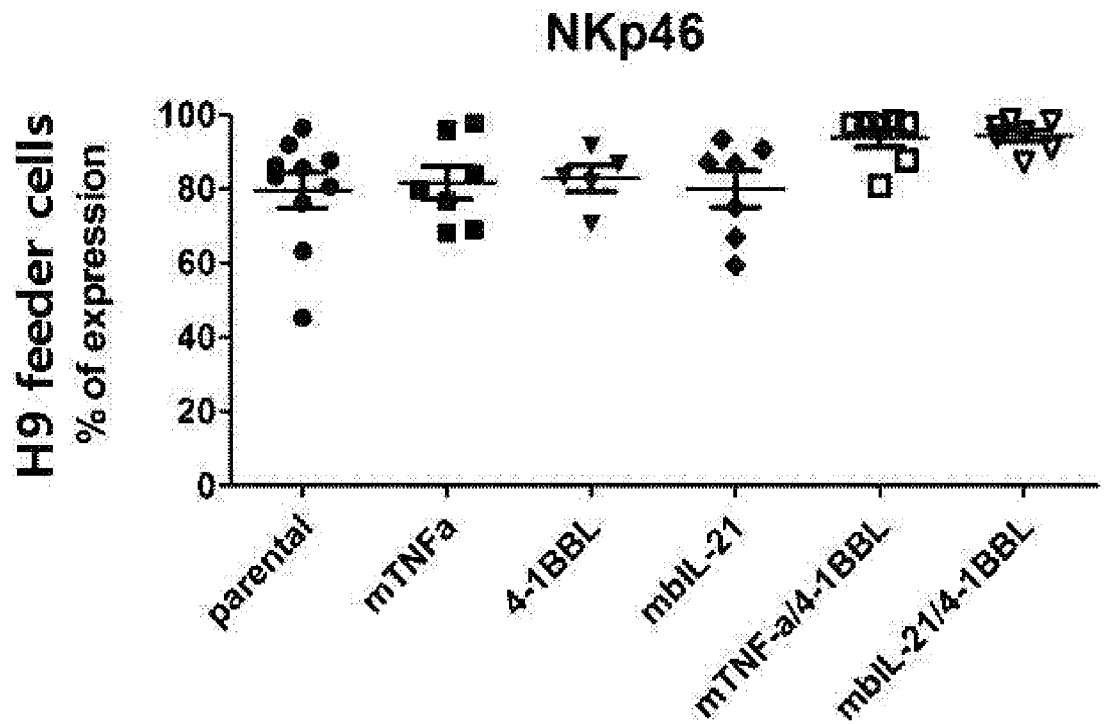
[Fig. 9f]
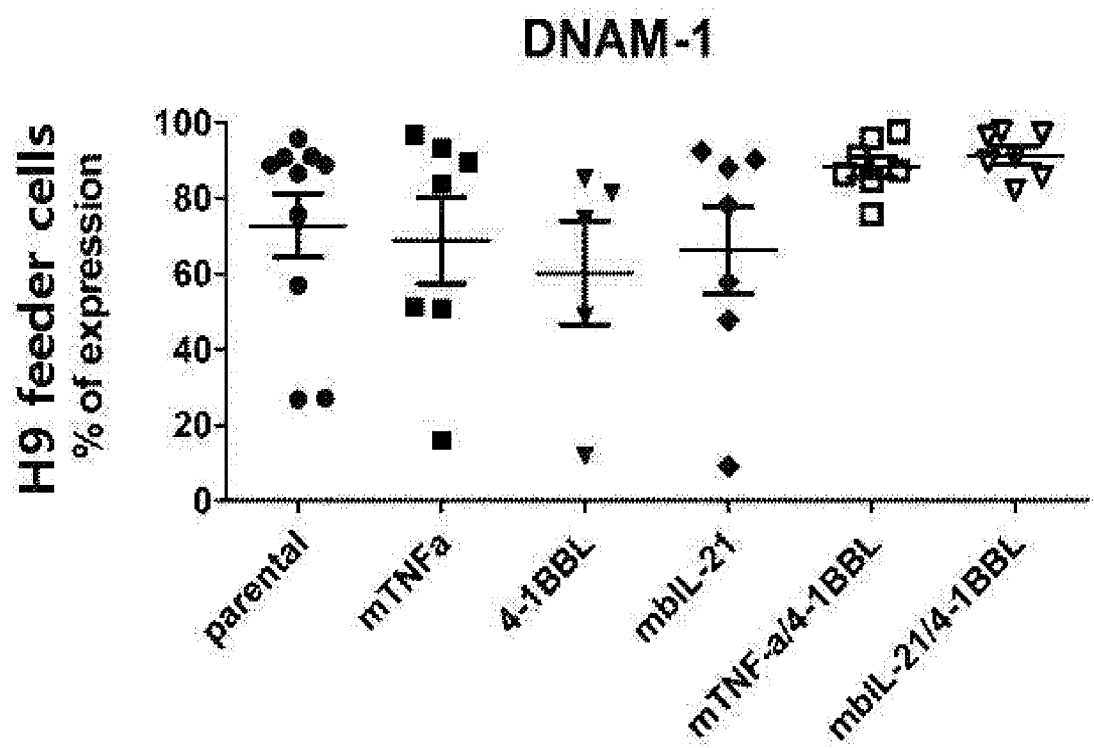

[Fig. 9g]
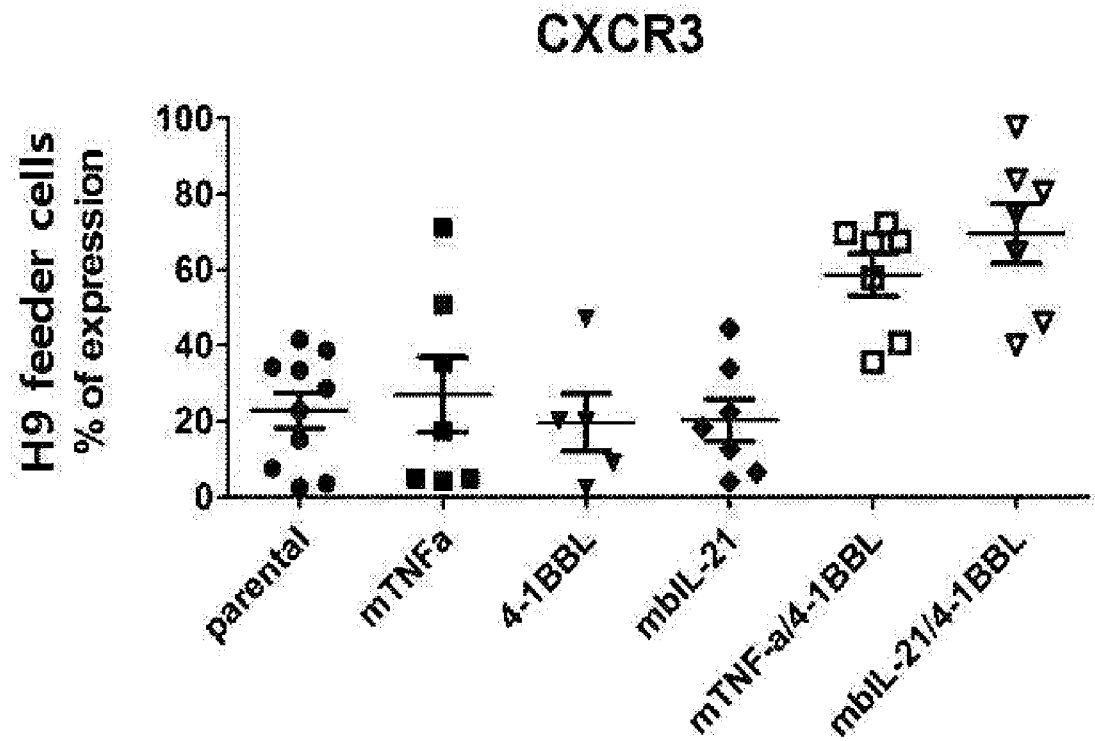
[Fig. 10a]
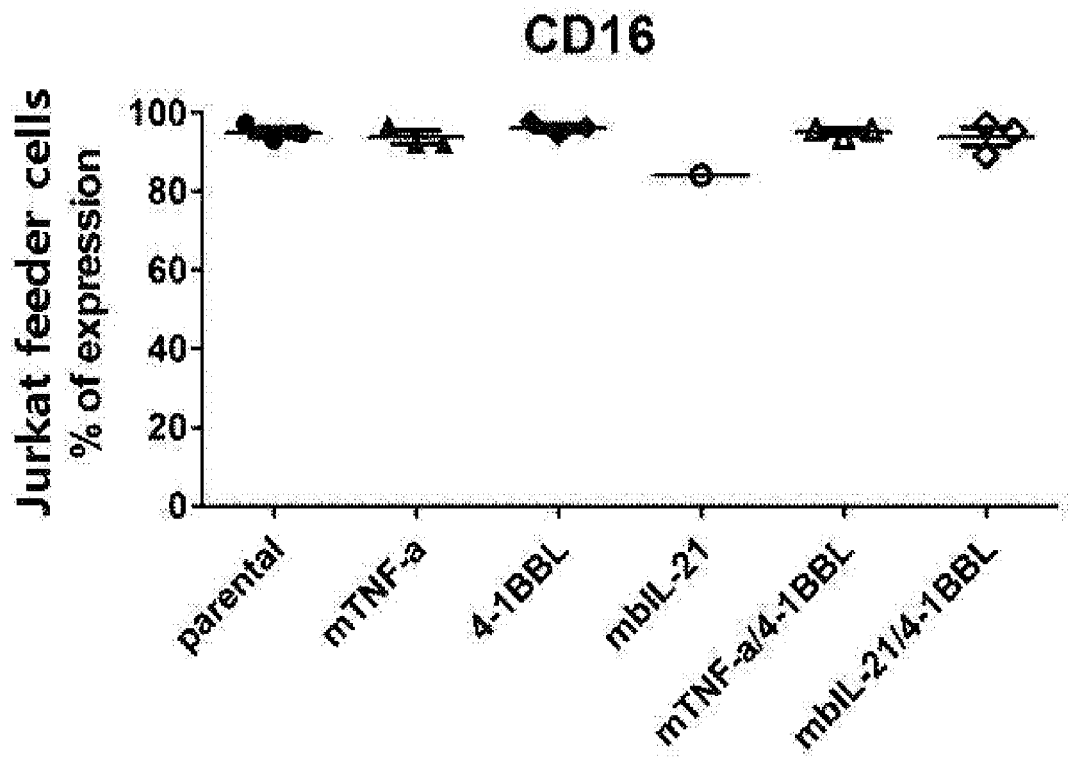

[Fig. 10b]
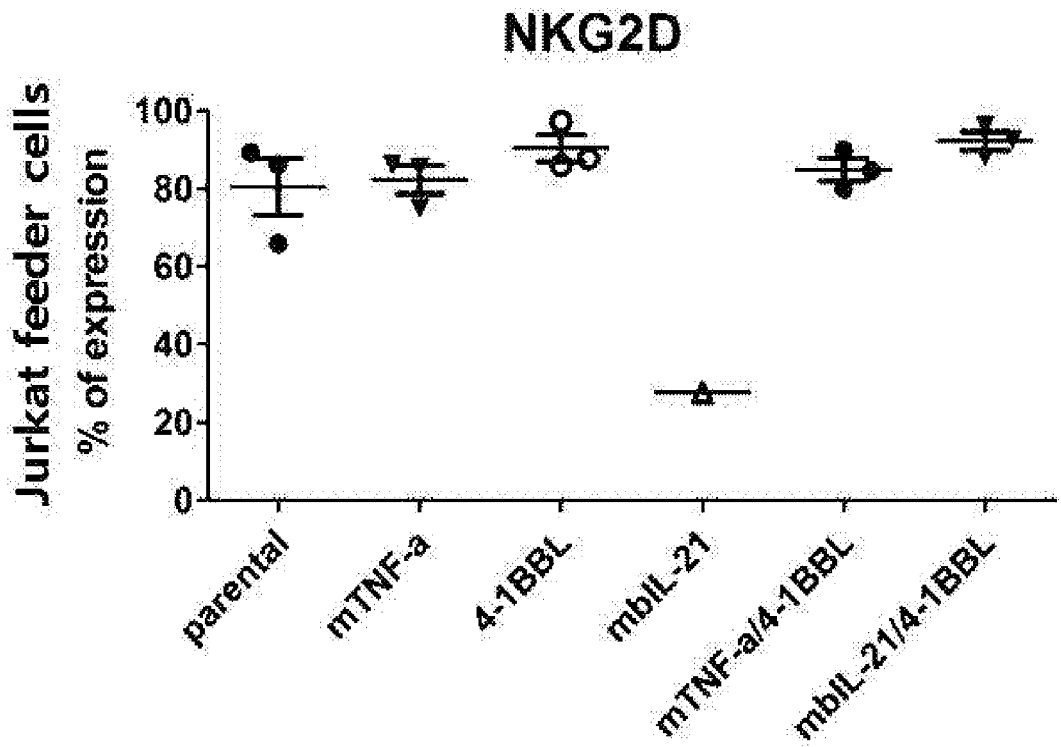
[Fig. 10c]
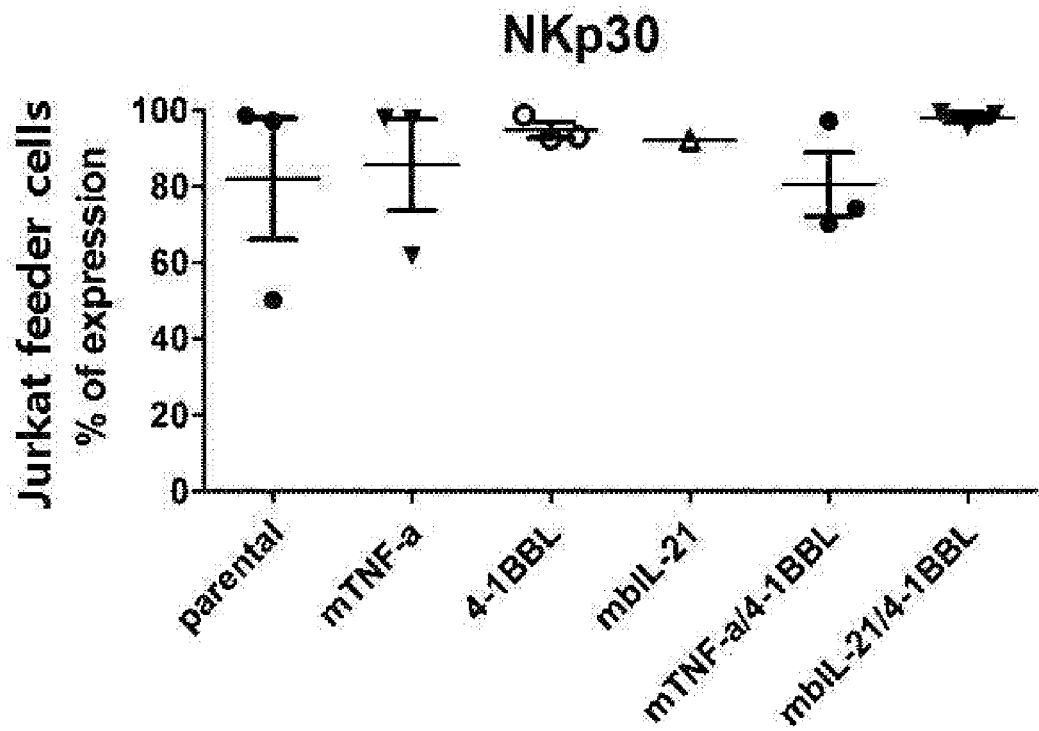

[Fig. 10d]
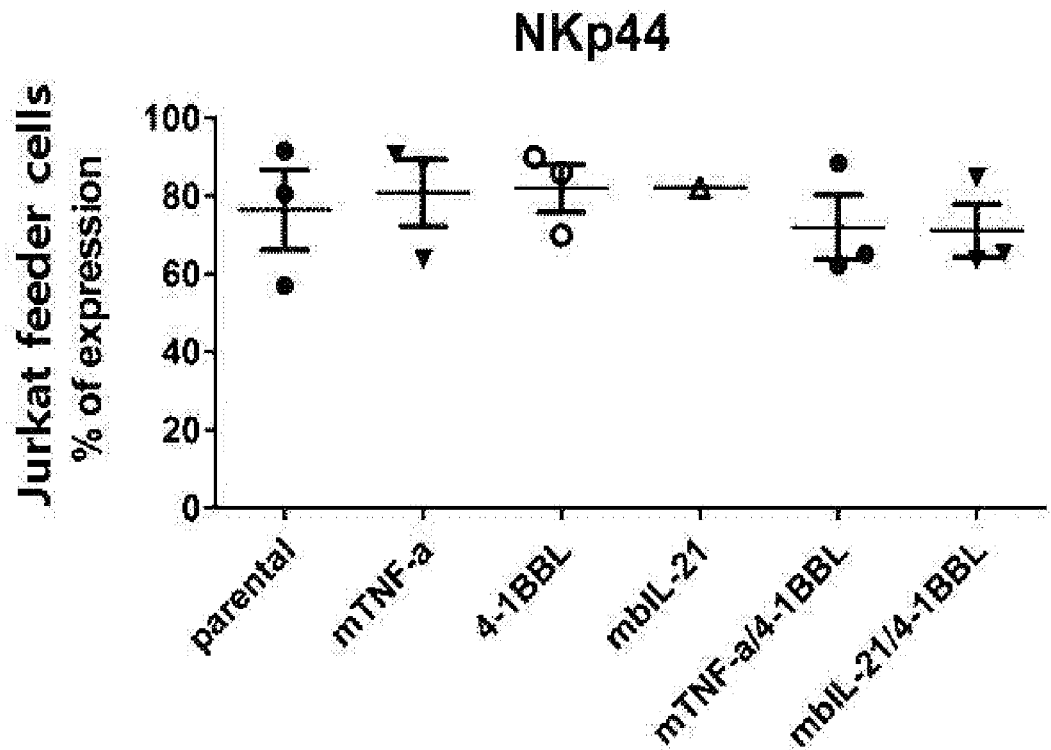
[Fig. 10e]
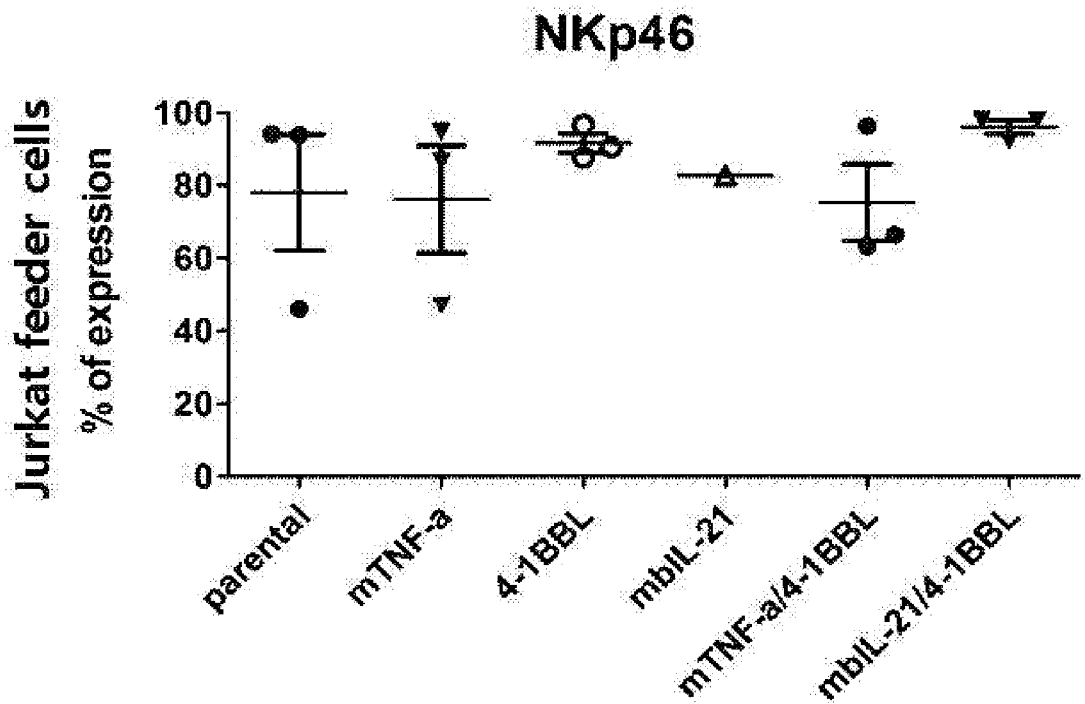

[Fig. 10f]
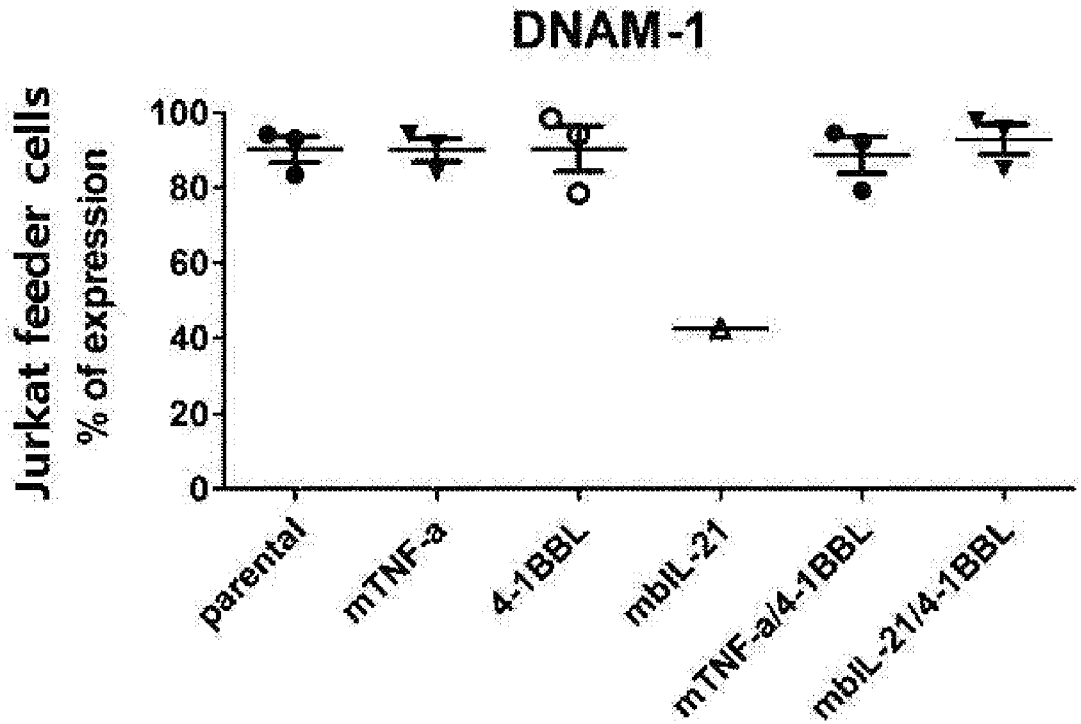
[Fig. 10g]
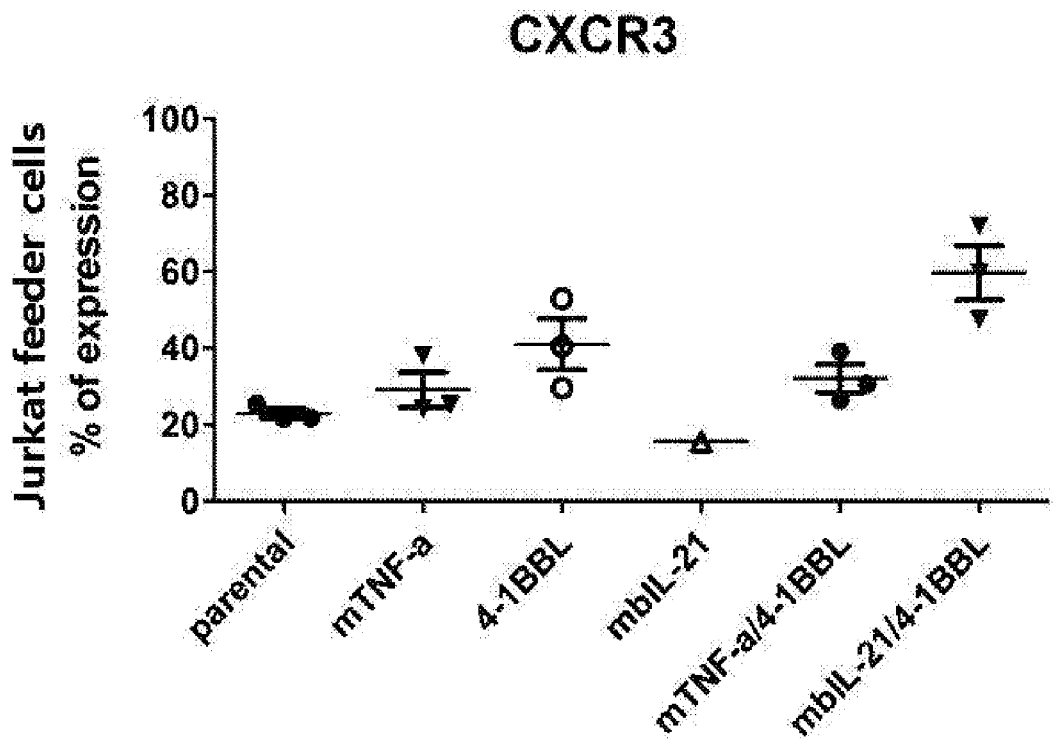

[Fig. 11a]
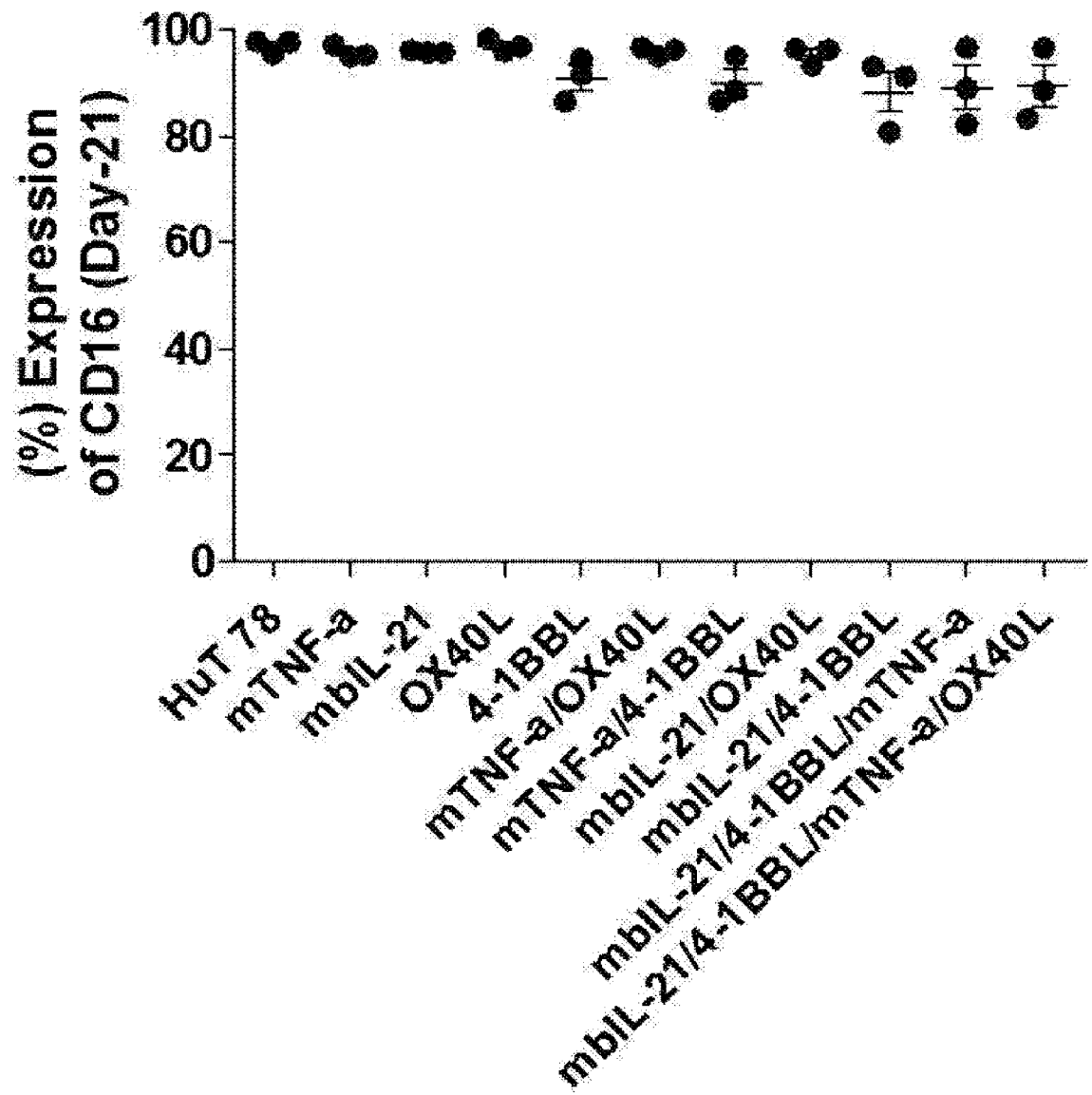

[Fig. 11b]
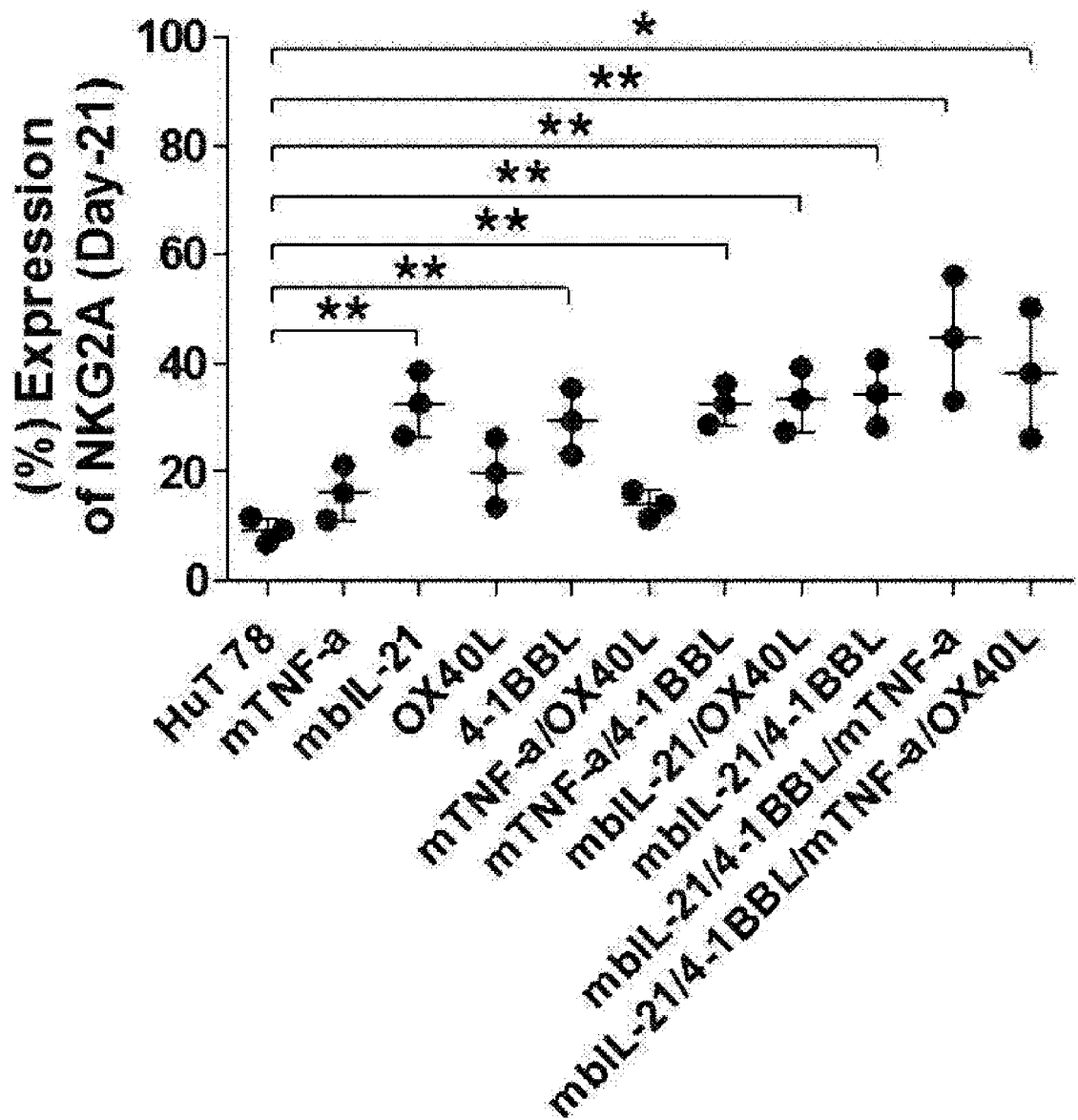

[Fig. 11c]
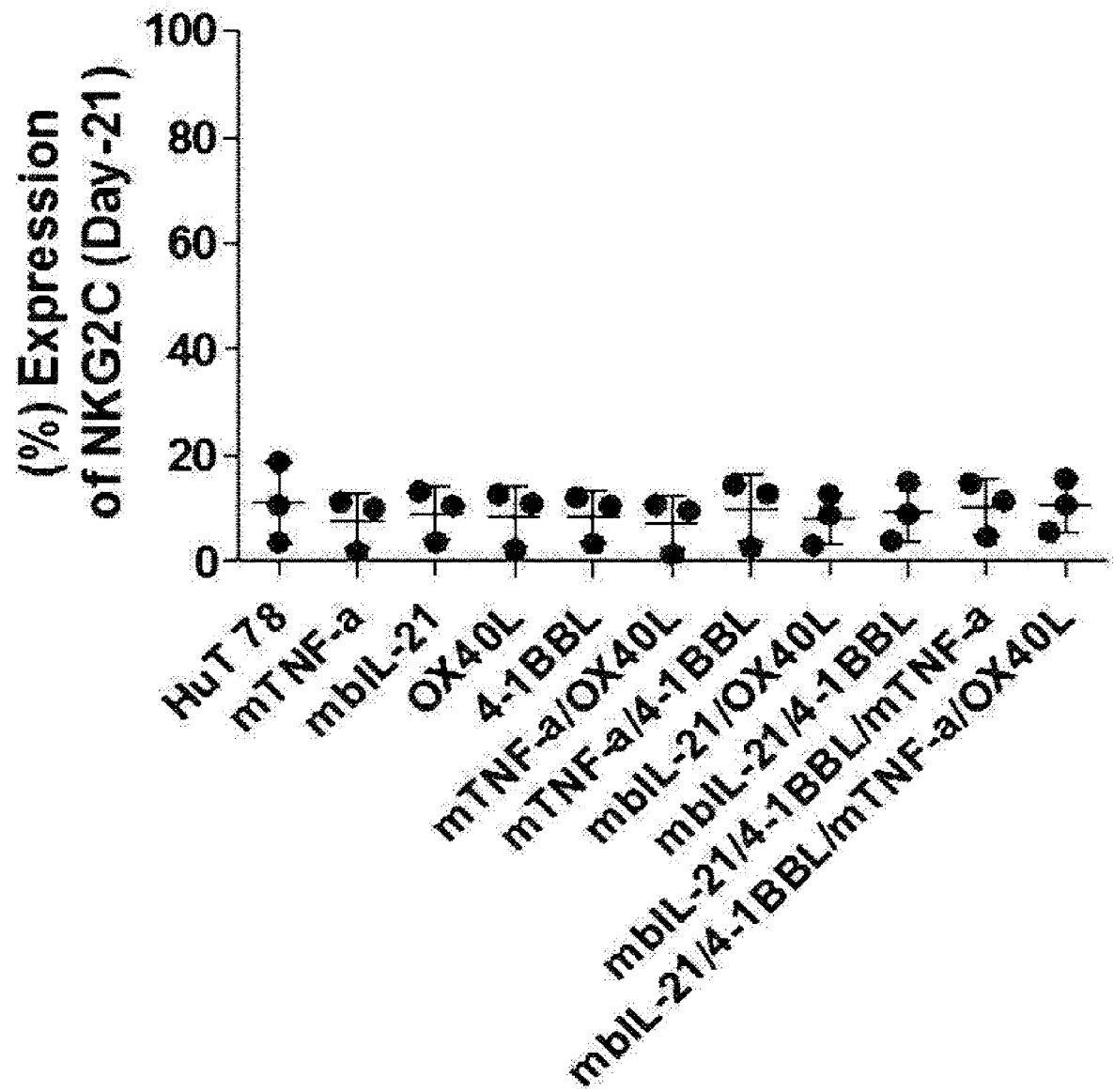

[Fig. 11d]
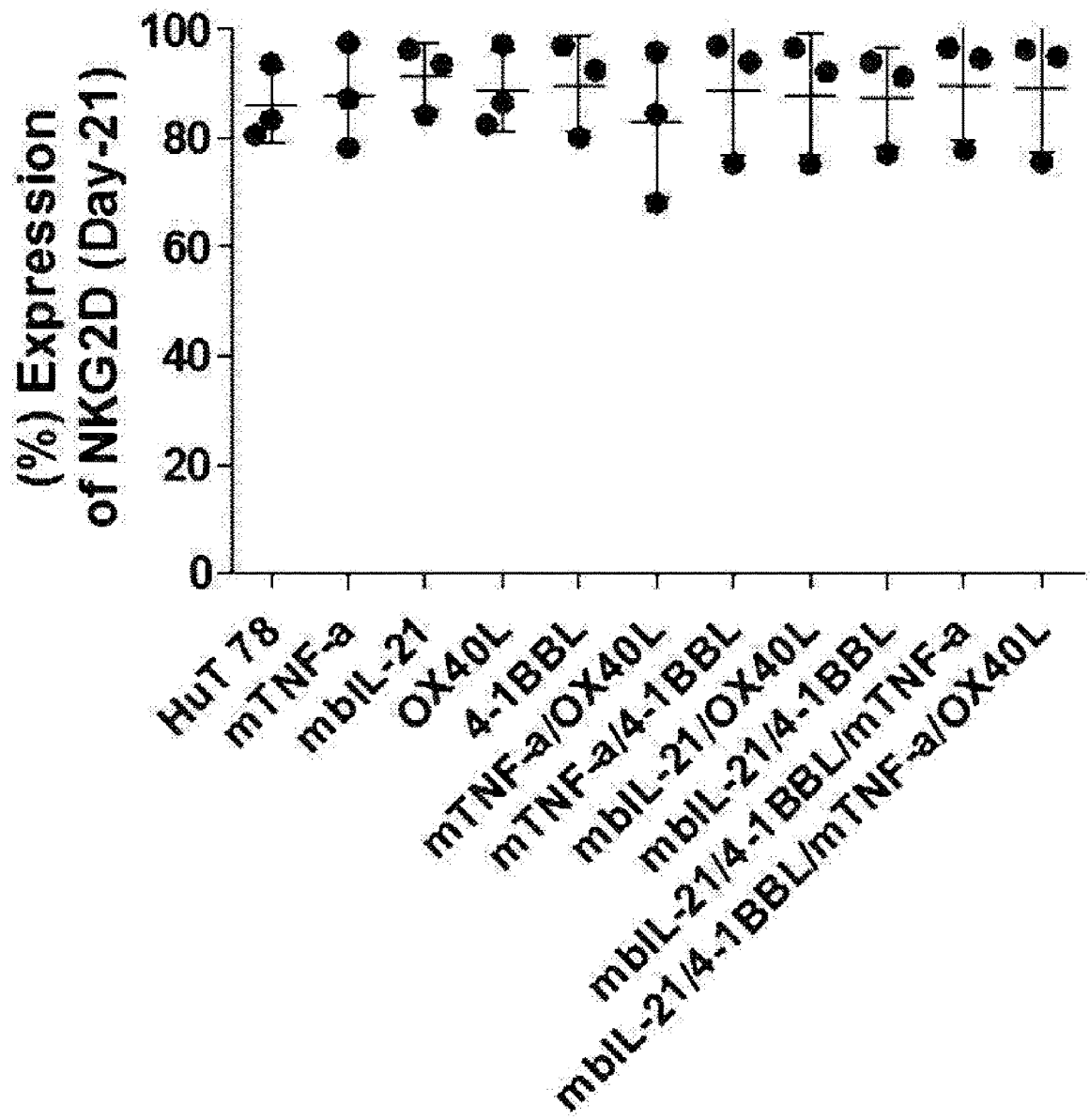

[Fig. 11e]
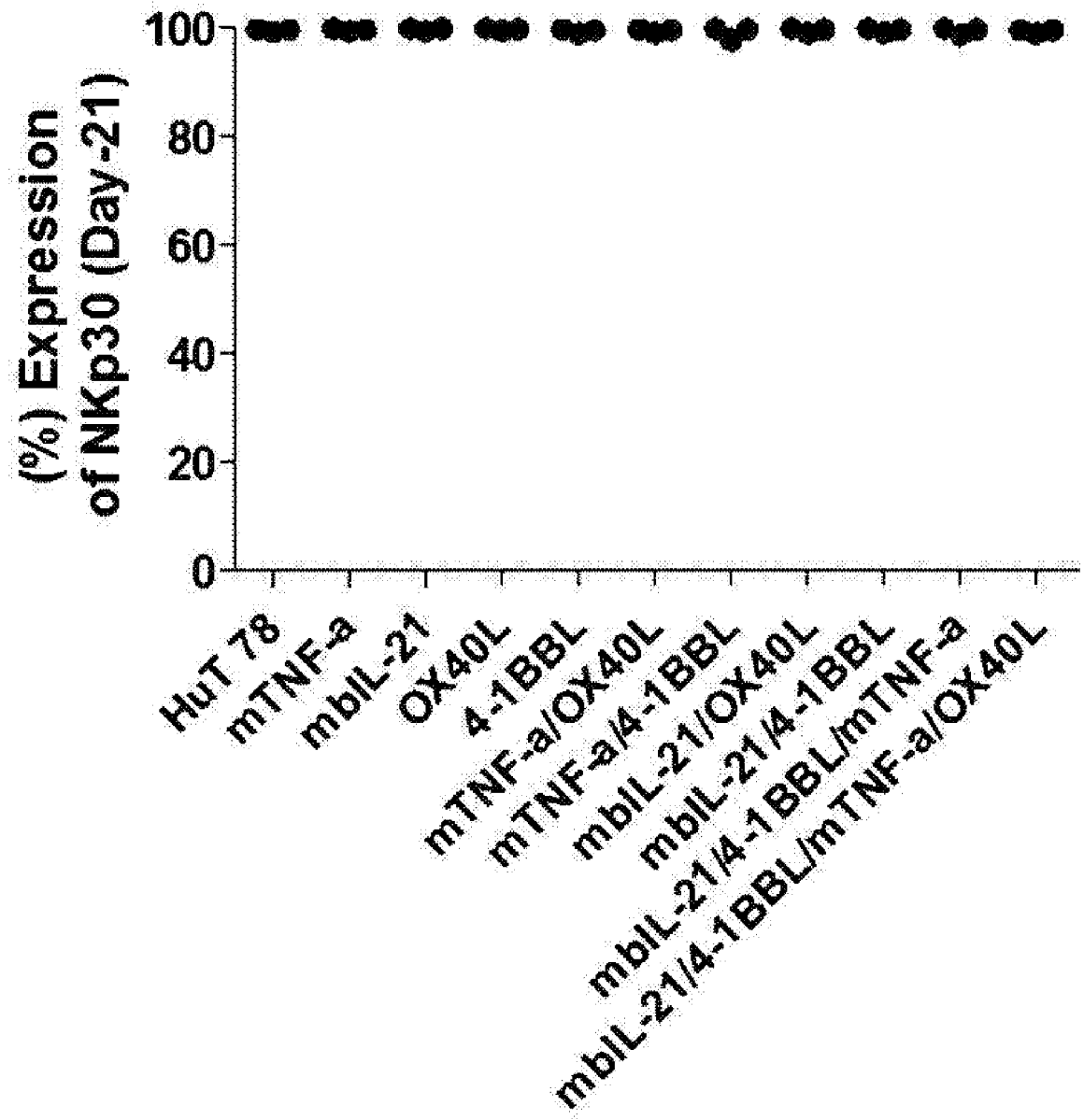

[Fig. 11f]
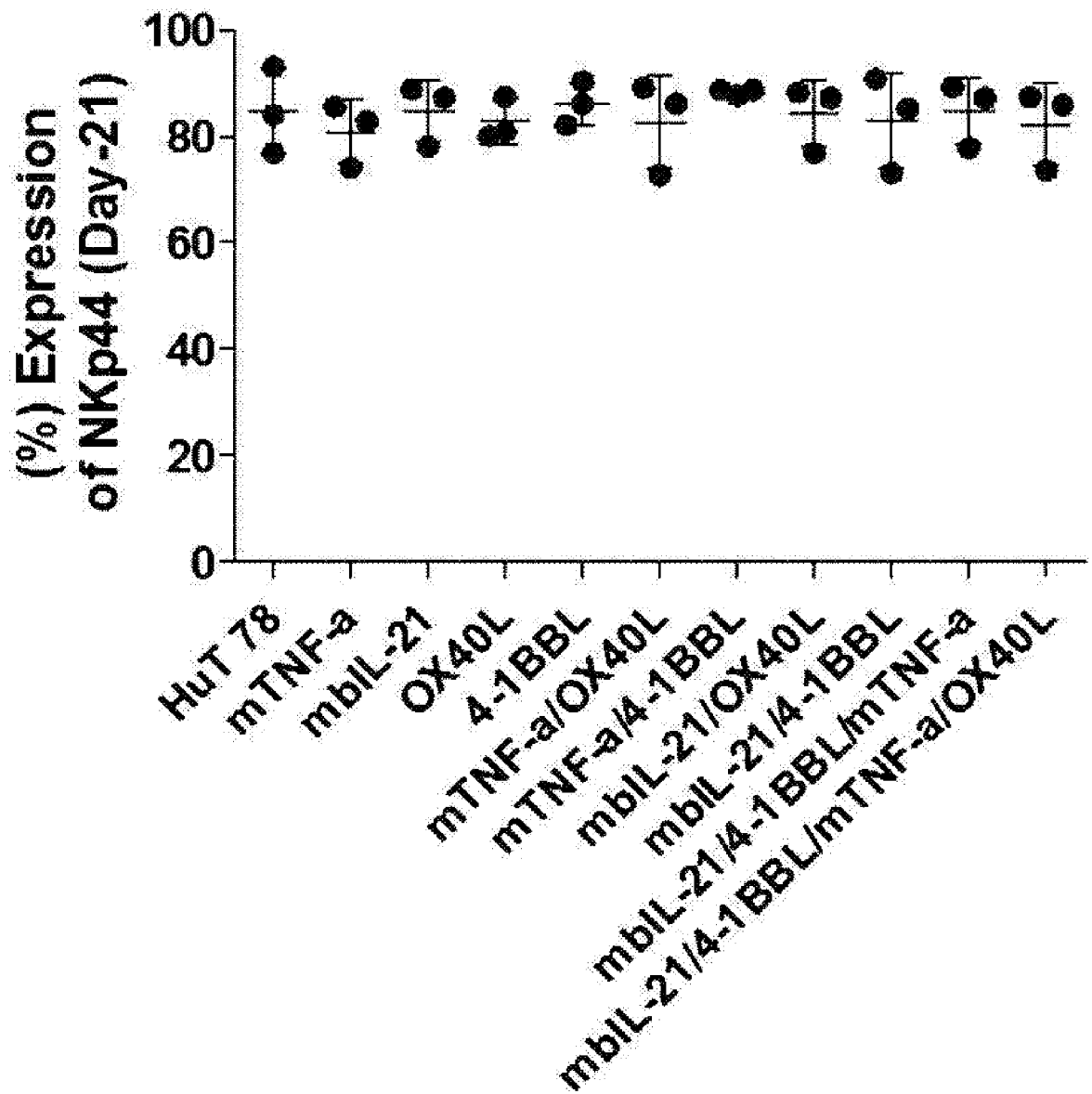

[Fig. 11g]
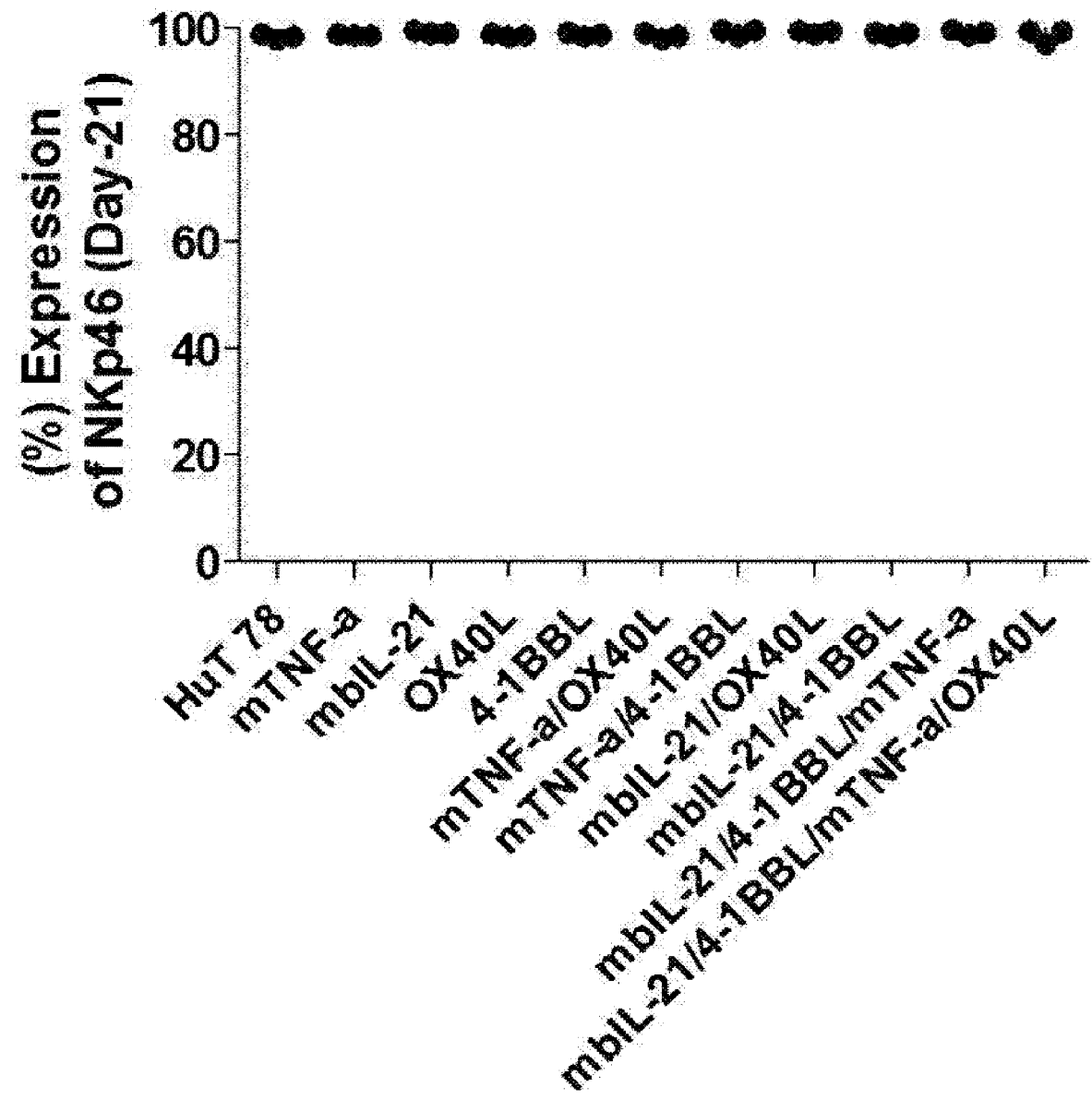

[Fig. 11h]
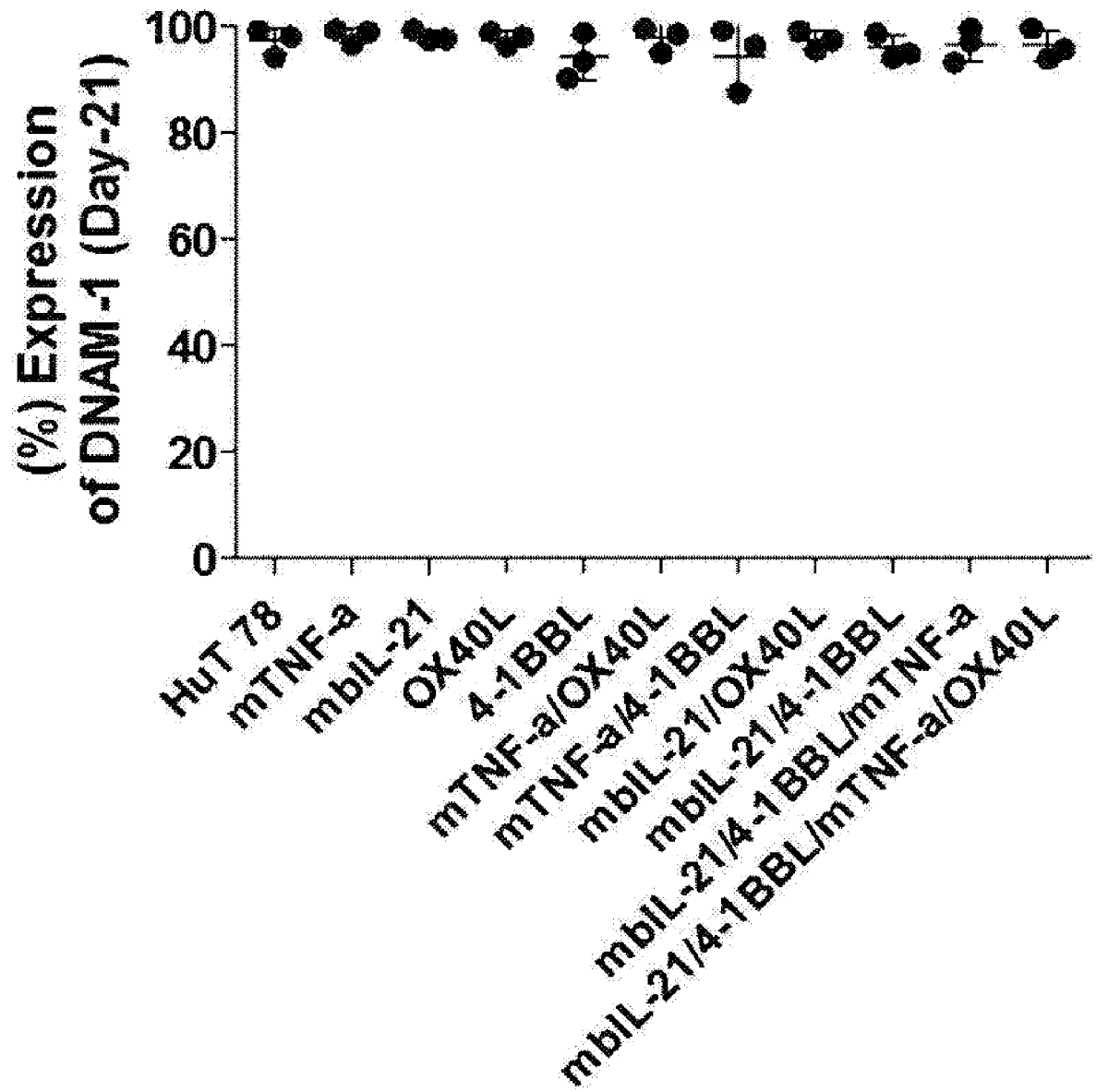

[Fig. 11i]
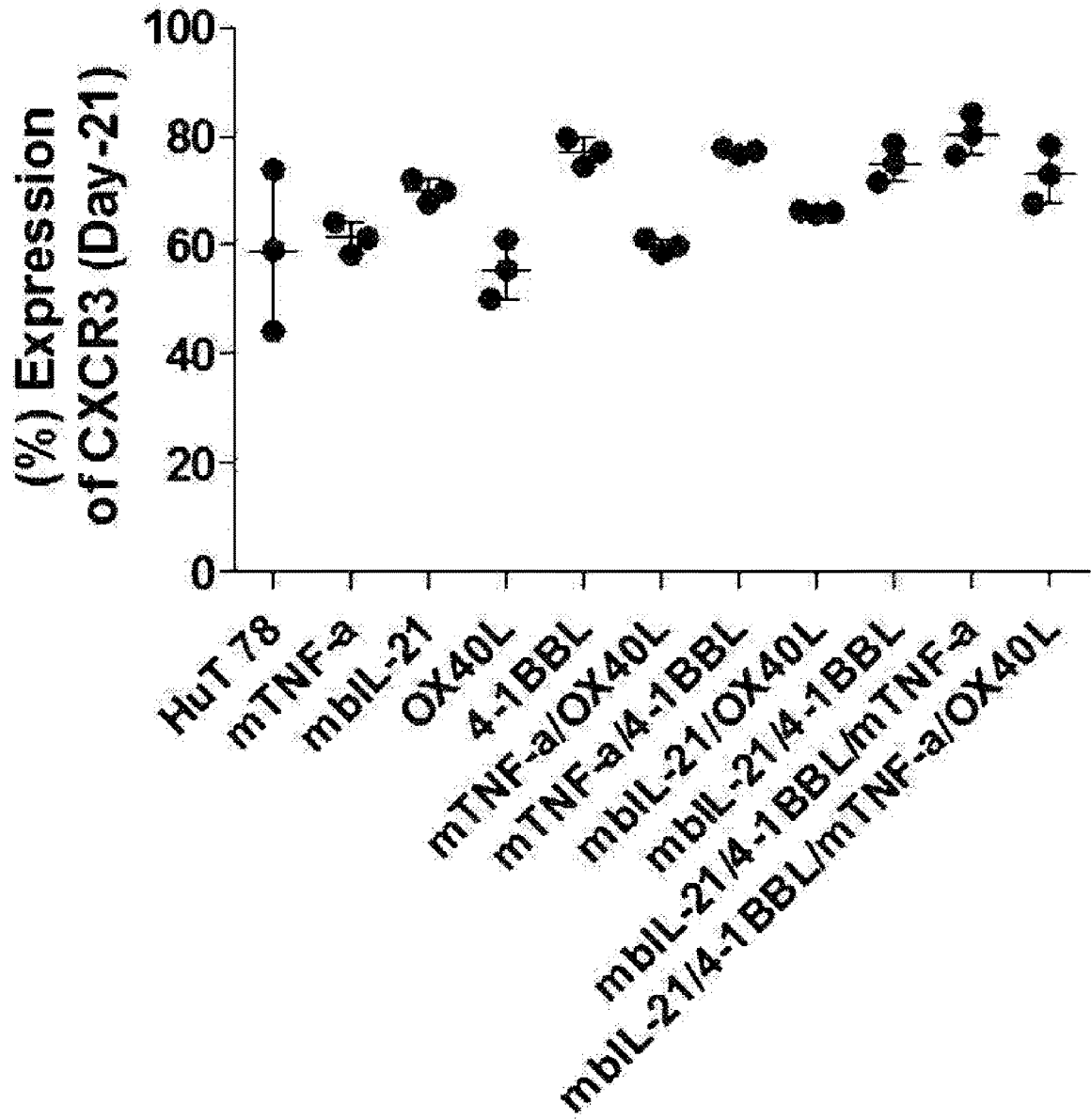

[Fig. 11j]
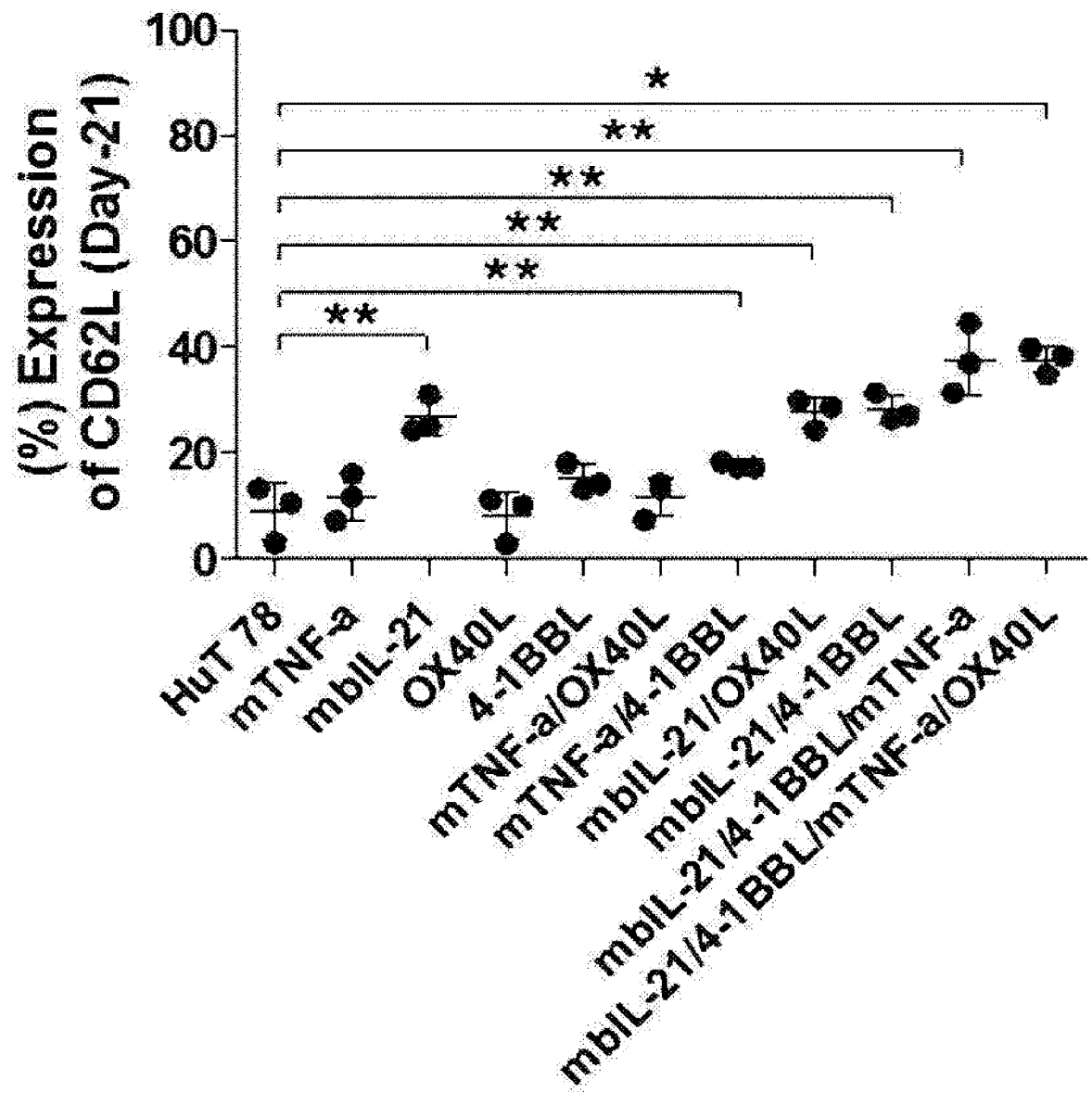

[Fig. 11k]
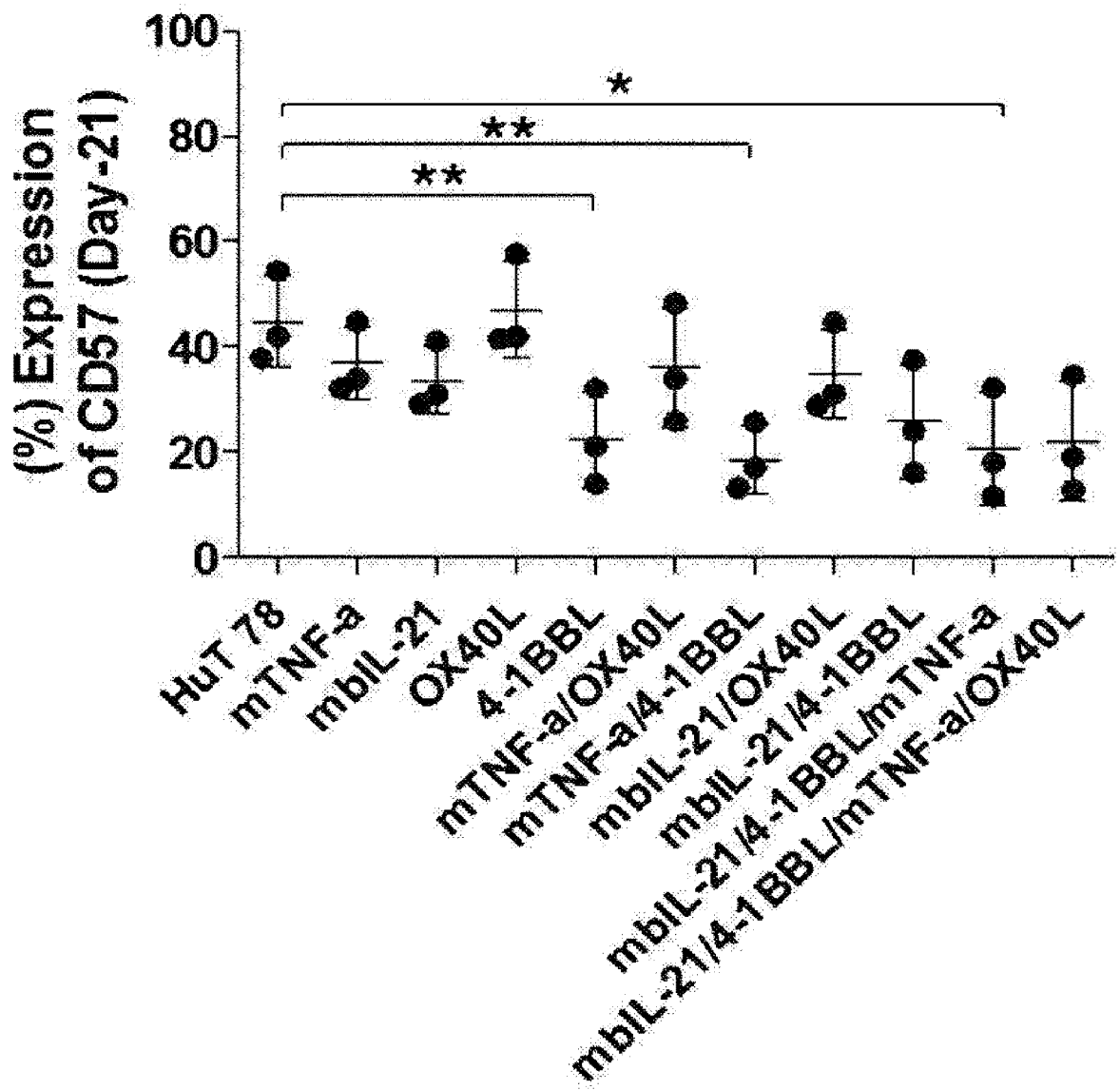

[Fig. 111]
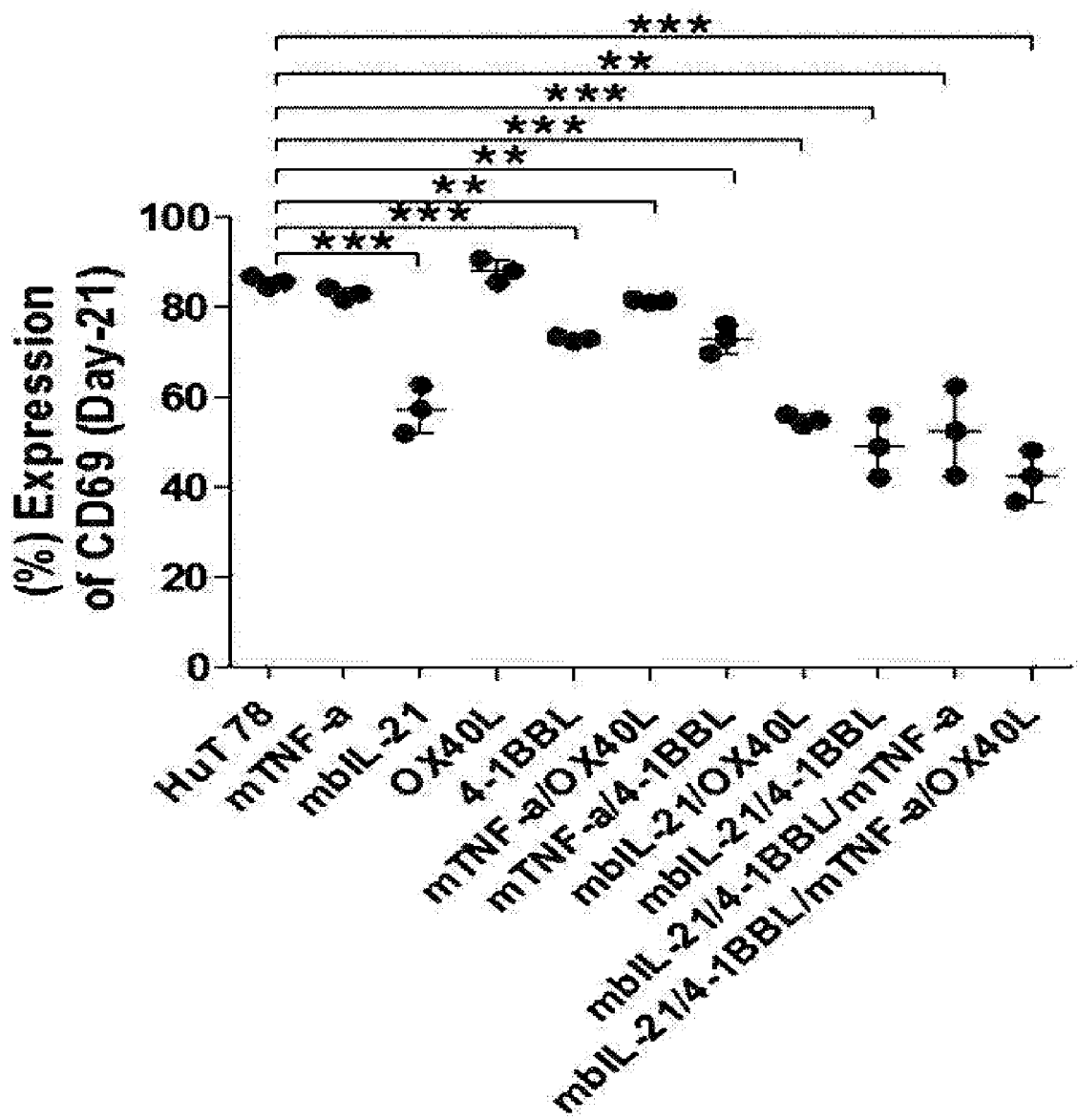

[Fig. 12a]
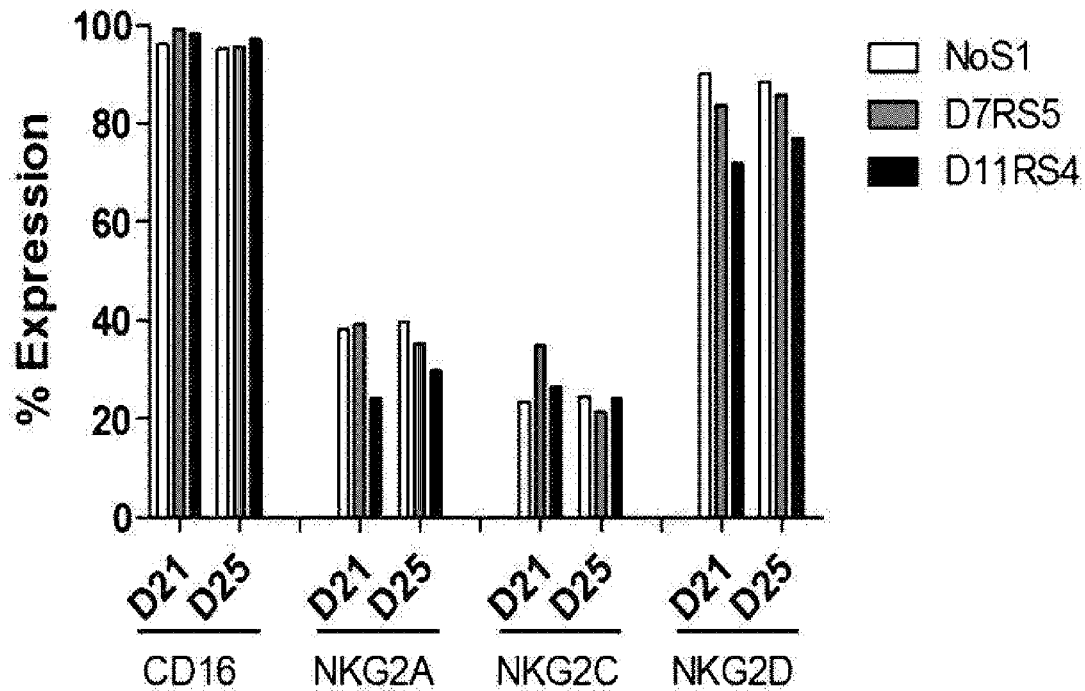
[Fig. 12b]
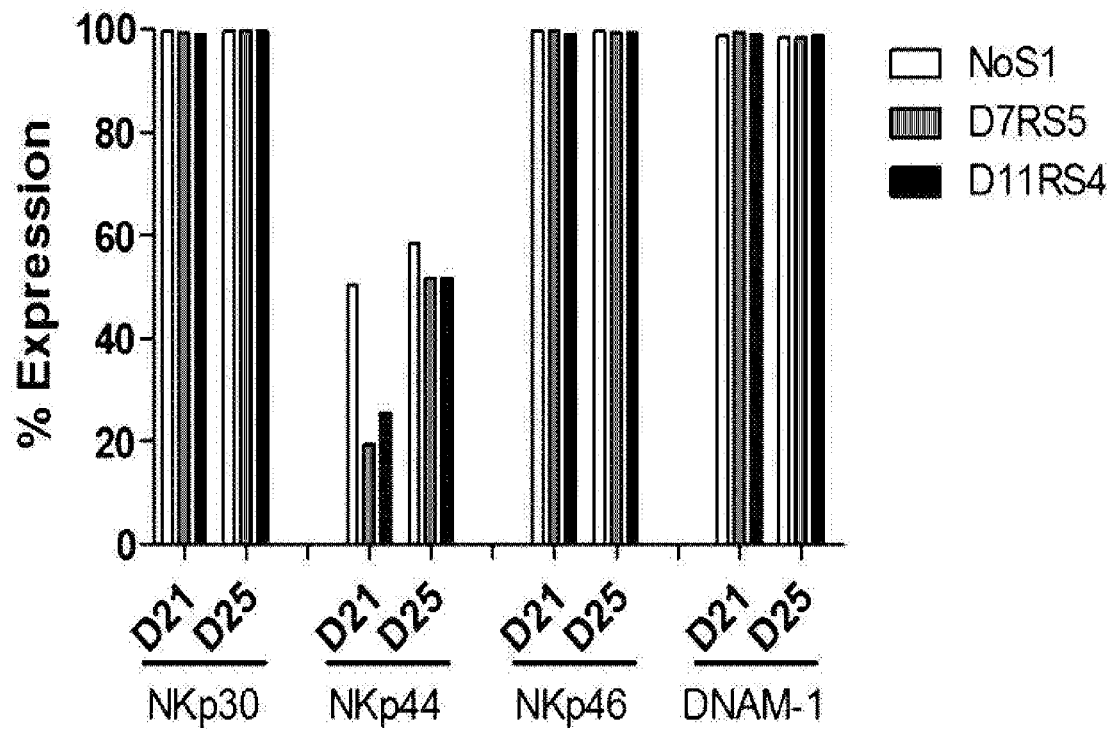

[Fig. 12c]
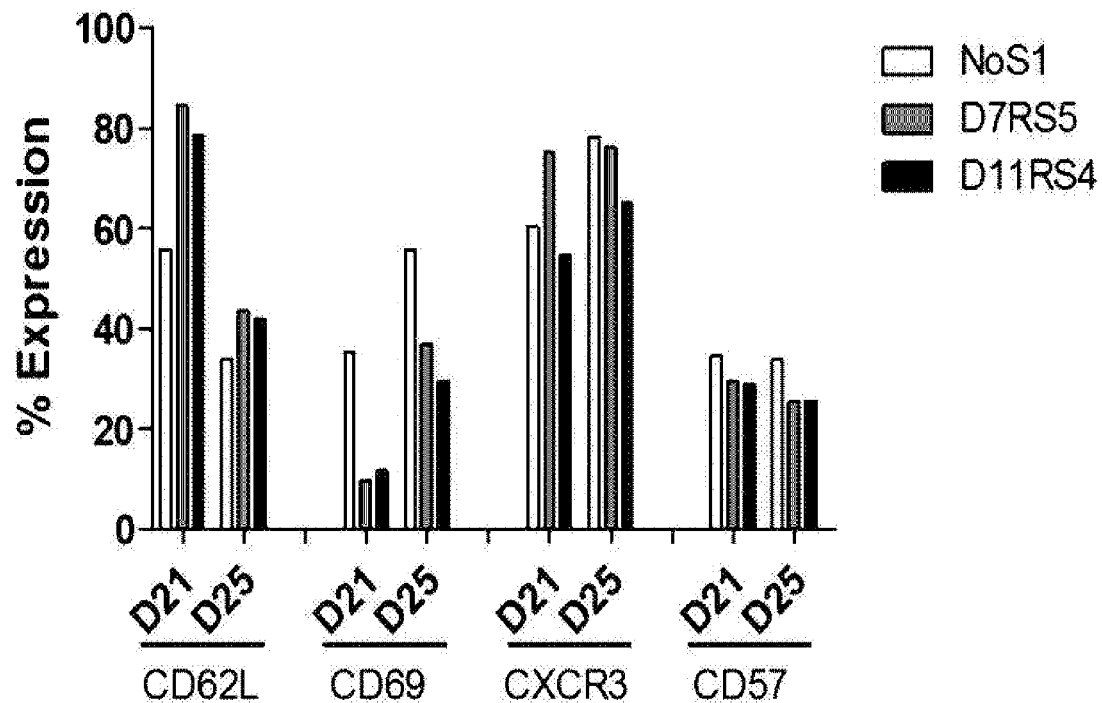
[Fig. 13a]
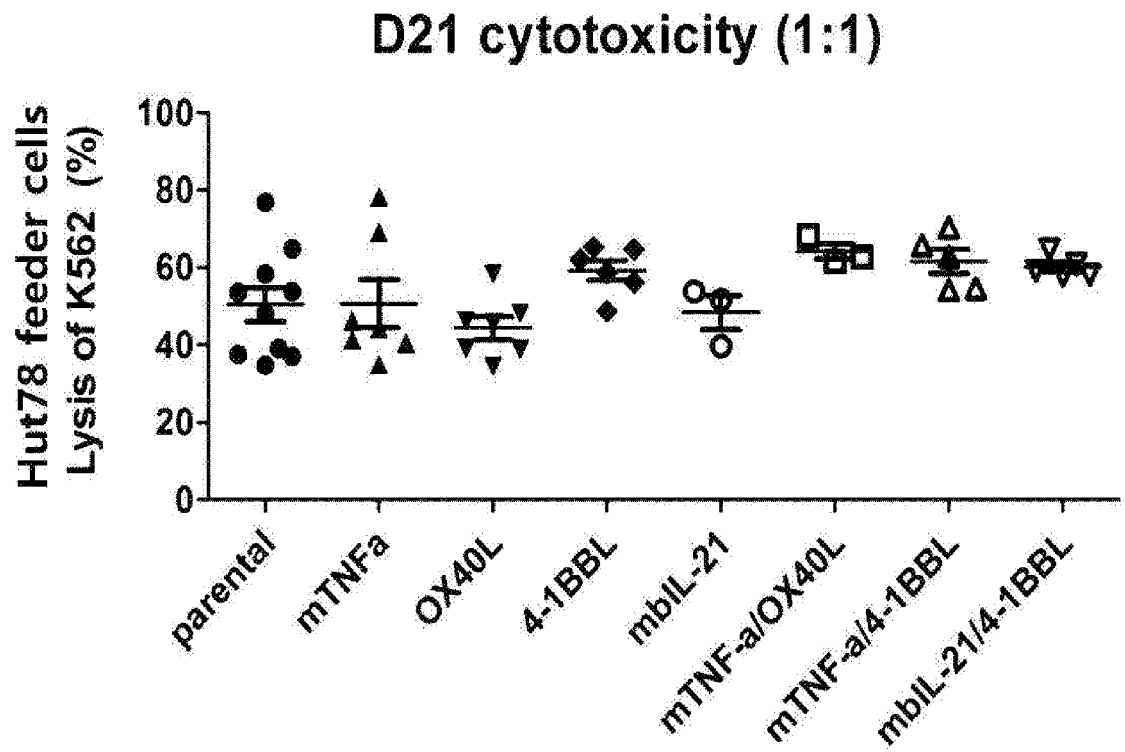

[Fig. 13b]
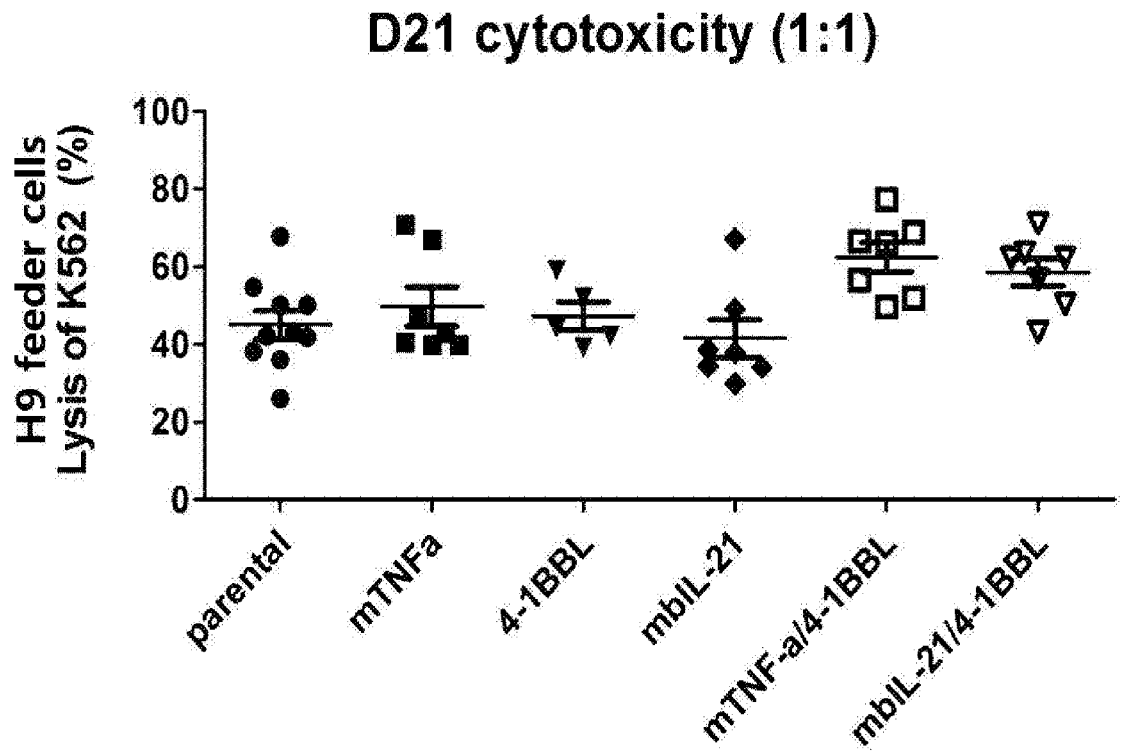
[Fig. 13c]
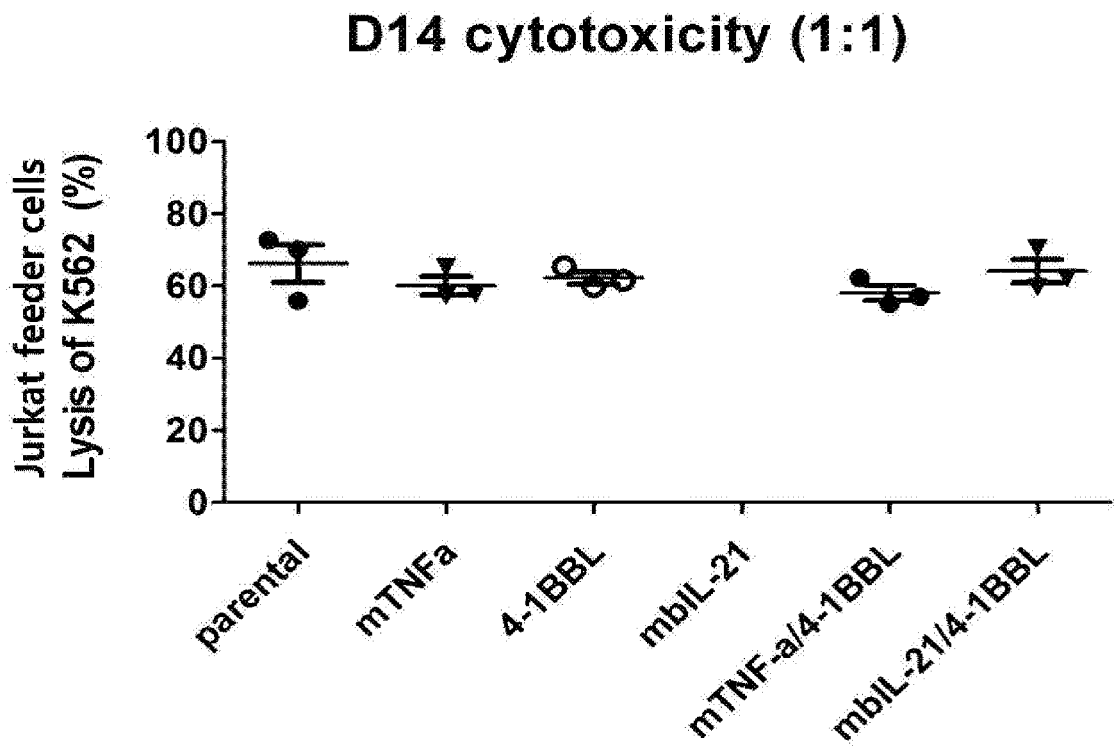

[Fig. 14a]
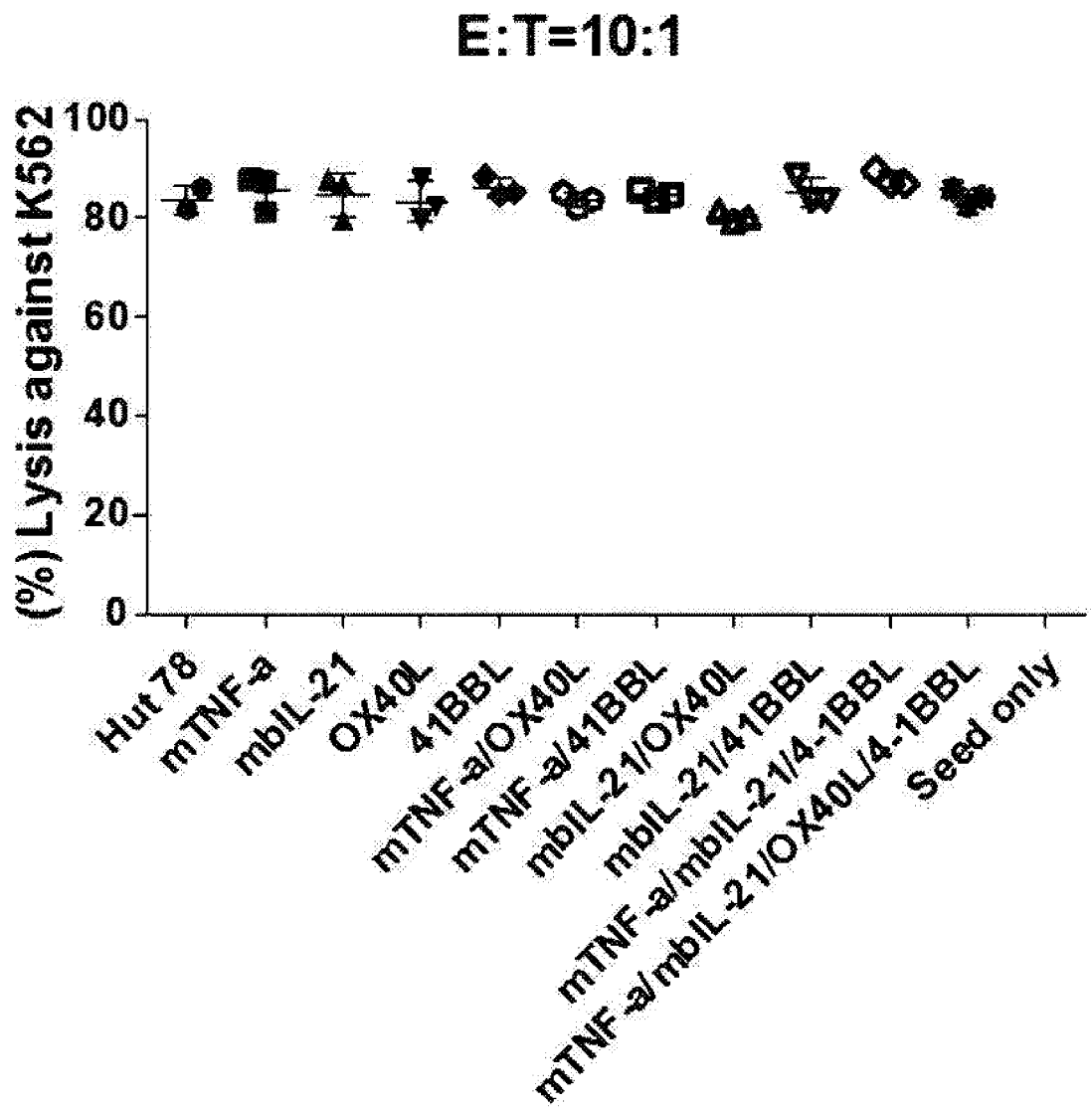

[Fig. 14b]
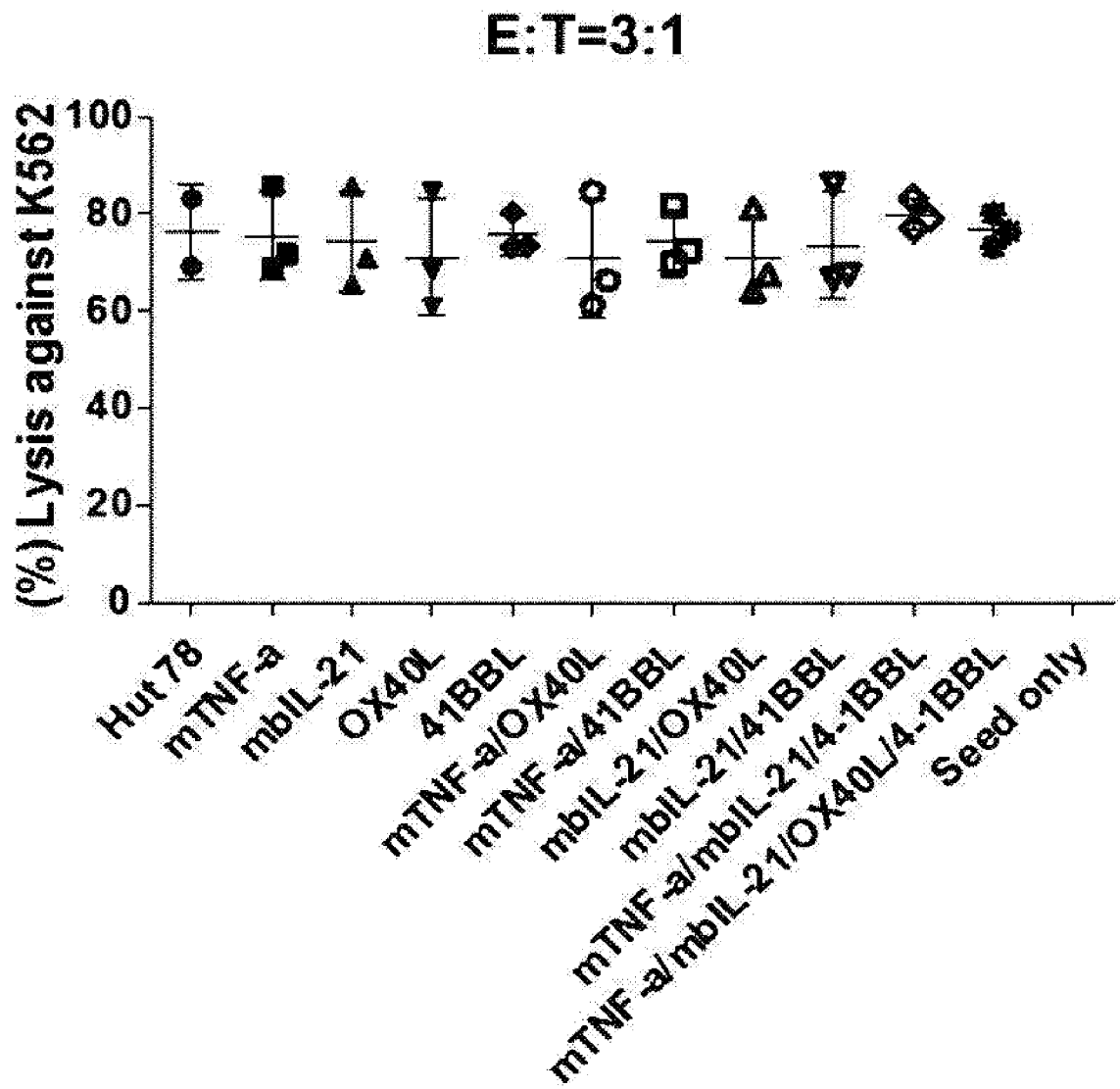

[Fig. 14c]
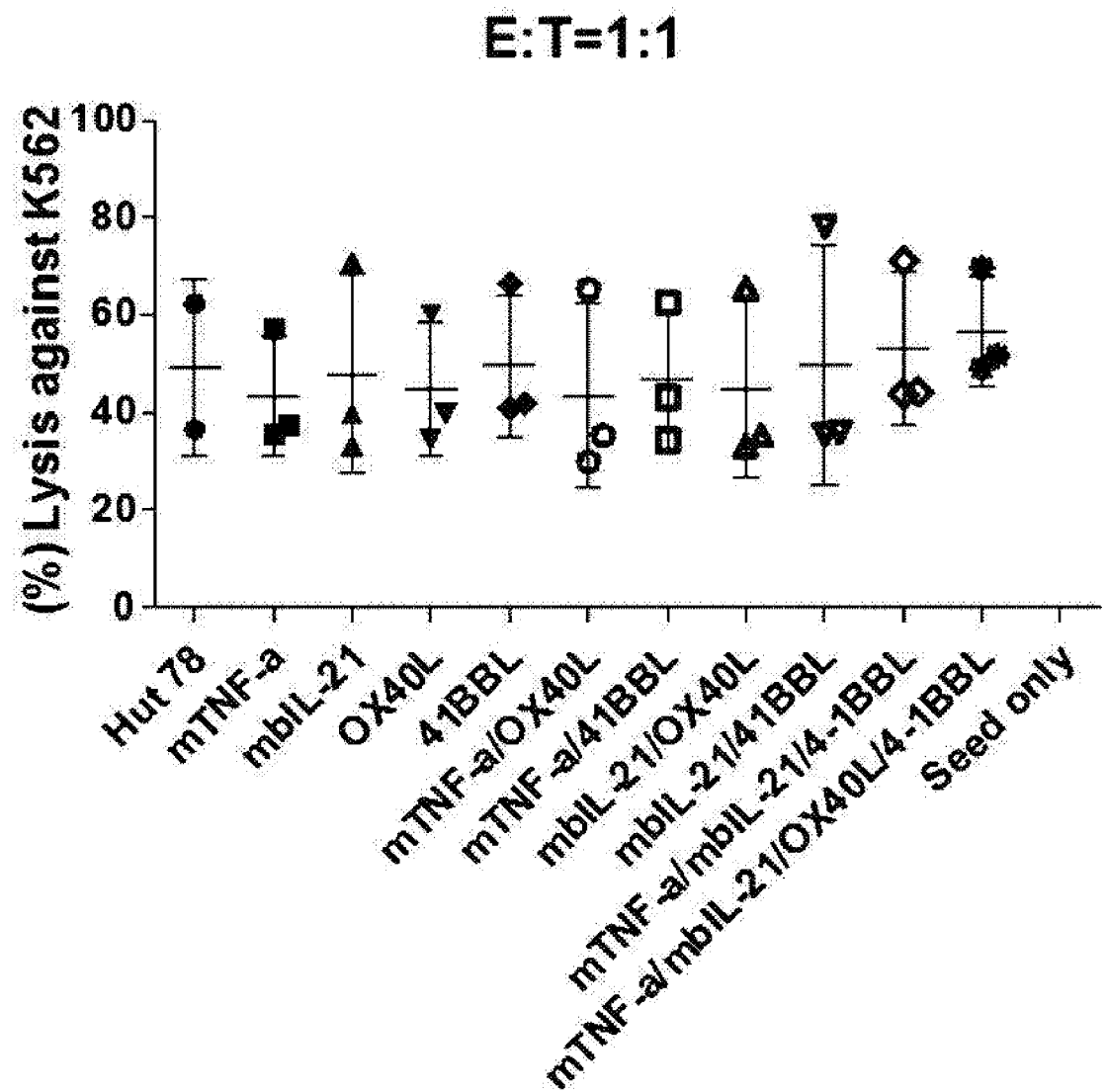

[Fig. 14d]
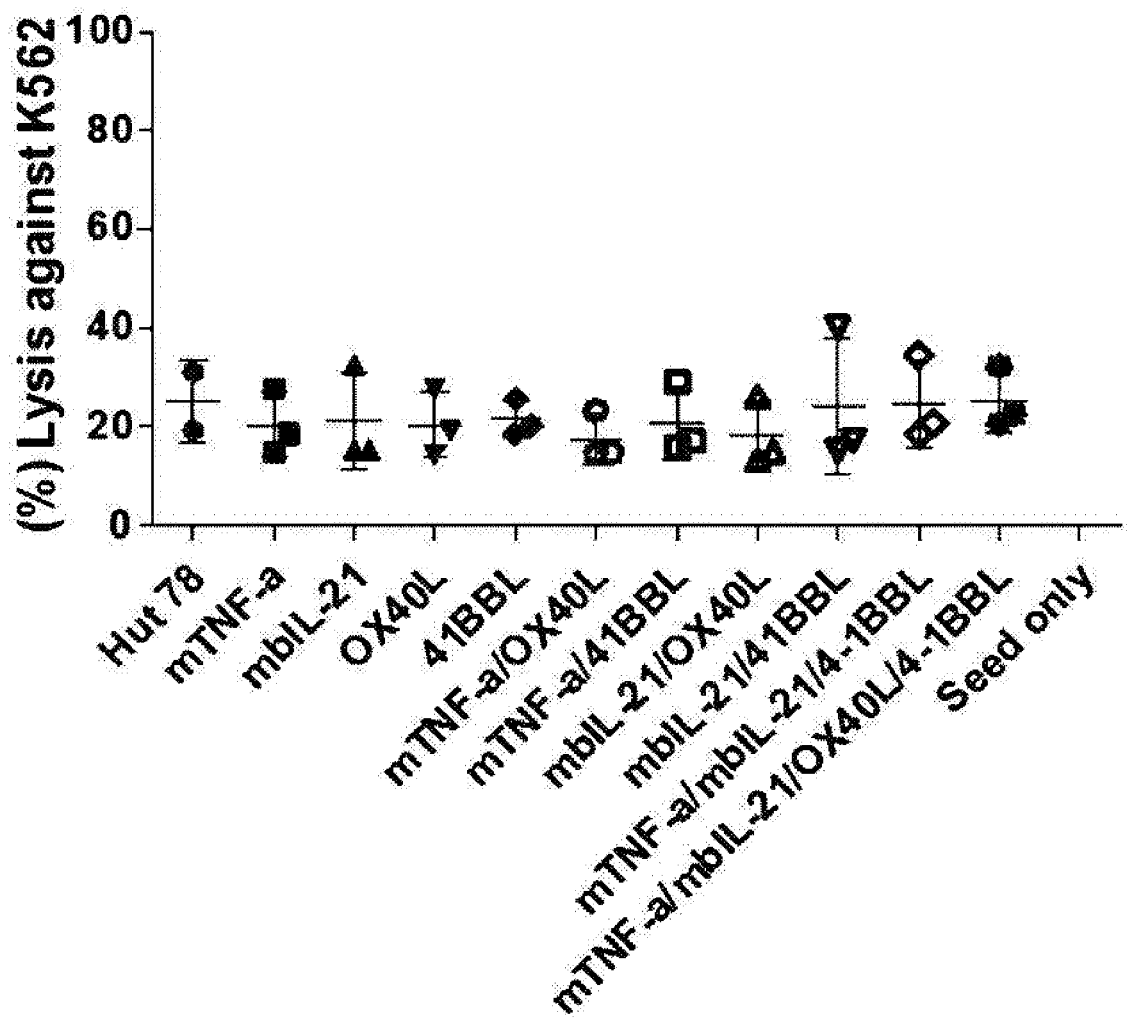

[Fig. 15a]
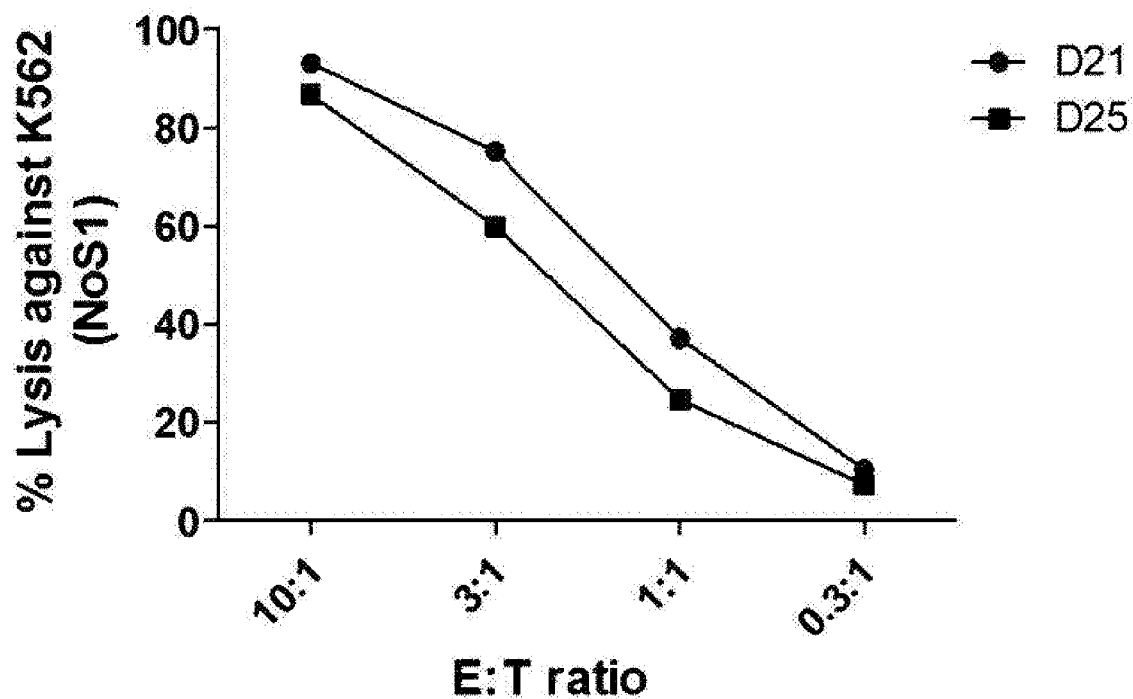
[Fig. 15b]
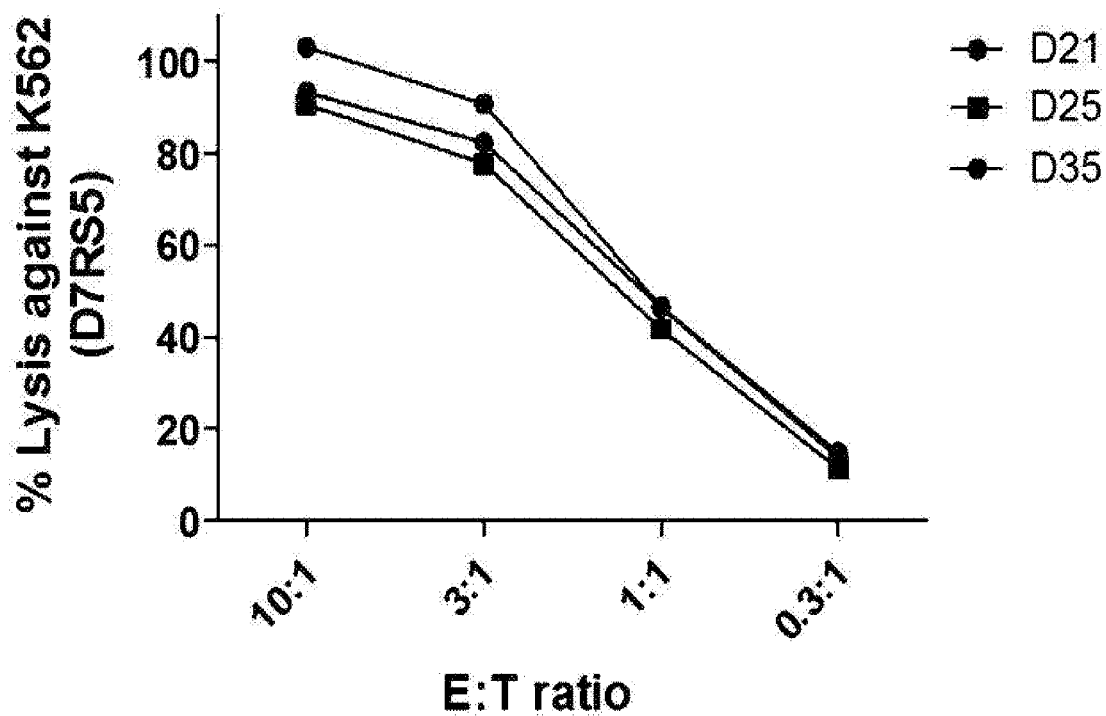

[Fig. 15c]
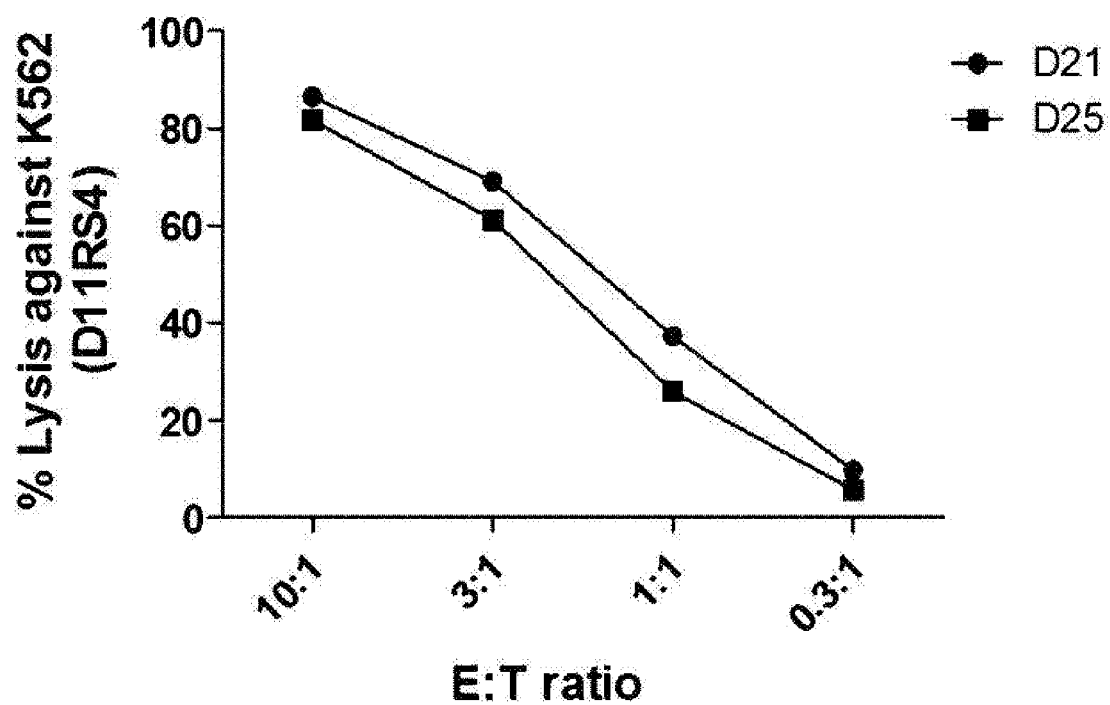

[Fig. 16a]
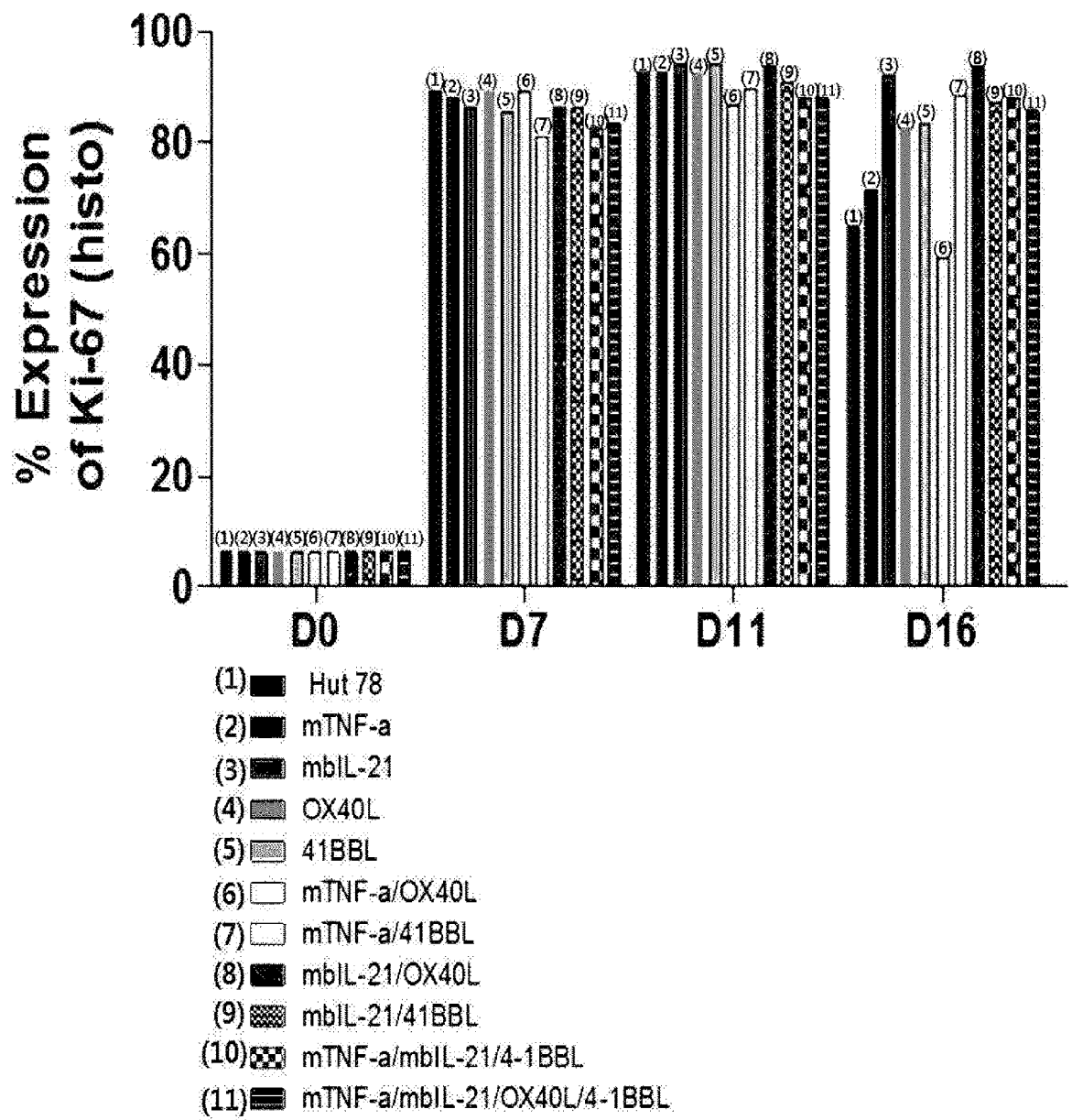

[Fig. 16b]
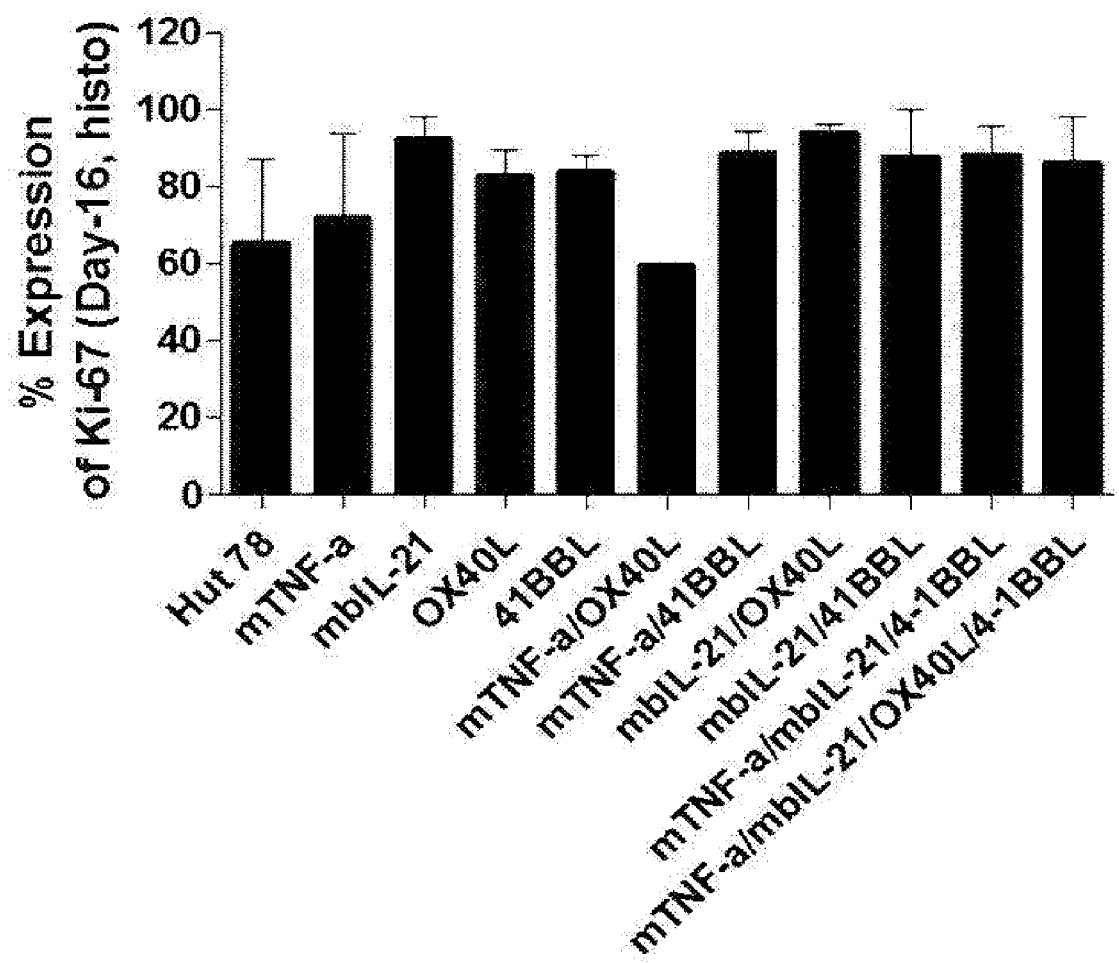

[Fig. 16c]
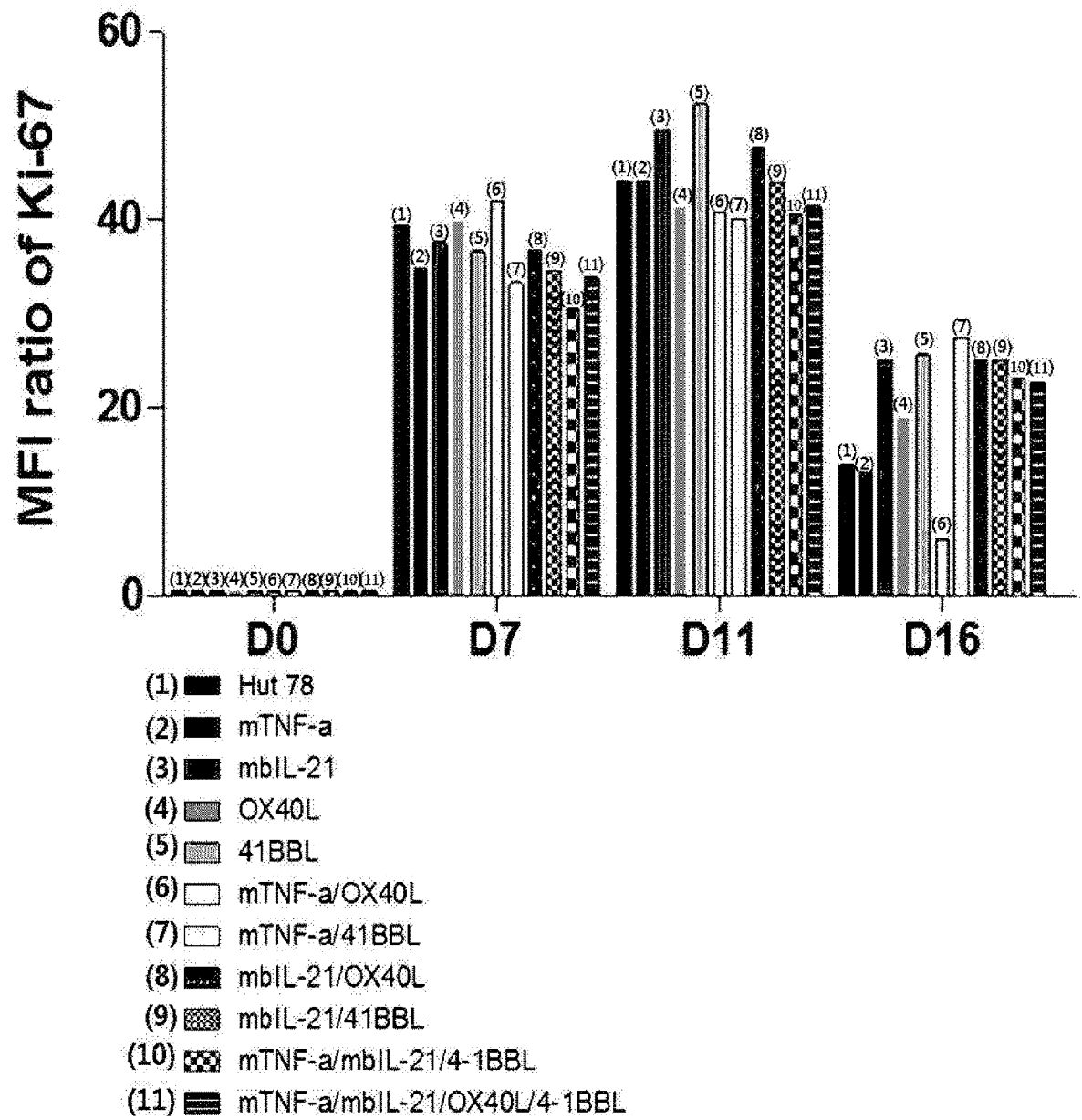

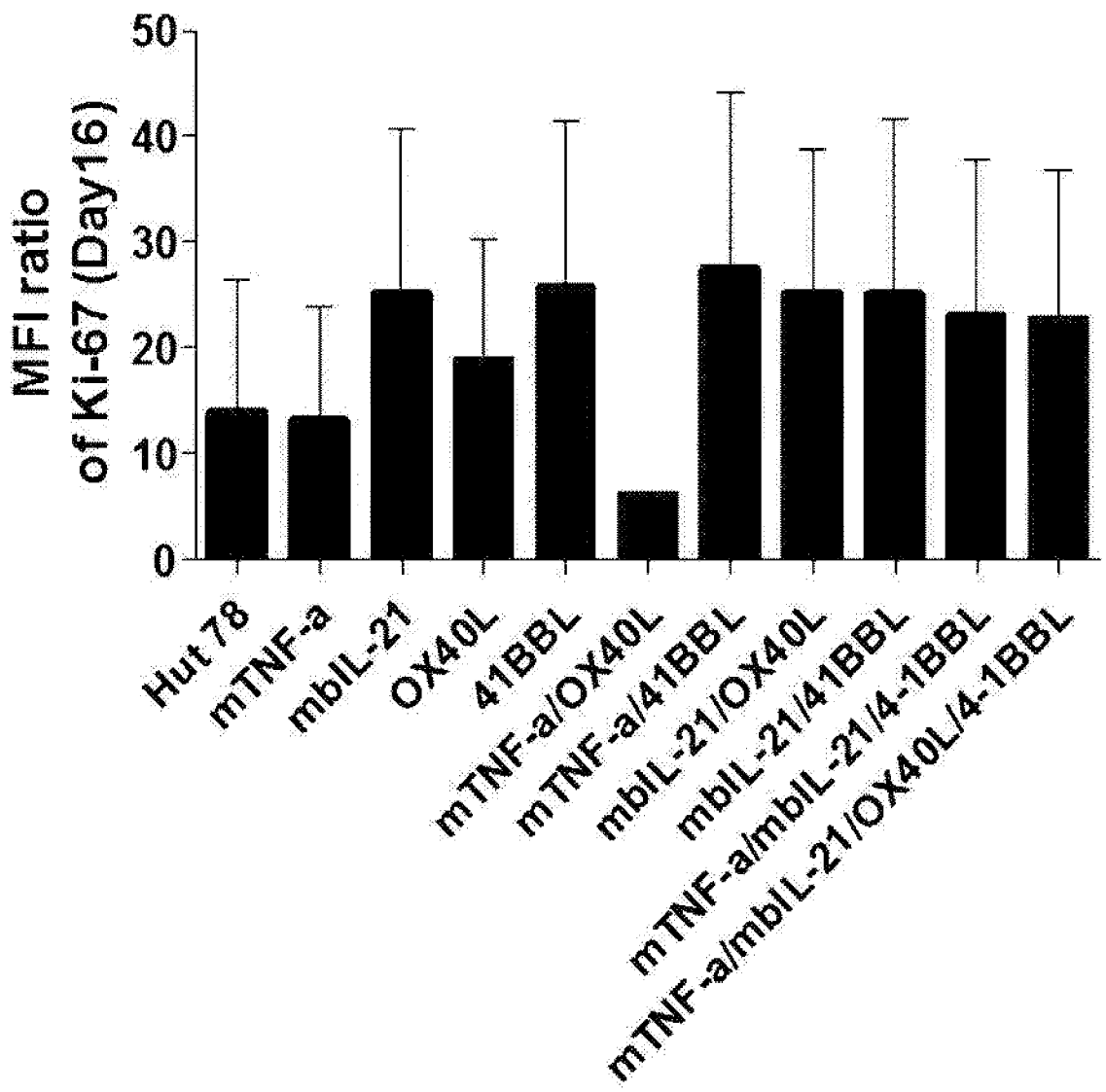
[Fig. 16d]

[Fig. 17a]
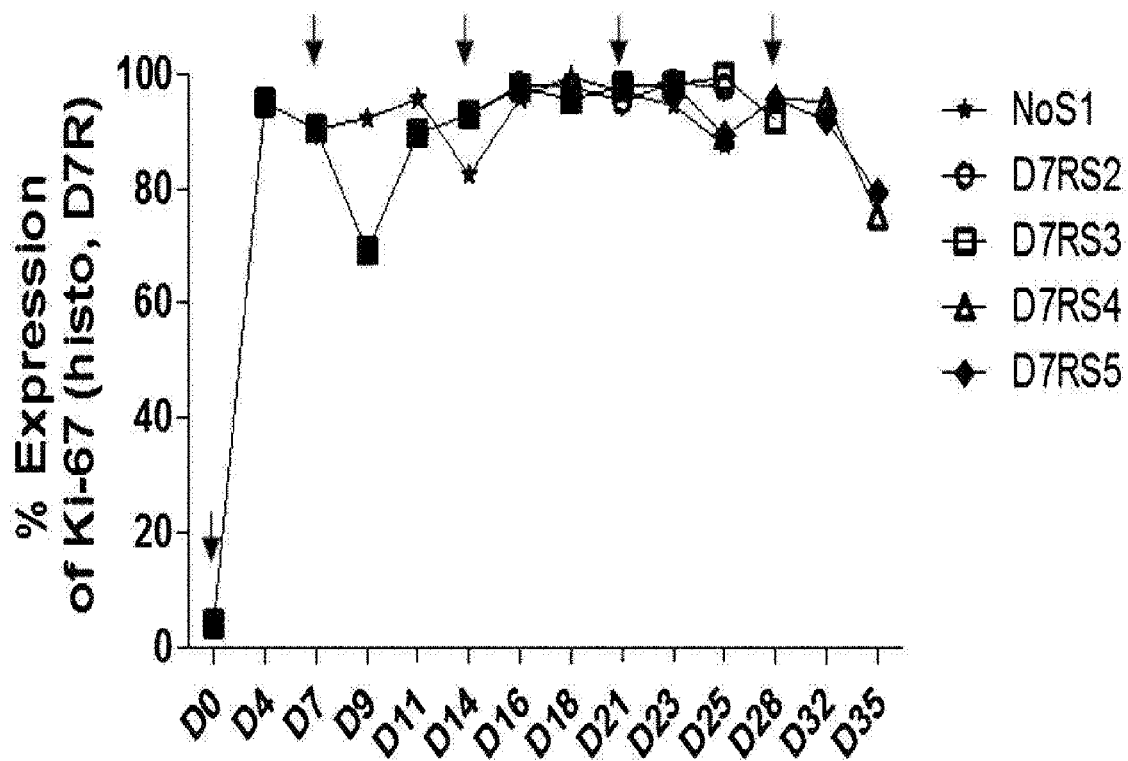
[Fig. 17b]
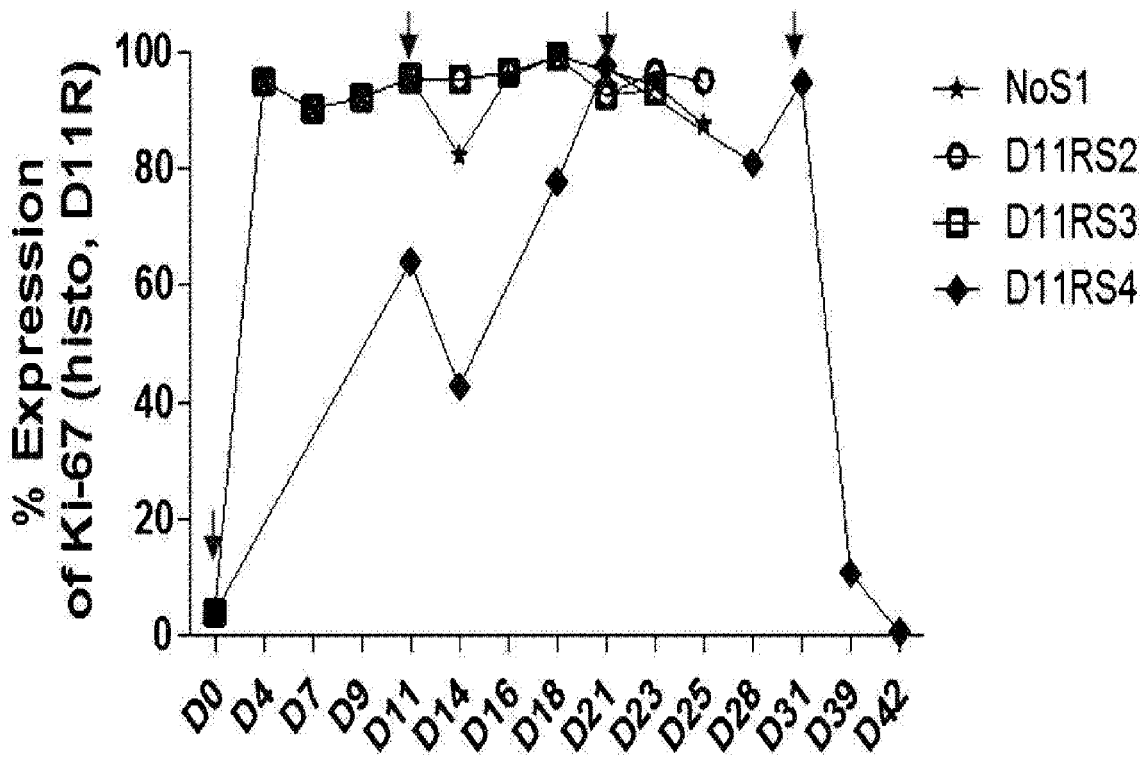

[Fig. 17c]
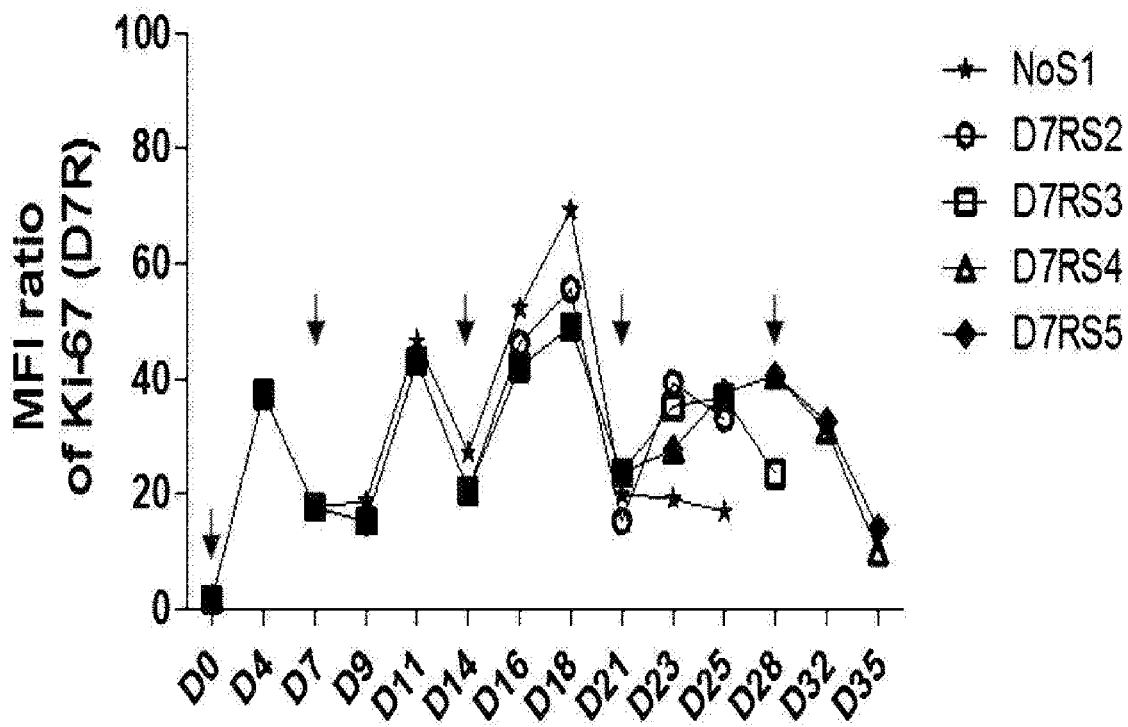
[Fig. 17d]
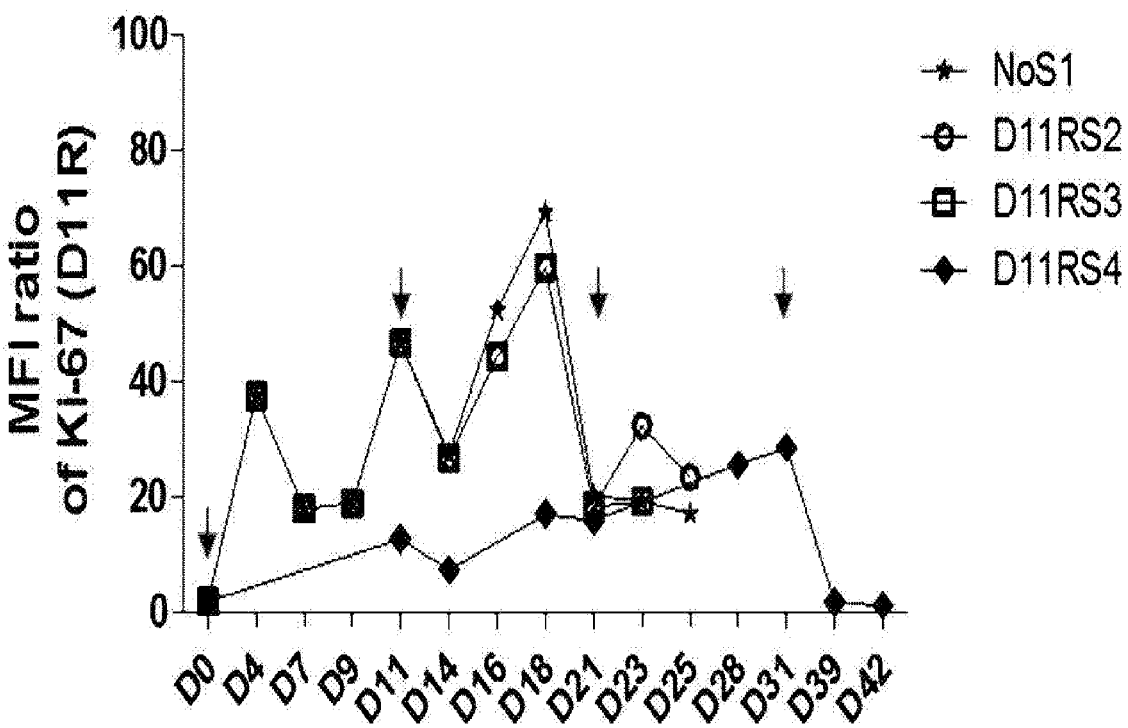

[Fig. 18a]
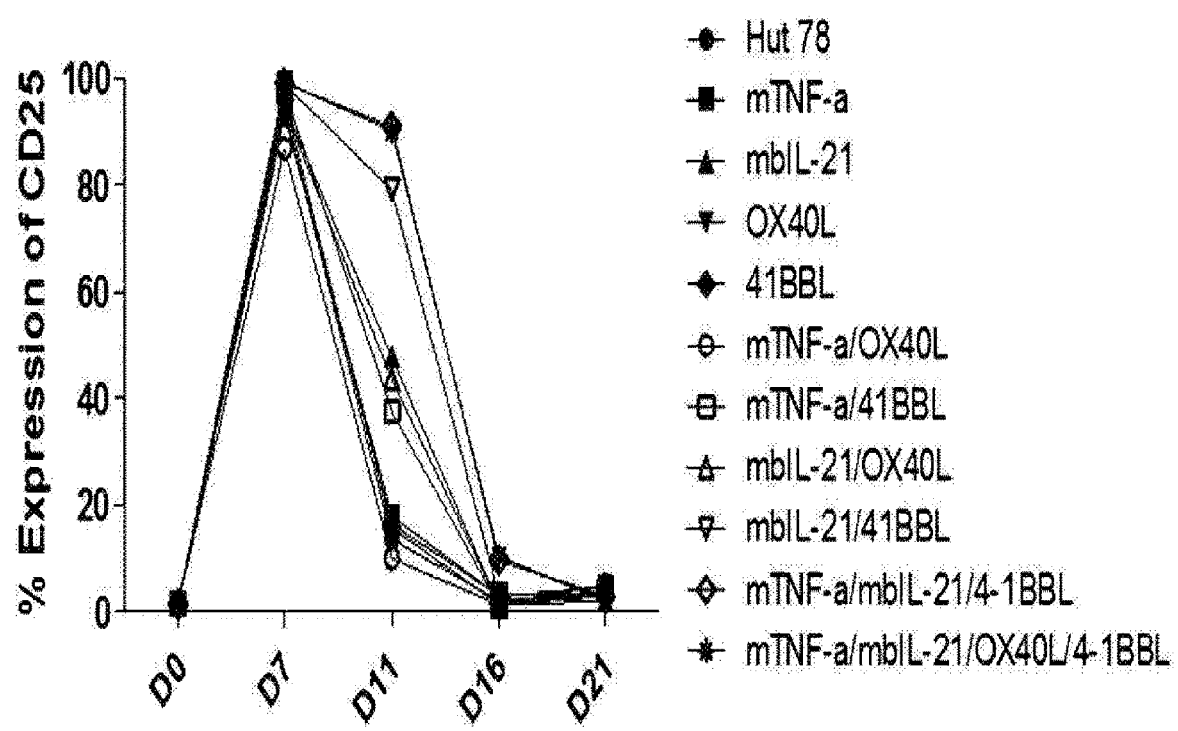

[Fig. 18b]
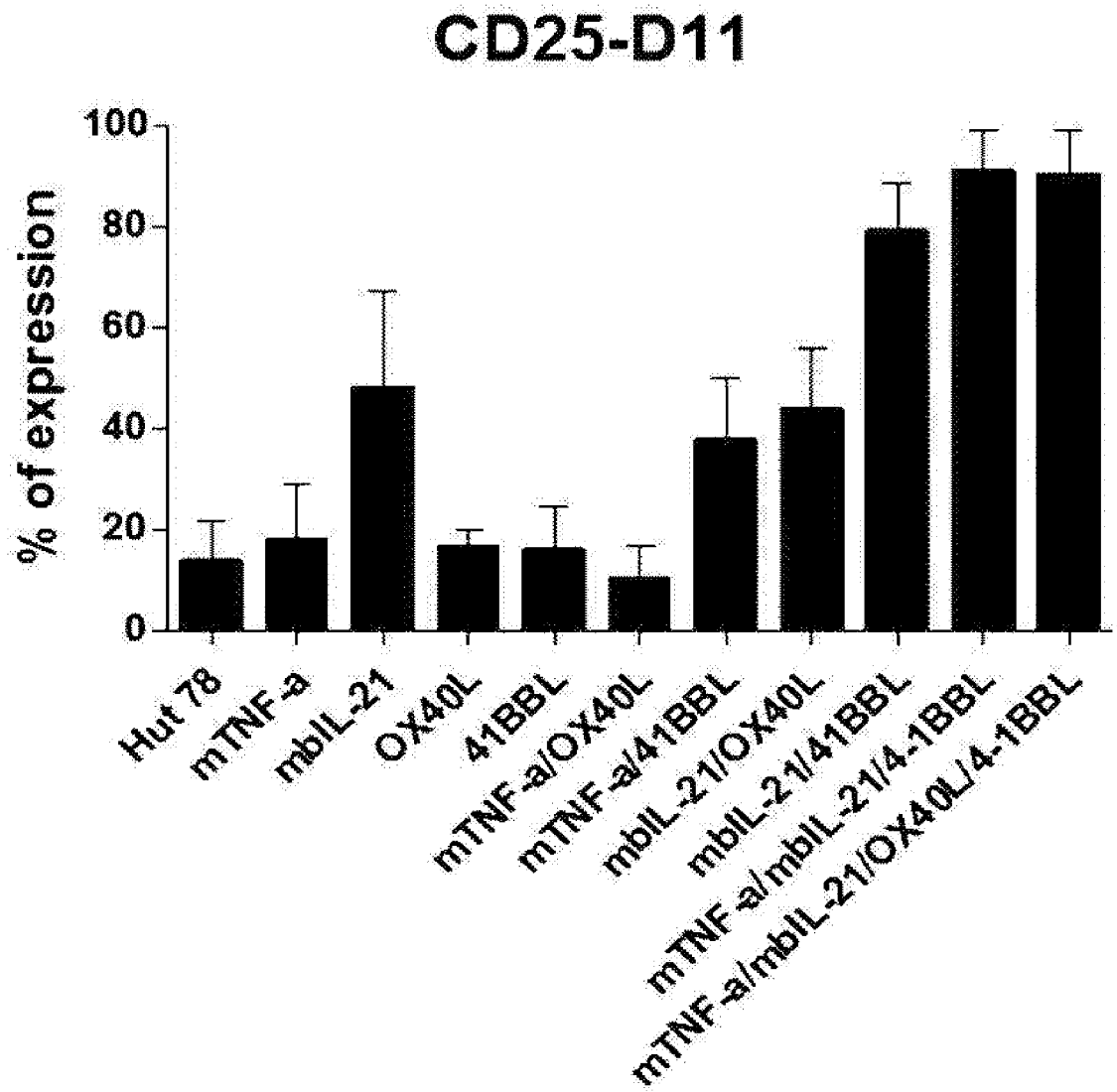

[Fig. 18c]
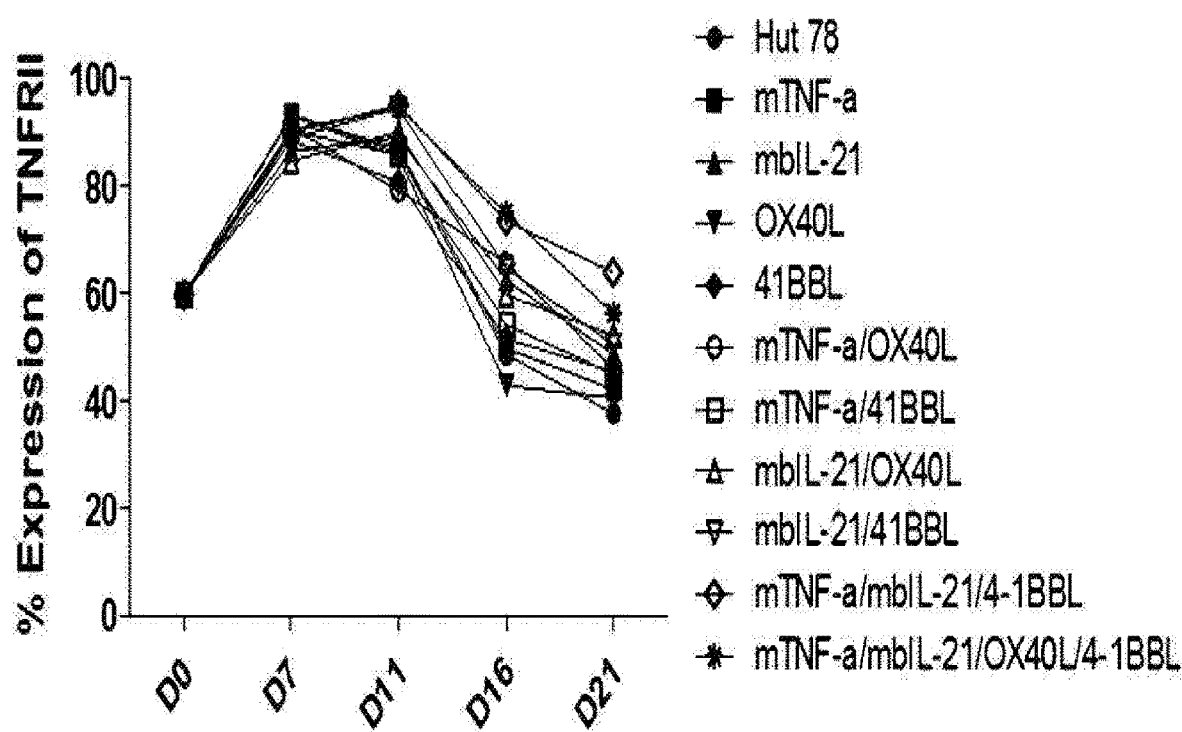

[Fig. 18d]
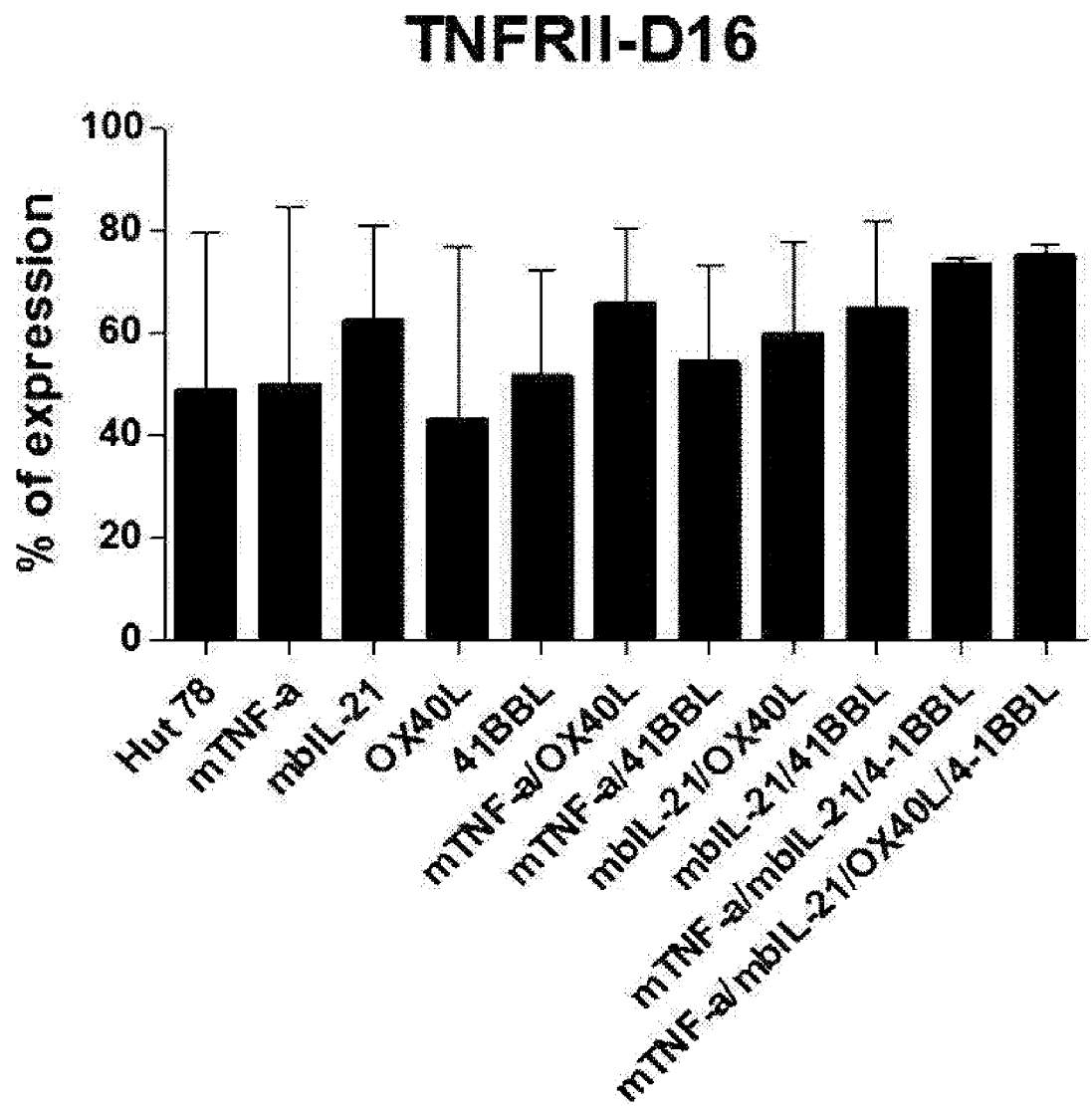

[Fig. 18e]
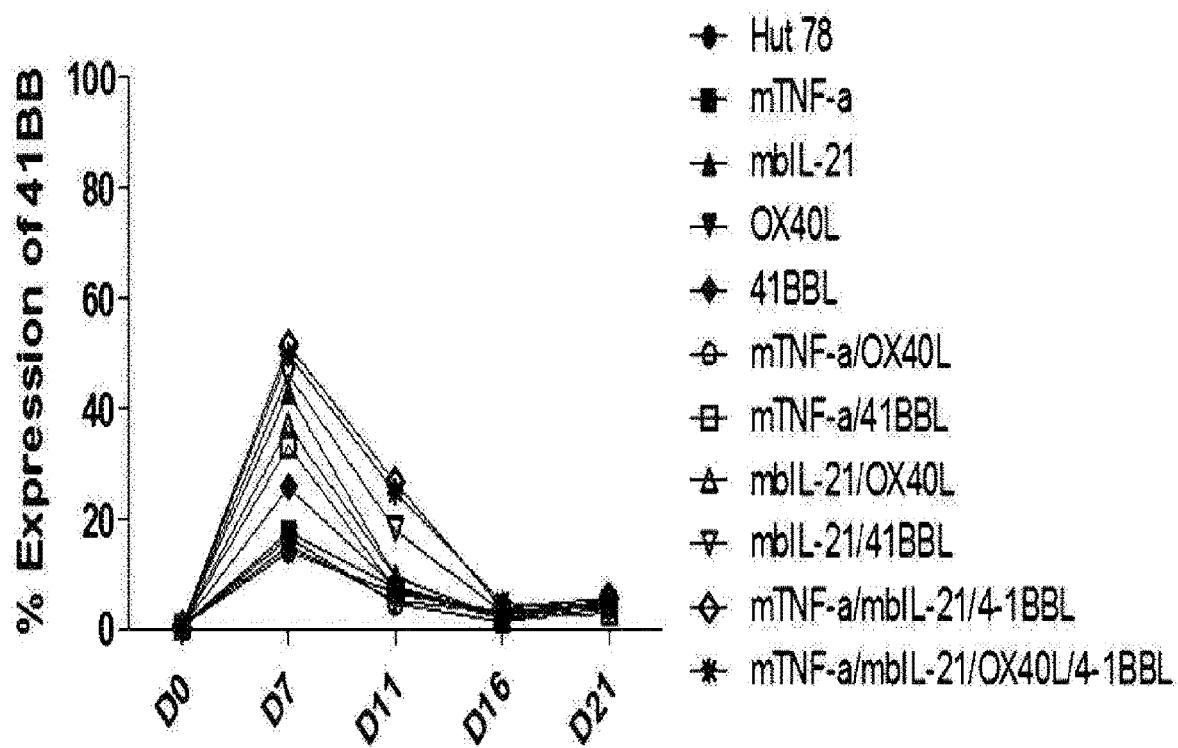

[Fig. 18f]
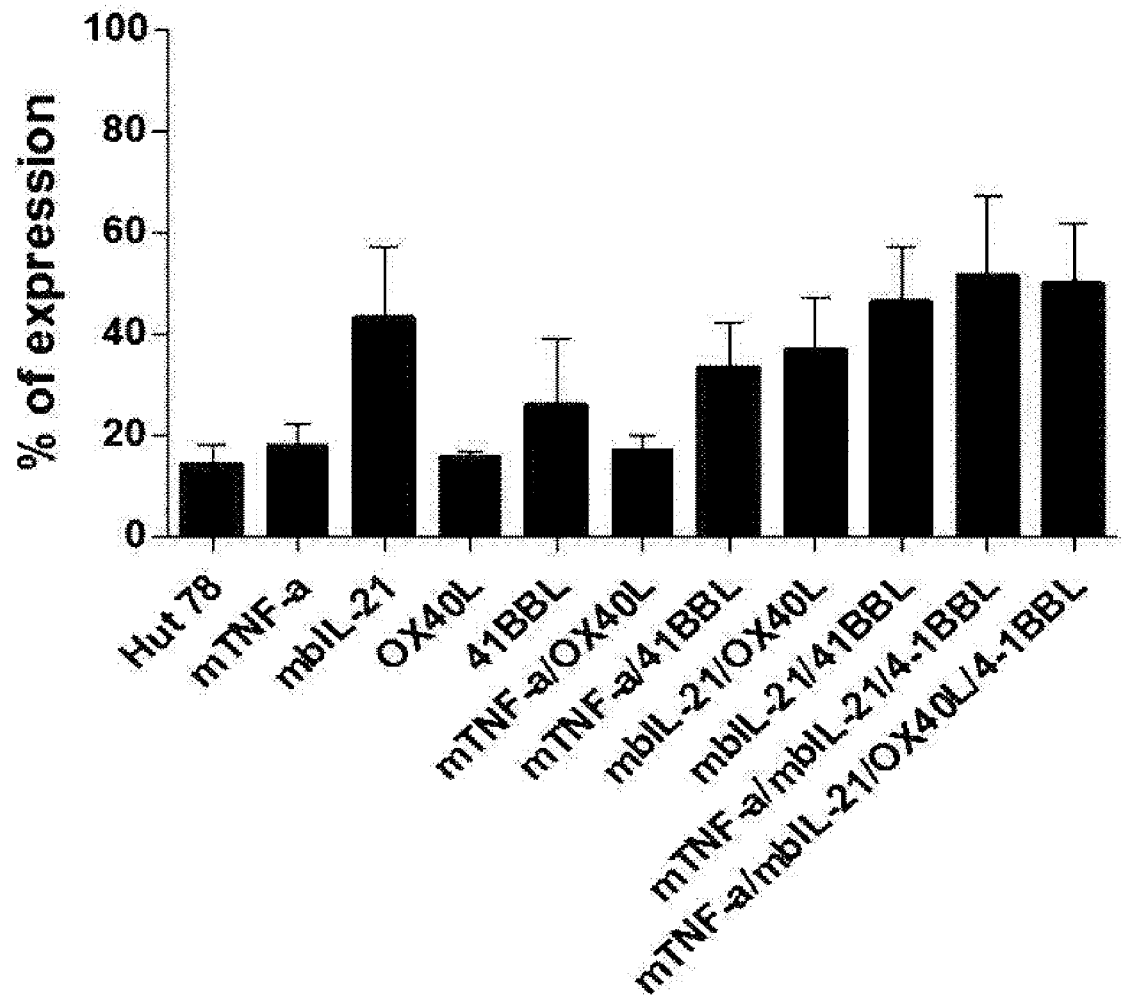

[Fig. 19a]
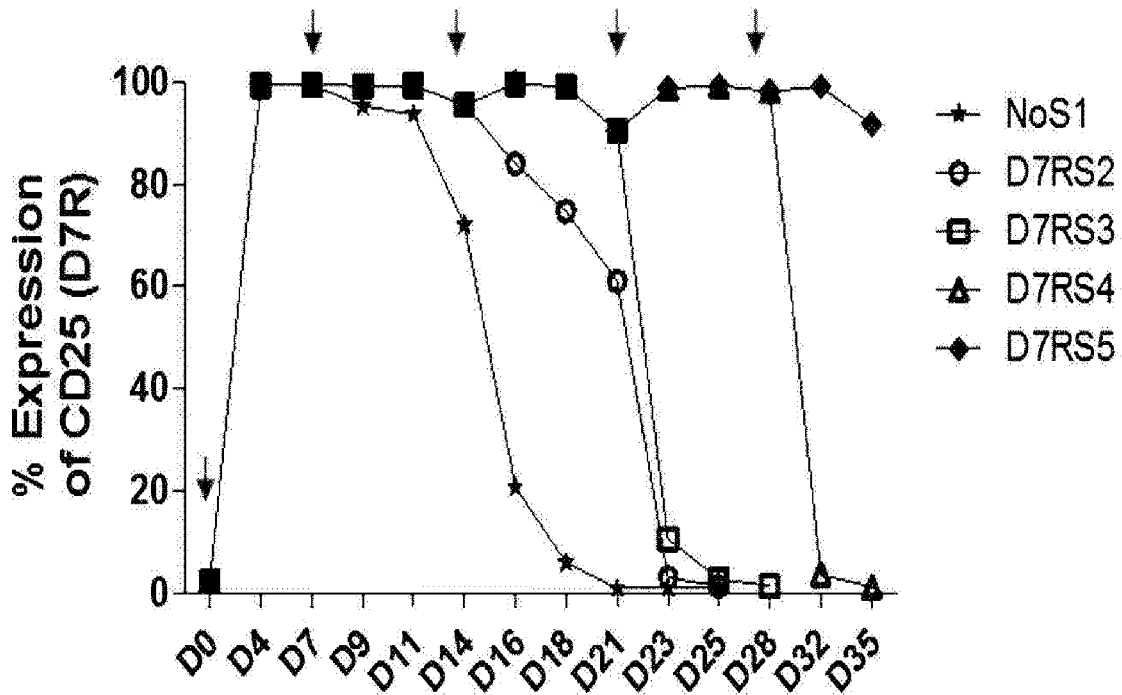
[Fig. 19b]
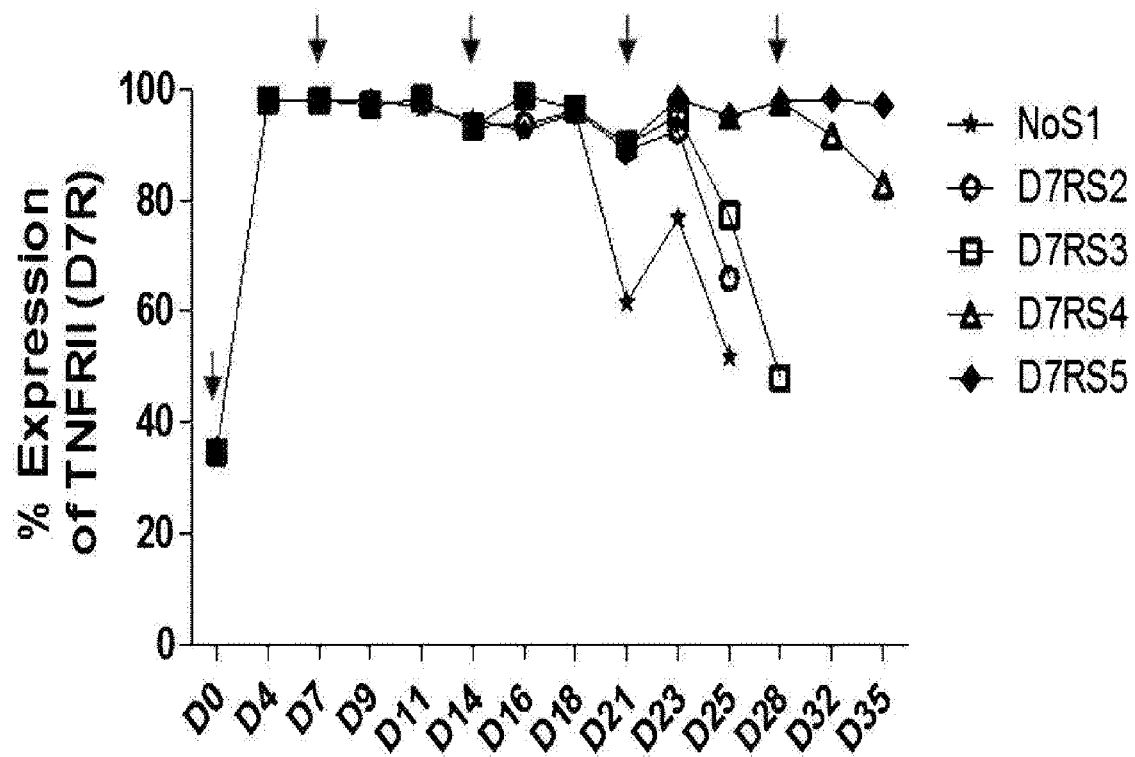

[Fig. 19c]
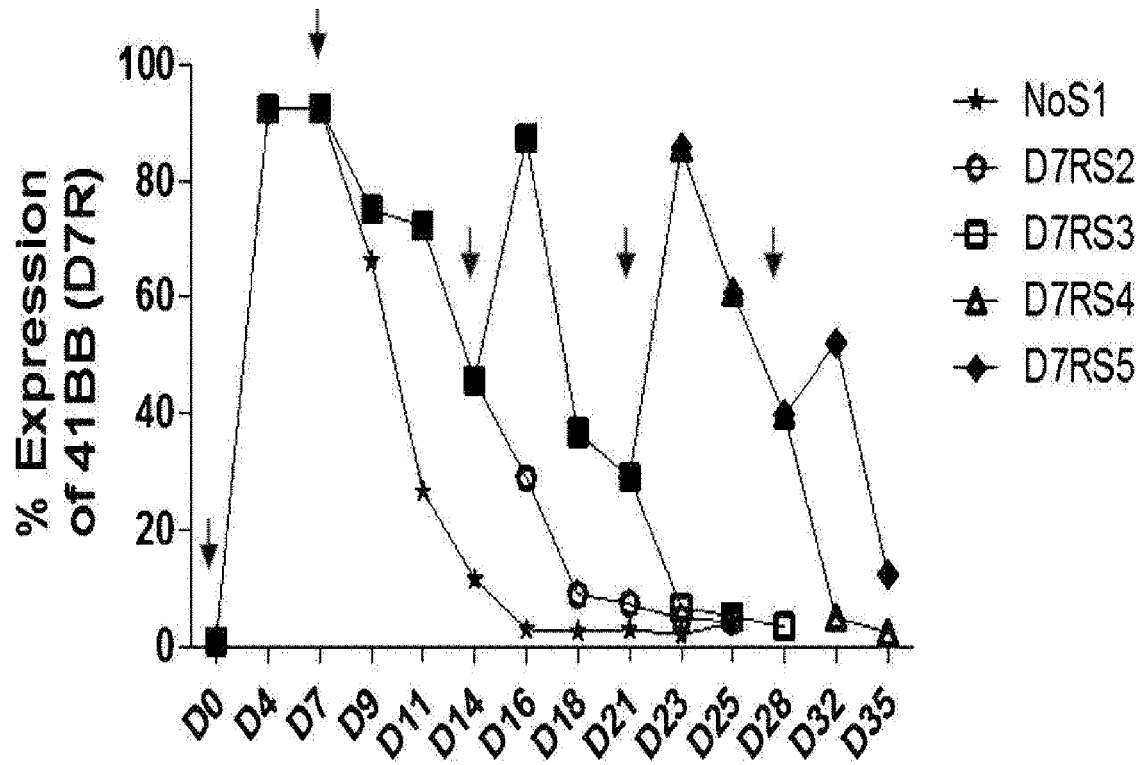
[Fig. 19d]
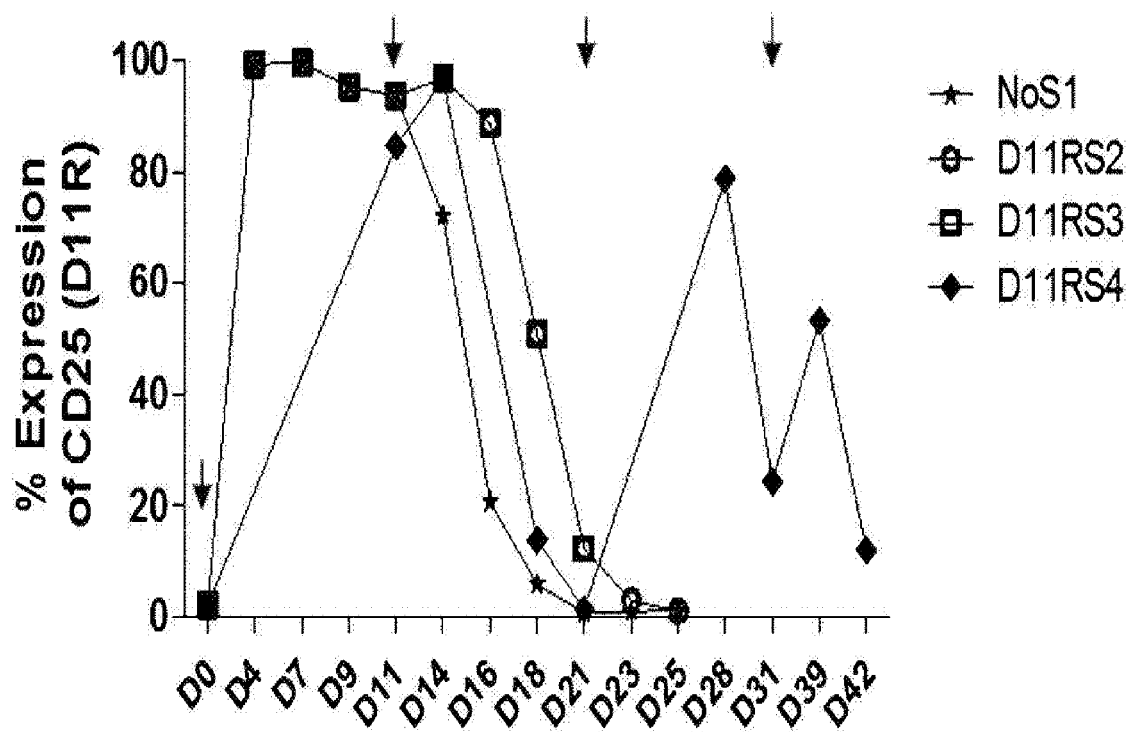

[Fig. 19e]
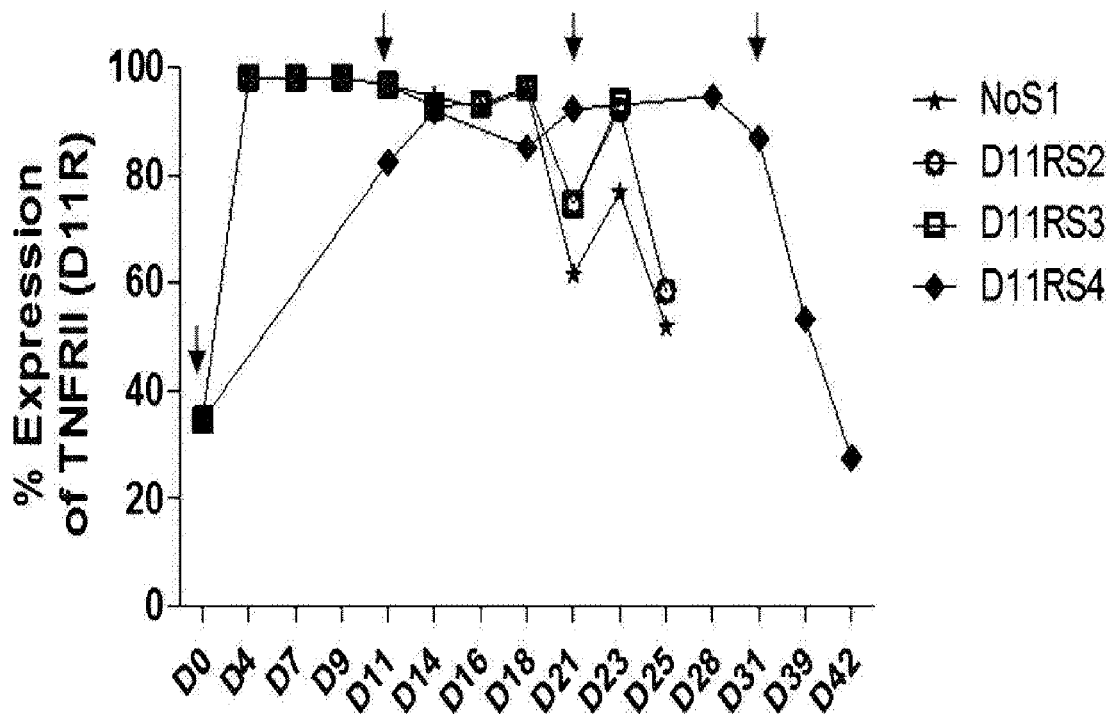
[Fig. 19f]
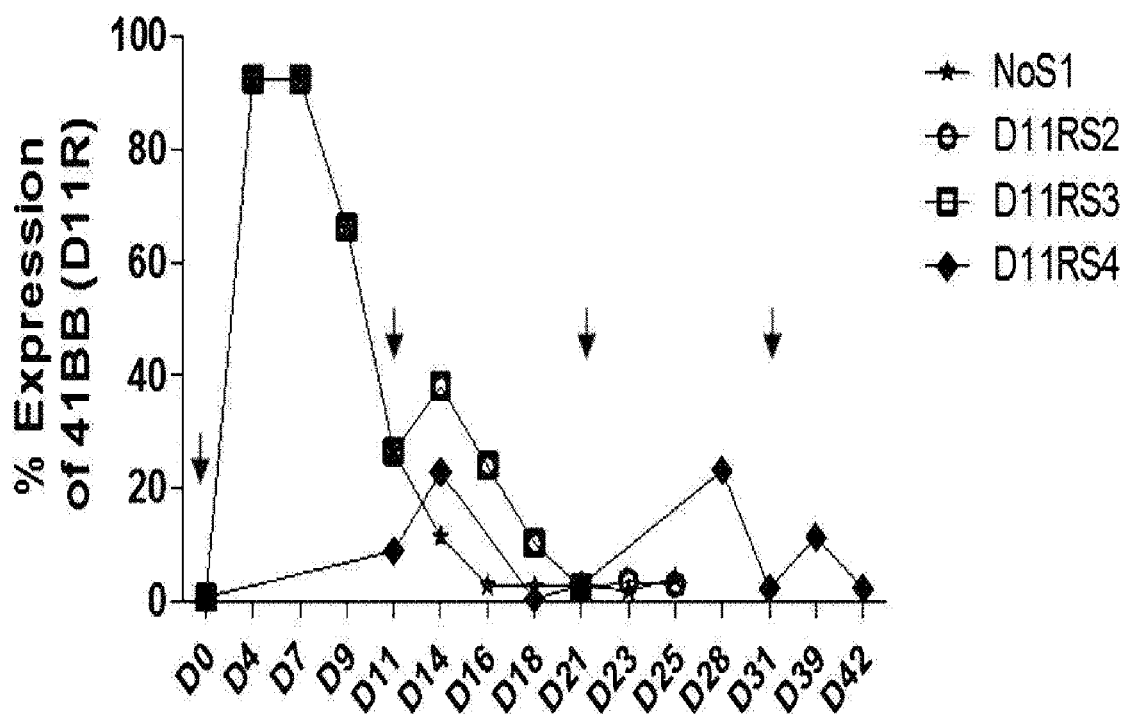

[Fig. 20a]
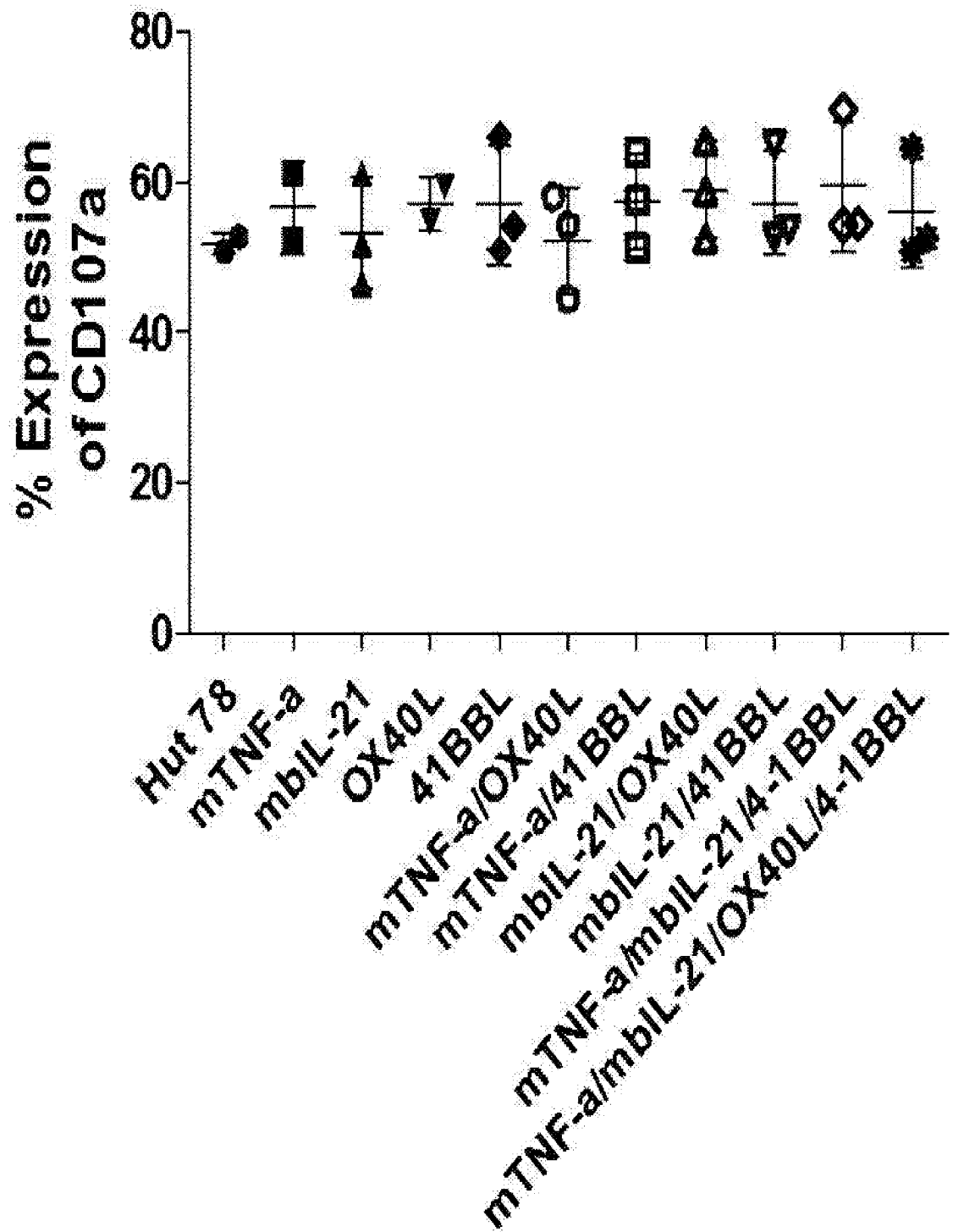

[Fig. 20b]
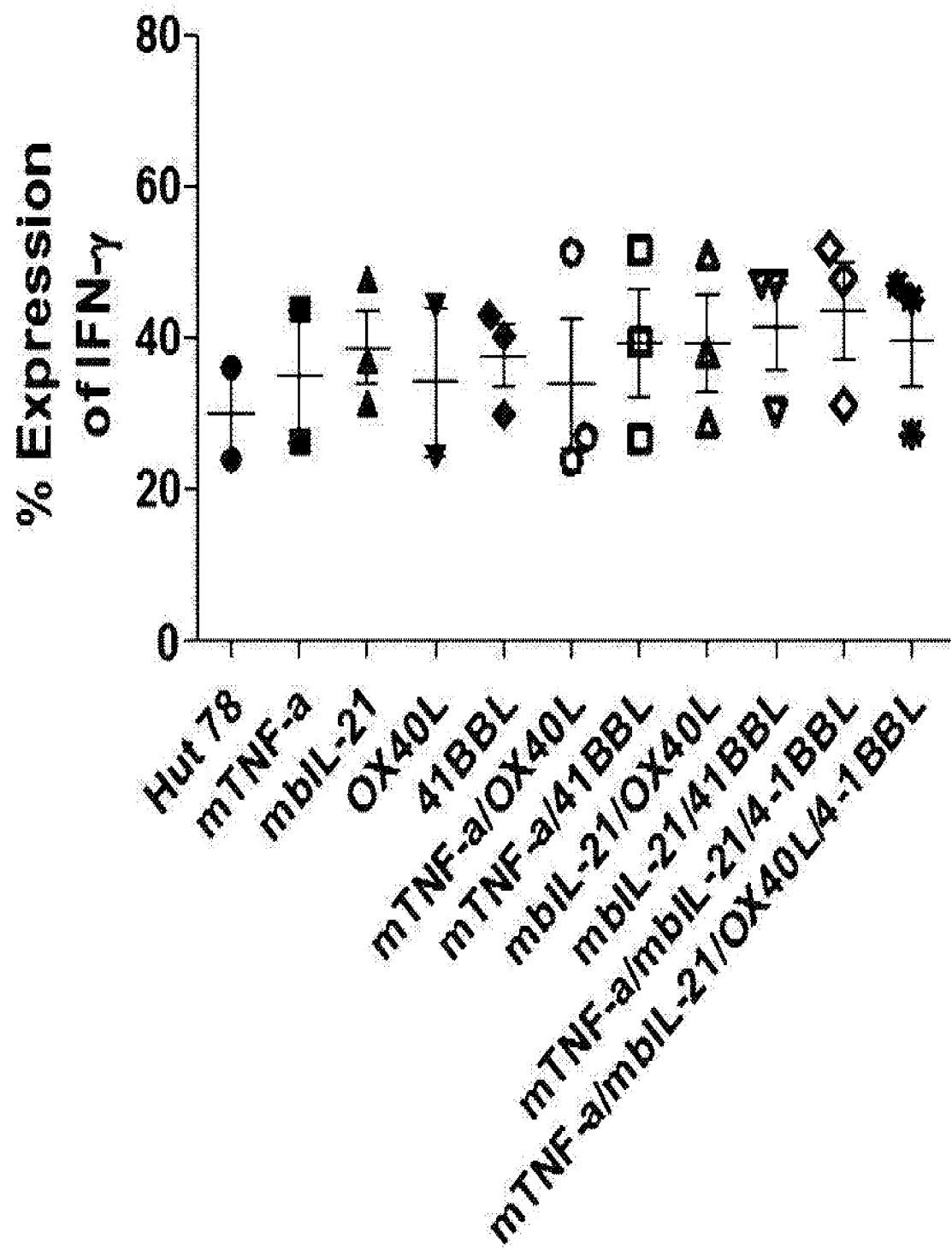

[Fig. 20c]
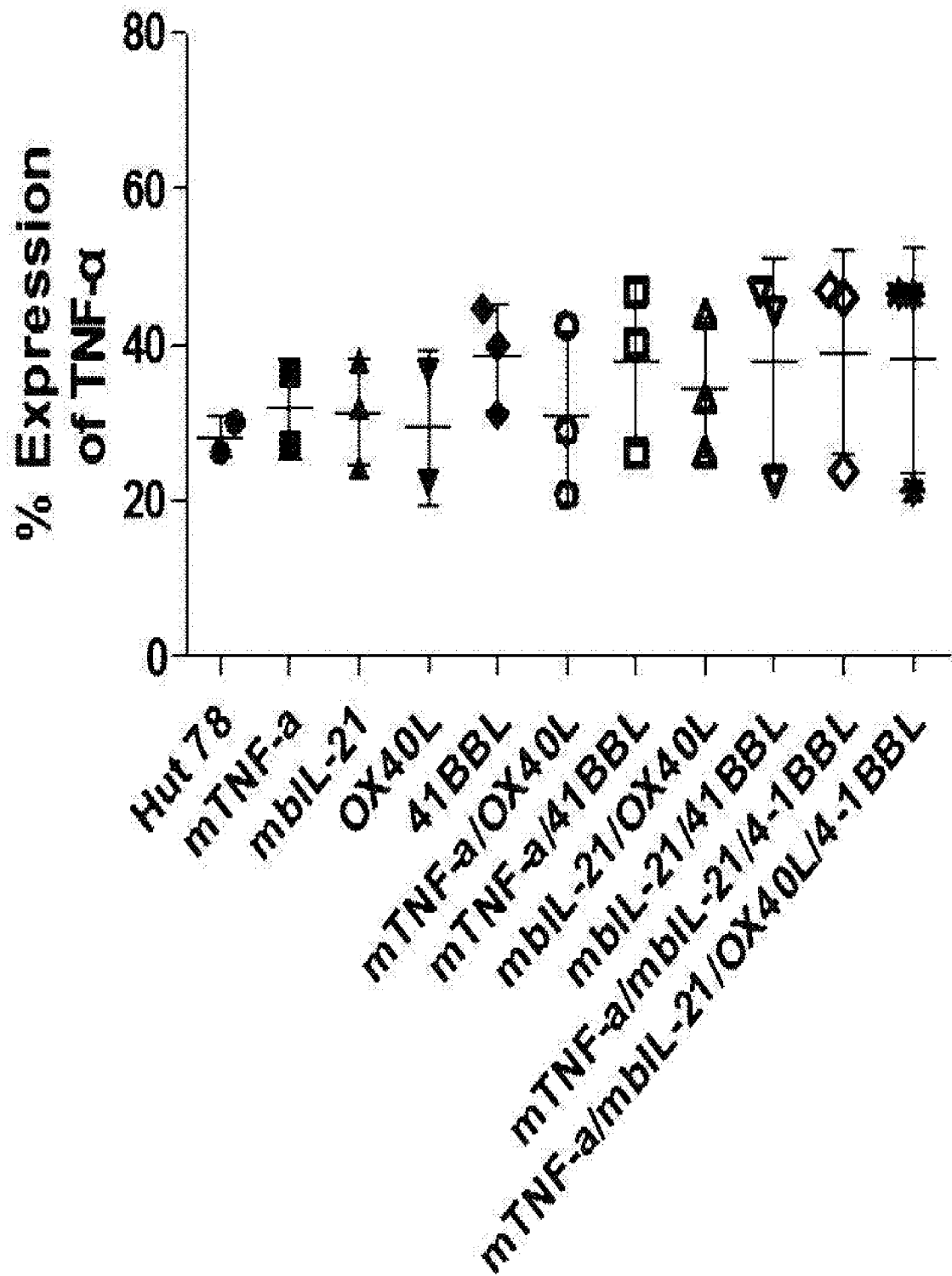

[Fig. 21a]
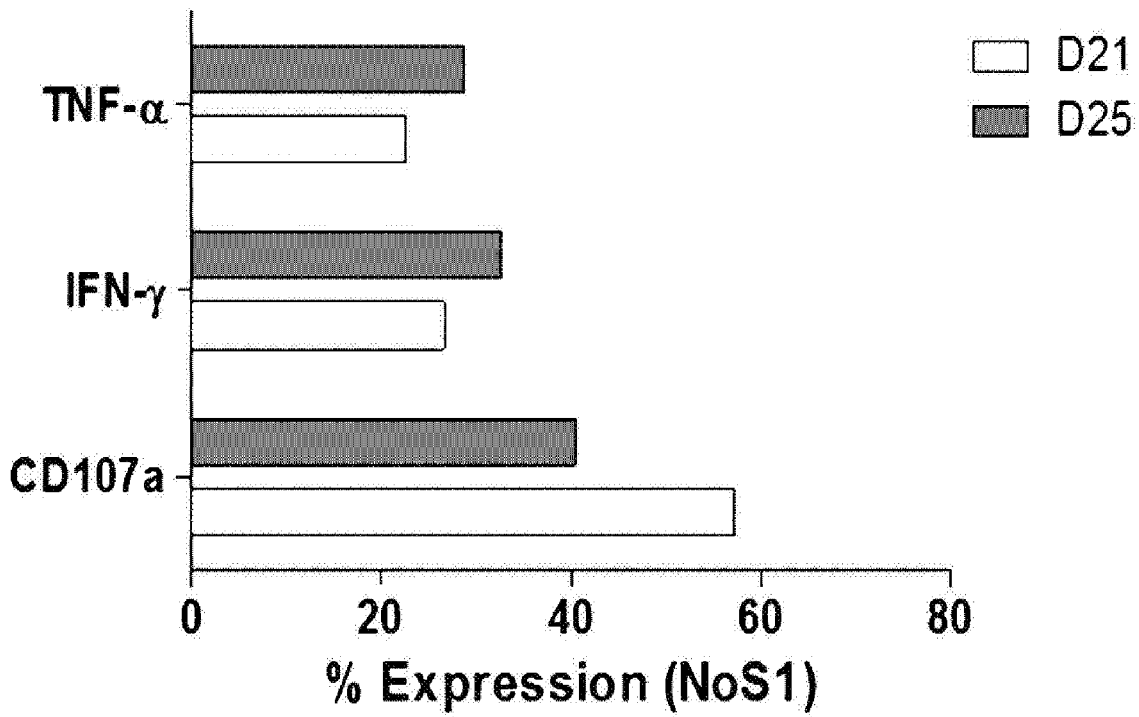
[Fig. 21b]
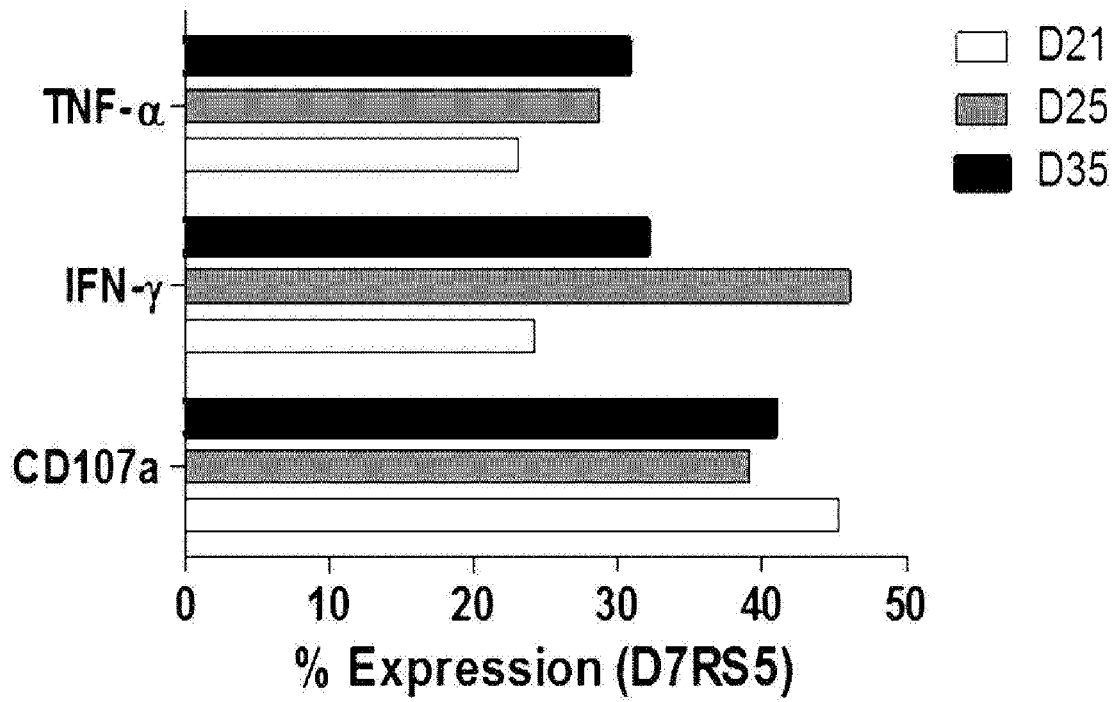

[Fig. 21c]
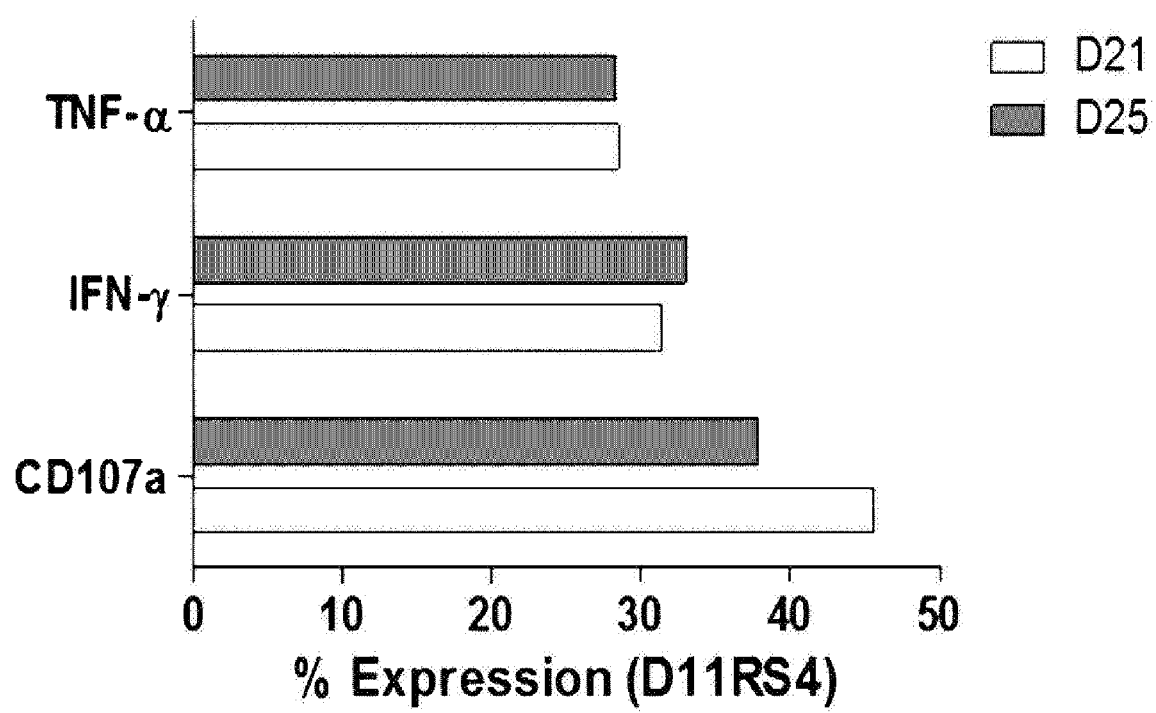

SEQUENCE LISTING

<160> NUMBER OF SEQ ID NOS: 17

<210> SEQ ID NO 1
<211> LENGTH: 254
<212> TYPE: PRT
<213> ORGANISM: Artificial Sequence
<220> FEATURE:
<223> OTHER INFORMATION: amino acid seqeunce for 4-1BBL

<400> SEQUENCE: 1

```
Met Glu Tyr Ala Ser Asp Ala Ser Leu Asp Pro Glu Ala Pro Trp Pro
1               5                   10                  15

Pro Ala Pro Arg Ala Arg Ala Cys Arg Val Leu Pro Trp Ala Leu Val
            20                  25                  30

Ala Gly Leu Leu Leu Leu Leu Leu Leu Ala Ala Ala Cys Ala Val Phe
        35                  40                  45

Leu Ala Cys Pro Trp Ala Val Ser Gly Ala Arg Ala Ser Pro Gly Ser
    50                  55                  60

Ala Ala Ser Pro Arg Leu Arg Glu Gly Pro Glu Leu Ser Pro Asp Asp
65                  70                  75                  80

Pro Ala Gly Leu Leu Asp Leu Arg Gln Gly Met Phe Ala Gln Leu Val
                85                  90                  95

Ala Gln Asn Val Leu Leu Ile Asp Gly Pro Leu Ser Trp Tyr Ser Asp
            100                 105                 110

Pro Gly Leu Ala Gly Val Ser Leu Thr Gly Gly Leu Ser Tyr Lys Glu
        115                 120                 125
```

```
Asp Thr Lys Glu Leu Val Val Ala Lys Ala Gly Val Tyr Tyr Val Phe
        130                 135                 140

Phe Gln Leu Glu Leu Arg Arg Val Val Ala Gly Glu Gly Ser Gly Ser
145                 150                 155                 160

Val Ser Leu Ala Leu His Leu Gln Pro Leu Arg Ser Ala Ala Gly Ala
            165                 170                 175

Ala Ala Leu Ala Leu Thr Val Asp Leu Pro Pro Ala Ser Ser Glu Ala
            180                 185                 190

Arg Asn Ser Ala Phe Gly Phe Gln Gly Arg Leu Leu His Leu Ser Ala
        195                 200                 205

Gly Gln Arg Leu Gly Val His Leu His Thr Glu Ala Arg Ala Arg His
        210                 215                 220

Ala Trp Gln Leu Thr Gln Gly Ala Thr Val Leu Gly Leu Phe Arg Val
225                 230                 235                 240

Thr Pro Glu Ile Pro Ala Gly Leu Pro Ser Pro Arg Ser Glu
                245                 250
```

<210> SEQ ID NO 2
<211> LENGTH: 765
<212> TYPE: DNA
<213> ORGANISM: Artificial Sequence
<220> FEATURE:
<223> OTHER INFORMATION: nucleotide sequence of 4-1BBL

<400> SEQUENCE: 2

```
atggaatacg cctctgacgc ttcactggac cccgaagccc cgtggcctcc cgcgccccgc      60
gctcgcgcct gccgcgtact gccttgggcc ctggtcgcgg ggctgctgct gctgctgctg     120
ctcgctgccg cctgcgccgt cttcctcgcc tgccccctgg gccgtgtccgg ggctcgcgcc    180
tcgcccggct ccgcggccag cccgagactc gcgagggtc ccgagctttc gcccgacgat      240
cccgccggcc tcttggacct gcggcagggc atgtttgcgc agctggtggc ccaaaatgtt     300
ctgctgatcg atgggcccct gagctggtac agtgacccag gcctggcagg cgtgtccctg     360
acggggggcc tgagctacaa agaggacacg aaggagctgg tggtggccaa ggctggagtc     420
tactatgtct tctttcaact agagctgcgg cgcgtggtgg ccggcgaggg ctcaggctcc     480
gtttcacttg cgctgcacct gcagccactg cgctctgctg ctggggccgc cgccctggct    540
ttgaccgtgg acctgccacc cgcctcctcc gaggctcgga actcggcctt cggttttccag   600
ggccgcttgc tgcacctgag tgccggccag cgcctgggcg tccatcttca cactgaggcc    660
agggcacgcc atgcctggca gcttacccag ggcgccacag tcttgggact cttccgggtg    720
accccccgaaa tcccagccgg actcccttca ccgaggtcgg aataa                   765
```

<210> SEQ ID NO 3
<211> LENGTH: 223
<212> TYPE: PRT
<213> ORGANISM: Artificial Sequence
<220> FEATURE:
<223> OTHER INFORMATION: amino acid seqeunce for membrane bound IL-21
      (mbIL-21)

<400> SEQUENCE: 3

```
Met Ala Leu Pro Val Thr Ala Leu Leu Leu Pro Leu Ala Leu Leu Leu
1               5                   10                  15

His Ala Ala Arg Pro Gln Asp Arg His Met Ile Arg Met Arg Gln Leu
            20                  25                  30

Ile Asp Ile Val Asp Gln Leu Lys Asn Tyr Val Asn Asp Leu Val Pro
```

```
                     35                  40                  45
Glu Phe Leu Pro Ala Pro Glu Asp Val Glu Thr Asn Cys Glu Trp Ser
 50                  55                  60

Ala Phe Ser Cys Phe Gln Lys Ala Gln Leu Lys Ser Ala Asn Thr Gly
 65                  70                  75                  80

Asn Asn Glu Arg Ile Ile Asn Val Ser Ile Lys Lys Leu Lys Arg Lys
                     85                  90                  95

Pro Pro Ser Thr Asn Ala Gly Arg Arg Gln Lys His Arg Leu Thr Cys
                100                 105                 110

Pro Ser Cys Asp Ser Tyr Glu Lys Lys Pro Pro Lys Glu Phe Leu Glu
                115                 120                 125

Arg Phe Lys Ser Leu Leu Gln Lys Met Ile His Gln His Leu Ser Ser
                130                 135                 140

Arg Thr His Gly Ser Glu Asp Ser Ala Lys Pro Thr Thr Thr Pro Ala
145                 150                 155                 160

Pro Arg Pro Pro Thr Pro Ala Pro Thr Ile Ala Ser Gln Pro Leu Ser
                165                 170                 175

Leu Arg Pro Glu Ala Cys Arg Pro Ala Ala Gly Gly Ala Val His Thr
                180                 185                 190

Arg Gly Leu Asp Phe Ala Cys Asp Ile Tyr Ile Trp Ala Pro Leu Ala
                195                 200                 205

Gly Thr Cys Gly Val Leu Leu Leu Ser Leu Val Ile Thr Leu Tyr
                210                 215                 220

<210> SEQ ID NO 4
<211> LENGTH: 672
<212> TYPE: DNA
<213> ORGANISM: Artificial Sequence
<220> FEATURE:
<223> OTHER INFORMATION: nucleotide sequence of membrane bound IL-21
      (mbIL-21)

<400> SEQUENCE: 4
atggctctgc ccgtcaccgc tctgctgctg cctctggccc tgctgctgca cgccgcaaga      60
ccacaggacc gccacatgat tcggatgagg cagctgatcg acattgtgga tcagctgaag     120
aactacgtga atgacctggt ccccgagttc ctgcccgctc ctgaggatgt cgaaacaaac     180
tgcgaatggt ctgcattcag ttgttttcag aaggctcagc tgaaatctgc aaacactgga     240
aacaatgagc gaatcattaa tgtgagcatc aagaaactga agcggaaacc cccttccact     300
aatgcaggcc ggagacagaa gcaccgactg acctgcccct catgtgacag ctatgaaaag     360
aaaccaccca agagttcct ggagcggttc aagagcctgc tccagaaaat gatccaccag     420
cacctgagca gccggaccca cggcagcgag gattctgcca agcctaccac aactccagct     480
ccccgccctc caaccctgc accaacaatt gccagtcagc ccctgtcact gaggcctgaa     540
gcatgccgcc agccgctgg cggagcagtc cacacacgag gcctggactt tgcttgtgat     600
atctacattt gggcacctct ggctggaact tgcggcgtcc tgctgctgtc cctggtcatc     660
accctgtatt ga                                                        672

<210> SEQ ID NO 5
<211> LENGTH: 183
<212> TYPE: PRT
<213> ORGANISM: Artificial Sequence
<220> FEATURE:
<223> OTHER INFORMATION: amino acid seqeunce for OX40L

<400> SEQUENCE: 5
```

```
Met Glu Arg Val Gln Pro Leu Glu Glu Asn Val Gly Asn Ala Ala Arg
1               5                   10                  15

Pro Arg Phe Glu Arg Asn Lys Leu Leu Leu Val Ala Ser Val Ile Gln
            20                  25                  30

Gly Leu Gly Leu Leu Cys Phe Thr Tyr Ile Cys Leu His Phe Ser
        35                  40                  45

Ala Leu Gln Val Ser His Arg Tyr Pro Arg Ile Gln Ser Ile Lys Val
    50                  55                  60

Gln Phe Thr Glu Tyr Lys Lys Glu Lys Gly Phe Ile Leu Thr Ser Gln
65                  70                  75                  80

Lys Glu Asp Glu Ile Met Lys Val Gln Asn Asn Ser Val Ile Ile Asn
                85                  90                  95

Cys Asp Gly Phe Tyr Leu Ile Ser Leu Lys Gly Tyr Phe Ser Gln Glu
            100                 105                 110

Val Asn Ile Ser Leu His Tyr Gln Lys Asp Glu Glu Pro Leu Phe Gln
            115                 120                 125

Leu Lys Lys Val Arg Ser Val Asn Ser Leu Met Val Ala Ser Leu Thr
    130                 135                 140

Tyr Lys Asp Lys Val Tyr Leu Asn Val Thr Thr Asp Asn Thr Ser Leu
145                 150                 155                 160

Asp Asp Phe His Val Asn Gly Gly Glu Leu Ile Leu Ile His Gln Asn
                165                 170                 175

Pro Gly Glu Phe Cys Val Leu
            180
```

```
<210> SEQ ID NO 6
<211> LENGTH: 552
<212> TYPE: DNA
<213> ORGANISM: Artificial Sequence
<220> FEATURE:
<223> OTHER INFORMATION: nucleotide sequence of OX40L

<400> SEQUENCE: 6
atggaacggg tgcaacctct ggaggagaat gtgggcaatg cagcccggcc aagatttgag    60
aggaacaagc tactgctggt ggcctctgtg atacagggac tggggctcct cctgtgcttc   120
acctacatct gcctgcactt cagcgctctt caggtgtcac accggtatcc ccgcatacaa   180
agtatcaagg tccagtttac cgagtataag aaagagaagg gtttcatcct cactagtcag   240
aaggaggatg aaatcatgaa ggtgcagaac aactcagtta ttattaactg tgacggcttt   300
tatctgatca gcctgaaggg ctacttctcc aggaagtaa acatcagcct gcattaccag   360
aaggatgagg agcccctgtt tcagctgaag aaggtccggt ccgtgaactc ccttatggtc   420
gcctctctga cgtacaagga caaggtgtac ctcaatgtga ccacagacaa tacatccctg   480
gatgacttcc atgtgaatgg cggagaactg attctgattc accagaaccc tggggagttc   540
tgtgtcttgt ga                                                       552

<210> SEQ ID NO 7
<211> LENGTH: 705
<212> TYPE: DNA
<213> ORGANISM: Homo sapiens

<400> SEQUENCE: 7
atgagcactg aaagcatgat ccgggacgtg gagctggccg aggaggcgct ccccaagaag    60 acagggggc cccagggctc caggcggtgc ttgttcctca gcctcttctc cttcctgatc   120
```

-continued

```
gtggcaggcg ccaccacgct cttctgcctg ctgcactttg gagtgatcgg cccccagagg    180
gaagagttcc ccagggacct ctctctaatc agccctctgg cccaggcagt cagatcatct    240
tctcgaaccc cgagtgacaa gcctgtagcc catgttgtag caaaccctca agctgagggg    300
cagctccagt ggctgaaccg ccgggccaat gccctcctgg ccaatggcgt ggagctgaga    360
gataaccagc tggtggtgcc atcagagggc ctgtacctca tctactccca ggtcctcttc    420
aagggccaag gctgcccctc cacccatgtg ctcctcaccc acaccatcag ccgcatcgcc    480
gtctcctacc agaccaaggt caacctcctc tctgccatca agagcccctg ccagagggag    540
accccagagg gggctgaggc caagccctgg tatgagccca tctatctggg aggggtcttc    600
cagctggaga agggtgaccg actcagcgct gagatcaatc ggcccgacta tctcgacttt    660
gccgagtctg ggcaggtcta ctttgggatc attgccctgt gagga                    705

<210> SEQ ID NO 8
<211> LENGTH: 233
<212> TYPE: PRT
<213> ORGANISM: Artificial Sequence
<220> FEATURE:
<223> OTHER INFORMATION: amino acid seqeunce for mutated TNF alpha
      (mTNF-a)

<400> SEQUENCE: 8

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
    50                  55                  60

Arg Asp Leu Ser Leu Ile Ser Pro Leu Ala Gln Pro Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
    130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225                 230

<210> SEQ ID NO 9
<211> LENGTH: 702
```

<212> TYPE: DNA
<213> ORGANISM: Artificial Sequence
<220> FEATURE:
<223> OTHER INFORMATION: nucleotide sequence of mutated TNF alpha
      (mTNF-a)

<400> SEQUENCE: 9

```
atgagcactg aaagcatgat ccgggacgtg gagctggccg aggaggcgct ccccaagaag      60
acagggggc cccagggctc caggcggtgc ttgttcctca gcctcttctc cttcctgatc     120
gtggcaggcg ccaccacgct cttctgcctg ctgcactttg gagtgatcgg ccccagagg     180
gaagagttcc cagggacct ctctctaatc agccctctgg cccagccggt cagatcatct     240
tctcgaaccc cgagtgacaa gcctgtagcc catgttgtag caaaccctca agctgagggg     300
cagctccagt ggctgaaccg ccgggccaat gccctcctgg ccaatggcgt ggagctgaga     360
gataaccagc tggtggtgcc atcagagggc ctgtacctca tctactccca ggtcctcttc     420
aagggccaag ctgcccctc acccatgtg ctcctcaccc acaccatcag ccgcatcgcc     480
gtctcctacc agaccaaggt caacctcctc tctgccatca gagcccctg ccagagggag     540
accccagagg gggctgaggc caagccctgg tatgagccca tctatctggg agggtcttc     600
cagctggaga agggtgaccg actcagcgct gagatcaatc ggcccgacta tctcgacttt    660
gccgagtctg ggcaggtcta ctttgggatc attgccctgt ga                      702
```

<210> SEQ ID NO 10
<211> LENGTH: 46
<212> TYPE: DNA
<213> ORGANISM: Artificial Sequence
<220> FEATURE:
<223> OTHER INFORMATION: Forward primer for 4-1BBL

<400> SEQUENCE: 10

```
tctagagcta gcgaattcgc caccatggaa tacgcctctg acgctt                     46
```

<210> SEQ ID NO 11
<211> LENGTH: 38
<212> TYPE: DNA
<213> ORGANISM: Artificial Sequence
<220> FEATURE:
<223> OTHER INFORMATION: Reverse primer for 4-1BBL

<400> SEQUENCE: 11

```
ttcgcggccg cggatcctta ttccgacctc ggtgaagg                              38
```

<210> SEQ ID NO 12
<211> LENGTH: 40
<212> TYPE: DNA
<213> ORGANISM: Artificial Sequence
<220> FEATURE:
<223> OTHER INFORMATION: Forward primer for mbIL-21

<400> SEQUENCE: 12

```
tagagctagc gaattcgcca ccgccaccat ggctctgccc                            40
```

<210> SEQ ID NO 13
<211> LENGTH: 35
<212> TYPE: DNA
<213> ORGANISM: Artificial Sequence
<220> FEATURE:
<223> OTHER INFORMATION: Reverse primer for mbIL-21

<400> SEQUENCE: 13

```
tcgcggccgc ggatcctcaa tacagggtga tgacc                                 35
```

```
<210> SEQ ID NO 14
<211> LENGTH: 38
<212> TYPE: DNA
<213> ORGANISM: Artificial Sequence
<220> FEATURE:
<223> OTHER INFORMATION: Forward primer for OX40L

<400> SEQUENCE: 14
tagagctagc gaattcgcca ccatggaacg ggtgcaac                              38

<210> SEQ ID NO 15
<211> LENGTH: 37
<212> TYPE: DNA
<213> ORGANISM: Artificial Sequence
<220> FEATURE:
<223> OTHER INFORMATION: Reverse primer for OX40L

<400> SEQUENCE: 15
tcgcggccgc ggatcctcac aagacacaga actcccc                               37

<210> SEQ ID NO 16
<211> LENGTH: 40
<212> TYPE: DNA
<213> ORGANISM: Artificial Sequence
<220> FEATURE:
<223> OTHER INFORMATION: Forward primer for mTNF-a

<400> SEQUENCE: 16
tagagctagc gaattcgcca ccgccaccat ggctctgccc                            40

<210> SEQ ID NO 17
<211> LENGTH: 34
<212> TYPE: DNA
<213> ORGANISM: Artificial Sequence
<220> FEATURE:
<223> OTHER INFORMATION: Reverse primer for mTNF-a

<400> SEQUENCE: 17
tcgcggccgc ggatcctcac agggcaatga tccc                                  34
```

METHOD FOR CULTURING NATURAL KILLER CELL, USING TRANSFORMED T CELL

CROSS REFERENCE TO RELATED APPLICATIONS

This application is a National Stage of International Application No. PCT/KR2018/005983 filed May 25, 2018, claiming priority based on Korean Patent Application No. 10-2017-0065180 filed May 26, 2017.

TECHNICAL FIELD

The present invention relates to a culture method for natural killer cells using transformed T cells.

BACKGROUND ART

As a therapeutic method for the treatment of cancer patients and the prevention of recurrence of cancer, immunotherapy using the patient's immune function has been developed. In particular, immunotherapy using natural killer cells that can be mass-produced and frozen has been studied. Natural killer cells are lymphoid cells that account for about 15% of peripheral blood lymphocytes, and play an important role in the innate immune response.

Specifically, natural killer cells activate dendritic cells and induce cytotoxic T lymphocytes (CTLs) to specifically respond to tumors, thereby eliminating tumor cells. Natural killer cells directly kill malignant tumors such as sarcoma, myeloma, carcinoma, lymphoma, and leukemia. However, most natural killer cells present in the bodies of normal subjects exist in an inactive state, and activated natural killer cells are required to eliminate tumors. In addition, in a case of natural killer cells present in the bodies of cancer patients, the natural killer cells have functional defects due to the immune evasion mechanism of cancer cells.

Therefore, in order to use natural killer cells as a therapeutic agent, it is very important to activate the natural killer cells. In addition, since the number of natural killer cells present in the body is limited, it is essential to develop a technique for massively proliferating and freezing natural killer cells in the blood from normal subjects or patients.

As a method for massively proliferating natural killer cells, an ex vivo expansion culture method is used. For ex vivo expansion culture of natural killer cells, Peripheral blood mononuclear cells (PBMCs), CD3- cells, CD3-CD56+ cells, CD56+ cells, and the like are used as seed cells, and cytokines such as IL-2, IL-12, IL-15, and IL-21, LPS (Goodier et al., J. Immunol. 165(1):139-147, 2000), OKT-3 antibodies that stimulate CD3 (Condiotti et al., Experimental Hematol. 29(1):104-113, 2001) are used as proliferation factors for natural killer cells. Using the above-mentioned proliferation factors only, it is possible to proliferate natural killer cells about 3 to 10 times. However, with the above proliferation rate, it is difficult to commercialize natural killer cells into a therapeutic agent.

Recently, methods for proliferating natural killer cells using various types of feeder cells have been studied. Representative cell lines used as feeder cells include PBMC, EBV-LCL, and K562 cell line. K562 cell line is a blood cancer-derived cell line that lacks HLA and is a representative target cell line that natural killer cells can easily attack. The culture method using K562-based feeder cells for NK cells are as follows; a method in which cultures NK cells using 4-1BBL and membrane-bound IL-15 expressed K562 cell line, (Fujisaki et al., Cancer Res. 69(9):4010-4017, 2009), a method in which cultures NK cells using MICA, 4-1BBL, and IL-15 expressed K562 cell line (Gong et al., Tissue Antigens, 76(6):467-475, 2010), and a method in which cultures NK cells using 4-1BBL and membrane-bound IL-21 expressed K562 cell (Cecele J D et al, PloSONE, 7(1):e30264, 2012)

DISCLOSURE OF INVENTION

Technical Problem

Accordingly, in order to activate and proliferate natural killer cells, the present inventors have developed a method for effectively proliferating natural killer cells ex vivo, comprising expressing co-stimulatory molecules and growth factors, which can enhance proliferation of the natural killer cells, in CD4+ T cells.

Specifically, in order to increase efficiency of a culturing method for natural killer cells using the CD4(+) T cells as feeder cells, the present inventors have established transformed or genetically modified CD4(+) T cells. The present inventors have identified that in a case where the genetically modified CD4(+) T cells are co-cultured with peripheral blood mononuclear cells, such co-culture increases proliferation and abnormal cell-killing activity of natural killer cells, and thus have completed the present invention. Therefore, there is provided a culture method for proliferating natural killer cells in an efficient and stable manner using the genetically modified CD4(+) T cells.

Solution to Problem

In an aspect of the present invention, there is provided a genetically modified or transformed CD4+ T cell that expresses at least one gene selected from the group consisting of 4-1BBL gene, mbIL-21 gene, OX40L gene, and mTNF-α gene.

In addition, in another aspect of the present invention, there is provided a culture method for natural killer cells, comprising a step of co-culturing the genetically modified CD4+ T cells and seed cells.

Furthermore, in yet another aspect of the present invention, there is provided a composition for culturing natural killer cells, comprising the genetically modified CD4+ T cell as an active ingredient.

In addition, in still yet another aspect of the present invention, there is provided a natural killer cell produced by the culture method.

Advantageous Effects of Invention

The culture method for natural killer cells using the genetically modified T cell of the present invention allows natural killer cells to be effectively proliferated and produced from a small number of seed cells. In addition, the culture method also improves abnormal cell-killing activity of natural killer cells. Therefore, the culture method for natural killer cells using the genetically modified T cell of the present invention can be usefully used for commercialization into a cell therapeutic agent. Furthermore, a natural killer cell produced by the culture method of the present invention can be usefully used as a cell therapeutic agent.

BRIEF DESCRIPTION OF DRAWINGS

FIG. 1a shows expression of single genes transduced into Hut78 cell line based on FACS.

FIG. 1b shows expression of double genes transduced into Hut78 cell line based on FACS.

FIG. 1c shows gene expression in Hut78 cell line based on FACS.

FIG. 1d shows expression of single genes transduced into Hut78 cell line based on FACS.

FIG. 1e shows expression of mTNF-α/OX40L and mTNFα/4-1BBL double genes transduced into Hut78 cell line based on FACS.

FIG. 1f shows expression of mbIL-21/OX40L and mbIL-21/4-1BBL double genes transduced into Hut78 cell line based on FACS.

FIG. 1g shows expression of triple genes transduced into Hut78 cell line based on FACS.

FIG. 1h shows expression of quadruple genes transduced into Hut78 cell line based on FACS.

FIG. 2a shows expression of single genes transduced into H9 cell line based on FACS.

FIG. 2b shows expression of double genes transduced into H9 cell line based on FACS.

FIG. 3a shows expression of single genes transduced into Jurkat T cell line based on FACS.

FIG. 3b shows expression of double genes transduced into Jurkat T cell line based on FACS.

FIG. 4a shows fold increase, for each transduced gene, of natural killer cells produced by co-culturing Hut78 T cells having undergone single gene or double gene transduction, and peripheral blood mononuclear cells.

FIG. 4b shows fold increase, for each transduced gene, of natural killer cells produced by co-culturing H9 T cells having undergone single gene or double gene transduction, and peripheral blood mononuclear cells.

FIG. 4c shows fold increase, for each transduced gene, of natural killer cells produced by co-culturing Jurkat T cells having undergone single gene or double gene transduction, and peripheral blood mononuclear cells.

FIG. 4d shows fold increase, for each transduced gene, of natural killer cells produced by co-culturing Hut78 T cell line having undergone single gene to quadruple gene transduction, and peripheral blood mononuclear cells.

FIG. 5a shows fold increase of natural killer cells (D7R) produced by co-culturing Hut78 T cell line having undergone triple gene transduction, and peripheral blood mononuclear cells.

FIG. 5b shows fold increase, calculated as log values, of natural killer cells (D7R) produced by co-culturing Hut78 T cell line having undergone triple gene transduction, and peripheral blood mononuclear cells.

FIG. 5c shows fold increases of natural killer cells (D11R) produced by co-culturing Hut78 T cell line having undergone triple gene transduction, and peripheral blood mononuclear cells.

FIG. 5d shows fold increase, calculated as log values, of natural killer cells (D11R) produced by co-culturing Hut78 T cell line having undergone triple gene transduction, and peripheral blood mononuclear cells.

FIG. 6a shows viability, for each transduced gene, of natural killer cells produced by co-culturing Hut78 T cell line having undergone single gene or double gene transduction, and peripheral blood mononuclear cells.

FIG. 6b shows viability, for each transduced gene, of natural killer cells produced by co-culturing H9 T cell line having undergone single gene or double gene transduction, and peripheral blood mononuclear cells.

FIG. 6c shows viability, for each transduced gene, of natural killer cells produced by co-culturing Jurkat T cell line having undergone single gene or double gene transduction, and peripheral blood mononuclear cells.

FIG. 6d shows viability, for each transduced gene, of natural killer cells produced by co-culturing Hut78 T cell line having undergone single gene to quadruple gene transduction, and peripheral blood mononuclear cells.

FIG. 7a shows purity (CD3-CD56+), for each transduced gene, of natural killer cells produced by co-culturing Hut78 T cell line having undergone single gene or double gene transduction, and peripheral blood mononuclear cells.

FIG. 7b shows activation (CD16+CD56+), for each transduced gene, of natural killer cells produced by co-culturing Hut78 T cell line having undergone single gene or double gene transduction, and peripheral blood mononuclear cells.

FIG. 7c shows purity (CD3-CD56+), for each transduced gene, of natural killer cells produced by co-culturing H9 T cell line having undergone single gene or double gene transduction, and peripheral blood mononuclear cells.

FIG. 7d shows activation (CD16+CD56+), for each transduced gene, of natural killer cells produced by co-culturing H9 T cell line having undergone single gene or double gene transduction, and peripheral blood mononuclear cells.

FIG. 7e shows purity (CD3-CD56+), for each transduced gene, of natural killer cells produced by co-culturing Jurkat T cell line having undergone single gene or double gene transduction, and peripheral blood mononuclear cells.

FIG. 7f shows activation (CD16+CD56+), for each transduced gene, of natural killer cells produced by co-culturing Jurkat cell line having undergone single gene or double gene transduction, and peripheral blood mononuclear cells.

FIG. 7g shows purity (CD3-CD56+), for each transduced gene, of natural killer cells produced by co-culturing Hut78 T cell line having undergone single gene to quadruple gene transduction, and peripheral blood mononuclear cells.

FIG. 7h shows activation (CD16+CD56+), for each transduced gene, of natural killer cells produced by co-culturing Hut78 T cell line having undergone single gene to quadruple gene transduction, and peripheral blood mononuclear cells.

FIG. 8a shows expression levels of the phenotypic marker CD16, for each transduced gene, in natural killer cells produced by co-culturing Hut78 T cell line having undergone single gene or double gene transduction, and peripheral blood mononuclear cells.

FIG. 8b shows expression levels of the phenotypic marker NKG2D, for each transduced gene, in natural killer cells produced by co-culturing Hut78 T cell line having undergone single gene or double gene transduction, and peripheral blood mononuclear cells.

FIG. 8c shows expression levels of the phenotypic marker NKp30, for each transduced gene, in natural killer cells produced by co-culturing Hut78 T cell line having undergone single gene or double gene transduction, and peripheral blood mononuclear cells.

FIG. 8d shows expression levels of the phenotypic marker NKp44, for each transduced gene, in natural killer cells produced by co-culturing Hut78 T cell line having undergone single gene or double gene transduction, and peripheral blood mononuclear cells.

FIG. 8e shows expression levels of the phenotypic marker NKp46, for each transduced gene, in natural killer cells produced by co-culturing Hut78 T cell line having undergone single gene or double gene transduction, and peripheral blood mononuclear cells.

FIG. 8f shows expression levels of the phenotypic marker DNAM-1, for each transduced gene, in natural killer cells produced by co-culturing Hut78 T cell line having undergone single gene or double gene transduction, and peripheral blood mononuclear cells.

FIG. 8g shows expression levels of the phenotypic marker CXCR3, for each transduced gene, in natural killer cells produced by co-culturing Hut78 T cell line having undergone single gene or double gene transduction, and peripheral blood mononuclear cells.

FIG. 9a shows expression levels of the phenotypic marker CD16, for each transduced gene, in natural killer cells produced by co-culturing H9 T cell line having undergone single gene or double gene transduction, and peripheral blood mononuclear cells.

FIG. 9b shows expression levels of the phenotypic marker NKG2D, for each transduced gene, in natural killer cells produced by co-culturing H9 T cell line having undergone single gene or double gene transduction, and peripheral blood mononuclear cells.

FIG. 9c shows expression levels of the phenotypic marker NKp30, for each transduced gene, in natural killer cells produced by co-culturing H9 T cell line having undergone single gene or double gene transduction, and peripheral blood mononuclear cells.

FIG. 9d shows expression levels of the phenotypic marker NKp44, for each transduced gene, in natural killer cells produced by co-culturing H9 T cell line having undergone single gene or double gene transduction, and peripheral blood mononuclear cells.

FIG. 9e shows expression levels of the phenotypic marker NKp46, for each transduced gene, in natural killer cells produced by co-culturing H9 T cell line having undergone single gene or double gene transduction, and peripheral blood mononuclear cells.

FIG. 9f shows expression levels of the phenotypic marker DNAM-1, for each transduced gene, in natural killer cells produced by co-culturing H9 T cell line having undergone single gene or double gene transduction, and peripheral blood mononuclear cells.

FIG. 9g shows expression levels of the phenotypic marker CXCR3, for each transduced gene, in natural killer cells produced by co-culturing H9 T cell line having undergone single gene or double gene transduction, and peripheral blood mononuclear cells.

FIG. 10a shows expression levels of the phenotypic marker CD16, for each transduced gene, in natural killer cells produced by co-culturing Jurkat T cell line having undergone single gene or double gene transduction, and peripheral blood mononuclear cells.

FIG. 10b shows expression levels of the phenotypic marker NKG2D, for each transduced gene, in natural killer cells produced by co-culturing Jurkat T cell line having undergone single gene or double gene transduction, and peripheral blood mononuclear cells.

FIG. 10c shows expression levels of the phenotypic marker NKp30, for each transduced gene, in natural killer cells produced by co-culturing Jurkat T cell line having undergone single gene or double gene transduction, and peripheral blood mononuclear cells.

FIG. 10d shows expression levels of the phenotypic marker NKp44, for each transduced gene, in natural killer cells produced by co-culturing Jurkat T cell line having undergone single gene or double gene transduction, and peripheral blood mononuclear cells.

FIG. 10e shows expression levels of the phenotypic marker NKp46, for each transduced gene, in natural killer cells produced by co-culturing Jurkat T cell line having undergone single gene or double gene transduction, and peripheral blood mononuclear cells.

FIG. 10f shows expression levels of the phenotypic marker DNAM-1, for each transduced gene, in natural killer cells produced by co-culturing Jurkat T cell line having undergone single gene or double gene transduction, and peripheral blood mononuclear cells.

FIG. 10g shows expression levels of the phenotypic marker CXCR3, for each transduced gene, in natural killer cells produced by co-culturing Jurkat T cell line having undergone single gene or double gene transduction, and peripheral blood mononuclear cells.

FIG. 11a shows expression levels of the phenotypic marker CD16, for each transduced gene, in natural killer cells produced by co-culturing Hut78 T cell line having undergone single gene to quadruple gene transduction, and peripheral blood mononuclear cells.

FIG. 11b shows expression levels of the phenotypic marker NKG2A, for each transduced gene, in natural killer cells produced by co-culturing Hut78 T cell line having undergone single gene to quadruple gene transduction, and peripheral blood mononuclear cells.

FIG. 11c shows expression levels of the phenotypic marker NKG2C, for each transduced gene, in natural killer cells produced by co-culturing Hut78 T cell line having undergone single gene to quadruple gene transduction, and peripheral blood mononuclear cells.

FIG. 11d shows expression levels of the phenotypic marker NKG2D, for each transduced gene, in natural killer cells produced by co-culturing Hut78 T cell line having undergone single gene to quadruple gene transduction, and peripheral blood mononuclear cells.

FIG. 11e shows expression levels of the phenotypic marker NKp30, for each transduced gene, in natural killer cells produced by co-culturing Hut78 T cell line having undergone single gene to quadruple gene transduction, and peripheral blood mononuclear cells.

FIG. 11f shows expression levels of the phenotypic marker NKp44, for each transduced gene, in natural killer cells produced by co-culturing Hut78 T cell line having undergone single gene to quadruple gene transduction, and peripheral blood mononuclear cells.

FIG. 11g shows expression levels of the phenotypic marker NKp46, for each transduced gene, in natural killer cells produced by co-culturing Hut78 T cell line having undergone single gene to quadruple gene transduction, and peripheral blood mononuclear cells.

FIG. 11h shows expression levels of the phenotypic marker DNAM-1, for each transduced gene, in natural killer cells produced by co-culturing Hut78 T cell line having undergone single gene to quadruple gene transduction, and peripheral blood mononuclear cells.

FIG. 11i shows expression levels of the phenotypic marker CXCR3, for each transduced gene, in natural killer cells produced by co-culturing Hut78 T cell line having undergone single gene to quadruple gene transduction, and peripheral blood mononuclear cells.

FIG. 11j shows expression levels of the phenotypic marker CD62L, for each transduced gene, in natural killer cells produced by co-culturing Hut78 T cell line having undergone single gene to quadruple gene transduction, and peripheral blood mononuclear cells.

FIG. 11k shows expression levels of the phenotypic marker CD57, for each transduced gene, in natural killer cells produced by co-culturing Hut78 T cell line having undergone single gene to quadruple gene transduction, and peripheral blood mononuclear cells.

FIG. 11*l* shows expression levels of the phenotypic marker CD69, for each transduced gene, in natural killer cells produced by co-culturing Hut78 T cell line having undergone single gene to quadruple gene transduction, and peripheral blood mononuclear cells.

FIG. 12*a* shows expression levels of the phenotypic markers CD16, NKG2A, NKG2C, and NKG2D in natural killer cells produced by co-culturing Hut78 T cell line having undergone triple gene transduction, and peripheral blood mononuclear cells.

FIG. 12*b* shows expression levels of the phenotypic markers NKp30, NKp44, NKp46, and DNAM-1 in natural killer cells produced by co-culturing Hut78 T cell line having undergone triple gene transduction, and peripheral blood mononuclear cells.

FIG. 12*c* shows expression levels of the phenotypic markers CD62L, CD69, CXCR3, and CD57 in natural killer cells produced by co-culturing Hut78 T cell line having undergone triple gene transduction, and peripheral blood mononuclear cells.

FIG. 13*a* shows tumor cell-killing activity, for each transduced gene, of natural killer cells produced by co-culturing Hut78 T cell line having undergone single gene or double gene transduction, and peripheral blood mononuclear cells.

FIG. 13*b* shows tumor cell-killing activity, for each transduced gene, of natural killer cells produced by co-culturing H9 T cell line having undergone single gene or double gene transduction, and peripheral blood mononuclear cells.

FIG. 13*c* shows tumor cell-killing activity, for each transduced gene, of natural killer cells produced by co-culturing Jurkat T cell line having undergone single gene or double gene transduction, and peripheral blood mononuclear cells.

FIG. 14*a* shows tumor cell-killing activity (E:T=10:1), for each transduced gene, of natural killer cells produced by co-culturing Hut78 T cell line having undergone single gene to quadruple gene transduction, and peripheral blood mononuclear cells.

FIG. 14*b* shows tumor cell-killing activity (E:T=3:1), for each transduced gene, of natural killer cells produced by co-culturing Hut78 T cell line having undergone single gene to quadruple gene transduction, and peripheral blood mononuclear cells.

FIG. 14*c* shows tumor cell-killing activity (E:T=1:1), for each transduced gene, of natural killer cells produced by co-culturing Hut78 T cell line having undergone single gene to quadruple gene transduction, and peripheral blood mononuclear cells.

FIG. 14*d* shows tumor cell-killing activity (E:T=0.3:1), for each transduced gene, of natural killer cells produced by co-culturing Hut78 T cell line having undergone single gene to quadruple gene transduction, and peripheral blood mononuclear cells.

FIG. 15*a* shows tumor cell-killing activity, for respective cell ratios, of natural killer cells (NoS1) produced by co-culturing Hut78 T cell line having undergone triple gene transduction, and peripheral blood mononuclear cells.

FIG. 15*b* shows tumor cell-killing activity, for respective cell ratios, of natural killer cells (D7RS5) produced by co-culturing Hut78 T cell line having undergone triple gene transduction, and peripheral blood mononuclear cells.

FIG. 15*c* shows tumor cell-killing activity, for respective cell ratios, of natural killer cells (D11RS4) produced by co-culturing Hut78 T cell line having undergone triple gene transduction, and peripheral blood mononuclear cells.

FIG. 16*a* shows, expression levels of the proliferation marker Ki-67, for each transduced gene, in natural killer cells produced by co-culturing Hut78 T cell line having undergone single gene to quadruple gene transduction, and peripheral blood mononuclear cells.

FIG. 16*b* shows expression levels of the proliferation marker Ki-67 on day 16, for each transduced gene, in natural killer cells produced by co-culturing Hut78 T cell line having undergone single gene to quadruple gene transduction, and peripheral blood mononuclear cells.

FIG. 16*c* shows expression levels of the proliferation marker Ki-67 for each transduced gene, in terms of mean fluorescence index (MFI) ratio values, in natural killer cells produced by co-culturing Hut78 T cell line having undergone single gene to quadruple gene transduction, and peripheral blood mononuclear cells.

FIG. 16*d* shows expression levels of the proliferation marker Ki-67 for each transduced gene, in terms of mean fluorescence index ratio values, in natural killer cells produced by co-culturing Hut78 T cell line having undergone single gene to quadruple gene transduction, and peripheral blood mononuclear cells.

FIG. 17*a* shows expression levels of the proliferation marker Ki-67 in natural killer cells (D7R) produced by performing re-stimulation at 7-day intervals when co-culturing Hut78 T cell line having undergone triple gene transduction, and peripheral blood mononuclear cells.

FIG. 17*b* shows expression levels of the proliferation marker Ki-67 in natural killer cells (D11R) produced by performing re-stimulation at 11-day intervals when co-culturing Hut78 T cell line having undergone triple gene transduction, and peripheral blood mononuclear cells.

FIG. 17*c* shows expression levels of the proliferation marker Ki-67, in terms of mean fluorescence index ratio values, in natural killer cells (D7R) produced by performing re-stimulation at 7-day intervals when co-culturing Hut78 T cell line having undergone triple gene transduction, and peripheral blood mononuclear cells.

FIG. 17*d* shows expression levels of the proliferation marker Ki-67, in terms of mean fluorescence index ratio values, in natural killer cells (D11R) produced by performing re-stimulation at 11-day intervals when co-culturing Hut78 T cell line having undergone triple gene transduction, and peripheral blood mononuclear cells.

FIG. 18*a* shows expression levels of the co-stimulatory molecule CD25, for each transduced gene, in natural killer cells produced by co-culturing Hut78 T cell line having undergone single gene to quadruple gene transduction, and peripheral blood mononuclear cells.

FIG. 18*b* shows expression levels of the co-stimulatory molecule CD25 on day 11, for each transduced gene, in natural killer cells produced by co-culturing Hut78 T cell line having undergone single gene to quadruple gene transduction, and peripheral blood mononuclear cells.

FIG. 18*c* shows expression levels of the co-stimulatory molecule TNFRII, for each transduced gene, in natural killer cells produced by co-culturing Hut78 T cell line having undergone single gene to quadruple gene transduction, and peripheral blood mononuclear cells.

FIG. 18*d* shows expression levels of the co-stimulatory molecule TNFRII on day 16, for each transduced gene, in natural killer cells produced by co-culturing Hut78 T cell line having undergone single gene to quadruple gene transduction, and peripheral blood mononuclear cells.

FIG. 18*e* shows expression levels of the co-stimulatory molecule 41BB, for each transduced gene, in natural killer cells produced by co-culturing Hut78 T cell line having undergone single gene to quadruple gene transduction, and peripheral blood mononuclear cells.

FIG. 18f shows expression levels of the co-stimulatory molecule 41BB on day 7, for each transduced gene, in natural killer cells produced by co-culturing Hut78 T cell line having undergone single gene to quadruple gene transduction, and peripheral blood mononuclear cells.

FIG. 19a shows expression levels of the co-stimulatory molecule CD25 in natural killer cells (D7R) produced by performing re-stimulation at 7-day intervals when co-culturing Hut78 T cell line having undergone triple gene transduction, and peripheral blood mononuclear cells.

FIG. 19b shows expression levels of the co-stimulatory molecule TNFRII in natural killer cells (D7R) produced by performing re-stimulation at 7-day intervals when co-culturing Hut78 T cell line having undergone triple gene transduction, and peripheral blood mononuclear cells.

FIG. 19c shows expression levels of the co-stimulatory molecule 41BB in natural killer cells (D7R) produced by performing re-stimulation at 7-day intervals when co-culturing Hut78 T cell line having undergone triple gene transduction, and peripheral blood mononuclear cells.

FIG. 19d shows expression levels of the co-stimulatory molecule CD25 in natural killer cells (D11R) produced by performing re-stimulation at 11-day intervals when co-culturing Hut78 T cell line having undergone triple gene transduction, and peripheral blood mononuclear cells.

FIG. 19e shows expression levels of the co-stimulatory molecule TNFRII in natural killer cells (D11R) produced by performing re-stimulation at 11-day intervals when co-culturing Hut78 T cell line having undergone triple gene transduction, and peripheral blood mononuclear cells.

FIG. 19f shows expression levels of the co-stimulatory molecule 41BB in natural killer cells (D11R) produced by performing re-stimulation at 11-day intervals when co-culturing Hut78 T cell line having undergone triple gene transduction, and peripheral blood mononuclear cells.

FIG. 20a shows expression levels of CD107a, for each transduced gene, in natural killer cells produced by co-culturing Hut78 T cell line having undergone single gene to quadruple gene transduction, and peripheral blood mononuclear cells.

FIG. 20b shows expression levels of IFN-γ, for each transduced gene, in natural killer cells produced by co-culturing Hut78 T cell line having undergone single gene to quadruple gene transduction, and peripheral blood mononuclear cells.

FIG. 20c shows expression levels of TNF-α, for each transduced gene, in natural killer cells produced by co-culturing Hut78 T cell line having undergone single gene to quadruple gene transduction, and peripheral blood mononuclear cells.

FIG. 21a shows expression levels of CD107a, IFN-γ, and TNF-α in natural killer cells (NoS1) produced by co-culturing Hut78 T cell line having undergone triple gene transduction, and peripheral blood mononuclear cells.

FIG. 21b shows expression levels of CD107a, IFN-γ, and TNF-α in natural killer cells (D7RS5) produced by co-culturing Hut78 T cell line having undergone triple gene transduction, and peripheral blood mononuclear cells.

FIG. 21c shows expression levels of CD107a, IFN-γ, and TNF-α in natural killer cells (D11RS4) produced by co-culturing Hut78 T cell line having undergone triple gene transduction, and peripheral blood mononuclear cells.

BEST MODE FOR CARRYING OUT THE INVENTION

Hereinafter, the present invention will be described in detail.

In an aspect of the present invention, there is provided a transformed CD4+ T cell that expresses at least one gene selected from the group consisting of 4-1BBL gene, mbIL-21 gene, OX40L gene, and mTNF-α gene.

Specifically, when one gene is transduced, the gene may be 4-1BBL, mbIL-21, OX40L, or mTNF-α. In addition, when two genes are transduced, a combination of the genes may be mbIL-21/4-1BBL, 4-1BBL/OX40L, mTNFα/4-1BBL, mbIL-21/OX40L, mbIL-21/mTNF-α, or mTNF-α/OX40L. In an embodiment of the present invention, combinations of genes, mbIL-21/4-1BBL, mTNF-α/OX40L, mTNF-α/4-1BBL, and mbIL-21/OX40L were transduced into T cells.

In addition, when three genes are transduced, a combination of the genes may be 4-1BBL/mbIL-21/OX40L, mbIL-21/OX40L/mTNF-α, mTNF-α/mbIL-21/4-1BBL, or 4-1BBL/OX40L/mTNF-α. In an embodiment of the present invention, a combination of genes, mTNF-α/mbIL-21/4-1BBL was transduced into T cells.

In addition, when four genes are transduced, a combination of the genes may be mTNF-α/mbIL-21/OX40L/4-1BBL. In an embodiment of the present invention, a combination of genes, mTNF-α/mbIL-21/OX40L/4-1BBL was transduced into T cells.

The term "4-1BBL" as used herein refers to one of TNF superfamily (TNFSF) called CD137L, and means a ligand that forms a trimer and binds to 4-1BB as a receptor. The 4-1BBL gene may be derived from human.

Specifically, the 4-1BBL gene may be NCBI Reference Sequence: NM_003811, but is not limited thereto. The 4-1BBL gene may have a nucleotide sequence encoding the amino acid sequence represented by SEQ ID NO: 1. The nucleotide sequence encoding the amino acid sequence represented by SEQ ID NO: 1 may be the nucleotide sequence represented by SEQ ID NO: 2.

The term "mbIL-21" as used herein may be IL-21 designed to be bound to a cell membrane. Here, mbIL-21 may be a fusion protein formed by binding between IL-21 and a transmembrane protein. The transmembrane protein may be CD8α. Specifically, the transmembrane protein may be a transmembrane domain of CD8α.

Specifically, the IL-21 gene may be NCBI Reference Sequence: NM_021803.3, but is not limited thereto. In addition, the CD8α gene may be NCBI Reference Sequence: NM_001768, but is not limited thereto. The mbIL-21 is expressed in the form of IL-21 bound to a cell membrane. In addition, the mbIL-21 gene may have a nucleotide sequence encoding the amino acid sequence represented by SEQ ID NO: 3. The nucleotide sequence encoding the amino acid sequence represented by SEQ ID NO: 3 may be the nucleotide sequence represented by SEQ ID NO: 4.

The term "OX40L" as used herein is also referred to as ACT-4 receptor, TNF4-human, GP34, or CD134L, and means a ligand that binds to OX40. Specifically, the OX40L gene may be NCBI Reference Sequence: NM_003326, but is not limited thereto. The OX40L gene may have a nucleotide sequence encoding the amino acid sequence represented by SEQ ID NO: 5. The nucleotide sequence encoding the amino acid sequence represented by SEQ ID NO: 5 may be the nucleotide sequence represented by SEQ ID NO: 6.

The term "mTNF-α" as used herein means a gene obtained by causing a point mutation to occur on DNA of tumor necrosis factor-alpha so that alanine-valine, a site recognized by tumor necrosis factor-alpha-converting enzyme (TACE) in the amino acid sequence of tumor necrosis factor-alpha, is changed to proline-valine. Mutation of alanine to proline is randomly selected.

Specifically, the mTNF-α gene may have a nucleotide sequence encoding the amino acid sequence represented by SEQ ID NO: 8. The nucleotide sequence encoding the amino acid sequence represented by SEQ ID NO: 8 may be the nucleotide sequence represented by SEQ ID NO: 9.

The 4-1BBL gene, mbIL-21 gene, OX40L gene, or mTNF-α gene may be transduced through a recombinant lentivirus. However, transduction is not limited thereto.

As a method of transfecting the gene into cells, a biochemical method, a physical method, or a virus-mediated transfection method may be used. In addition, as the biochemical method, FuGene6 (Roche, USA), lipofectamine (Lipofectamine™ 2000, Invitrogen, USA), or ExGen 500 (MBI Fermentas International Inc., CANADA) may be used. In addition, a lipid-mediated method using lipofectamine may be used.

The term "vector" as used herein is an expression vector capable of expressing a gene of interest in a cell into which the vector is transduced, and refers to a gene construct containing an essential regulatory element operably linked so that a gene insert transduced into the vector is expressed.

In addition, as the expression vector containing the gene, any expression vector capable of expressing the gene in CD4+ T cell line may be used, and pCDH-CMV-MCS-EF1-Puro (SBI, CD510B-1) or pCDH-CMV-MCS-EF1-Neo (SBI, CD514B-1) lentiviral vector was used in a specific embodiment of the present invention.

The lentivirus means a virus which belongs to a retrovirus family and is characterized by a long latency period. The lentivirus can deliver genetic information into DNA of a host cell. Use of the lentivirus is one of the most effective methods of using gene delivery vectors that can replicate in non-dividing cells.

The CD4+ T cells may be ex vivo isolated CD4+ T cells, ex vivo expansion-cultured CD4+ T cells, or CD4+ T cell line (T lymphoma cell line). In addition, the CD4+ T cells may be auxiliary T cells, and may be a hybridoma obtained by fusing CD4+ T cells with cancer cells. Specifically, the CD4+ T cells may be any one selected from the group consisting of Hut78, H9, Jurkat, Loucy, Molt-3, Molt-13, PEER, RPMI8402, and TALL-01 cells. Hut78, H9, or Jurkat T cells may be preferred.

In another aspect of the present invention, there is provided a culture method for natural killer cells, comprising a step of co-culturing the transformed CD4+ T cells and seed cells.

The term "feeder cell" as used herein is also referred to as an auxiliary cell for culture, and means a cell which does not proliferate but has metabolic activity so that the cell produces various metabolites and thus helps proliferation of a target cell. The feeder cell may be a transformed CD4+ T cell that expresses at least one gene selected from the group consisting of 4-1BBL gene, mbIL-21 gene, OX40L gene, and mTNF-α gene.

T cells used as the feeder cells may be inactivated cells whose division/proliferation is inhibited or cells which have not been inactivated. Preferably, the T cells may be inactivated to ensure safety. As an inactivation method, a conventional method known in the art may be used. For example, a gamma ray-irradiation method may be used. In a case where T cells which have not been inactivated are used, most of them are tumor cells, and thus may be killed by activated natural killer cells during culture.

The term "seed cell" as used herein means a cell capable of proliferating to natural killer cells through appropriate culture. Specifically, the seed cells may be any one selected from the group consisting of peripheral blood, peripheral blood leukocytes, peripheral blood mononuclear cells (PBMCs), enriched natural killer cells, and isolated natural killer cells. The seed cells may preferably be, but are not limited to, CD3(−) cells from which CD3(+) cells have been eliminated.

In a culture method for natural killer cells, culture may be performed by mixing the feeder cells and the seed cells at a ratio of 0.1 or higher. Specifically, the feeder cells and the seed cells may be at a ratio of 0.1:1 to 50:1. More specifically, the ratio may be 0.5:1 to 40:1.

Even more specifically, the ratio may be 1:1 to 30:1. Most specifically, the ratio may be 2:1 to 20:1. In an embodiment, the feeder cells and the seed cells may be at a ratio of 5:1, but is not particularly limited thereto. The "ratio" means a ratio based on the number of cells.

In the culture method for natural killer cells, the seed cells may be mixed once with the feeder cells and culture may be performed for 5 days to 60 days, or may be mixed two or more times with the feeder cells and culture may be performed for 60 days or longer. Preferably, the seed cells may be mixed once with the feeder cells and culture was performed for 14 days to 21 days. However, the culture method is not limited thereto.

In the culture method for natural killer cells, natural killer cells and T lymphoma cell line are co-cultured in conventional animal cell culture medium such as AIM-V medium, RPMI1640, CellGro SCGM, X-VIVO20, IMDM, and DMEM. In co-culture, culture may be performed with addition of an antibody that has low affinity for T cells and stimulates T cells, and an interleukin. However, the culture method is not limited thereto.

The term "antibody which has low affinity for T cells and stimulates T cells" as used herein means a protein that specifically responds to CD3 antigens, a group of molecules each of which associates with T cell receptor (TCR) to form an antigen recognition complex. As compared with TCR, the CD3 molecule has a longer intracellular region and plays a role in delivering an antigen recognition signal into a cell.

The antibody that has low affinity for T cells and stimulates T cells, which can be used in the present invention, may preferably be an anti-CD3 antibody. Specifically, the anti-CD3 antibody may be OKT-3, UCHT1, or HIT3a.

The term "interleukin (IL)" as used herein refers to a group belonging to cytokines, and means a proteinaceous biologically-active substance produced by immunocompetent cells such as lymphocytes, monocytes, and macrophages. The interleukin may be IL-2, IL-15, IL-12, IL-18, or IL-21.

In an embodiment of the present invention, culture was performed with addition of OKT-3 antibody and IL-2. A concentration of the OKT-3 antibody to be added may be 0.1 ng/ml to 100 ng/ml. Preferably, the concentration of the OKT-3 antibody may be 10 ng/μl. A concentration of IL-2 may be 10 U/ml to 2,000 U/ml. Preferably, the concentration of IL-2 may be 500 U/ml. In addition, serum or plasma and an additional growth factor that supports growth of lymphocytes may be added and culture may be performed. The type of serum or plasma to be added to the medium is not particularly limited, and a variety of commercially available animal-derived serum or plasma may be used. Preferably, human-derived serum or plasma, in particular, self-derived serum or plasma may be used.

The term "culture" as used herein means a method of growing cells under an environmental condition that is appropriately artificially regulated. The method of culturing the genetically modified CD4+ T cells may be carried out using methods well known in the art. Specifically, the culture may be performed in a batch or fed-batch process, or may be continuously performed in a repeated fed-batch process.

In addition, precursors suitable for the culture medium may be used. The above-mentioned raw materials may be added to a culture, during a culture process, in a batch, fed-batch, or continuous manner by an appropriate method. However, the present invention is not particularly limited thereto. A pH of the culture can be regulated by using, in an appropriate manner, basic compounds such as sodium hydroxide, potassium hydroxide, and ammonia, or acidic compounds such as phosphoric acid or sulfuric acid.

The culture method using the T cells as feeder cells allows natural killer cells to be selectively cultured from seed cells such as PBMCs, and enables a stable culture due to the fact that there is no difference in proliferation of natural killer cells as compared with a case where PBMC feeder cells are used depending on donors.

Therefore, a large amount of natural killer cell therapeutic agents can be efficiently and stably obtained.

In addition, in yet another aspect of the present invention, there is provided a composition for culturing natural killer cells, comprising the genetically modified CD4+ T cell as an active ingredient.

Furthermore, in still yet another aspect of the present invention, there is provided a natural killer cell produced by the culture method for natural killer cells.

The natural killer cells cultured according to the culture method for natural killer cells can be frozen and do not exhibit impaired cell function even in a case of being thawed again. In addition, due to high expression of an activating receptor such as NKp46, the natural killer cells exhibit increased killing activity against a tumor cell line and increased cytokine secretion, and thus an excellent anticancer effect can be expected. Therefore, it is possible to prepare a cell therapeutic agent effective for tumor treatment, using a large number of activated natural killer cells which can be clinically applied.

In addition, in a composition for the prevention or treatment of an infectious disease, comprising, as an active ingredient, the natural killer cell produced by the culture method for natural killer cells, the natural killer cell may be contained in an amount of 10% to 95% by weight with respect to the total weight of the composition. In addition, the composition for the prevention or treatment of an infectious disease of the present invention may further comprise, in addition to the active ingredient, one or more active ingredients that exhibit the same or similar functions.

The composition for the prevention or treatment of an infectious disease may be formulated into a pharmaceutical composition for administration by further including one or more pharmaceutically acceptable carriers in addition to the above-mentioned active ingredients.

A dose of the pharmaceutical composition for the prevention or treatment of an infectious disease may be regulated depending on various factors including type of disease, severity of disease, types and amounts of active ingredients and other ingredients included in the composition, type of formulation and the patient's age, weight, general health condition, sex, and diet, time of administration, route of administration and secretion rate of composition, duration of treatment, and simultaneously used drugs. However, for desired effects, a dose of the natural killer cells according to the present invention may be $0.01 \times 10^7$ cells/kg to $1.0 \times 10^9$ cells/kg, and may be $0.5 \times 10^7$ cells/kg to $1.0 \times 10^8$ cells/kg. Here, the dose may be administered once a day or may be divided into several times a day.

In addition, the pharmaceutical composition for the prevention or treatment of an infectious disease may be administered to an individual by various methods known in the art. The route of administration may be appropriately selected by those skilled in the art in consideration of administration method, body fluid volume, viscosity, and the like.

MODE FOR THE INVENTION

Hereinafter, the present invention will be described in detail by way of examples. However, the following examples are only for illustrating the present invention, and the present invention is not limited to the following examples.

EXAMPLE 1

Construction of Recombinant Lentivirus

EXAMPLE 1.1

Construction of Recombinant Lentiviral Vector

As a lentiviral vector, pCDH-CMV-MCS-EF1-Puro (SBI, CD510B-1) or pCDH-CMV-MCS-EF1-Neo (SBI, CD514B-1) was used. As genes for transduction, 4-1BBL (TNF superfamily member 9, TNFSF9), mbIL-21 (membrane-bound IL-21), OX40L (TNF superfamily member 4 (TNFSF4) transcript variant 1) and mTNF-α (membrane-bound TNF alpha) genes were used.

Specifically, for the 4-1BBL gene (SEQ ID NO: 2), 4-1BBL gene expression vector (OriGene, RC211160) was used. For the mbIL-21 gene (SEQ ID NO: 4), pcDNA3.1 vector (GenScript, US) into which a codon-optimized mbIL-21 gene sequence is inserted was used. For the OX40L gene (SEQ ID NO: 6), a request for synthesis thereof was made to BIONEER CORPORATION.

For the mTNF-α gene (SEQ ID NO: 9), RNA was extracted from peripheral blood mononuclear cells (PBMCs), and then CDS was obtained therefrom by reverse transcriptase (RT)-PCR. In order for TNF-α to be secreted, TNF-α was cleaved by tumor necrosis factor-alpha-converting enzyme (TACE); however, a point mutation was caused to occur on DNA of TNF-α so that alanine-valine (A-V), a site recognized by TACE in the amino acid sequence of TNF-α, became proline-valine (P-V), thereby allowing TNF-α to remain attached to a cell membrane. The point mutation was performed, in human mTNF-α gene represented by SEQ ID NO: 7, by replacing guanine, which is the $226^{th}$ base, with cytosine, and replacing adenine, which is the $228^{th}$ base, with guanine.

Primers suitable for each gene for transducrion were used to amplify, through PCR, the coding sequence (CDS) of the transgene (Table 1).

TABLE 1

| | Primer | Sequence information (5'→3') | SEQ ID NO |
|---|---|---|---|
| 4-1BBL | 4-1BBL Forward | TCTAGAGCTAGCGAATTCGCCACCATGGAATACGCCTCTGACGCTT | SEQ ID NO: 10 |
| | 4-1BBL Reverse | TTCGCGGCCGCGGATCCTTATTCCGACCTCGGTGAAGG | SEQ ID NO: 11 |
| mbIL-21 | mbIL-21 Forward | TAGAGCTAGCGAATTCGCCACCGCCACCATGGCTCTGCCC | SEQ ID NO: 12 |
| | mbIL-21 Reverse | TCGCGGCCGCGGATCCTCAATACAGGGTGATGACC | SEQ ID NO: 13 |
| OX40L | OX40L Forward | TAGAGCTAGCGAATTCGCCACCATGGAACGGGTGCAAC | SEQ ID NO: 14 |
| | OX40L Reverse | TCGCGGCCGCGGATCCTCACAAGACACAGAACTCCCC | SEQ ID NO: 15 |
| mTNF-α | mTNF-α Forward | TAGAGCTAGCGAATTCGCCACCGCCACCATGGCTCTGCCC | SEQ ID NO: 16 |
| | mTNF-α Reverse | TCGCGGCCGCGGATCCTCACAGGGCAATGATCCC | SEQ ID NO: 17 |

Table 1 shows the primers used in the experiment.

The transgene and the lentiviral vector were treated with EcoRI and BamHI restriction enzymes. Thereafter, ligation was performed using an In-Fusion HD cloning kit (Clontech, 639649). The ligated lentiviral vector was transformed into DH5α competent cells and culture was performed. Plasmid DNA was obtained from the transformed DH5α competent cells using a plasmid mini-prep kit (MACHEREY-NAGEL/740422.50). For all plasmid DNA, a request for sequencing thereof was made to an outside company, and it was confirmed that DNA sequences thereof were accurate.

EXAMPLE 1.2

Construction of Enriched Lentiviruses

For recombinant lentiviral production, 293T cell line was inoculated into a 75T flask (Nunc, 156499) at $1.5 \times 10^6$ to $2 \times 10^6$ cells two days prior to transfection, and incubated in an incubator at a condition of 5% $CO_2$ and 37° C. When cell confluency of the 293T cells reached about 80% to 90%, the medium was replaced with 6 ml of OPTI-MEM (Gibco, 31985-088) and incubated for 30 minutes under a 5% $CO_2$ condition at a temperature of 37° C. A DNA mixed solution and a lipofectamine (lipofectamine 2000, Life technologies, 11668500) mixed solution were prepared (Table 2).

TABLE 2

| Category | Ingredient |
|---|---|
| DNA mixed solution | 6 μg of target DNA, 6 μg of Gag, 6 μg of REV, 3 μg of VSVG, 1 ml of OPTI-MEM |
| Lipofectamine mixed solution | 36 μl of lipofectamine 2000, 1 ml of OPTI-MEM |

Table 2 shows the DNA mixed solution and the lipofectamine (lipofectamine 2000, Life technologies, 11668500) mixed solution.

Ingredients of the respective mixed solutions were mixed well using a vortexer and allowed to stand at room temperature for 3 minutes. Then, the two mixed solutions were mixed and allowed to stand at room temperature for 20 minutes or longer. The 293T cells for which medium replacement had been made were subjected to treatment with 2 ml of the mixed solution of DNA and lipofectamine. After 4 hours, the medium was replaced with DMEM (Gibco, 11995073) medium supplemented with 10% (v/v) FBS, and incubation was performed for 48 hours under a condition of 5% $CO_2$ at a temperature of 37° C.

8 ml of culture of the 293T cells obtained by performing incubation for 48 hours was collected and filtered with a 0.45 μm filter (Millipore, SLHP033RS). The filtered culture was enriched to 250 μl or less using the Amicon Ultra-15 Centrifugal Filter Unit with Ultracel-100 membrane (Merckmillipore, UFC910096). The enriched viruses were aliquoted in appropriate amounts and stored at a temperature of −80° C.

EXAMPLE 2

Construction of T Cells Having Transduced Genes

EXAMPLE 2.1

Lentiviral Infection $0.5 \times 10^6$ cells of T cell line in culture, 1 ml of OPTI-MEM, 50 μl of lentiviral thaw, 10 μg/ml of polybrene (Santa Cruz, C2013) were mixed. The mixture was placed in a 6-well plate (Nunc, 140675), and spinoculation was performed at 1800 g and a temperature of 32° C. for 90 minutes. Then, incubation was performed for 2 hours in an incubator at a condition of 5% $CO_2$ and 37° C. Thereafter, the medium was replaced with the same culture medium and incubation was performed for 48 hours.

Hut78 cell line (ATCC, TIB-161™) was cultured in IMDM (ATCC, 30-2005) medium containing 20% (v/v) FBS. In subculture, the cell concentration thereof was maintained at $1.5 \times 10^5$ cells/ml to $2.0 \times 10^5$ cells/ml. H9 cell line (ATCC, HTB-176™) and Jurkat T cell line (ATCC, TIB-152™) were cultured in RPMI1640 (ATCC, 30-2001) medium containing 10% (v/v) FBS. In subculture, the cell concentrations thereof were maintained at $1.0 \times 10^5$ cells/ml to $1.5 \times 10^5$ cells/ml and $0.5 \times 10^5$ cells/ml to $1.0 \times 10^5$ cells/ml, respectively. Subculture of all cell lines was performed at 2-day to 3-day intervals. As a culture vessel, a 75T flask was used, and the medium volume was maintained at 15 ml to 20 ml.

The recombinant lentivirus-infected cell line was selected using antibiotics (Table 3).

TABLE 3

| Combination of transduced genes | Cell line | Antibiotic concentration used |
|---|---|---|
| mTNF-α | Hut78 | 1 μg/ml of puromycin |
| mbIL-21 | H9 | (Life technologies, A1113802) |
|  | Jurkat | or 6 μg/ml of blasticidin (Gibco, R210-01) |
| OX40L | Hut78 | 1 μg/ml of puromycin |
| 4-1BBL | H9 | or 50 μg/ml of G418 (Sigma Aldrich, G8168) |
|  | Jurkat | 1 mg/ml of G418 |
| mTNF-α/OX40L | Hut78 | 1 μg/ml of puromycin or 6 μg/ml of blasticidin |
| mbIL-21/OX40L | H9 | 50 μg/ml of G418 |
| mbIL-21/4-1BBL | Jurkat | 0.5 μg/ml of puromycin |
|  |  | 1 mg/ml of G418 |
| mTNF-α/mbIL-21/4-1BBL | Hut78 | 1 μg/ml of puromycin |
| mTNF-α/mbIL-21/OX40L/4-1BBL |  | 6 μg/ml of blasticidin |
|  |  | 50 μg/ml of G418 |

Table 3 shows antibiotics used for the cell lines having transduced genes.

EXAMPLE 2.2

Identification of Expression of Transduced Genes

The T cell line subcultured in Example 2.1. was collected and centrifuged at 1,200 rpm for 5 minutes. Then, the culture was removed by suction. FACS buffer was made by adding 2% (v/v) FBS to PBS. Dilution with 1 ml of the FACS buffer was performed and the cell number was measured. Dilution with the FACS buffer was performed so as to give a concentration of $5 \times 10^6$ cells/ml. 100 μl of the diluted cell solution was added to each 5 ml FACS tube (Falcon, 352052). Staining was performed with anti-human TNF-α (membrane)-PE (R&D Systems, FAB210P), anti-human OX40L-PE (BD, 558184), anti-human 4-1BBL-PE (BD, 559446), anti-human IL-21-PE (eBioscience, 12-7219-42), 7-AAD (Beckman Coulter, Inc., IM3630c), PE mouse IgG1 k isotype control (BD Pharmingen, 555749), PerCP-Cy5.5 mouse IgG1 k isotype control (BD, 550795) antibodies, and then an expression rate of each gene was analyzed using FACS equipment (FIGS. 1a to 3b).

EXAMPLE 3

Co-Culture of CD3(−) PBMCs and T Cells Having Transduced Genes

EXAMPLE 3.1

Preparation of CD3(−) PBMC Seed Cells

Phosphate buffered saline (PBS, LONZA, 17-516Q) was added, at a 1:1 ratio, to PBMCs collected from healthy donors and centrifugation was performed at 1,500 rpm and a temperature of 4° C. for 10 minutes. 2% (v/v) FBS and 2 mM EDTA were added to PBS, to make MACS running buffer. The PBMC pellets were suspended in 10 ml of the MACS running buffer and the cell number was measured using an Adam cell counter system.

In order to obtain the seed cells from which CD3(+) cells have been eliminated, $5 \times 10^7$ PBMCs were transferred to a new 50-ml tube, and then centrifuged at 1,200 rpm and a temperature of 4° C. for 10 minutes. 400 μl of the MACS running buffer and 100 μl of CD3 magnetic beads (Miltenyi Biotech, 130050101) were added to $5 \times 10^7$ PBMC cell pellets and reaction was allowed to occur at a temperature of 4° C. for 20 minutes. 10 ml to 20 ml of the MACS running buffer was added thereto and washing was performed. Then, centrifugation was performed at 1,200 rpm and a temperature of 4° C. for 10 minutes, and the resultant was suspended again in 2 ml of the MACS running buffer.

The cells were isolated using VarioMACS (Miltenyi Biotech) equipped with a CS column (Miltenyi Biotech, 130-041-305). The cells were recovered by washing the column until it reached a final volume of 20 ml. The cell number was measured using the Adam cell counter system. $1 \times 10^7$ cells were placed in a new 50-ml tube, and centrifuged at 1,200 rpm and a temperature of 4° C. for 10 minutes. The cell pellets were suspended in freezing medium, and freezing was performed in liquid nitrogen to achieve $1 \times 10^7$ cells per vial.

One frozen CD3(−) PBMC vial was thawed and transferred to a 50-ml tube. CD3(−) PBMCs were suspended in PBS containing 0.6% (v/v) ACD (citrate-dextrose solution, Sigma-Aldrich, C3821), 0.2% (v/v) fetal serum bovine (FBS), and 2 mM EDTA, and centrifuged at 1,200 rpm and a temperature of 4° C. for 10 minutes. CD3(−) PBMC pellets were suspended in 1% (v/v) CellGro medium (Cellgenix, 20802-0500), and the cell number was measured using the Adam cell counter system. CD3(−) PBMC seed cells were suspended in 1% (v/v) CellGro medium at a concentration of $1 \times 10^6$ cells/ml.

EXAMPLE 3.2

Co-Culture of CD3(−) PBMC Seed Cells and T Feeder Cells Having Transduced Genes T cells having transduced gene were recovered from the culture flask and centrifuged at 1,200 rpm and a temperature of 4° C. for 10 minutes. Thereafter, the cells were suspended in 1% (v/v) CellGro medium, and the cell number was measured using the Adam cell counter system. T feeder cells having transduced gene(s) were prepared by being suspended in 1% (v/v) CellGro medium at a concentration of $5 \times 10^6$ cells/ml and then being irradiated with 20,000 cGy in a gamma-ray irradiator and inactivated.

In culture of natural killer cells, 500 IU of IL-2 (Proleukin Inj., Novartis Korea) and 10 ng/ml of OKT-3 (eBioscience, 16-0037-85) were added to a culture plastic plate. On day 0 of culture, the CD3(−) PBMC seed cells and the T feeder cells having transduced gene(s) were added in a volume of 0.5 ml to 1 ml each at a ratio of 1:5 or 1:2.5, and CellGro medium containing 1% (v/v) human plasma was added thereto in a volume of 0.25 ml to 0.5 ml. The resultant was subjected to static culture in an incubator at a temperature condition of 37° C. for 4 to 7 days while adding the medium.

On days 4 to 5 of culture, the cell number was measured so that the cells had a concentration of about $0.5\times10^6$ to $1\times10^6$ cells/ml. Thereafter, the cells were diluted with CellGro medium containing 500 IU of IL-2 and 1% (v/v) autologous plasma, and placed in an appropriate culture vessel. The cells were again subjected to static culture.

After that, the cell number was measured at 2-day to 3-day intervals so that the cells had a concentration of $0.5\times10^5$ to $1\times10^6$ cells/ml. Thereafter, the cells were subjected to suspension culture until day 21 while performing dilution with CellGro medium containing 500 IU of IL-2 and 1% (v/v) autologous plasma. On day 21 of suspension culture, natural killer cells were obtained.

As a result of comparing proliferation rates of the cultured natural killer cells, it was possible to identify that culture with the cell line into which one or more genes (mTNF-α, OX40L, 4-1BBL, or mbIL-21) have been transduced results in increased proliferation of natural killer cells, in terms of proliferation rate based on total nucleated cells (TNC), as compared with the cell line having no transduced gene (76-fold in H9, 382-fold in Hut78, 26-fold in Jurkat). In particular, as compared with single transduction of the 4-1BBL gene or the mbIL-21 gene, in case of the cell line into which the mbIL-21/4-1BBL gene is transduced, remarkably high proliferation rates for natural killer cells, which are 4,169-fold in Hut78-mbIL-21/4-1BBL, 3,758-fold in H9-mbIL-21/4-1BBL, 258-fold in Jurkat-mbIL-21/4-1BBL, were induced regardless of types of T cells (Table 4, FIGS. 4a to 4c). That is, it was identified that a synergistic effect was observed when the mbIL-21 gene and the 4-1BBL gene were transduced.

TABLE 4

| Transduced gene(s) | Hut78 feeder cell Fold increase (D21) | H9 feeder cell Fold increase (D21) | Jurkat feeder cell Fold increase (D14) |
|---|---|---|---|
| Parental | 382.0 ± 379.78 | 79.3 ± 38.60 | 26.1 ± 15.45 |
| mTNF-α | 532.5 ± 315.48 | 147.7 ± 101.04 | 19.1 ± 8.84 |
| OX40L | 541.4 ± 353.22 | — | — |
| 4-1BBL | 992.3 ± 423.75 | 689.8 ± 541.60 | 121.7 ± 30.46 |
| mbIL-21 | 979.2 ± 745.36 | 277.8 ± 71.00 | 1.4 ± 1.05 |
| mTNF-α/OX40L | 916.0 ± 204.52 | — | — |
| mTNF-α/4-1BBL | 1871.7 ± 701.68 | 985.3 ± 705.35 | 60.7 ± 20.09 |
| mbIL-21/4-1BBL | 4169.5 ± 2795.10 | 3758.5 ± 3232.39 | 258.5 ± 121.36 |

Table 4 shows proliferation rates of the natural killer cells cultured with T cell line having undergone single or double gene transduction.

In order to identify a synergistic effect obtained when a combination of two or more genes is transduced, a proliferative effect of the natural killer cells cultured with Hut78 T cell line having undergone triple gene (mTNF-α/mbIL-21/4-1BBL) or quadruple gene (mTNF-α/mbIL-21/OX40L/4-1BBL) transduction was compared together with combinations of genes for which experiments were previously made. Among the cell lines having undergone double gene transduction, the cell line that induced the highest proliferation of natural killer cells was the cell line (998-fold) into which the mbIL-21/4-1BBL gene had been transduced. However, when cultured with a cell line having undergone triple gene transduction (1,607-fold) or a cell line having undergone quadruple gene transduction (1,640-fold), it was identified that a higher synergistic effect was observed than the cell line (998-fold) into which the mbIL-21/4-1BBL gene was transduced (Table 5 and FIG. 4d).

TABLE 5

| Transduced gene(s) | Hut78 feeder cell Fold increase(D21) |
|---|---|
| Parental | 72.1 ± 71.5 |
| mTNF-α | 121.9 ± 103.0 |
| OX40L | 212.4 ± 297.2 |
| 4-1BBL | 235.1 ± 195.1 |
| mbIL-21 | 737.2 ± 393.6 |
| mTNF-α/OX40L | 77.8 ± 67.3 |
| mTNF-α/4-1BBL | 385.4 ± 293.3 |
| mbIL-21/4-1BBL | 998.3 ± 911.2 |
| mbIL-21/OX40L | 743.0 ± 411.7 |
| mTNF-α/mbIL-21/4-1BBL | 1607.3 ± 845.0 |
| mTNF-α/mbIL-21/OX40L/4-1BBL | 1640.6 ± 1191.6 |
| Single culture of seed cells | 0.8 |

Table 5 shows proliferation rates of the natural killer cells cultured with T cell lines having undergone multiple gene transduction.

Experiments were conducted to identify whether culture of natural killer cells can be continuously maintained with repeated re-stimulation by T cell line due to gene transduction.

Hut78 cells having undergone triple gene transduction were recovered from the culture flask and centrifuged at 1,200 rpm and a temperature of 4° C. for 10 minutes. Thereafter, the cells were suspended in 1% (v/v) CellGro medium, and the cell number was measured using the Adam cell counter system. Hut78 feeder cells having undergone triple gene transduction were prepared by being suspended in 1% (v/v) CellGro medium at a concentration of $2.5\times10^6$ cells/ml and then being irradiated with 20,000 cGy in a gamma-ray irradiator and inactivated.

In culture of natural killer cells, 500 IU of IL-2 (Proleukin Inj., Novartis Korea) and 10 ng/ml of OKT-3 (eBioscience, 16-0037-85) were added to a culture plastic plate.

On day 0 of culture, the CD3(−) PBMC seed cells and the Hut78 feeder cells having undergone triple gene transduction were added in a volume of 0.5 ml to 1 ml each at a ratio of 1:2.5, and CellGro medium containing 1% (v/v) human plasma was added thereto in a volume of 0.5 ml to 1 ml. The cells were subjected to static culture in an incubator at a temperature condition of 37° C. for 4 to 7 days. On day 2 or 3 of culture, half of the medium was removed and CellGro medium containing 1% (v/v) human plasma was added thereto as much as the removed volume. On day 4 or 5 of culture, the cell number was measured so that the cells had a concentration of about $0.5\times10^6$ cells/ml to $1\times10^6$ cells/ml.

On day 7 or 11 of culture, the cell number was measured and the cells were suspended in 1% (v/v) CellGro medium at a concentration of $1\times10^6$ cells/ml. For re-stimulation, the Hut78 feeder cells having undergone triple gene transduction were added thereto in a volume of 0.5 ml to 1 ml each at a ratio of 1:2.5, and CellGro medium containing 500 IU of IL-2 (Proleukin Inj., Novartis Korea), 10 ng/ml of OKT-3 (eBioscience, 16-0037-85), and 1% (v/v) human plasma was added thereto in a volume of 0.5 ml to 1 ml. The cells were subjected to static culture in an incubator at a temperature condition of 37° C. for 3 to 4 days. After that, the cell number was measured at 2-day or 3-day intervals so that the cells had a concentration of $0.5\times10^5$ cells/ml to $1\times10^6$ cells/ml.

The re-stimulation process was repeated at 7-day or 11-day intervals, so that a total of 4 re-stimulations at 7-day intervals (D7RS5) and a total of 3 re-stimulations at 11-day intervals (D11RS4) were given.

As a result of comparing proliferation rates of cultured natural killer cells, it was possible to identify that culture with one or more re-stimulations resulted in increased proliferation of natural killer cells, in terms of proliferation based on total nucleated cells (TNC), as compared with a proliferation obtained in a case where no re-stimulation was given (FIGS. 5a to 5d). When being stimulated once with Hut78-mTNF-α/4-1BBL/mbIL-21 cell line on day 0 of culture, culture was continued up to day 25 and 2,124-fold proliferation was achieved. When stimulated 5 times with Hut78-mTNFα/4-1BBL/mbIL-21 cell line at 7-day intervals, culture was continued up to day 35 day and 436,032-fold proliferation was achieved. When stimulated 4 times with Hut78-mTNF-α/4-1BBL/mbIL-21 cell line at 11-day intervals, culture was continued up to day 42 and 2,628,153-fold proliferation was achieved. Therefore, it was possible to identify that repeated stimulation with Hut78-mTNF-α/4-1BBL/mbIL-21 T cell line at 7-day or 11-day intervals resulted in a continuous increase in proliferation of natural killer cells.

EXPERIMENTAL EXAMPLE 1

Identification of Cell Viability of Natural Killer Cells Depending on Transduced Gene(s)

In order to compare and evaluate in-vitro cell viability, the Adam cell counter system, which is one of cell counters using PI staining solution capable of binding to intracellular nuclei, was used. After the number of viable cells was calculated by subtracting the number of dead cells from the measured total number of cells, cell viability was calculated using the following Expression I.

Cell viability (%)=(Number of viable cells/number of total cells)×100      [Expression I]

As a result of measuring viability of the natural killer cells after 21 days of culture, high cell viability of about 80% or more was observed under all conditions (FIGS. 6a to 6d).

EXPERIMENTAL EXAMPLE 2

Cell Phenotypic Analysis in Natural Killer Cells Depending on Transduced Gene(s)

The natural killer cells cultured for 21 days or the natural killer cells cultured with repeated re-stimulation were collected and centrifuged at 1,200 rpm for 5 minutes. The culture was removed by suction. Dilution with 1 ml of FACS buffer was performed and the cell number was measured. Dilution with the FACS buffer was performed so as to give a concentration of $5 \times 10^6$ cells/ml. 100 μl of the diluted cell solution was added to each 5-ml FACS tube (Falcon, 352052), and phenotypic analysis was performed with the following antibodies.

Tube 1: Anti-human CD3-FITC (BD Pharmingen, 555332), anti-human CD16-PE (BD Pharmingen, 555407), anti-human CD56-PE-Cy5 (BD Pharmingen, 555517) or anti-human CD56-PE Cy7 (BD Pharmingen, 557747), anti-human CD56-BV421 (BD Pharmingen, 562751)

Tube 2: Anti-human CD14-FITC (BD Pharmingen, 555397), anti-human CD19-PE (BD Pharmingen, 555413), anti-human CD3-PE-Cy5 (BD Pharmingen, 555341) or anti-human CD3-PE Cy7 (eBioscience, 25-0038-42), anti-human CD3-BV421 (BD Pharmingen, 562438)

Tube 3: Anti-human CD3-FITC, anti-human NKG2D-PE (R&D Systems, FAB139P), anti-human CD56-PE-Cy5 or anti-human CD56-PE-Cy7, anti-human CD56-BV421

Tube 4: Anti-human CD3-FITC, anti-human NKp30-PE (BD Pharmingen, 558407), anti-human CD56-PE-Cy5 or anti-human CD56-PE-Cy7, anti-human CD56-BV421

Tube 5: Anti-human CD3-FITC, anti-human NKp44-PE (BD Pharmingen, 558563), anti-human CD56-PE-Cy5 or anti-human CD56-PE-Cy7, anti-human CD56-BV421

Tube 6: Anti-human CD3-FITC, anti-human NKp46-PE (BD Pharmingen, 557991), anti-human CD56-PE-Cy5 or anti-human CD56-PE-Cy7, anti-human CD56-BV421

Tube 7: Anti-human CD3-FITC, anti-human DNAM-1-PE (BD Pharmingen, 559789), anti-human CD56-PE-Cy5 or anti-human CD56-PE-Cy7, anti-human CD56-BV421

Tube 8: Anti-human CD3-FITC, anti-human CXCR3-PE (BD Pharmingen, 557185), anti-human CD56-PE-Cy5 or anti-human CD56-PE-Cy7, anti-human CD56-BV421

Tube 9: Anti-human CD3-FITC, PE mouse IgG1 k isotype control (BD Pharmingen, 555749), anti-human CD56-PE-Cy5 or anti-human CD56-PE-Cy7, anti-human CD56-BV421

Tube 10: FITC mouse IgG1 k isotype control (BD Pharmingen, 555748), PE mouse IgG1 k isotype control, PE-Cy5 mouse IgG1 k isotype control (BD Pharmingen, 555750) or PE-Cy7 mouse IgG1 k isotype control (BD Pharmingen, 557872), BV421 mouse IgG1 k isotype control (BD Pharmingen, 562438)

Tube 11: Anti-human CD3-FITC, anti-human NKG2A-PE (R&D Systems, FAB1059P), anti-human CD56-PE-Cy5 or anti-human CD56-PE-Cy7, anti-human CD56-BV421

Tube 12: Anti-human CD3-FITC, anti-human NKG2C-PE (R&D Systems, FAB138P), anti-human CD56-PE-Cy5 or anti-human CD56-PE-Cy7, anti-human CD56-BV421

Tube 13: Anti-human CD3-FITC, anti-human CD62L-PE (eBioscience, 12-0629-42), anti-human CD56-PE-Cy5 or anti-human CD56-PE-Cy7, anti-human CD56-BV421

Tube 14: Anti-human CD3-FITC, anti-human CD69-PE (R&D Systems, FAB23591P), anti-human CD56-PE-Cy5 or anti-human CD56-PE-Cy7, anti-human CD56-BV421

Tube 15: Anti-human CD3-FITC, anti-human CD57-PE (BD Pharmingen, 560844), anti-human CD56-PE-Cy5 or anti-human CD56-PE-Cy7, anti-human CD56-BV421

In Tube 1, Staining with anti-human CD56 was performed by selecting one of three fluorescences, and thus the same fluorescence was selected for CD3 of Tube 2 and CD56 of Tubes 3 to 9 and 11 to 15, and isotype control of Tube 10.

The cells in the above tubes were stained at refrigeration temperature for 30 minutes. Thereafter, 2 ml of FACS buffer was added to the stained cells, and centrifugation was performed at 1,500 rpm for 5 minutes. The supernatant was removed, and 2 ml of FACS buffer was added again. Centrifugation was performed at 1,500 rpm for 5 minutes. The supernatant was removed again, and placed and suspended in 200 μl of fixation buffer (BD, 554655). Then, identification of the cells and examination for purity and phenotype thereof were performed using FACS LSRII Fortessa (BD).

Identification and purity analysis were performed on the natural killer cells cultured for 21 days. As a result, it was identified that the NK cell (CD3-CD56+) content was 95% or more under all conditions, and that an expression level of CD56+CD16+ marker for evaluating activation of the natural killer cells was highly maintained using the T feeder cells having undergone double gene transduction (FIGS. 7a to 7h).

In addition, expression of representative receptors in natural killer cells was analyzed. It was identified that all natural killer cells expressed CD16 at a high level, and expressed the activation markers NKG2D, NKp30, NKp44, NKp46, and DNAM-1 at high levels, without variation among donors, under a condition of feeder cells having undergone double gene transduction, as compared with a condition where no gene has been transduced or a condition of feeder cells having undergone single gene transduction. In particular, it was possible to identify that the amount of CXCR3 was greatly increased under a condition of feeder cells having undergone double gene transduction. Therefore, it was identified that the feeder cells having undergone double gene transduction were useful feeder cells capable of increasing activation and tumor targeting of NK cells (FIGS. 8a to 11l).

As a result of identifying receptors and activation markers of the natural killer cells cultured with repeated re-stimulation by T cell line due to gene transduction, it was identified that under both the condition where no re-stimulation was performed and the condition where repeated re-stimulation was performed, the activation markers (CD16, NKG2D, NKp30, NKp44, NKp46, DNAM-1) were expressed with no large difference even when a re-stimulation interval or a culture period increased (FIGS. 12a to 12c).

EXPERIMENTAL EXAMPLE 3

Identification of Abnormal Cell-Killing Activity of Natural Killer Cells Depending on Transduced Gene(s) for T Cells $1 \times 10^6$ cells of K562 cancer cell line were placed in a 15-ml tube and centrifugation was performed. The cell pellets were suspended in RPMI1640 medium supplemented with 1 ml of 10% (v/v) FBS. Thereafter, 30 µl of 1 mM Calcein-AM (Molecular probe, C34852) was added thereto. Then, silver foil was used to block the light, and staining was performed for 1 hour in an incubator at a temperature condition of 37° C.

The Calcein-AM-stained tumor cell line was washed by adding thereto 10 ml to 15 ml of RPMI1640 medium supplemented with 10% (v/v) FBS, and centrifugation was performed. Then, the pellets were suspended in 10 ml of RPMI1640 medium supplemented with 10% (v/v) FBS so that the cells had a concentration of $1 \times 10^5$ cells/ml. Natural killer cells were placed in a 15-ml tube at $1 \times 10^6$ cells, and centrifugation was performed. The pellets were suspended in RPMI1640 medium supplemented with 10% (v/v) FBS at a desired ratio (1:1) with respect to K562 cancer cell line. The prepared K562 cancer cell line and natural killer cell line were mixed using 100 µl each and dispensed into a 96-well U-bottom plate (Nunc, 163320). Each well was prepared in triplicate and a mean value thereof was obtained.

To spontaneous release wells were added 100 µl of the stained K562 cancer cell line and 100 µl of RPMI1640 medium supplemented with 10% (v/v) FBS. To maximum release wells were added 100 µl of the stained K562 cancer cell line and 100 µl of triple distilled water supplemented with 2% (v/v) Triton-X 100.

In order to correct auto-fluorescence present in RPMI1640 medium supplemented with 10% (v/v) FBS and RPMI1640 medium supplemented with 2% (v/v) Triton-X 100, 200 µl of RPMI1640 medium supplemented with 10% (v/v) FBS was added to prepare a medium value; and 100 µl of RPMI1640 medium supplemented with 2% (v/v) Triton-X 100 was added to 100 µl of RPMI1640 medium supplemented with 10% (v/v) FBS, to prepare a mixed solution value of the two solutions. The auto-fluorescence was corrected by adding, to the maximum release value, the difference (A) obtained by subtracting the mixed solution value from the medium value.

The light was blocked and reaction was allowed to occur for 4 hours in an incubator at a temperature condition of 37° C., and then the plate was centrifuged at 2,000 rpm for 3 minutes. The supernatant was dispensed at 100 µl each into 96-well black plate (Nunc, 237108). Fluorescence values ($OD_{480/535}$ nm) were measured using a fluorescence plate reader (Perkin Elmer, VICTOR X3), and tumor cell-killing ability of natural killer cells was calculated using the following Expression II.

% of killing=(Sample well mean fluorescence value −Spon well mean fluorescence value)/{(Max well mean fluorescence value+A)−Spon well mean fluorescence value}×100   [Expression II]

The natural killer cells cultured with various feeder cells were reacted with K562 cancer cell line to measure their direct cell-killing activity. As compared with other conditions, the killing activity against the K562 cancer cell line was increased on average under a condition of feeder cells having undergone double gene transduction (FIGS. 13a to 14d).

The natural killer cells cultured with re-stimulation by T cell line due to gene transduction were reacted with K562 cancer cell line to measure their direct cell-killing activity. It was identified that under both the condition where no re-stimulation was performed and the condition where repeated re-stimulation was performed, the killing activity against K562 was well maintained even when a culture period was prolonged and fold expansion was increased (FIGS. 15a to 15c).

EXPERIMENTAL EXAMPLE 4

Analysis of Proliferation Marker (Ki-67) in Natural Killer Cells Depending on Transduced Gene(s) for T Cells The natural killer cells cultured for 21 days or the natural killer cells cultured with repeated re-stimulation were collected and centrifuged at 1,200 rpm for 5 minutes. The culture was removed by suction. Dilution with 1 ml of FACS buffer was performed and the cell number was measured. Dilution with FACS buffer was performed so as to give a concentration of $5 \times 10^6$ cells/ml. 100 µl of the diluted cell solution was added to each 5-ml FACS tube (Falcon, 352052), and proliferation marker analysis was performed with the following antibodies.

Tube 1: Anti-human CD3-FITC (BD Pharmingen, 555332), anti-human CD56-PE-Cy7 (BD Pharmingen, 557747), 7-AAD (Beckman Coulter, Inc., A07704)

Tube 2: Anti-human CD3-FITC (BD Pharmingen, 555332), anti-human CD56-PE-Cy7 (BD Pharmingen, 557747), 7-AAD (Beckman Coulter, Inc., A07704)

Tube 3: FITC Mouse IgG1 k isotype control (BD Pharmingen, 555748), PE-Cy7 Mouse IgG1 k isotype control (BD Pharmingen, 557872)

The cells in the above tubes were stained at refrigeration temperature for 30 minutes. Thereafter, 2 ml of FACS buffer was added to the stained cells, and centrifugation was performed at 1,500 rpm for 5 minutes. The supernatant was removed, and 2 ml of FACS buffer was added again. Centrifugation was performed at 1,500 rpm for 5 minutes. The supernatant was removed again, and placed and suspended in 200 μl of fixation/permeabilization buffer (eBioscience, 00-5521-00). Then, reaction was allowed to occur at refrigeration temperature for 30 minutes or longer. 2 ml of 1× Perm/wash buffer was added and centrifugation was performed at 1,500 rpm for 5 minutes. The supernatant was removed, and 2 ml of FACS buffer was added again. Centrifugation was performed at 1,500 rpm for 5 minutes. Anti-human Ki-67-V450 (BD Pharmingen, 561281) was added to the tube 1, and V450 mouse IgG1 k isotype control (BD Pharmingen, 561504) was added to the tubes 2 and 3. Staining was performed at room temperature for 30 minutes.

Thereafter, 2 ml of 1× Perm/wash buffer was added to the stained cells, and centrifugation was performed at 1,500 rpm for 5 minutes. The supernatant was removed, and 2 ml 1× Perm/wash buffer was added again. Centrifugation was performed at 1,500 rpm for 5 minutes. The supernatant was removed again, and placed and suspended in 200 μl of fixation buffer (BD, 554655). Then, FACS LSRII Fortessa (BD) was used to examine the proliferation marker in the cells.

It was identified that expression of Ki-67 in the natural killer cells cultured with HuT 78 cell lines into which one or more genes have been transduced was maintained at a relatively high level, except for Hut78-mTNF-α/OX40L, as compared with the HuT 78 cell line having no gene transduction (FIGS. 16a to 16d).

Analysis was performed on the proliferation marker in the natural killer cells cultured through re-stimulation by Hut78-mTNFα/4-1BBL/mbIL-21 feeder cells. As a result, it was identified that expression of Ki-67 which had been decreasing increased with stimulation by feeder cells at 7-day or 11-day intervals. In addition, it was identified that expression of Ki-67 could be sustained through repeated re-stimulation (FIGS. 17a to 17d).

EXPERIMENTAL EXAMPLE 5

Analysis of Co-Stimulatory Molecules in Natural Killer Cells Depending on Transduced Gene(s) for T Cells The natural killer cells cultured for 21 days or the natural killer cells cultured with repeated re-stimulation were collected and centrifuged at 1,200 rpm for 5 minutes. The culture was removed by suction. Dilution with 1 ml of FACS buffer was performed and the cell number was measured. Dilution with FACS buffer was performed so as to give a concentration of $5 \times 10^6$ cells/ml. 100 μl of the diluted cell solution was added to each 5-ml FACS tube (Falcon, 352052), and phenotypic analysis was performed with the following antibodies.

Tube 1: Anti-human CD3-FITC (BD Pharmingen, 555332), anti-human CD25-PE (BD Pharmingen, 555432), anti-human CD56-PE-Cy5 (BD Pharmingen, 555517) or anti-human CD56-PE Cy7 (BD Pharmingen, 557747), anti-human CD56-BV421 (BD Pharmingen, 562751)

Tube 2: Anti-human CD3-FITC, anti-human TNFRII-PE (R&D Systems, FAB226P), anti-human CD56-PE-Cy5 or anti-human CD56-PE-Cy7, anti-human CD56-BV421

Tube 3: Anti-human CD3-FITC, anti-human 4-1BB-PE (BD Pharmingen, 559446), anti-human CD56-PE-Cy5 or anti-human CD56-PE-Cy7, anti-human CD56-BV421

Tube 4: Anti-human CD3-FITC, PE mouse IgG1 k isotype control (BD Pharmingen, 555749), anti-human CD56-PE-Cy5 or anti-human CD56-PE-Cy7, anti-human CD56-BV421

Tube 5: FITC mouse IgG1 k isotype control (BD Pharmingen, 555748), PE mouse IgG1 k isotype control, PE-Cy5 mouse IgG1 k isotype control (BD Pharmingen, 555750) or PE-Cy7 mouse IgG1 k isotype control (BD Pharmingen, 557872), BV421 mouse IgG1 k isotype control (BD Pharmingen, 562438)

In Tube 1, Staining with anti-human CD56 was performed by selecting one of three fluorescences, and thus the same fluorescence was selected for CD56 of Tubes 2 to 4, and isotype control of Tube 5.

The cells in the above tubes were stained at refrigeration temperature for 30 minutes. Thereafter, 2 ml of FACS buffer was added to the stained cells, and centrifugation was performed at 1,500 rpm for 5 minutes. The supernatant was removed, and 2 ml of FACS buffer was added again. Centrifugation was performed at 1,500 rpm for 5 minutes. The supernatant was removed again, and placed and suspended in 200 μl of fixation buffer (BD, 554655). Then, FACS LSRII Fortessa (BD) was used to perform identification of the cells and examination for co-stimulatory molecules.

Analysis was performed on co-stimulatory molecules in the natural killer cells cultured for 21 days using Hut78 cell lines having various gene combinations. As a result, it was identified that expression of the co-stimulatory molecules in the natural killer cells cultured with the Hut78 cell lines into which one or more genes have been transduced is maintained at a relatively high level as compared with the non-transgenic Hut78 cell line. In particular, it was identified that the cell lines into which a single gene or combinations of multiple genes including the mbIL-21 gene have been transduced exhibited higher expression of co-stimulatory molecules than other cell lines (FIGS. 18a to 18f).

Analysis was performed on co-stimulatory molecules in the natural killer cells cultured after one stimulation by Hut78-mTNF-α/4-1BBL/mbIL-21 cell line on day 0 of culture or the natural killer cells cultured through repeated re-stimulation by Hut78-mTNF-α/4-1BBL/mbIL-21 cell line at 7-day or 11-day intervals. As a result, expression of the co-stimulatory molecules increased and then remained in a decreased state, unless additional re-stimulation is performed after the first stimulation. On the other hand, expression of the co-stimulatory molecules was continued during the culture period while repeatedly showing that upon repeated stimulation by feeder cells, expression of the co-stimulatory molecules increased at a time point of stimulation and then decreased after a certain time elapsed (FIGS. 19a to 19f).

EXPERIMENTAL EXAMPLE 6

Identification of Cytokine-Secretion of Natural Killer Cells Depending on Transduced Gene(s) for T Cells $2.5 \times 10^6$ cells of K562 cancer cell line were placed in a 15-ml tube and centrifuged. The cell pellets were suspended in 1 ml of RPMI1640 medium supplemented with 10% (v/v) FBS.

Natural killer cells were placed at $2.5 \times 10^6$ cells in a 15-ml tube and centrifuged. The cell pellets were suspended in RPMI1640 medium supplemented with 1 ml of 10% (v/v) FBS. In order to identify, within the cells, cytokines to be secreted out of the cells, the protein transport inhibitors Golgiplug (BD, 555029) and Golgistop (BD, 554724) were added thereto.

The prepared cells were dispensed into a 96-well U-bottom plate (Nunc, 163320), in which the natural killer cells and the medium were added in 100 μl each to well 1, and the K562 cancer cell line and the natural killer cell line were mixed using 100 μl each and added to wells 2 and 3.

Wells 1, 2: Anti-human CD107a-APC (BD Pharmingen, 560664)

Well 3: APC mouse IgG1 k isotype control (BD Pharmingen, 555751)

The light was blocked and reaction was allowed to occur for 4 hours in an incubator at a temperature condition of 37° C., and then the plate was centrifuged at 2,000 rpm for 3 minutes. The supernatant was removed and cytokine-secreting ability analysis was performed with the following antibodies.

Wells 1, 2, 3: Anti-human CD3-PerCP-Cy5.5 (eBioscience, 45-0036-42), anti-human CD56-APC-Cy7 (eBioscience, 47-0567-42), 7-AAD (Beckman Coulter, Inc., A07704)

The plate was stained at refrigeration temperature for 30 minutes. Thereafter, 100 μl of FACS buffer was added to the stained cells, and centrifugation was performed at 2,000 rpm for 3 minutes. The supernatant was removed and 200 μl FACS buffer was added again thereto. Centrifugation was performed at 2,000 rpm for 3 minutes. The supernatant was removed again, and placed and suspended in 200 μl of fixation/permeabilization buffer (BD Pharmingen, 554714). Then, reaction was allowed to occur at refrigeration temperature for 30 minutes or longer.

200 μl of 1× Perm/wash buffer was added thereto, and centrifugation was performed at 1,500 rpm for 5 minutes. The supernatant was removed, and 2 ml of FACS buffer was added again. Centrifugation was performed at 2,000 rpm for 3 minutes. Anti-human IFN-γ-FITC (BD Pharmingen, 554700), anti-human TNFα-PE-Cy7 (eBioscience, 25-7349-82) were added to wells 1 and 2, and FITC mouse IgG1 k isotype control (BD Pharmingen, 555748), PE-Cy7 mouse IgG1 k isotype control (BD Pharmingen, 557872) were added to well 3. Staining was performed at refrigeration temperature for 30 minutes.

Thereafter, 100 μl of 1× Perm/wash buffer was added to the stained cells, and centrifugation was performed at 2,000 rpm for 3 minutes. The supernatant was removed and 100 μl of 1× Perm/wash buffer was added again thereto. Centrifugation was performed at 2,000 rpm for 3 minutes. The supernatant was removed again, and placed and suspended in 200 μl of fixation buffer (BD, 554655). Then, FACS LSRII Fortessa (BD) was used to examine cytokine-secreting ability of the cells.

Measurements were performed on the cytokine-secreting ability, against K562 cancer cell line, of the natural killer cells cultured for 21 days using Hut78 cell lines having various gene combinations. As a result, it was identified that when being cultured with cell lines into which one or more genes have been transduced, a similar level of cytokine-secreting ability was observed despite large difference in expansion fold, as compared with the cell line having no gene transduction (FIGS. 20a to 20c).

The cytokinesecretion of the natural killer cells cultured after one stimulation by Hut78-mTNFα/4-1BBL/mbIL-21 cell line on day 0 of culture or the natural killer cells cultured through repeated re-stimulation by Hut78-mTNFα/4-1BBL/mbIL-21 cell line at 7-day or 11-day intervals was measured by reaction with K562 cancer cell line. It was identified that as compared with the natural killer cells cultured with one stimulation, the cytokine-secreting ability against K562 was maintained, without large difference, in the natural killer cells cultured with repeated re-stimulation, despite a long culture period and high expansion fold (FIGS. 21a to 21c).

The invention claimed is:

1. A genetically modified CD4+T cell that expresses a TNF-α gene mutated to encode an amino acid other than Alanine at the amino acid corresponding to P76 of SEQ ID NO: 8 and/or an amino acid other than Valine at the amino acid corresponding to V77 of SEQ ID NO: 8; wherein the cell is inactivated.

2. The genetically modified CD4+T cell of claim 1, wherein the CD4+T cell is a Hut78, H9, or Jurkat cell.

3. The genetically modified CD4+T cell of claim 1, wherein the CD4+T cell is a Hut78 cell.

4. The genetically modified CD4+T cell of claim 1, wherein the TNF-α gene comprises a nucleotide sequence encoding the amino acid of SEQ ID NO: 8.

5. The genetically modified CD4+T cell of claim 1, wherein the cell further expresses a membrane-bound IL-21 gene.

6. The genetically modified CD4+T cell of claim 5, wherein the membrane-bound IL-21 gene comprises a nucleotide sequence encoding the amino acid of SEQ ID NO: 3.

7. The genetically modified CD4+T cell of claim 1, wherein the cell further expresses a 4-1BBL gene.

8. The genetically modified CD4+T cell of claim 7, wherein the 4-1BBL gene comprises a nucleotide sequence encoding the amino acid of SEQ ID NO: 1.

9. The genetically modified CD4+T cell of claim 1, wherein the cell further expresses an OX40L gene.

10. The genetically modified CD4+T cell of claim 9, wherein the OX40L gene comprises a nucleotide sequence encoding the amino acid of SEQ ID NO: 5.

11. The genetically modified CD4+T cell of claim 5, wherein the cell further expresses a 4-1BBL gene.

12. The genetically modified CD4+T cell of claim 11, wherein the 4-1BBL gene comprises a nucleotide sequence encoding the amino acid of SEQ ID NO: 1.

13. The genetically modified CD4+T cell of claim 6, wherein the cell further expresses a 4-1BBL gene.

14. The genetically modified CD4+T cell of claim 13, wherein the 4-1BBL gene comprises a nucleotide sequence encoding the amino acid of SEQ ID NO: 1.

15. The genetically modified CD4+T cell of claim 5, wherein the cell further expresses an OX40L gene.

16. The genetically modified CD4+T cell of claim 15, wherein the OX40L gene comprises a nucleotide sequence encoding the amino acid of SEQ ID NO: 5.

17. The genetically modified CD4+T cell of claim 6, wherein the cell further expresses an OX40L gene.

18. The genetically modified CD4+T cell of claim 17, wherein the OX40L gene comprises a nucleotide sequence encoding the amino acid of SEQ ID NO: 5.

19. The genetically modified CD4+T cell of claim 7, wherein the cell further expresses an OX40L gene.

20. The genetically modified CD4+T cell of claim 19, wherein the OX40L gene comprises a nucleotide sequence encoding the amino acid of SEQ ID NO: 5.

21. The genetically modified CD4+T cell of claim 8, wherein the cell further expresses an OX40L gene.

22. The genetically modified CD4+T cell of claim 21, wherein the OX40L gene comprises a nucleotide sequence encoding the amino acid of SEQ ID NO: 5.

23. The genetically modified CD4+T cell of claim 11, wherein the cell further expresses an OX40L gene.

24. The genetically modified CD4+T cell of claim 23, wherein the OX40L gene comprises a nucleotide sequence encoding the amino acid of SEQ ID NO: 5.

25. The genetically modified CD4+T cell of claim 12, wherein the cell further expresses an OX40L gene.

26. The genetically modified CD4+T cell of claim 25, wherein the OX40L gene comprises a nucleotide sequence encoding the amino acid of SEQ ID NO: 5.

27. The genetically modified CD4+T cell of claim 13, wherein the cell further expresses an OX40L gene.

28. The genetically modified CD4+T cell of claim 27, wherein the OX40L gene comprises a nucleotide sequence encoding the amino acid of SEQ ID NO: 5.

29. The genetically modified CD4+T cell of claim 14, wherein the cell further expresses an OX40L gene.

30. The genetically modified CD4+T cell of claim 29, wherein the OX40L gene comprises a nucleotide sequence encoding the amino acid of SEQ ID NO: 5.

* * * * *